US012790435B2

(12) United States Patent
Zhou et al.

(10) Patent No.: US 12,790,435 B2
(45) Date of Patent: Nov. 10, 2026

(54) ARTIFICIAL MELANIN NANOPARTICLES AND METHODS INCLUDING POROUS MELANIN MATERIALS

(71) Applicant: Northwestern University, Evanston, IL (US)

(72) Inventors: Xuhao Zhou, Evanston, IL (US); Zhao Wang, Evanston, IL (US); Naneki C. McCallum, Evanston, IL (US); Nathan C. Gianneschi, Evanston, IL (US); Zofia E. Siwicka, Evanston, IL (US)

(73) Assignee: Northwestern University, Evanston, IL (US)

(*) Notice: Subject to any disclaimer, the term of this patent is extended or adjusted under 35 U.S.C. 154(b) by 864 days.

(21) Appl. No.: 17/621,908

(22) PCT Filed: Jun. 26, 2020

(86) PCT No.: PCT/US2020/039769
§ 371 (c)(1),
(2) Date: Dec. 22, 2021

(87) PCT Pub. No.: WO2021/021350
PCT Pub. Date: Feb. 4, 2021

(65) Prior Publication Data

US 2022/0332670 A1 Oct. 20, 2022

Related U.S. Application Data

(60) Provisional application No. 62/868,369, filed on Jun. 28, 2019.

(51) Int. Cl.

| | |
|---|---|
| ***C08G 61/10*** | (2006.01) |
| ***B29B 9/00*** | (2006.01) |
| ***B82Y 5/00*** | (2011.01) |

(52) U.S. Cl.
CPC ................ *C08G 61/10* (2013.01); *B29B 9/00* (2013.01); *B82Y 5/00* (2013.01); *C08G 2261/11* (2013.01);
(Continued)

(58) Field of Classification Search
None
See application file for complete search history.

(56) References Cited

U.S. PATENT DOCUMENTS 4,861,760 A 8/1989 Mazuel et al.
4,911,920 A 3/1990 Jani et al.
(Continued)

FOREIGN PATENT DOCUMENTS

CN 107298873 A * 10/2017 ............ C09B 61/00
KR 10-2016-0072590 A 6/2016
(Continued)

OTHER PUBLICATIONS

Machine translation of CN 107298873A (Year: NA).*
(Continued)

*Primary Examiner* — Rachel Kahn
(74) *Attorney, Agent, or Firm* — Leydig, Voit & Mayer, Ltd.

(57) ABSTRACT

In an aspect, a plurality of artificial melanin nanoparticles are provided, wherein: each melanin nanoparticle of the plurality of artificial melanin nanoparticles comprises a plurality of melanin oligomers; each melanin oligomer comprises a plurality of covalently-bonded melanin base units; and each melanin base unit comprises substituted or unsubstituted naphthalene. In an aspect, porous artificial melanin materials and methods of synthesizing porous artificial melanin materials are provided.

20 Claims, 67 Drawing Sheets

1,8-DHN
2-4' dimer
4-4' dimer
2-2' dimer
DHN-based Allomelanin Nanoparticle (AMNP)

(52) U.S. Cl.
CPC ................ *C08G 2261/1422* (2013.01); *C08G 2261/226* (2013.01); *C08G 2261/314* (2013.01); *C08G 2261/362* (2013.01); *C08G 2261/43* (2013.01)

(56) References Cited

U.S. PATENT DOCUMENTS

| | | | |
|---|---|---|---|
| 5,212,162 | A | 5/1993 | Missel et al. |
| 5,403,841 | A | 4/1995 | Lang et al. |
| 5,441,542 | A | 8/1995 | Prota et al. |
| 5,547,658 | A | 8/1996 | Hansenne et al. |
| 8,067,044 | B2 | 11/2011 | Henry et al. |
| 8,586,090 | B2 | 11/2013 | Dadachova et al. |
| 11,045,493 | B2 | 6/2021 | Gianneschi et al. |
| 2009/0178209 | A1 | 7/2009 | Koike et al. |
| 2011/0236325 | A1 | 9/2011 | Mitchell et al. |
| 2013/0078205 | A1 | 3/2013 | Dayan et al. |
| 2013/0177616 | A1 | 7/2013 | de Olivera et al. |
| 2014/0044789 | A1 | 2/2014 | Dadachova et al. |
| 2015/0093342 | A1 | 4/2015 | Domloge et al. |
| 2021/0393673 | A1 | 12/2021 | Gianneschi et al. |

FOREIGN PATENT DOCUMENTS

| | | | |
|---|---|---|---|
| WO | WO 1993/005759 | A1 | 4/1993 |
| WO | WO 2009/003037 | A1 | 12/2008 |
| WO | WO 2017/064672 | A1 | 4/2017 |
| WO | WO 2018/013609 | A2 | 1/2018 |
| WO | WO 2021/021350 | A2 | 2/2021 |
| WO | WO 2021/087076 | A1 | 5/2021 |
| WO | WO 2021/096692 | A1 | 5/2021 |

OTHER PUBLICATIONS

Extended European Search Report dated Jun. 12, 2023 in corresponding European Application No. 20848583.9.
"NanoComposix's Guide to Dynamic Light Scattering Measurement and Analysis" [dated Feb. 2015 (version 1.4), published by nanoComposix of San Diego, CA, and available at nanoComposix_Guidelines_for_DLS_Measurements_and_Analysis (last accessed Jun. 26, 2019), pp. 1-8.
Abcam Flow cytometric analysis of cell cycle with propidium iodide DNA staining. https://www.abcam.com/protocols/flow-cytometric-analysis-of-cell-cycle-with-propidium-iodide-dna-staining.
Akiladevi et al. (2010) "Ethosomes—A noninvasive approach for transdermal drug delivery," Int J Current Pharm Res 2(4): 1-4.
Alikhan et al. (2011) "Vitiligo: a comprehensive overview: part I. Introduction, epidemiology, quality of life, diagnosis, differential diagnosis, associations, histopathology, etiology, and work-up," J. Am. Acad. Dermatol. 65(3): 473-491.
Al-Muhammed et al. (1996) "In-vivo studies on dexamethasone sodium phosphate liposomes," J. Microencapsul. 13(3): 293-306.
Ando et al. (2007) "Approaches to identify inhibitors of melanin biosynthesis via the quality control of tyrosinase," J. Invest. Dermatol. 127(4): 751-761.
Ando et al. (2012) "Melanosomes are transferred from melanocytes to keratinocytes through the processes of packaging, release, uptake, and dispersion," J. Invest. Dermatol. 132(4): 1222-1229.
Apte et al. (2013) "Psychrotrophic yeast Yarrowia lipolytica NCYC 789 mediates the synthesis of antimicrobial silver nanoparticles via cell-associated melanin," AMB Express 3:32, pp. 1-8.
Bardestani et al. (2019) "Experimental methods in chemical engineering: specific surface area and pore size distribution measurements—BET, BJH, and DFT," The Canadian Journal of Chemical Engineering 97(11): 2781-2791.
Battistella et al. (2020) "Mimicking Natural Human Hair Pigmentation with Synthetic Melanin," ACS Cent. Sci. 6(7): 1179-1188.
Beltran-Garcia et al. (2014) "Singlet Molecular Oxygen Generation by Light-Activated DHN-Melanin of the Fungal Pathogen Mycosphaerella fijiensis in Black Sigatoka Disease of Bananas," PLOS ONE 9(3): e91616, pp. 1-15.
Berge et al. (1977) "Pharmaceutical Salts," Journal of Pharmaceutical Sciences 66(1): 1-19.
Bernard et al. (2016) "Consumption of hair dye products by the French women population: Usage pattern and exposure assessment," Food and Chemical Toxicology 88: 123-132.
Bikle et al. (2012) "Calcium Regulation of Keratinocyte Differentiation," Expert Rev. Endocrinol. Metab. 7(4): 461-472.
Borowska et al. (2015) "Metals in cosmetics: implications for human health," J Appl Toxicol 35(6): 551-572.
Boulton et al. (2001) "Retinal Photodamage," J. Photochem. Photobiol. B: Biol. 64(2-3): 144-161.
Brenner et al. (2008) "The Protective Role of Melanin Against UV Damage in Human Skin," Photochem. Photobiol. 84(3): 539-549.
Byers et al. (2003) "Role of Cytoplasmic Dynein in Perinuclear Aggregation of Phagocytosed Melanosomes and Supranuclear Melanin Cap Formation in Human Keratinocytes," J. Invest. Dermatol. 121(4): 813-820.
Byers et al. (2007) "Requirement of dynactin p150$^{Glued}$ subunit for the functional integrity of the keratinocyte microparasol," J. Investi. Dermatol. 127(7): 1736-1744.
Cecchini et al. (2017) "Modeling Fungal Melanin Buildup: Biomimetic Polymerization of 1,8-Dihydroxynaphthalene Mapped by Mass Spectrometry," Chem. Eur. J. 23: 8092-8098.
Chen et al. (2014) "Engineering fluorescent poly(dopamine) capsules," Langmuir 30(10): 2921-2925.
Chen et al. (2016) "Nanoscale Polydopamine (PDA) Meets π-π Interactions: An Interface-Directed Coassembly Approach for Mesoporous Nanoparticles," Langmuir 32(46): 12119-12128.
Chonn et al. (1995) "Recent advances in liposomal drug-delivery systems," Curr. Opin. Biotechnol. 6(6): 698-708.
Chung (Sep. 2016) "Azo dyes and human health: A review," J Environ Sci Health C Environ Carcinog Ecotoxicol Rev 34: 233-261.
Cordero et al. (2020) "Melanin." Curr Biol 30 (4), R142-R143.
Dadachova et al. (2007) "Ionizing Radiation Changes the Electronic Properties of Melanin and Enhances the Growth of Melanized Fungi," Plos One 2(5): e457, pp. 1-13.
Dadachova et al. (2008) "Ionizing Radiation: How Fungi Cope, Adapt, and Exploit with the Help of Melanin," Curr. Opin. Microbiol. 11(6): 525-531.
Dadachova et al. (2008) "The radioprotective properties of fungal melanin are a function of its chemical composition, stable radical presence and spatial arrangement," Pigment Cell Melanoma Res 21(2): 192-199.
D'Alba et al. (2019) " Melanosomes: Biogenesis, Properties, and Evolution of an Ancient Organelle," Physiol. Rev. 99: 1-19.
Dell'Angelica et al. (2000) "Lysosome-related organelles," FASEB J. 14(10): 1265-1278.
D'Ischia et al. (2015) "Melanins and Melanogenesis: from Pigment Cells to Human Health and Technological Applications," Pigm. Cell Melanoma Res. 28(5): 520-544.
Dong et al. (2019) "Melanin-mimetic multicolor and low-toxicity hair dye," RSC Adv 9: 33617.
Durante et al. (2011) Physical basis of radiation protection in space travel. Rev. Mod. Phys. 83, (4), 1245-1281.
Eisenman et al. (2005) "Microstructure of Cell Wall-Associated Melanin in the Human Pathogenic Fungus Cryptococcus neoformans," Biochemistry 44(10): 3683-3693.
Etebari et al. (2015) "Evaluation of protective effect of amifostine on dacarbazine induced genotoxicity" Res Pharm Sci 10, (1), 68-74.
Eyles et al. (1997) "Oral Delivery and Fate of Poly(lactic acid) Microsphere-encapsulated Interferon in Rats," J. Pharm. Pharmacol. 49(7): 669-674.
Fan et al. (2014) "Transferring biomarker into molecular probe: melanin nanoparticle as a naturally active platform for multimodality imaging," J. Am. Chem. Soc. 136(43): 15185-15194.
Foote et al. (1996) Active Oxygen in Chemistry (Book).
Gago-Dominguez et al. (2001) "Use of permanent hair dyes and bladder-cancer risk," Int J Cancer 91(4): 575-579.

(56) References Cited

OTHER PUBLICATIONS

Gao (1995) "Controlled Release of a Contraceptive Steroid from Biodegradable and Injectable Gel Formulations: In Vitro Evaluation," Pharm. Res. 12(6): 857-863.
Gao et al. (2013) "Mussel-Inspired Synthesis of Polydopamine-Functionalized Graphene Hydrogel as Reusable Adsorbents for Water Purification," ACS Applied Materials & Interfaces 5(2): 425-432.
Gao et al. (2019) "Rapid preparation of polydopamine coating as a multifunctional hair dye," Rsc Adv 9: 20492-20496.
Ghiani et al. (2008) "Characterization of human hair melanin and its degradation products by means of magnetic resonance techniques," Magn Reson Chem 46(5): 471-479.
Glass et al. (2012) "Direct chemical evidence for eumelanin pigment from the Jurassic period" Proc. Natl. Acad. Sci. U. S. A. 109, (26), 10218-23.
Guerra-Tapia et al. (2014) "Hair cosmetics: dyes," Actas Dermo-Sifiliograficas 105(9): 833-839.
Haining et al. (2017) "Neuromelanin, One of the Most Overlooked Molecules in Modern Medicine, is not a Spectator," Neural Regen. Res. 12(3): 372-375.
Hall et al. (2016) "Protection against Radiotherapy-Induced Toxicity," Antioxidants (Basel) 5(3): 22, pp. 1-18.
Han et al. (2015) "Dual-Stage-Light-Guided Tumor Inhibition by Mitochondria-Targeted Photodynamic Therapy," Adv. Funct. Mater. 25(20): 2961-2971.
Harrison et al. (2003) "Hair colouring, permanent styling and hair structure," J Cosmet Dermatol 2(3-4): 180-185.
Hasegawa et al. (2015) "Health effects of radiation and other health problems in the aftermath of nuclear accidents, with an emphasis on Fukushima." Lancet 386, (9992), 479-488.
Haveli et al. (2012) "Hair Fiber as a Nanoreactor in Controlled Synthesis of Fluorescent Gold Nanoparticles," Nano Lett 12(12): 6212-6217.
Hennessy et al. (2005) "Eumelanin and Pheomelanin Concentrations in Human Epidermis before and after UVB Irradiation," Pigm. Cell Res. 18(3): 220-223.
Hong et al. (2004) "Binding of Metal lons to Melanin and Their Effects on the Aerobic Reactivity," Photochem. Photobiol. 80(3): 477-481.
Hong et al. (2007) "Current Understanding of the Binding Sites, Capacity, Affinity, and Biological Significance of Metals in Melanin," J. Phys. Chem. B 111(28): 7938-7947.
Huang et al. (2017) "Mimicking Melanosomes: Polydopamine Nanoparticles as Artificial Microparasols," and Suppl. Info., ACS Cent. Sci. (Jun. 2017) 3(6): 564-569 (22 pp. total).
Huang et al. (2018) "Recent Advances and Progress on Melanin-like Materials and Their Biomedical Applications," Biomacromolecules 19: 1858-1868.
Hunt et al. (1995) "Eumelanin and phaeomelanin contents of human epidermis and cultured melanocytes," Pigment Cell Res. 8(4): 202-208.
Im et al. (2017) "Metal-Chelation-Assisted Deposition of Polydopamine on Human Hair: A Ready-to-Use Eumelanin-Based Hair Dyeing Methodology," Acs Biomater Sci Eng 3(4): 628-636.
International Preliminary Report on Patentability, dated Jan. 24, 2019, corresponding to International Application No. PCT/US2017/041596 (filed Jul. 11, 2017), 10 pp.
Ito et al. (1980) "Co-polymerization of dopa and cysteinyldopa in melanogenesis in vitro," Experientia 36(7): 822-823.
Ito et al. (1985) "Microanalysis of eumelanin and pheomelanin in hair and melanomas by chemical degradation and liquid chromatography," Anal. Biochem. 144(2): 527-536.
Ito et al. (2003) "Quantitative analysis of eumelanin and pheomelanin in humans, mice, and other animals: a comparative review," Pigment Cell Res. 16(5): 523-531.
Ito et al. (2008) "Chemistry of Mixed Melanogenesis—Pivotal Roles of Dopaquinone," Photochem. Photobiol. 84(3): 582-592.
Ito S. (1989) "Optimization of conditions for preparing synthetic pheomelanin." Pigment Cell Res 2, (1), 53-6.
Iwamoto et al. (1999) "Different cell cycle mechanisms between UV-induced and X-ray-induced apoptosis in WiDr colorectal carcinoma cells," Apoptosis 4(1): 59-66.
Jin et al. (2012) "Genome-wide association analyses identify 13 new susceptibility loci for generalized vitiligo," Nat. Genet. 44(6): 676-680.
Johnson (2017) Safety Assessment of Ammonia and Ammonium Hydroxide as Used in Cosmetics, Cosmetic Ingredient Review, 42 pages.
Ju et al. (2011) "Bioinspired polymerization of dopamine to generate melanin-like nanoparticles having an excellent free-radical-scavenging property," Biomacromolecules 12(3): 625-632.
Ju et al. (2013) "Bio-Inspired, Melanin-Like Nanoparticles as a Highly Efficient Contrast Agent for T1-Weighted Magnetic Resonance Imaging," Biomacromolecules 14(10): 3491-3497.
Ju et al. (2015) "Bio-inspired Development of a Dual-Mode Nanoprobe for MRI and Raman Imaging," Small 11(1): 84-89.
Kang et al. (2018) "Reverse Engineering To Characterize Redox Properties: Revealing Melanin's Redox Activity through Mediated Electrochemical Probing," Chem. Mater. 30: 5814-5826.
Kasraee et al. (2012) "Ebselen is a new skin depigmenting agent that inhibits melanin biosynthesis and melanosomal transfer," Exp. Dermatol. 21: 19-24.
Kawamura et al. (2016) "Full-Color Biomimetic Photonic Materials with Iridescent and Non-Iridescent Structural Colors." Sci Rep 6, 33984.
Keogh et al. (1965) "Rate of Greying of Human Hair," Nature 207: 877-878.
Kim et al. (2010) "Biomimetic Approach to Confer Redox Activity to Thin Chitosan Films," Adv. Funct. Mater. 20(16): 2683-2694.
Kim et al. (2011) "Development of a high-content screening method for chemicals modulating DNA damage response," J. Biomol. Screen. 16(2): 259-265.
Kim et al. (2018) "Enzymatic film formation of nature-derived phenolic amines" Nanoscale 10 (28), 13351-13355.
Kim et al. (2017) "Spectroelectrochemical Reverse Engineering Demonstrates That Melanin's Redox and Radical Scavenging Activities Are Linked," Biomacromolecules 18(12): 4084-4098.
Kobayashi et al. (1993) "Melanin Reduces Ultraviolet-Induced DNA Damage Formation and Killing Rate in Cultured Human Melanoma Cells," J. Invest. Dermatol. 101(5): 685-689.
Kobayashi et al. (1998) "Supranuclear melanin caps reduce ultraviolet induced DNA photoproducts in human epidermis," J. Invest. Dermatol. 110(5): 806-810.
Korner et al. (1982) "Mammalian tyrosinase catalyzes three reactions in the biosynthesis of melanin," Science 217(4565): 1163-1165.
Kumar (2005) "Exploratory analysis of global cosmetic industry: major players, technology and market trends," Technovation 25(11): 1263-1272.
Lampel et al. (2017) "Polymeric Peptide Pigments with Sequence-Encoded Properties," Science 356(6342): 1064-1068.
Lee et al. (2007) "A reversible wet/dry adhesive inspired by mussels and geckos." Nature 448, (7151), 338-41.
Lee et al. (2007) "Mussel-Inspired Surface Chemistry for Multifunctional Coatings," Science 318(5849): 426-430.
Lee et al. (2015) "Retinal development in albinism: a prospective study using optical coherence tomography in infants and young children," Lancet. 385(Suppl 1): p. S14.
Lemaster et al. (2019) "Gadolinium Doping Enhances the Photoacoustic Signal of Synthetic Melanin Nanoparticles: A Dual Modality Contrast Agent for Stem Cell Imaging," Chem. Mater. 31(1): 251-259.
Lent et al. (2017) "Acute and subacute oral toxicity of periodate salts in rats," Regul Toxicol Pharmacol 83: 23-37.
Li et al. (2016) "Polycatechol Nanoparticle MRI Contrast Agents," Small 12(5): 668-677.
Liebscher et al. (2013) "Structure of polydopamine: a never-ending story?" Langmuir 29(33): 10539-10548.
Lin et al. (2016) "Multimodal-Imaging-Guided Cancer Phototherapy by Versatile Biomimetic Theranostics with UV and γ-Irradiation Protection," Adv Mater 28(17): 3273-3279.

(56) References Cited

OTHER PUBLICATIONS

Liu et al. (2003) "Comparison of the Structural and Physical Properties of Human Hair Eumelanin Following Enzymatic or Acid/Base Extraction." Pigment Cell Res. 16, (4), 355-365.
Liu et al. (2004) "Ion-Exchange and Adsorption of Fe(III) by Sepia Melanin," Pigm. Cell Res. 17(3): 262-269.
Liu et al. (2013) "Mussel-Inspired Polydopamine: a Biocompatible and Ultrastable Coating for Nanoparticles in vivo," ACS Nano 7(10): 9384-9395.
Liu et al. (2014) "Polydopamine and its derivative materials: synthesis and promising applications in energy, environmental, and biomedical fields," Chem. Rev. 114(9): 5057-5115.
Liu et al. (2019) "Role of Polydopamine's Redox-activity on Its Pro-oxidant, Radical-scavenging, and Antimicrobial Activities," Acta Biomater. 88: 181-196.
Liu et al. (2017) "Comprehensive Insights into the Multi-Antioxidative Mechanisms of Melanin Nanoparticles and Their Application To Protect Brain from Injury in Ischemic Stroke," J. Am. Chem. Soc. 139(2): 856-862.
Luo et al. (2018) "Multifunctional Graphene Hair Dye," Chem-US 4: 784-794.
Lusic et al. (2013) "X-ray-computed tomography contrast agents" Chem. Rev. 113, (3), 1641-1666.
MacLeod et al. (2015) "PEGylated N-Heterocyclic Carbene Anchors Designed To Stabilize Gold Nanoparticles in Biologically Relevant Media," J. Am. Chem. Soc. 137(25): 7974-7977.
Maia et al. (2013) "Key ornamental innovations facilitate diversification in an avian radiation." Proc. Natl. Acad. Sci. U. S. A. 110, (26), 10687-10692.
Manini et al. (2018) "Characterization and Fate of Hydrogen-Bonded Free-Radical Intermediates and Their Coupling Products from the Hydrogen Atom Transfer Agent 1,8-Naphthalenediol," ACS Omega 3: 3918-3927.
Manini et al. (2019) "A Robust Fungal Allomelanin Mimic: An Antioxidant and Potent pi-Electron Donor with Free-Radical Properties that can be Tuned by lonic Liquids," Chempluschem 84(9): 1331-1337.
Manini et al. (2020) "Synthetic mycomelanin thin films as emergent bio-inspired interfaces controlling the fate of embryonic stem cells," J Mater Chem B 8(20): 4412-4418.
Marks et al. (2001) "The melanosome: membrane dynamics in black and white," Nat. Rev. Mol. Cell Biol. 2: 738-748 (11 pages).
Martinez et al. (2019) "Production of Melanins With Recombinant Microorganisms" Front Bioeng Biotechnol 7, 285.
Mbonyiryivuze et al. (2015) "Fourier Transform Infrared Spectroscopy for Sepia Melanin" Phys. Mater. Chem. 3, (2), 25-29.
McFadden et al. (2007) "Allergy to hair dye—Its incidence is rising, as more and younger people dye their hair," Brit Med J 334: 220-220.
Meredith et al. (2006) "The physical and chemical properties of eumelanin," Pigment Cell Res. 19(6): 572-594.
Mironenko et al. (2000) "Intraspecific variation in gamma-radiation resistance and genomic structure in the filamentous fungus Alternaria alternata: a case study of strains inhabiting Chernobyl reactor No. 4," Ecotoxicol Environ Saf 45(2): 177-187.
Montoliu et al. (2014) "Increasing the complexity: new genes and new types of albinism," Pigment Cell Melanoma Res. 27(1): 11-18.
Morel et al. (2011) "Current Trends in the Chemistry of Permanent Hair Dyeing," Chem Rev 111(4): 2537-2561.
Mostert et al. (2018) "The photoreactive free radical in eumelanin," Science Advances 4(3).
Mouret et al. (2006) "Cyclobutane pyrimidine dimers are predominant DNA lesions in whole human skin exposed to UVA radiation," Proc. Natl. Acad. Sci. 103(37): 13765-13770.
Mutsaers (2004) "The mesothelial cell," Int. J. Biochem. Cell Biol. 36(1): 9-16.
Nambiar et al. (2012) "Polymer-composite materials for radiation protection," ACS Appl Mater Interfaces 4(11): 5717-5726.
Napolitano et al. (2013) "Red Hair Benzothiazines and Benzothiazoles: Mutation-Inspired Chemistry in the Quest for Functionality," Acc. Chem. Res. 46(2): 519-528.
Ni et al. (2020) "Chemoenzymatic elaboration of the Raper-Mason pathway unravels the structural diversity within eumelanin pigments" Chem Sci 11, 7836-7841.
Nishimura et al. (2005) "Mechanisms of hair graying: Incomplete melanocyte stem cell maintenance in the niche," Science 307(5710): 720-724.
Nosanchuk et al. (2003) "The Contribution of Melanin to Microbial Pathogenesis," Cell. Microbiol. 5(4): 203-223.
Nosanchuk et al. (2015) "Fungal Melanin: What do We Know About Structure?" Front. Microbiol. 6, 1463: pp. 1-7.
Ochs et al. (2011) "Dopamine-mediated continuous assembly of biodegradable capsules," Chem. Mater. 23(13): 3141-3143.
Orlow (1995) "Melanosomes are specialized members of the lysosomal lineage of organelles," J. Invest. Dermatol. 105(1): 3-7.
Pacelli et al. (2017) "Melanin is Effective in Protecting Fast and Slow Growing Fungi from Various Types of Ionizing Radiation," Environ. Microbiol. 19(4): 1612-1624.
Panzella et al. (2013) "Atypical structural and pi-electron features of a melanin polymer that lead to superior free-radical-scavenging properties." Angew. Chem. Int. Ed. 2013, 52, (48), 12684-7.
Park et al. (2017) "Novel Neuroprotective Effects of Melanin-Concentrating Hormone in Parkinson's Disease," Mol. Neurobiol. 54: 7706-7721.
Patel et al. (2013) "Trends in use of hair dye: a cross-sectional study," Int J Trichology 5(3): 140-143, 9 pages.
Pezzella et al. (1997) "Identification of Partially Degraded Oligomers of 5, 6-Dihydroxyindole-2-carboxylic Acid in Sepia Melanin by Matrix-assisted Laser Desorption/lonization Mass Spectrometry," Rapid Commun. Mass Spectrom. 11(4): 368-372.
Pihet et al. (2009) "Melanin is an Essential Component for the Integrity of the Cell Wall of Aspergillus Fumigatus Conidia," BMC Microbiol. 9: 177, pp. 1-11.
Premi et al. (2015) "Chemiexcitation of melanin derivatives induces DNA photoproducts long after UV exposure" Science 347, (6224), 842-847.
Prota, G. (2000) "Melanins, melanogenesis and melanocytes: looking at their functional significance from the chemist's viewpoint" Pigment Cell Res 13 (4), 283-93.
Pyo et al. (2016) "Artificial pheomelanin nanoparticles and their photo-sensitization properties," J Photochem Photobiol B 160: 330-335.
Qstio, Am. J Hasp. Pharm. 46: 1576-1587, 1989.
Rao (1995) "Recent developments of collagen-based materials for medical applications and drug delivery systems," J Biomater Sci. Polym. Ed 7(7): 623-645.
Raposo et al. (2007) "Melanosomes—dark organelles enlighten endosomal membrane transport," Nat. Rev. Mol. Cell Biol. 8(10): 786-797.
Ren et al. (2013) "High level production of tyrosinase in recombinant *Escherichia coli*" BMC Biotechnol 13, 18.
Ricci et al. (2016) "Drug-induced hair colour changes," Eur J Dermatol 26(6): 531-536.
Riley (1997) "Melanin," Int J Biochem Cell B 29(11): 1235-1239.
Robertson et al. (2012) "Adaptation of the Black Yeast Wangiella dermatitidis to Ionizing Radiation: Molecular and Cellular Mechanisms," Plos One 7(11): e48674, pp. 1-18.
Rouse et al. (2007) "Effects of Mechanical Flexion on the Penetration of Fullerene Amino Acid-Derivatized Peptide Nanoparticles through Skin," Nano Letters 7(1): 155-160.
Ryu et al. (2018) "Polydopamine Surface Chemistry: A Decade of Discovery," ACS Appl Mater Interfaces 10(9): 7523-7540.
Schmaler-Ripcke et al. (2009) "Production of Pyomelanin, a Second Type of Melanin, via the Tyrosine Degradation Pathway in Aspergillus fumigatus," Appl. Environ. Microbiol. 75(2): 493-503.
Schweitzer et al. (2009) "Physico-Chemical Evaluation of Rationally Designed Melanins as Novel Nature-Inspired Radioprotectors," PLOS ONE 4(9): e7229, pp. 1-8.
Schweitzer et al. (2010) "Melanin-Covered Nanoparticles for Protection of Bone Marrow during Radiation Therapy of Cancer," Int. J. Radiat. Oncol. Biol. Phys. 78(5): 1494-1502.

(56) References Cited

OTHER PUBLICATIONS

Scott et al. (2002) "Filopodia are conduits for melanosome transfer to keratinocytes," J. Cell Sci. 115(7): 1441-1451.
Seagle et al. (2005) "Melanin photoprotection in the human retinal pigment epithelium and its correlation with light-induced cell apoptosis," Proceedings of the National Academy of Sciences of the United States of America 102(25): 8978-8983.
Seagle et al. (2005) "Time-Resolved Detection of Melanin Free Radicals Quenching Reactive Oxygen Species," J. Am. Chem. Soc. 127(32): 11220-11221.
Sealy et al. (1982) "Eumelanins and pheomelanins: characterization by electron spin resonance spectroscopy," Science 217(4559): 545-547—Abstract Only.
Search Report and Written Opinion, dated Feb. 26, 2021, corresponding to International Patent Application No. PCT/US2020/039769, 13 pages.
Search Report and Written Opinion, dated Jan. 26, 2021, corresponding to International Patent Application No. PCT/US2020/057902, 11 pages.
Search Report and Written Opinion, dated Jan. 30, 2018, corresponding to International Application No. PCT/US2017/041596 (filed Jul. 11, 2017), 12pp.
Search Report and Written Opinion, dated Mar. 4, 2021, corresponding to International Patent Application No. PCT/US2020/057939, 16 pages.
Seo et al. (2003) "Mushroom tyrosinase: Recent prospects" J Agr Food Chem 51 (10), 2837-2853.
Seo et al. (2012) "Hydrogen peroxide and monoethanolamine are the key causative ingredients for hair dye-induced dermatitis and hair loss," J Dermatol Sci 66(1): 12-19.
Simon et al. (2010) "The Red and the Black," Acc. Chem. Res. 43(11): 1452-1460.
Sing et al. (1985) "Reporting physisorption data for gas/solid systems with special reference to the determination of surface area and porosity," Pure Appl. Chem. 57(4): 603-619.
Smyth et al. (1951) "A study of pigments from red, brown, and buff feathers and hair." Physiol Zool 24, (3), 205-16.
Solano (2014) "Melanins: Skin Pigments and Much More-Types, Structural Models, Biological Functions, and Formation Routes," New J. Sci. 2014, 498276: 1-28.
Solano (2016) "Photoprotection versus photodamage: updating an old but still unsolved controversy about melanin," Polym. Int. 65(11): 1276-1287.
Song et al. (2007) "Supramolecular Nanofibers by Self-Organization of Bola-amphiphiles through a Combination of Hydrogen Bonding and π-π Stacking Interactions," Adv. Mater. 19(3): 416-420.
Søsted et al. (2005) "Contact dermatitis to hair dyes in a Danish adult population: an interview-based study," Brit J Dermatol 153(1): 132-135.
Strube et al. (2015) "Site-Specific In Situ Synthesis of Eumelanin Nanoparticles by an Enzymatic Autodeposition-like Process," Biomacromolecules. 16(5): 1608-1613.
Sun et al. (2019) "Melanin-dot-mediated delivery of metallacycle for NIR-II/photoacoustic dual-modal imaging-guided chemo-photothermal synergistic therapy," Proc Natl Acad Sci USA 116(34): 16729-16735.
Tada et al. (2010) "Scavenging or Quenching Effect of Melanin on Superoxide Anion and Singlet Oxygen," J. Clin. Biochem. Nutr. 46(3): 224-228.
Tadokoro et al. (2003) "UV-induced DNA damage and melanin content in human skin differing in racial/ethnic origin," FASEB J. 17(9): 1177-1179.
Taieb et al. "Melanins and Melanosomes: Biosynthesis, Biogenesis, Physiological, and Pathological Functions," Wiley-VCR Verlag GmbH & Co., Weinheim, (2011).
Takkouche et al. (2005) "Personal use of hair dyes and risk of cancer—A meta-analysis," Jama—J Am Med Assoc 293(20): 2516-2525.
Thomson (1974) "The Pigments of Reddish Hair and Feathers," Angew. Chem., Int. Ed. 13(5): 305-312.
Thureau et al. (2012) "Probing the motional behavior of eumelanin and pheomelanin with solid-state NMR spectroscopy: new insights into the pigment properties." Chem.: Eur. J. 18, (34), 10689-700.
Tokura et al. (2018) "Fabrication of Defined Polydopamine Nanostructures by DNA Origami-Templated Polymerization," Angew. Chem. Int. Ed. Engl. 57: 1587-1591.
Tran et al. (2006) "Chemical and structural disorder in eumelanins: a possible explanation for broadband absorbance," Biophys. J. 90(3): 743-752.
Van Neste et al. (2004) "Hair cycle and hair pigmentation: dynamic interactions and changes associated with aging," Micron 35(3): 193-200.
Velasco et al. (2009) "Hair fiber characteristics and methods to evaluate hair physical and mechanical properties," Braz J Pharm Sci 45(1): 153-162.
Vliegenthart et al. (2011) "Compression, crumpling and collapse of spherical shells and capsules," New J. Phys. 13: 045020, pp. 1-24.
Wakamatsu et al. (2003) "The Structure of Neuromelanin as Studied by Chemical Degradative Methods," J. Neurochem. 86(4): 1015-1023.
Walter et al. (2006) "Early use of PbS nanotechnology for an ancient hair dyeing formula," Nano Lett 6(10): 2215-2219.
Wang et al. (2018) "Skin Pigmentation-Inspired Polydopamine Sunscreens," Adv. Funct. Mater. 28: 1802127: 1-9.
Wang et al. (2019) "Characterization and application of melanin produced by the fast-growing marine bacterium Vibrio natriegens through heterologous biosynthesis." Appl Environ Microbiol DOI: 10.1128/AEM.02749-19.
Wang et al. (2017) "A Novel UV-Shielding and Transparent Polymer Film: When Bioinspired Dopamine-Melanin Hollow Nanoparticles Join Polymers," Acs Appl Mater Inter 9(41): 36281-36289.
Wang et al. (2017) "Tunable, Metal-Loaded Polydopamine Nanoparticles Analyzed by Magnetometry," Chem. Mater. 29(19): 8195-8201.
Watt et al. (2009) "The supramolecular structure of melanin," Soft Matter 5(19): 3754-3760.
Wogelius et al. (2011) "Trace metals as biomarkers for eumelanin pigment in the fossil record," Science 333(6049): 1622-1626.
Wu et al. (2012) "Melanoregulin regulates a shedding mechanism that drives melanosome transfer from melanocytes to keratinocytes," Proc. Natl. Acad. Sci. 109(31): E2101-E2109.
Xiao et al. (2015) "Bio-Inspired Structural Colors Produced via Self-Assembly of Synthetic Melanin Nanoparticles," ACS nano 9(5): 5454-5460.
Xiao et al. (2017) "Bioinspired Bright Noniridescent Photonic Melanin Supraballs," Sci. Adv. 3(9): e1701151.
Yi et al. (2017) "Liquid-immune structural colors with angle-independence inspired from hollow melanosomes," Chem Commun 53(66): 9234-9237.
Yu et al. (2014) "Formation of polydopamine nanofibers with the aid of folic acid," Angew. Chem. Int. Ed. 53(46): 12600-12604.
Zaidi et al. (2014) "Purification and characterization of melanogenic enzyme tyrosinase from button mushroom" Enzyme Res 120739.
Zanoni et al. (2018) "Allergens of permanent hair dyes induces epidermal damage, skin barrier loss and IL-1 alpha increase in epidermal in vitro model," Food Chem Toxicol 112: 265-272.
Zhang et al. (2012) "Biocompatible Polydopamine Fluorescent Organic Nanoparticles: Facile Preparation and Cell Imaging," Nanoscale 4(18): 5581-5584.
Zhang et al. (2016) "CuSO4/H2O2-Induced Rapid Deposition of Polydopamine Coatings with High Uniformity and Enhanced Stability," Angew Chem Int Ed Engl 55(9): 3054-3057.
Zhou et al. (2014) "Rapidly-Deposited Polydopamine Coating via High Temperature and Vigorous Stirring: Formation, Characterization and Biofunctional Evaluation," Plos One 9(11): e113087, pp. 1-10.
Zhou et al. (2019) "Artificial Allomelanin Nanoparticles," ACS Nano 13(10): 10980-10990.
Zhu et al. (2018) "A rapid deposition of polydopamine coatings induced by iron (III) chloride/hydrogen peroxide for loose nanofiltration," J Colloid Interf Sci 523: 86-97.

(56) References Cited

OTHER PUBLICATIONS

Zucca et al. (2014) "Neuromelanin of the human substantia nigra: an update," Neurotox. Res. 25: 13-23.

* cited by examiner

AMNP-1
Structural colors after centrifuge
FIG. 43A
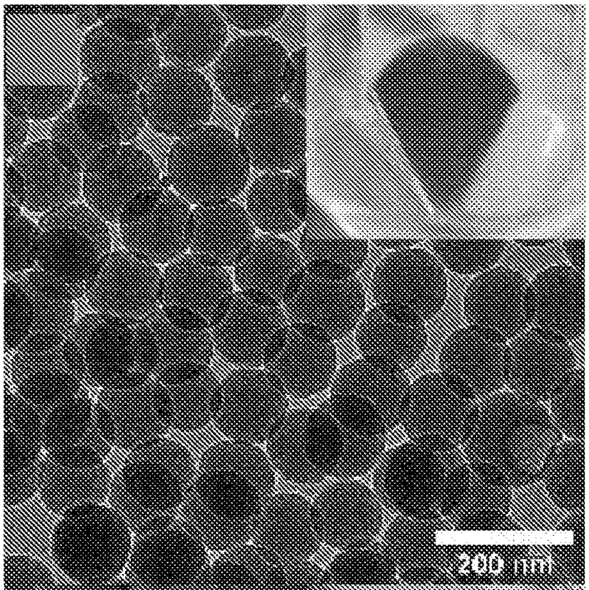
FIG. 43B
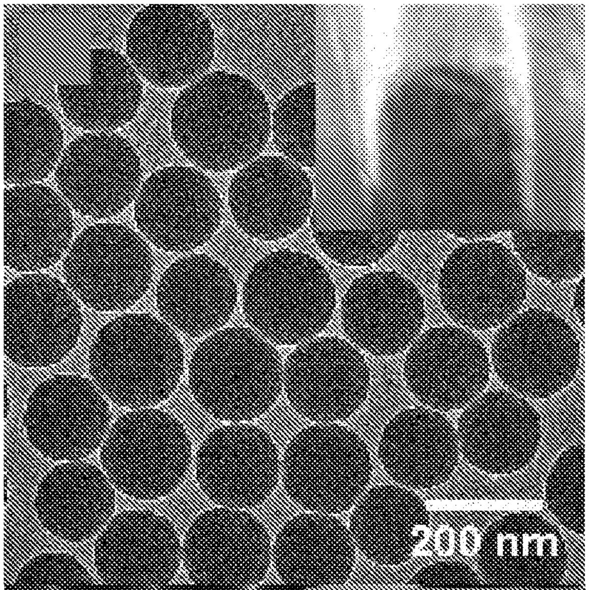
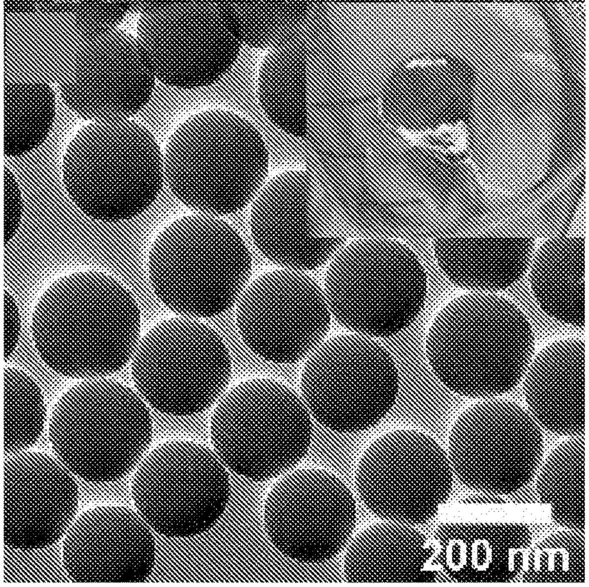
FIG. 43C
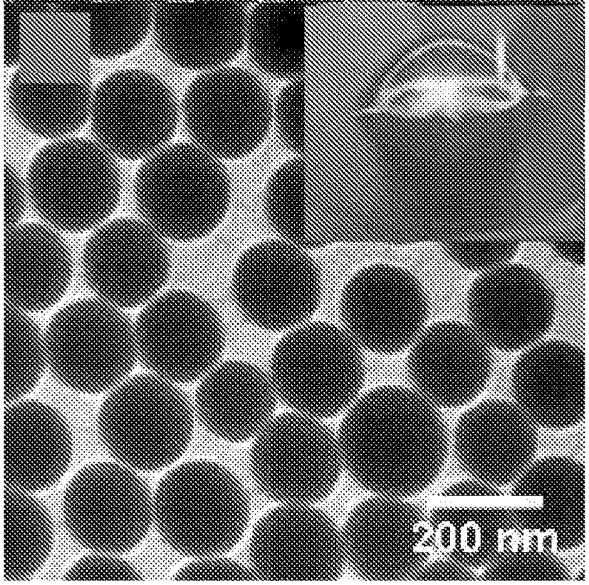
FIG. 43D

ARTIFICIAL MELANIN NANOPARTICLES AND METHODS INCLUDING POROUS MELANIN MATERIALS

CROSS-REFERENCE TO RELATED APPLICATIONS

This application is a U. S. National Stage Application filed under 35 U.S.C. § 371 of International Application No. PCT/US2020/039769, filed Jun. 26, 2020 (Published as WO 2021/021350), which claims the benefit of priority to U.S. Provisional Patent Application No. 62/868,369 filed Jun. 28, 2019, which are hereby incorporated by reference in their entireties.

STATEMENT REGARDING FEDERALLY SPONSORED RESEARCH OR DEVELOPMENT

This invention was made with government support under FA9550-18-1-0142 awarded by the Air Force Office of Scientific Research (AFOSR). The government has certain rights in the invention.

SUMMARY OF THE INVENTION

Provided herein are artificial melanin nanoparticles (AMNPs or AMNP) and associated methods, including methods for making artificial melanin nanoparticles. These methods for making AMNPs are advantageous at least because they are scalable, utilize aqueous solutions, low cost materials, and do not require highly toxic reagents. These AMNPs are advantageous at least because they have ordered and uniform morphologies which are reproducibly controllable, such as with regard to particle size, polydispersity, and shape. Also included herein are methods for producing structural color using the AMNPs disclosed herein.

In an aspect, a material comprising artificial melanin nanoparticles is provided, wherein: each melanin nanoparticle of the plurality of artificial melanin nanoparticles comprises a plurality of melanin oligomers; each melanin oligomer comprises a plurality of covalently-bonded melanin base units; and each melanin base unit comprises substituted or unsubstituted naphthalene.

In an aspect, a material comprising artificial melanin nanoparticles is provided, wherein: each melanin nanoparticle of the plurality of artificial melanin nanoparticles comprises a plurality of melanin oligomers; each melanin oligomer comprises a plurality of covalently-bonded melanin base units; and the plurality of artificial melanin nanoparticles are characterized by a peak size selected from the range of 100 nm to 300 nm and a polydispersity index selected to be less than or equal to 0.10, and optionally for some embodiments a polydispersity index selected to be less than or equal to 0.3 and optionally for some embodiments a polydispersity index selected to be less than or equal to 0.2. Optionally, the plurality of artificial melanin nanoparticles are characterized by a peak size selected from the range of 100 nm to 200 nm and a polydispersity index selected to be less than or equal to 0.10.

In an aspect, a material comprising artificial melanin nanoparticles is provided, wherein: each melanin nanoparticle of the plurality of artificial melanin nanoparticles comprises a plurality of melanin oligomers; each melanin oligomer comprises a plurality of covalently-bonded melanin base units; and the plurality of artificial melanin nanoparticles exhibits structural color. Optionally, the plurality of artificial melanin nanoparticles exhibits structural color when the plurality of artificial melanin nanoparticles are in the form of a layer or film, such as a monolayer or thicker, or in the form of a pellet, such as a free-standing pellet, for example. Optionally, the plurality of artificial melanin nanoparticles exhibits structural color when the plurality of artificial melanin nanoparticles are in the form of a packed and/or ordered structure. Optionally, the plurality of artificial melanin nanoparticles exhibits structural color when the plurality of artificial melanin nanoparticles are dried or otherwise deposited onto a substrate.

In an aspect, a material comprising artificial melanin nanoparticles is provided, wherein: each melanin nanoparticle of the plurality of artificial melanin nanoparticles comprises a plurality of melanin oligomers; each melanin oligomer comprises a plurality of covalently-bonded melanin base units; and at least 50% of the plurality of melanin oligomers are selected from the group consisting of monomers, dimers, trimers, tetramers, pentamers, and any combination thereof. The monomers, dimers, trimers, tetramers, and pentamers have one, two, three, four, and five melanin base units, respectively. Optionally, at least 30%, optionally at least 40%, optionally at least 50%, optionally at least 60%, optionally at least 80%, of the plurality of melanin oligomers are selected from the group consisting of dimers, trimers, tetramers, pentamers, and any combination thereof, and the artificial melanin nanoparticles further comprise monomers. Optionally, at least 50% of the plurality of melanin oligomers are selected from the group consisting of dimers, trimers, tetramers, pentamers, and any combination thereof, and the artificial melanin nanoparticles further comprise monomers. Optionally, at least 30%, optionally at least 40%, optionally at least 50%, optionally at least 60%, optionally at least 80%, of the plurality of melanin oligomers are selected from the group consisting of dimers, trimers, tetramers, and any combination thereof, and the artificial melanin nanoparticles further comprise monomers. Optionally, at least 50% of the plurality of melanin oligomers are selected from the group consisting of dimers, trimers, tetramers, and any combination thereof, and the artificial melanin nanoparticles further comprise monomers. Optionally, at least 30% by mass, optionally at least 40% by mass, optionally at least 50% by mass, optionally at least 60% by mass, optionally at least 80% by mass, of each or of each of at least 80% of the plurality of artificial melanin nanoparticles is the monomers (each monomer having only one melanin base unit) and/or the melanin oligomers selected from the group consisting of dimers, trimers, tetramers, pentamers and any combination thereof. Optionally, at least 30% by mass, optionally at least 40% by mass, optionally at least 50% by mass, optionally at least 60% by mass, optionally at least 80% by mass, of each or of each of at least 80% of the plurality of artificial melanin nanoparticles is the monomers (each monomer having only one melanin base unit) and the melanin oligomers selected from the group consisting of dimers, trimers, tetramers, pentamers and any combination thereof. Optionally, at least 30% by mass, optionally at least 40% by mass, optionally at least 50% by mass, optionally at least 60% by mass, optionally at least 80% by mass, of each or of each of at least 80% of the plurality of artificial melanin nanoparticles is the monomers (each monomer having only one melanin base unit) and/or the melanin oligomers selected from the group consisting of dimers, trimers, tetramers, and any combination thereof. Optionally, at least 30% by mass, optionally at least 40% by mass, optionally at least 50% by mass, optionally at least 60% by mass, optionally at least 80% by mass, of each or of each of at least 80% of the plurality of artificial melanin nanoparticles is the monomers (each monomer having only one melanin base unit) and the melanin oligomers selected from the group consisting of dimers, trimers, tetramers, and any combination thereof.

In an aspect, a material comprising artificial melanin nanoparticles is provided, wherein: each melanin nanoparticle of the plurality of artificial melanin nanoparticles comprises a plurality of melanin oligomers; each melanin oligomer comprises a plurality of covalently-bonded melanin base units; and each nanoparticle has a sphericity of less than 0.90 and has a shape characterized as at least one of: walnut-like, a collapsed sphere or collapsed ellipsoid, and a sphere or ellipsoid having a plurality of indentations.

In an aspect, a material comprising artificial melanin nanoparticles is provided, wherein: each melanin nanoparticle of the plurality of artificial melanin nanoparticles comprises a plurality of melanin oligomers; each melanin oligomer comprises a plurality of covalently-bonded melanin base units; and the plurality of artificial melanin nanoparticles are characterized by a radical scavenging activity greater than that of polydopamine nanoparticles having the same diameter as the plurality of artificial melanin nanoparticles under otherwise identical condition. Optionally, the plurality of artificial melanin nanoparticles are characterized by a radical scavenging activity at least 5%, optionally at least 10%, optionally at least 15%, optionally at least 20%, greater than that of polydopamine nanoparticles having the same diameter as the plurality of artificial melanin nanoparticles under otherwise identical condition.

According to certain embodiments, each melanin base unit comprises substituted or unsubstituted naphthalene. According to certain embodiments, each melanin base unit comprises dihydroxynaphthalene. According to certain embodiments, each melanin base unit comprises 1,8-dihydroxynaphthalene. According to certain embodiments, each melanin base unit comprises a structure having the formula FX1:

(FX1)

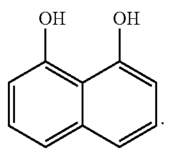

According to certain embodiments, each melanin oligomer is free of nitrogen. According to certain embodiments, at least 20%, optionally at least 40%, optionally at least 50%, optionally at least 80% of the plurality of melanin oligomers are dimers having two covalently-bonded melanin base units. According to certain embodiments, 20% to 80% of the plurality of melanin oligomers are dimers having two covalently-bonded melanin base units. According to certain embodiments, at least 50% of the plurality of melanin oligomers are selected from the group consisting of monomers, dimers, trimers, tetramers, pentamers, and any combination thereof. The monomers, dimers, trimers, tetramers, and pentamers have one, two, three, four, and five melanin base units, respectively. Optionally, at least 30%, optionally at least 40%, optionally at least 50%, optionally at least 60%, optionally at least 80%, of the plurality of melanin oligomers are selected from the group consisting of dimers, trimers, tetramers, pentamers, and any combination thereof, and the artificial melanin nanoparticles further comprise monomers. According to certain embodiments, at least 40% of the plurality of melanin oligomers are selected from the group consisting of monomers, dimers, trimers, tetramers, pentamers, and any combination thereof. According to certain embodiments, at least 20%, optionally at least 40%, optionally at least 80%, of the plurality of melanin oligomers are selected from the group consisting of monomers, dimers, and trimers, and any combination thereof. According to certain embodiments, at least 50% of the plurality of melanin oligomers are selected from the group consisting of monomers, dimers, and trimers, and any combination thereof. According to certain embodiments, at least 30% by mass, optionally at least 40% by mass, optionally at least 50% by mass, optionally at least 60% by mass, optionally at least 80% by mass, of each or of each of at least 80% of the plurality of artificial melanin nanoparticles is the monomers (each monomer having only one melanin base unit) and/or the melanin oligomers selected from the group consisting of dimers, trimers, tetramers, pentamers and any combination thereof. According to certain embodiments, at least 30% by mass, optionally at least 40% by mass, optionally at least 50% by mass, optionally at least 60% by mass, optionally at least 80% by mass, of each or of each of at least 80% of the plurality of artificial melanin nanoparticles is the monomers (each monomer having only one melanin base unit) and the melanin oligomers selected from the group consisting of dimers, trimers, tetramers, pentamers and any combination thereof. According to certain embodiments, at least 30% by mass, optionally at least 40% by mass, optionally at least 50% by mass, optionally at least 60% by mass, optionally at least 80% by mass, of each or of each of at least 80% of the plurality of artificial melanin nanoparticles is the monomers (each monomer having only one melanin base unit) and/or the melanin oligomers selected from the group consisting of dimers, trimers, tetramers, and any combination thereof. According to certain embodiments, at least 30% by mass, optionally at least 40% by mass, optionally at least 50% by mass, optionally at least 60% by mass, optionally at least 80% by mass, of each or of each of at least 80% of the plurality of artificial melanin nanoparticles is the monomers (each monomer having only one melanin base unit) and the melanin oligomers selected from the group consisting of dimers, trimers, tetramers, and any combination thereof. According to certain embodiments, each melanin oligomer is non-covalently associated with at least one other melanin oligomer via at least one of hydrogen bonding and π-π stacking of naphthalene rings. According to certain embodiments, each melanin oligomer is non-covalently associated with at least one other melanin oligomer or melanin monomer via at least one of hydrogen bonding and π-π stacking of naphthalene rings. A melanin monomer comprises the melanin base unit.

According to certain embodiments, each nanoparticle is characterized by a sphericity of greater than 0.90. According to certain embodiments, at least 50%, optionally at least 75%, optionally at least 90%, optionally at least 95%, of the plurality of nanoparticles is characterized by a sphericity of greater than 0.90. According to certain embodiments, each nanoparticle is characterized by a sphericity of greater than 0.99. According to certain embodiments, at least 50%, optionally at least 75%, optionally at least 90%, optionally at least 95%, of the plurality of nanoparticles is characterized by a sphericity of greater than 0.95. According to certain embodiments, each nanoparticle is characterized by a sphericity of greater than 0.99. According to certain embodiments, at least 50%, optionally at least 75%, optionally at least 90%, optionally at least 95%, of the plurality of nanoparticles is characterized by a sphericity of greater than 0.99. According to certain embodiments, the plurality nanoparticles is characterized by a polydispersity index less than or equal to 0.10. According to certain embodiments, each nanoparticle has a size characteristics, such as diameter, selected from the range of 100±50 nm to 300±50 nm. According to certain embodiments, each nanoparticle has a size characteristics, such as diameter, selected from the range of 100 nm to 300 nm. According to certain embodiments, each nanoparticle has a size characteristics, such as diameter, selected from the range of 20 nm to 300±50 nm. According to certain embodiments, the plurality of artificial melanin nanoparticles are characterized by a peak size selected from the range of 100 nm to 300 nm. According to certain embodiments, the plurality of artificial melanin nanoparticles are characterized by a peak size selected from the range of 100 nm to 200 nm. According to certain embodiments, the plurality of artificial melanin nanoparticles are characterized by a peak size selected from the range of 50 nm to 300 nm, optionally 50 nm to 200 nm.

According to certain embodiments, each nanoparticle has a sphericity of less than 0.90 and has a shape characterized as at least one of: walnut-like, a collapsed sphere or collapsed ellipsoid, and a sphere or ellipsoid having a plurality of indentations. According to certain embodiments, at least 50%, optionally at least 75%, optionally at least 90%, optionally at least 95%, of the plurality of nanoparticles has a sphericity of less than 0.90 and has a shape characterized as at least one of: walnut-like, a collapsed sphere or collapsed ellipsoid, and a sphere or ellipsoid having a plurality of indentations.

According to certain embodiments, the plurality of artificial melanin nanoparticles are dispersed in a solvent or solvent mixture, thereby forming an artificial nanoparticle dispersion. According to certain embodiments, the solvent or solvent mixture is at least 50% water, optionally at least 75% water, optionally at least 90% water, optionally at least 95%, by volume. According to certain embodiments, the solvent or solvent mixture comprises an organic solvent. According to certain embodiments, the solvent or solvent mixture comprises a buffer. According to certain embodiments, the organic solvent comprises methanol, ethanol, acetonitrile, acetone dichloromethane, dimethylformamide, ethyl acetate, acetone, or any combination thereof. In some embodiments, artificial melanin nanoparticles are allowed to further age or further oxidize after synthesis. In some embodiments, aging or further oxidation of the nanoparticles affects the solubility or dispersibility, such as increasing stability in the presence of organic solvents. According to certain embodiments, the nanoparticles in the artificial nanoparticle dispersion are characterized by a zeta potential or an average zeta potential selected from the range of −50 mV to −10 mV, optionally −40 to −20 mV, optionally in a solvent or solvent solution that is at least 95% water by volume. According to certain embodiments, the nanoparticles in the artificial nanoparticle dispersion are stably dispersed without forming precipitates after at least 5 hours at a concentration selected from the range of 0.01 mg/mL to 5 mg/mL, optionally 0.01 mg/mL to 1 mg/mL, optionally within 20% of 0.1 mg/mL. According to certain embodiments, the nanoparticles in the artificial nanoparticle dispersion are stably dispersed without forming precipitates after at least 12 hours at a concentration selected from the range of 0.01 mg/mL to 5 mg/mL, optionally 0.01 mg/mL to 1 mg/mL, optionally within 20% of 0.1 mg/mL.

According to certain embodiments, the plurality of artificial melanin nanoparticles is internalized in one or more viable biological cells. According to certain embodiments, the plurality of artificial melanin nanoparticles form a plurality of perinuclear caps in one or more viable biological cells. According to certain embodiments, internalization of the plurality of nanoparticles in biological cells provides a cell viability of at least 80%, optionally at least 90%, with respect to water as a control. In some embodiments, aging or further oxidation of the nanoparticles affects the toxicity of the plurality of artificial melanin nanoparticles, such as decreasing their toxicity with aging or further oxidation.

According to certain embodiments, the plurality of artificial melanin nanoparticles is characterized by a radical scavenging activity greater than that of polydopamine nanoparticles having the same diameter as the plurality of artificial melanin nanoparticles under otherwise identical condition. According to certain embodiments, the plurality of artificial melanin nanoparticles is characterized by a radical scavenging activity at least 10%, optionally at least 15%, optionally at least 50%, greater than that of polydopamine nanoparticles having the same diameter as the plurality of artificial melanin nanoparticles under otherwise identical condition. According to certain embodiments, the plurality of artificial melanin nanoparticles is characterized by a radical scavenging activity of at least 0.012 mol/g using an assay of 2,2-diphenyl-1-(2,4,6-trinitrophenyl) hydrazyl (DPPH).

Also disclosed herein are processes for forming any plurality of artificial melanin nanoparticles disclosed herein, including any one or any combination of embodiments disclosed herein. The processes for forming any plurality of artificial melanin nanoparticles include polymerizing a plurality of melanin monomers via oxidative oligomerization, each melanin monomer comprising the melanin base unit.

Also disclosed herein are methods for making any plurality of artificial melanin nanoparticles disclosed herein, including any one or any combination of embodiments disclosed herein. The methods for making a plurality of artificial melanin nanoparticles include polymerizing a plurality of melanin monomers via oxidative oligomerization, each melanin monomer comprising the melanin base unit. According to certain embodiments, the step of polymerizing comprising reacting the plurality of melanin monomers with one or more oxidation agents. According to certain embodiments, the step of polymerizing comprising dissolving the plurality of melanin monomers and the one or more oxidation agents in a solvent or solvent mixture. According to certain embodiments, the solvent or solvent mixture comprises water. The solvent or solvent mixture optionally comprises water and an organic solvent and/or buffer. According to certain embodiments, the step of dissolving comprises rapidly injecting the one or more oxidation agents into a stirred monomer solution comprising the plurality of melanin monomers in the solvent or solvent mixture. According to certain embodiments, the step of reacting comprises the plurality of melanin monomers and the one or more oxidation agents being reacted in the solvent or solvent mixture for a time selected from the range of 1 to 24 hours. According to certain embodiments, the method comprises isolating the polymerized artificial melanin nanoparticles. According to certain embodiments, the step of dissolving is characterized by a molar ratio of one or more oxidation agents to melanin monomers selected from the range of 0.08 to 1.5, optionally 0.2 to 1.5, optionally 0.08 to 0.6, optionally 0.1 to 1, optionally 0.1 to 2, optionally 0.05 to 2.5, optionally 0.05 to 5. The molar ratio of one or more oxidation agents to melanin monomers may be selected to be different depending on the particular selected oxidation agent(s) and melanin monomers. According to certain embodiments, each nanoparticle is characterized by a sphericity of greater or equal to than 0.90 when the molar ratio of one or more oxidation agents to melanin monomers is less than 1. According to certain embodiments, each nanoparticle is characterized by a sphericity of less than 0.90 when the molar ratio of one or more oxidation agents to melanin monomers is greater than or equal to 1. The characteristics, such as shape, of the artificial melanin nanoparticles may vary and be controlled by selected of particular oxidation agent(s) and melanin monomers, as well as by selection of the molar ratio of one or more oxidation agents to melanin monomers. For example, to obtain a particle with a particular sphericity, different molar ratios of one or more oxidation agents to melanin monomers may be selected for different oxidation agent(s). According to certain embodiments, the step of dissolving further comprises dissolving a buffer solution in the solvent or solvent mixture. According to certain embodiments, the one or more oxidation agents is a salt, optionally an inorganic salt, which is soluble in the solvent or solvent mixture. According to certain embodiments, the one or more oxidation agents selected from the group consisting of $NaIO_4$, $KMnO_4$, a persulfate salt, ammonium persulfate, and any combination thereof. According to certain embodiments, the one or more oxidation agents is $NaIO_4$ or $KMnO_4$. According to certain embodiments, each melanin monomer comprises substituted or unsubstituted naphthalene. According to certain embodiments, each melanin monomer comprises dihydroxynaphthalene. According to certain embodiments, each melanin monomer comprises 1,8-dihydroxynaphthalene. According to certain embodiments, each melanin monomer is free of nitrogen. According to certain embodiments, the method does not comprise deriving or extracting the at least one of the plurality of melanin base units, the plurality of melanin oligomers, and the plurality of artificial melanin nanoparticles from a biological source or a living organism.

In an aspect, the invention provides compositions comprising porous melanin materials. In an embodiment, for example, a porous artificial melanin material comprises: (i) one or more melanin oligomers, polymers or a combination thereof; wherein the one or more melanin oligomers and/or polymers comprise a plurality of covalently-bonded melanin base units; wherein the melanin oligomers and/or polymers are arranged to form an internal structure having a plurality of pores; wherein the porous artificial melanin material is characterized by a pore volume per mass of material greater than or equal to 0.1 $cm^3/g$, optionally greater than or equal to 0.3 $cm^3/g$, and wherein at least a portion of the pores have at least one size dimension, such as cross section dimension or longitudinal dimension, greater than or equal to 0.5 nm.

The porous melanin materials may include a range of physical, chemical and structural characteristics, such as relating to porosity, chemical composition, phase and physical state or condition (e.g., particle, film, dispersion, etc.).

In an embodiment, for example, the porous artificial melanin material is characterized by an average pore volume per mass of material selected from the range of 0.1 $cm^3/g$ to 0.6 $cm^3/g$, and optionally 0.1-1 $cm^3/g$ and optionally 0.3 $cm^3/g$ to 0.6 $cm^3/g$. In an embodiment, for example, the porous artificial melanin material is a microporous material or a mesoporous material. In an embodiment, for example, the pores of the porous artificial melanin material include micropores each having at least one average size dimension, such as a cross sectional dimension and/or longitudinal dimension, selected from the range of 0.5 nm to 2.5 nm, and optionally 0.5 nm to 1.3 nm. In an embodiment, for example, the pores of the porous artificial melanin material include mesopores each having at least one average size dimension, such as a cross sectional dimension and/or longitudinal dimension, selected from the range of 2 nm to 50 nm, and optionally 2 nm to 25 nm. In an embodiment, for example, the pores are characterized by a distribution of pore sizes over the range of 0.5 nm to 50 nm.

In some embodiments, for example, the pores of the internal structure are formed by organization of the melanin oligomers and/or polymers of the porous artificial melanin material. In some embodiments, for example, the pores of the internal structure are formed by close packing and/or self-assembly of the melanin oligomers and/or polymers of the porous artificial melanin material. In some embodiments, for example, the pores of the internal structure are formed by templating of the melanin oligomers and/or polymers of the porous artificial melanin material.

In some embodiments, for example, the pores are not uniformly distributed throughout the porous melanin materials, for example, because the material is non-crystalline and/or amorphous. In an embodiment, for example, the porous artificial melanin material is an at least partially non-crystalline material and/or an amorphous material. In some embodiments, for example, the pores of the internal structure are randomly distributed. In some embodiments, for example, the pores of the internal structure are provided in repeating structures the amorphous porous artificial melanin material provided in an at least partial non-crystalline or amorphous state.

In some embodiments, for example, the pores of porous artificial melanin material include one or more pore types selected from the group of cylindrical pores, channel-like pores, slit-shape pores, ink-bottle pores and any combination of these.

The porous artificial melanin material may be provided in a range of physical states and or as components of materials or systems. In some embodiments, for example, the porous artificial melanin material comprise porous melanin particles, such as nanoparticles. In some embodiments, for example, the porous melanin particles are characterized by an average size selected from the range of 20 nm to 500 nm in diameter. In some embodiments, for example, the porous melanin particles are one or more of solid particles, hollow particles, lacey particles, and any combinations of these. In an embodiment, the porous artificial melanin material is a solid porous artificial melanin particle, for example, with pores distributed throughout the particle, for example uniformly distributed or randomly distributed, and without a hollow configuration. In an embodiment, the porous artificial melanin material is a lacey porous artificial melanin particle, for example, with pores distributed throughout the particle, for example uniformly distributed or randomly distributed, and without a hollow configuration. In an embodiment, the porous artificial melanin material is not a hollow particle, for example is not a hollow sphere particle.

In an embodiment, the porous melanin particles are purified or isolated. In an embodiment, the porous melanin particles are provided as a film or a coating. In an embodiment, the porous melanin particles are provided as a dispersion comprising the porous melanin particles dispersed in a continuous phase.

The porous artificial melanin material may encompass a range of chemical compositions. In some embodiments, for example, the melanin base units are one or more substituted or unsubstituted catechol-based monomers, substituted or unsubstituted polyol-based monomers, substituted or unsubstituted phenol-based monomers, substituted or unsubstituted indole-based monomers, substituted or unsubstituted benzothiazine-based monomers, substituted or unsubstituted benzothiazole-based monomers, substituted or unsubstituted dopamine-based monomers or any combination of these.

In some embodiments, for example, the porous artificial melanin material comprises allomelanin. In some embodiments, for example, at least a portion of, and optionally all of, the melanin base units each independently comprises substituted or unsubstituted naphthalene. In some embodiments, for example, at least a portion of, and optionally all of, the melanin base units each independently comprises dihydroxynaphthalene. In some embodiments, for example, at least a portion of, and optionally all of, the melanin base units each independently comprises 1,8-dihydroxynaphthalene. In some embodiments, for example, at least a portion of, and optionally all of, the melanin base units each independently comprises a structure having the formula FX1:

(FX1)

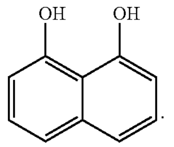

In some embodiments, for example, each melanin oligomer is free of nitrogen.

In some embodiments, for example, the porous artificial melanin material comprises polydopamine. In some embodiments, for example, at least a portion of, and optionally all of, the melanin base units each independently comprises a substituted or unsubstituted dopamine monomer. In some embodiments, for example, at least a portion of, and optionally all of, the melanin base units each independently are selected from the group consisting of substituted or unsubstituted dihydroxydopamine monomers, substituted or unsubstituted dioxydopamine monomers, substituted or unsubstituted dihydroxynaphthalene monomers, substituted or unsubstituted dioxydopamine monomers and any combination of these. In some embodiments, for example, at least a portion of, and optionally all of, the melanin base units each independently are selected from the group consisting of 3,4-dihydroxydopamine monomers, 3,4-dioxydopamine monomers, 3,4-dihydroxynaphthalene monomers, and any combination of these.

In an aspect, methods for making porous artificial melanin materials are providing including etching, dissolution, incubating and templating synthetic approaches.

In an embodiment, for example, a method of making a porous artificial melanin material employing a dissolution or etching approach comprises: (i) polymerizing artificial melanin precursors in a first aqueous solution, thereby generating a first intermediate melanin product comprising one or more melanin oligomers and/or polymers; (ii) contacting the first intermediate melanin product with a nonaqueous solvent, thereby resulting in partial dissolution or materials removal so as to generate a second intermediate melanin product; and (iii) contacting second intermediate melanin product with water or a second aqueous solution, thereby resulting in the porous artificial melanin material.

In an embodiment, for example, the step of polymerizing the artificial melanin precursors in a first aqueous solution comprises oxidative oligomerization or polymerization. In an embodiment, for example, the artificial melanin precursors are provided in the first aqueous solution at a concentration selected from the range of 0.1 mg/mL to 10 mg/mL. In an embodiment, for example, the step of polymerizing the artificial melanin precursors in the first aqueous solution is carried out at a temperature selected from the range of 15° C. to 30° C. In an embodiment, for example, the step of polymerizing the artificial melanin precursors in the first aqueous solution is carried out for a time duration selected over the range of 4 hours to 24 hours. In an embodiment, for example, the step of contacting the first intermediate melanin product with the nonaqueous solvent comprises removing the first intermediate melanin product from contact with at least a portion of, and optionally all of, the first aqueous solution and contacting the removed first intermediate melanin product with the nonaqueous solvent.

In an embodiment, for example, the method further comprises removing water from the first intermediate melanin product prior to the step of contacting the first intermediate melanin product with the nonaqueous solvent. In an embodiment, for example, the nonaqueous solvent is one or more of an alcohol, hydrocarbon, organic solvent or any combination of these. In an embodiment, for example, the one or more alcohol is methanol, ethanol, propyl alcohol, butyl alcohol or any combination of these. In an embodiment, for example, the nonaqueous solvent is acetonitrile, acetic acid, acetone or any combination of these. In an embodiment, for example, the step of contacting the first intermediate melanin product with the nonaqueous solvent is carried out at a temperature selected from the range of 15° C. to 30° C. In an embodiment, for example, the step of contacting the first intermediate melanin product with the nonaqueous solvent is carried out for a time duration selected over the range of 1 second to 1 week.

In an embodiment, for example, the step of contacting the second intermediate melanin product with water or a second aqueous solution comprises diluting the second intermediate melanin product with the water or second aqueous solution. In an embodiment, for example, the step of contacting second intermediate melanin product with water or a second aqueous solution comprises dialyzing the second intermediate melanin product into the water or second aqueous solution.

In an embodiment, for example, the artificial melanin precursors are one or more substituted or unsubstituted catechol-based monomers, substituted or unsubstituted polyol-based monomers, substituted or unsubstituted phenol-based monomers, substituted or unsubstituted indole-based monomers, substituted or unsubstituted benzothiazine-based monomers, substituted or unsubstituted benzothiazole-based monomers, substituted or unsubstituted dopamine-based monomers or any combination of these.

In an embodiment, for example, at least a portion of, and optionally all of, the artificial melanin precursors each independently comprises substituted or unsubstituted naphthalene. In an embodiment, for example, at least a portion of, and optionally all of, the artificial melanin precursors each independently comprises dihydroxynaphthalene. In an embodiment, for example, at least a portion of, and optionally all of, the artificial melanin precursors each independently comprises 1,8-dihydroxynaphthalene. In an embodiment, for example, at least a portion of, and optionally all of, the artificial melanin precursors each independently comprises a structure having the formula FX1:

(FX1)

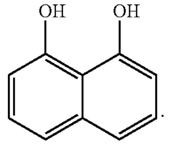

In an embodiment, for example, each melanin oligomer and/or polymer is free of nitrogen.

In an embodiment, for example, the porous artificial melanin material comprises allomelanin.

In an embodiment, for example, the porous artificial melanin material made by methods using a dissolution or etching approach is characterized by a pore volume per mass of material greater than or equal to 0.1 $cm^3/g$ and wherein at least a portion of the pores have at least one size dimension, such as a cross sectional dimension and/or longitudinal dimension, greater than or equal to 0.5 nm. In an embodiment, for example, the porous artificial melanin material made by methods using a dissolution or etching approach is characterized by an average pore volume per mass of material selected from the range of 0.1 $cm^3/g$ to 1 $cm^3/g$. In an embodiment, for example, the porous artificial melanin material made by methods using a dissolution or etching approach is a microporous material or a mesoporous material. In an embodiment, for example, the pores of the porous artificial melanin material made by methods using a dissolution or etching approach include primary pores having at least one average size dimension, such as a cross sectional dimension and/or longitudinal dimension, selected from the range of 0.5 nm to 2 nm.

In an embodiment, for example, a method of making a porous artificial melanin material employing a templating approach comprises: (i) combining artificial melanin precursors and a templating agent in a first aqueous solution; and (ii) polymerizing the artificial melanin precursors in the presence of the templating agent, thereby generating an intermediate melanin product comprising one or more melanin oligomers and/or polymers incorporated with the templating agent, thereby resulting in the porous artificial melanin material. A wide range of templating agents are useful in the present methods including materials with a defined structure that may be coated with or accommodated by the melanin monomer or polymerization products thereof.

In some embodiments, the method further comprising the step of removing the templating agent, for example, using chemical or thermal removal process(es). In some embodiments the template is not removed and thus remains a component of the porous artificial melanin material.

In an embodiment, for example, the step of polymerizing the artificial melanin precursors in a first aqueous solution comprises oxidative oligomerization or polymerization. In an embodiment, for example, the artificial melanin precursors are provided in the first aqueous solution at a concentration selected from the range of 0.1 to 10 mg/mL. In an embodiment, for example, the templating agent is provided in the first aqueous solution at a concentration selected from the range of 0.1 to 10 mg/mL. In an embodiment, for example, the mass ratio of artificial melanin precursors to templating agent is selected from the range of 1:100 to 100:1. In an embodiment, for example, the step of polymerizing the artificial melanin precursors in the first aqueous solution is carried out at a temperature selected from the range of 15° C. to 30° C. In an embodiment, for example, the step of polymerizing the artificial melanin precursors in the first aqueous solution is carried out for a time duration selected over the range of 1 hour to 1 week.

In an embodiment, for example, at least a portion of the artificial melanin precursors each independently comprises a substituted or unsubstituted dopamine monomer. In an embodiment, for example, at least a portion of the artificial melanin precursors each independently are selected from the group consisting of substituted or unsubstituted dihydroxydopamine monomers, substituted or unsubstituted dioxydopamine monomers, substituted or unsubstituted dihydroxynaphthalene monomers, substituted or unsubstituted dioxydopamine monomers and any combination of these. In an embodiment, for example, at least a portion of the artificial melanin precursors each independently are selected from the group consisting of 3,4-dihydroxydopamine monomers, 3,4-dioxydopamine monomers, 3,4-dihydroxynaphthalene monomers, and any combination of these.

In an embodiment, for example, the templating agent is a microporous or mesoporous templating agent. In an embodiment, for example, the templating agent is a porous silicon dioxide material, a porous ceramic material, porous metal material, porous carbon material, porous polymer material, an organic framework, a metal organic framework, a covalent organic framework, a porous polystyrene material, a hydrogel, one or more surfactants or any combination of these. In an embodiment, for example, the templating agent is silica, alumina, titania, gold, silver, platinum, copper, cobalt, palladium, nickel, zinc, iron, calcium, carbon, polystyrene, polydimethylsiloxane, poly (acrylic acid), poly (methyl methacrylate), poly (vinyl pyrrolidone), ethylene glycol dimethacrylate, polyurethane, divinylbenzene, bis(2-ethylhexyl) sulfosuccinate, ethylene trimethacrylate, acrylamide, bisacrylamide, covalent organic framework, metal organic framework, porous aromatic framework, polymer with intrinsic microporosity, hyper-conjugated polymer, conjugate microporous polymer, amino acids, poloxamers, trimethyl benzene, cetyl trimethyl ammonium bromide, ammonium sulfate, sodium dodecyl sulfate or any combination of these.

In an embodiment, for example, the templating agent is removed via etching, dissolution, calcination, dehydration, denaturation or any combination of these processes.

In an embodiment, for example, the porous artificial melanin material generated by the templating method is characterized by a pore volume per mass of material greater than or equal to 0.1 $cm^3/g$ and wherein at least a portion of the pores have at least one size dimension, such as a cross sectional dimension and/or longitudinal dimension, greater than or equal to 0.5 nm. In an embodiment, for example, the porous artificial melanin material generated by the templating method is characterized by an average pore volume per mass of material selected from the range of 0.1 $cm^3/g$ to 1 $cm^3/g$. In an embodiment, for example, the porous artificial melanin material generated by the templating method is a microporous material or a mesoporous material. In an embodiment, for example, the porous artificial melanin material generated by the templating method includes primary pores having an average size dimension, such as a cross sectional dimension and/or longitudinal dimension, selected from the range of 0.5 to 50 nm.

In an embodiment, for example, the porous artificial melanin material generated by the templating method comprises a templated structure. In an embodiment, for example, the porous artificial melanin material generated by the templating method comprises polydopamine.

Without wishing to be bound by any particular theory, there may be discussion herein of beliefs or understandings of underlying principles relating to the devices and methods disclosed herein. It is recognized that regardless of the ultimate correctness of any mechanistic explanation or hypothesis, an embodiment of the invention can nonetheless be operative and useful.

BRIEF DESCRIPTION OF THE DRAWINGS

(FIG. 3B) 0.5:1.0; (FIG. 3C) 1.0:1.0; (FIG. 3D) 1.5:1.0. Scale bars 200 nm. SEM images of the corresponding AMNP-1 with molar ratios of $NaIO_4$ to 1,8-DHN at (FIG. 3E) 0.2:1.0; (FIG. 3F) 0.5:1.0; (FIG. 3G) 1.0:1.0; (FIG. 3H) 1.5:1.0. Scale bars 400 nm.

FIG. 6A. DPPH radical scavenging activity of antioxidants. In FIG. 6A, the PDA-NPs are size-matched with the AMNP-1. FIG. 6B. Calculated amount of quenched DPPH per gram of antioxidant.

FIG. 16A. Electrical input (voltage) and electrical output (current); FIG. 16B. time domain; FIG. 16C. potential domain (single cycle); and FIG. 16D. potential domain (30 cycles). The electrical outputs reveal amplified mediator currents indicating signatures of redox cycling and redox activity. (Mediators: 300 μM Fc and 300 μM $Ru^{3+}$ in 0.1 M, pH 7.0 phosphate buffer. Scan rate=25 mV/s.)

(FIG. 17C) 227 nm with a polydispersity index of 0.09 for AMNP-2; (FIG. 17E) 970 nm with a polydispersity index of 0.36 for AMNP-3. Zeta potential of (FIG. 17B) AMNP-1; (FIG. 17D) AMNP-2; (FIG. 17F) AMNP-3.

(FIG. 19B) Acetonitrile; (FIG. 19C) Methanol (FIG. 19D) Ethanol; (FIG. 19E) Dimethylformamide (DMF). Scale bars 3 μm.

(FIG. 20B) Acetonitrile; (FIG. 20C) Methanol (FIG. 20D) Ethanol; (FIG. 20E) DMF. Scale bars 3 μm.

(FIG. 21B) AMNP-2 with 0.2 molar ratio of $KMnO_4$ to DHN (retention time at 15.0 min corresponds to DHN monomer). AMNP-3 could not be dispersed in any of the organic solvents tested.

(FIG. 23B) 0.5:1.0; (FIG. 23C) 1.0:1.0; (FIG. 23D) 1.5:1.0.

(FIG. 25A) electrical input (voltage) and electrical output (current), (FIG. 25B) time domain, (FIG. 25C) potential domain (single cycle) and (FIG. 25D) potential domain (30 cycles).

(FIG. 26A) electrical input (voltage) and electrical output (current), (FIG. 26B) time domain, (FIG. 26C) potential domain (single cycle) and (FIG. 26D) potential domain (30 cycles).

(FIG. 29A) DPPH radical scavenging activity of antioxidants; (FIG. 29B)

Figure 3A:
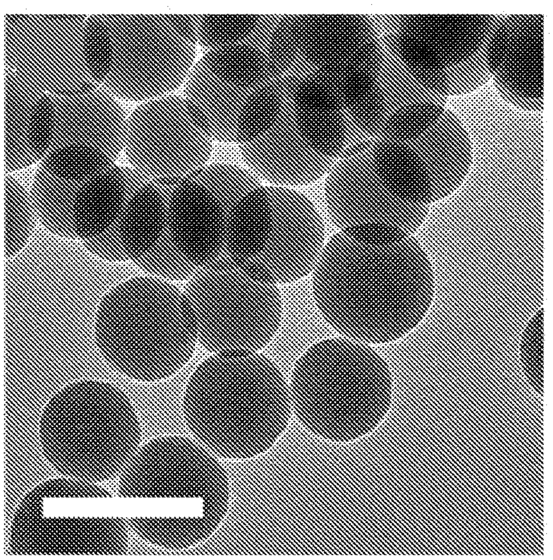
FIGS. 3A-3H. TEM images of AMNP-1 with different molar ratios of $NaIO_4$ to 1,8-DHN monomer at (FIG. 3A) 0.2:1.0.
Figure 3B:
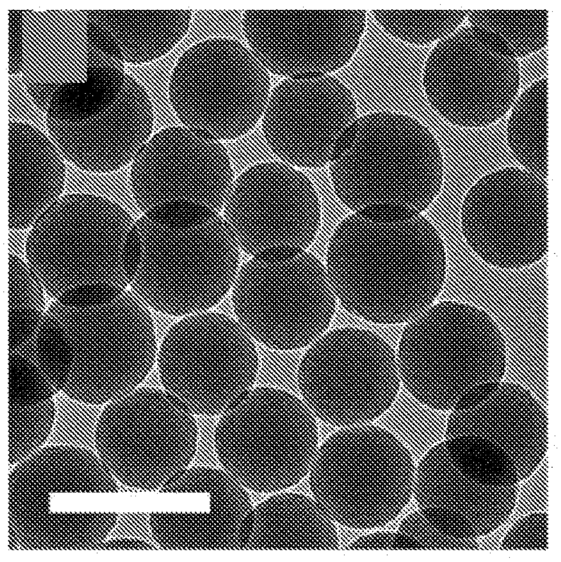
Figure 3C:
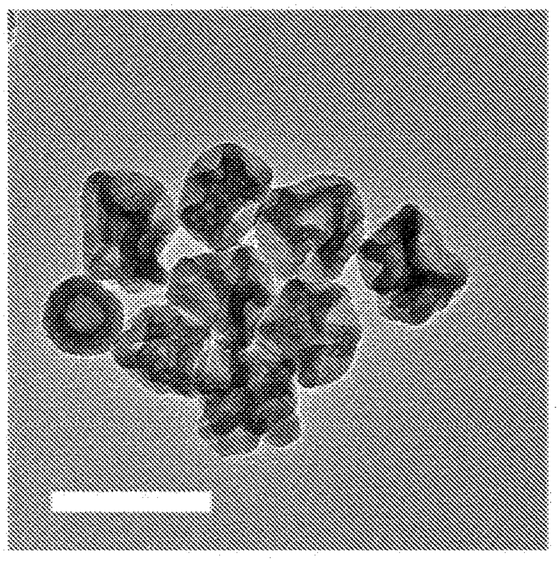
Figure 3D:
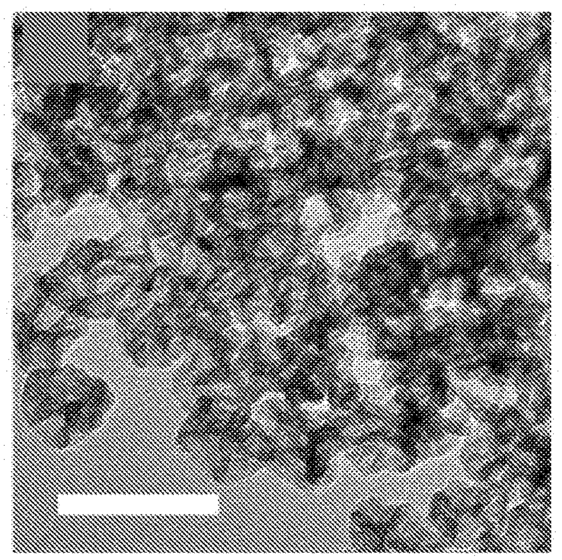
Figure 3E:
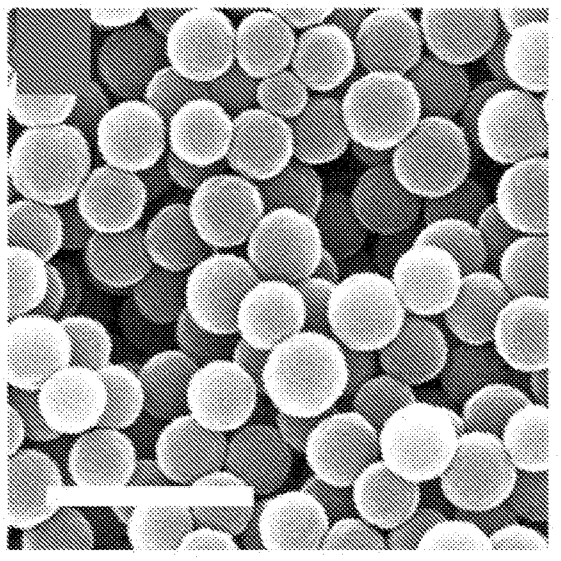
Figure 3F:
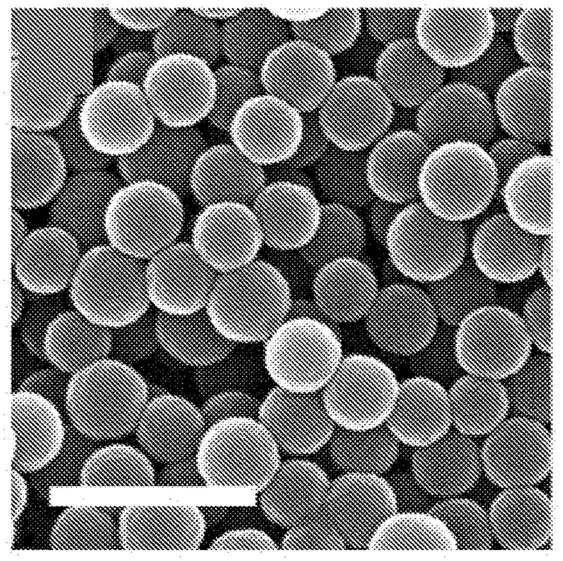
Figure 3G:
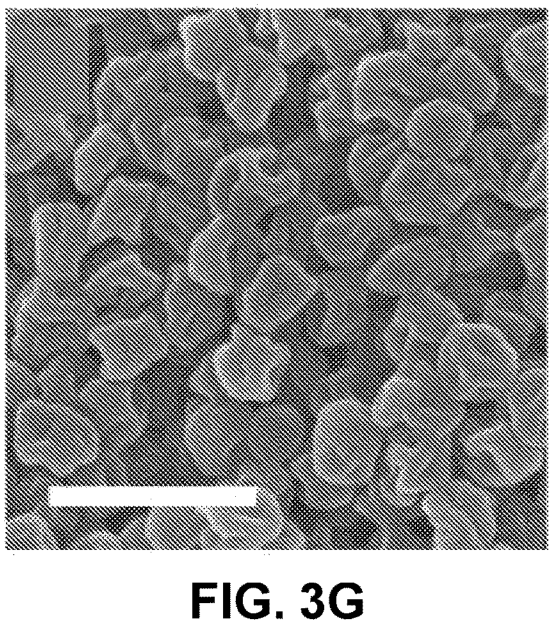
Figure 3H:
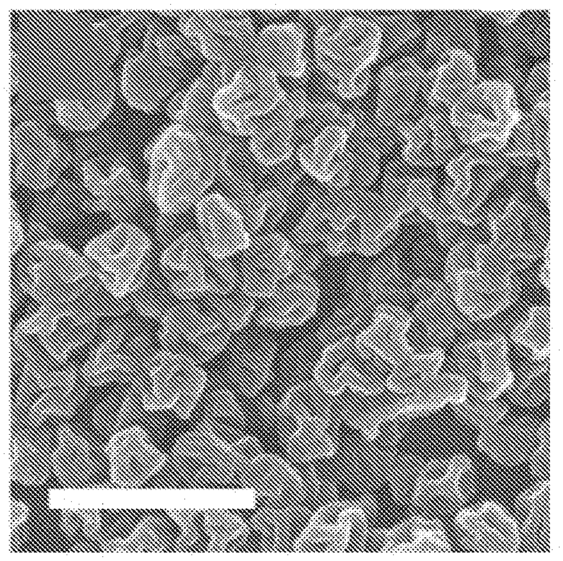

Calculated amount of quenched DPPH per gram of antioxidant (walnut[1] AMNP-1 in FIG. 3C and walnut[2] AMNP-1 in FIG. 3D).

Figure 30A:
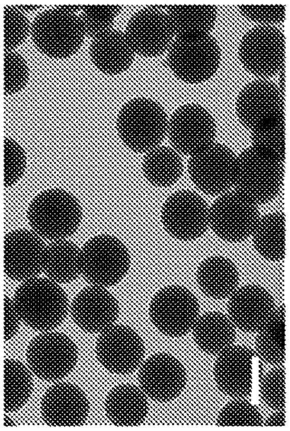
Figure 30B:
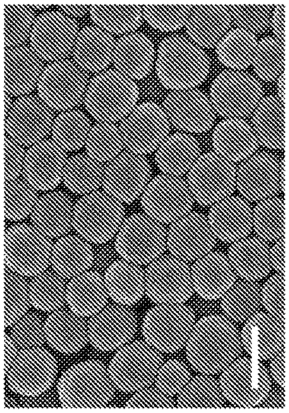
Figure 30C:
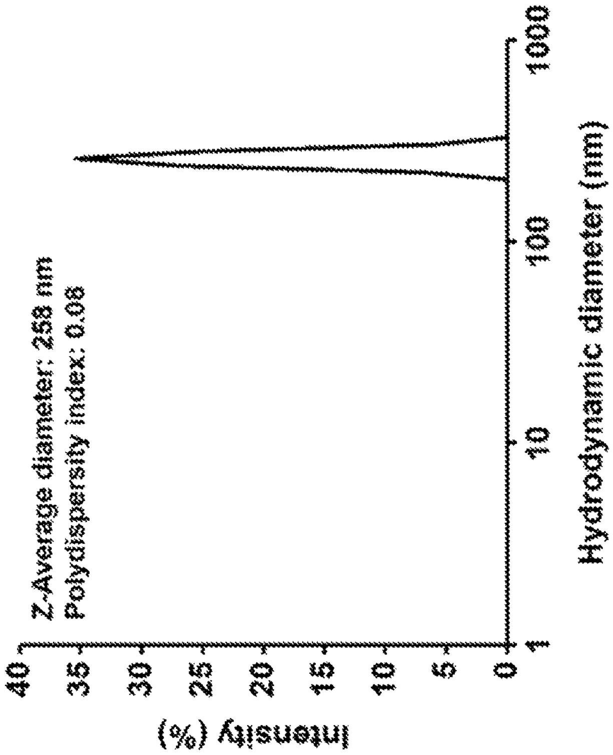
Figure 30D:
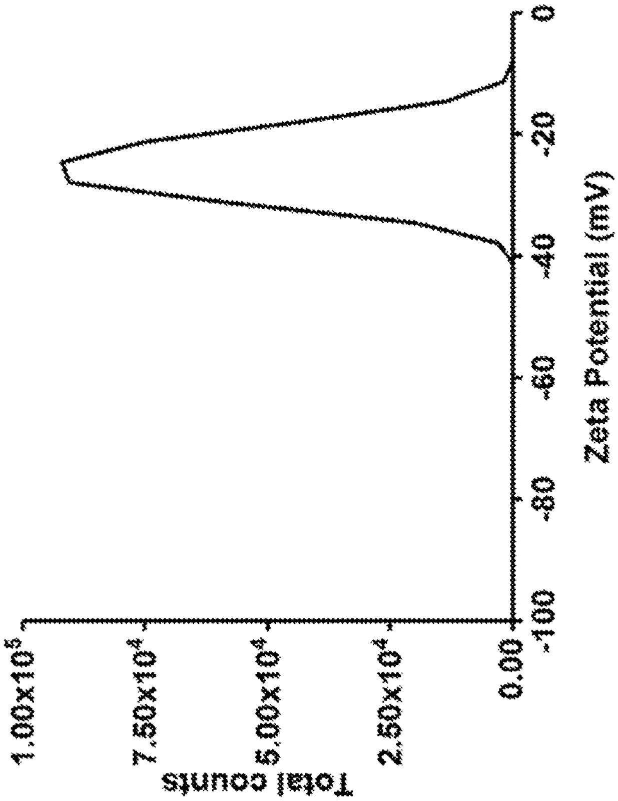

FIG. 30A. TEM and (FIG. 30B) SEM micrographs of PDA-NPs, scale bars 200 nm. Average size of PDA-NPs was determined via dynamic light scattering in ultrapure water to be (FIG. 30C) 258 nm with polydispersity index of 0.08; (FIG. 30D) Zeta potential.

Figure 31A:
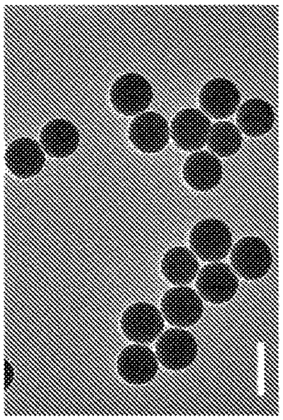
Figure 31B:
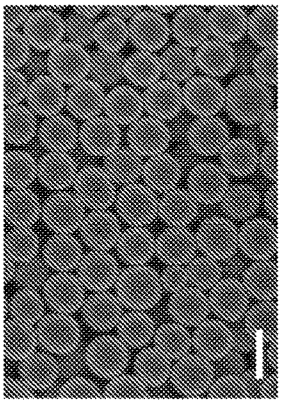
Figure 31C:
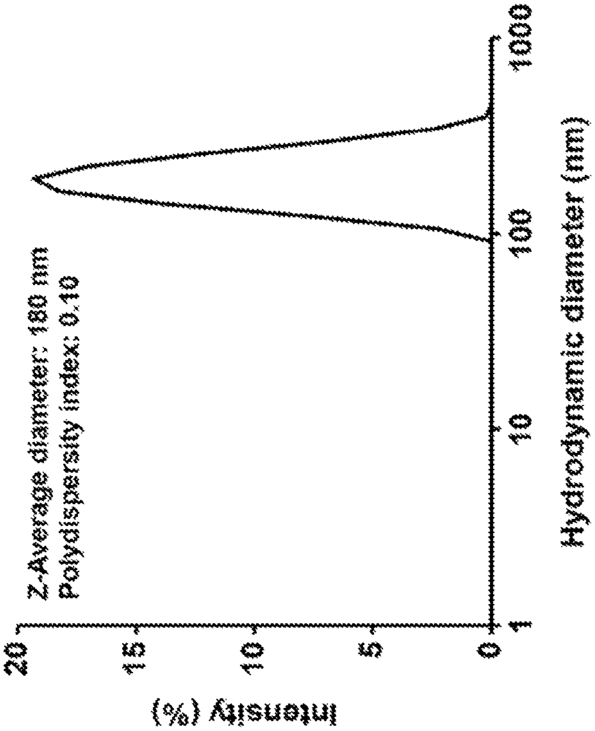
Figure 31D:
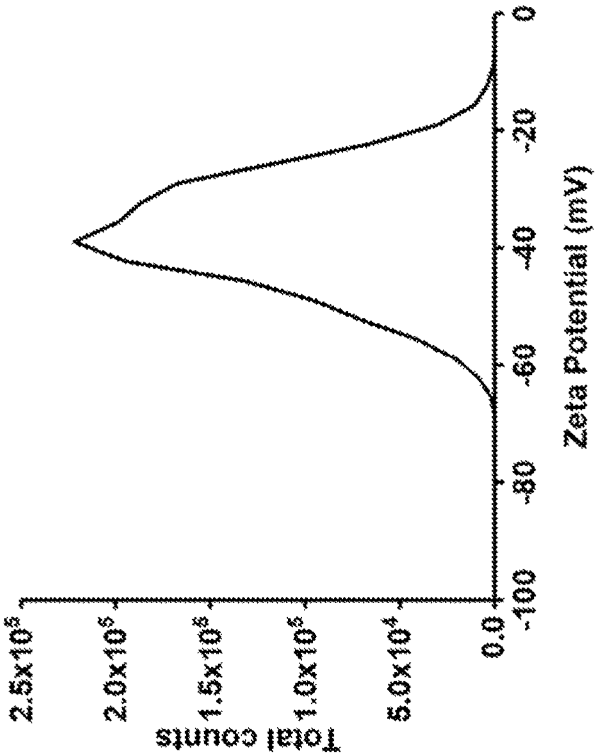

FIG. 31A. TEM and (FIG. 31B) SEM micrographs of silica nanoparticles, scale bars 200 nm. Average size of silica nanoparticles was determined via dynamic light scattering in ultrapure water to be (FIG. 31C) 180 nm with polydispersity index of 0.10; (FIG. 31D) Zeta potential.

Figure 32A:
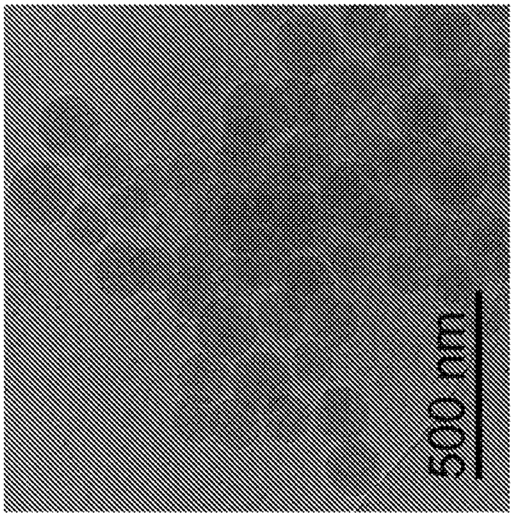
Figure 32B:
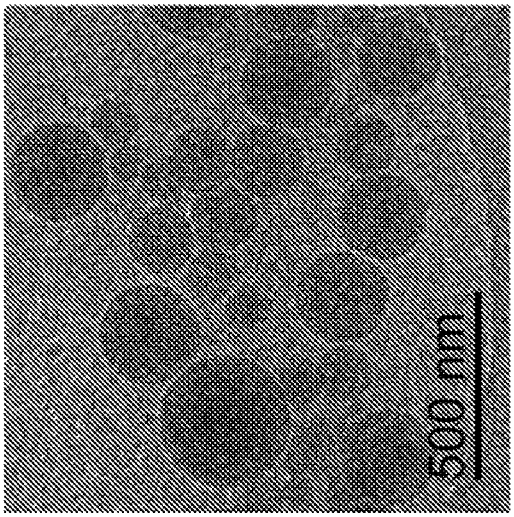
Figure 32C:
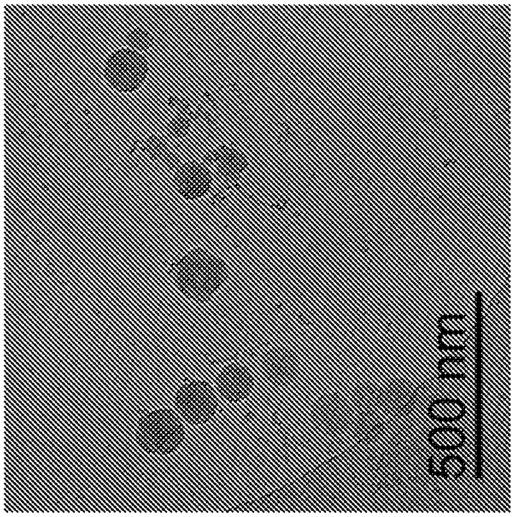

FIGS. 32A-32C. CryoTEM of AMNPs in cell media, (FIG. 32A) AMNP-1; (FIG. 32B) AMNP-2; (FIG. 32C) AMNP-3. Particles were incubated in cell culture media at 0.04 mg/mL for 48 hours, then 4 μL of suspended AMNP particles was vitrified using a Vitrobot Mark III (ThermoFisher Scientific) operating at 8° C. with >95% relative humidity. TEM grids were surface plasma treated before the vitrification procedure.

Figure 33:
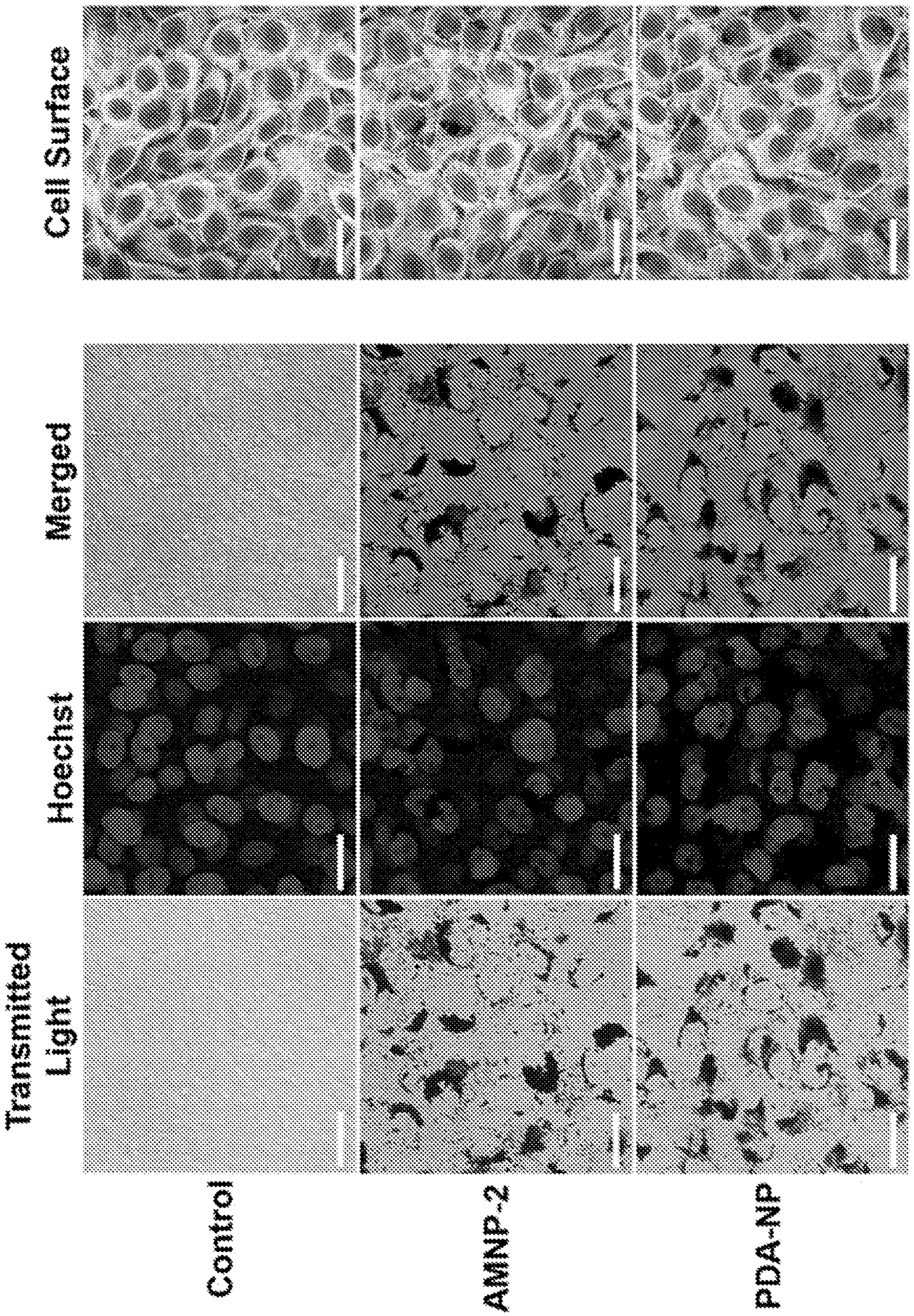

FIG. 33. NHEK cells were differentiated in 1.2 mM $CaCl_2$) for 24 hours and then incubated with the vehicle, or 0.04 mg/mL AMNP-2 or PDA-NP. Perinuclear caps are apparent as black crescents in the transmitted light images. Nuclei are stained with Hoechst (blue). Images show a single section through the center of the cell layer (left three columns). To better view the morphological changes at the surface of the differentiating cells, they were stained with CellTracker™ Orange CMRA dye (ThermoFisher), shown in yellow (rightmost column). Scale bars 25 μm.

Figure 34A:
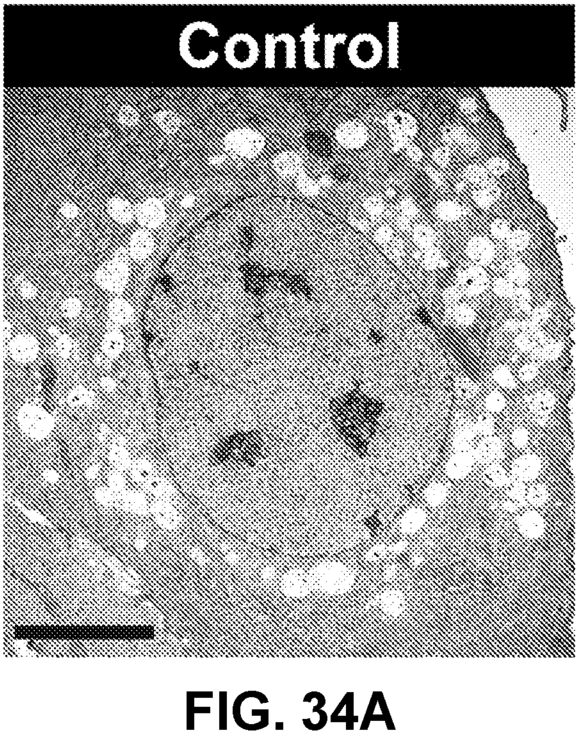
Figure 34B:
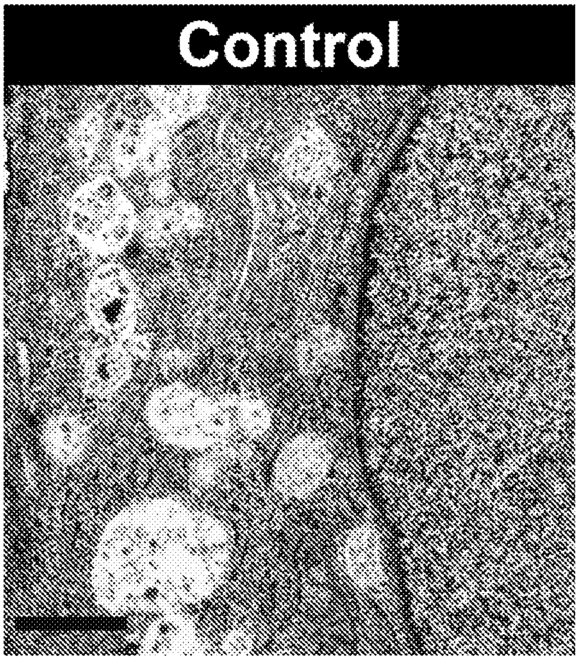

FIGS. 34A-34B. STEM micrographs of monolayer NHEK cells treated with the vehicle (water) for 48 hours, resin-embedded, and sectioned to 60 nm thick. Images were acquired using a high-angle annular dark field (HAADF) detector and image contrast inverted to simulate traditional bright-field TEM images. (FIG. 34A) scale bar 5 μm, (FIG. 34B) scale bar 1 μm.

Figure 35A:
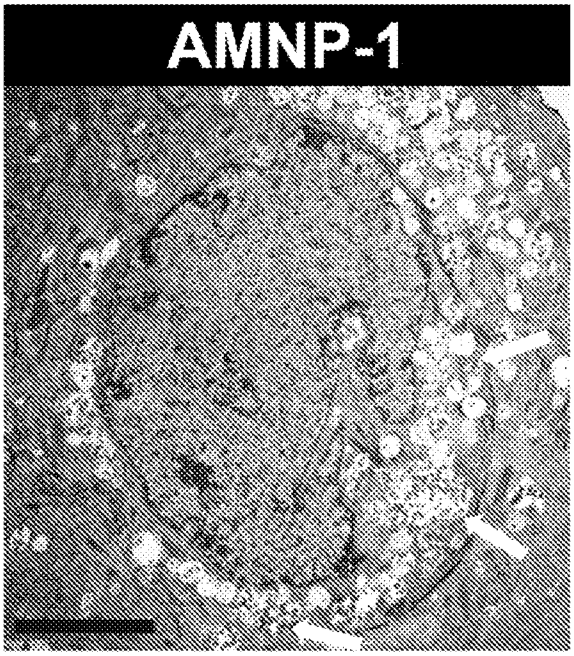
Figure 35B:
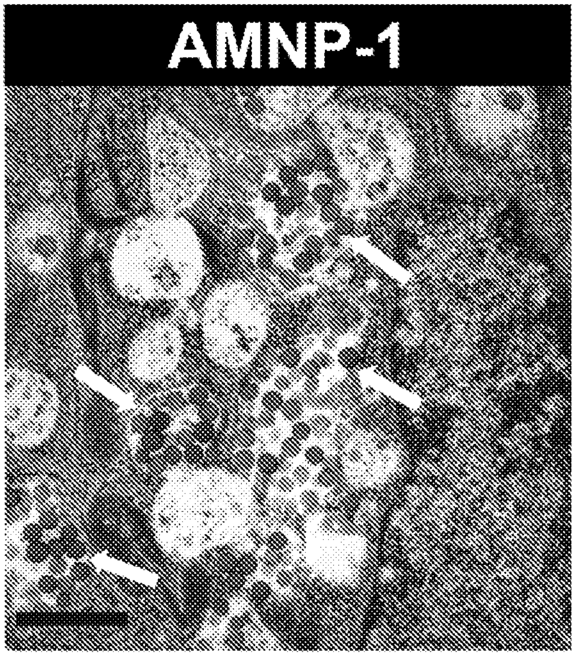

FIGS. 35A-35B. STEM micrographs of monolayer NHEK cells treated with 0.04 mg/mL AMNP-1 for 48 hours, resin-embedded, and sectioned to 60 nm thick. Images were acquired using an HAADF detector and image contrast inverted to simulate traditional bright-field TEM images. (FIG. 35A) scale bar 5 μm, (FIG. 35B) scale bar 1 μm. Arrows point to nanoparticles inside the cell.

Figure 36A:
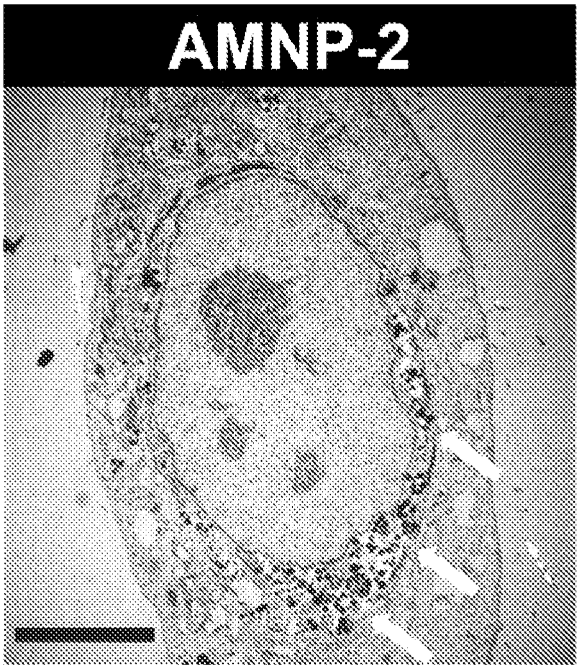
Figure 36B:
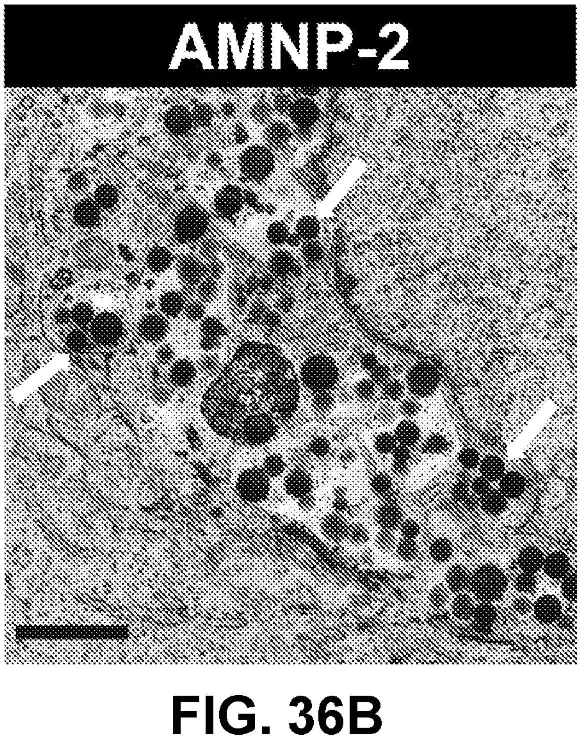

FIGS. 36A-36B. STEM micrographs of monolayer NHEK cells treated with 0.04 mg/mL AMNP-2 for 48 hours, resin-embedded, and sectioned to 60 nm thick. Images were acquired using an HAADF detector and image contrast inverted to simulate traditional bright-field TEM images. (FIG. 36A) scale bar 5 μm, (FIG. 36B) scale bar 1 μm. Arrows point to nanoparticles inside the cell.

Figure 37A:
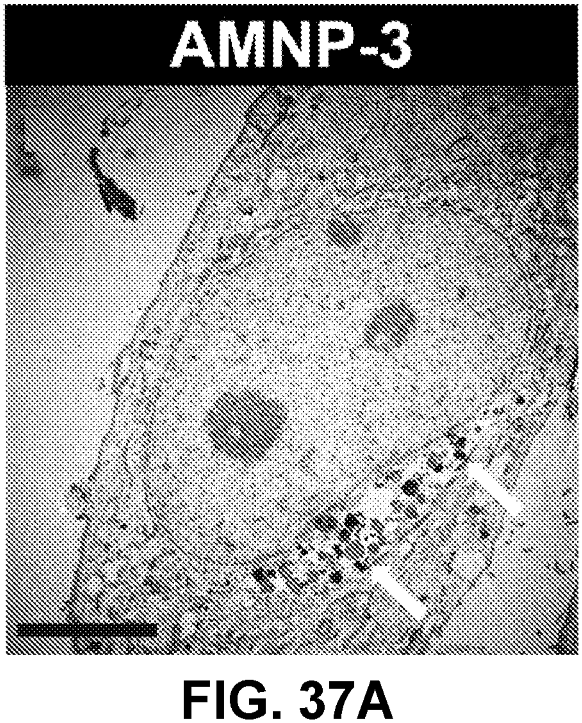
Figure 37B:
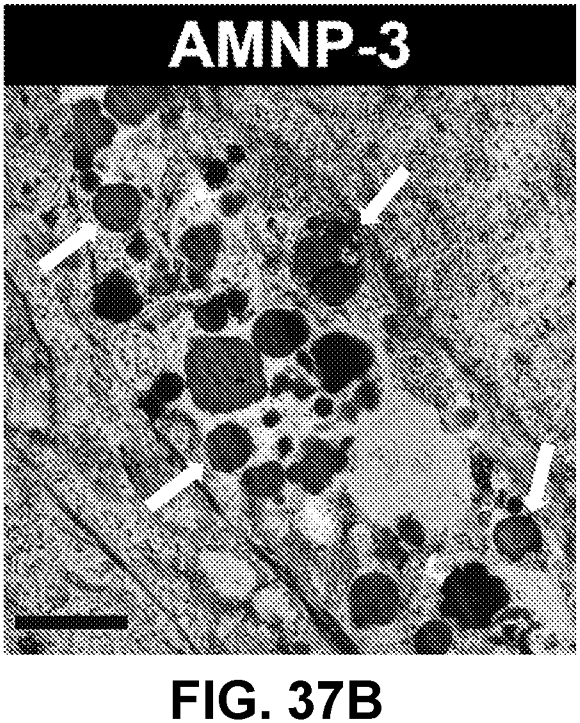

FIGS. 37A-37B. STEM micrographs of monolayer NHEK cells treated with 0.04 mg/mL AMNP-3 for 48 hours, resin-embedded, and sectioned to 60 nm thick. Images were acquired using an HAADF detector and image contrast inverted to simulate traditional bright-field TEM images. (FIG. 37A) scale bar 5 μm, (FIG. 37B) scale bar 1 μm. Arrows point to nanoparticles inside the cell.

Figure 38A:
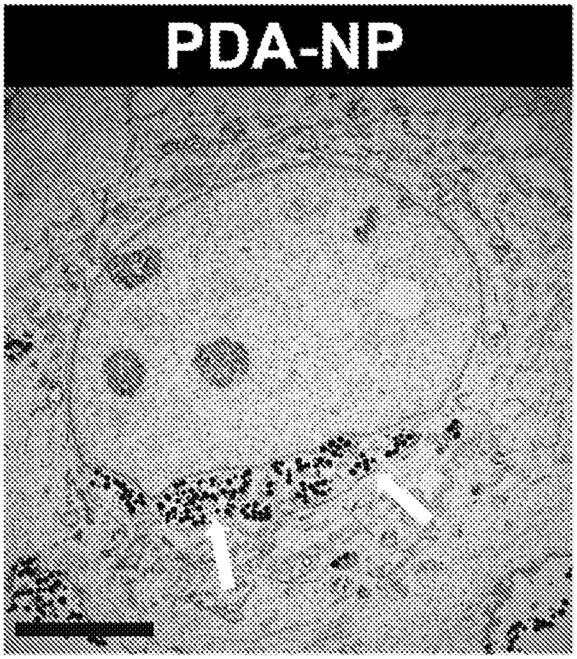
Figure 38B:
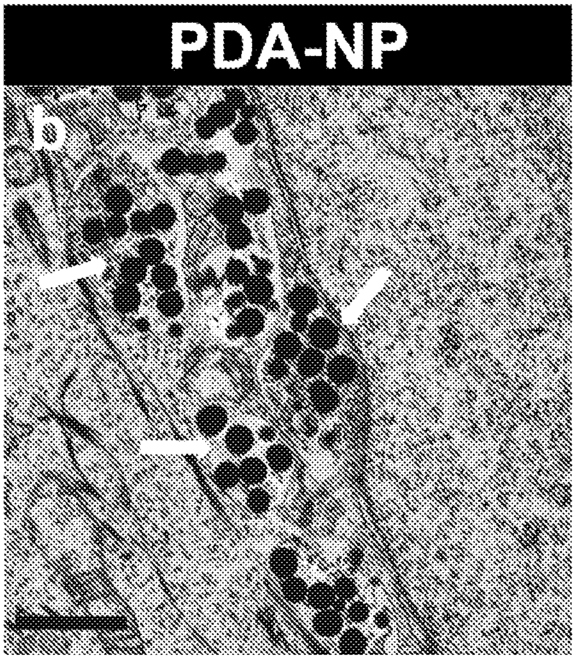

FIGS. 38A-38B. STEM micrographs of monolayer NHEK cells treated with 0.04 mg/mL PDA-NP for 48 hours, resin-embedded, and sectioned to 60 nm thick. Images were acquired using an HAADF detector and image contrast inverted to simulate traditional bright-field TEM images. (FIG. 38A) scale bar 5 μm, (FIG. 38B) scale bar 1 μm. Arrows point to nanoparticles inside the cell.

Figure 39A:
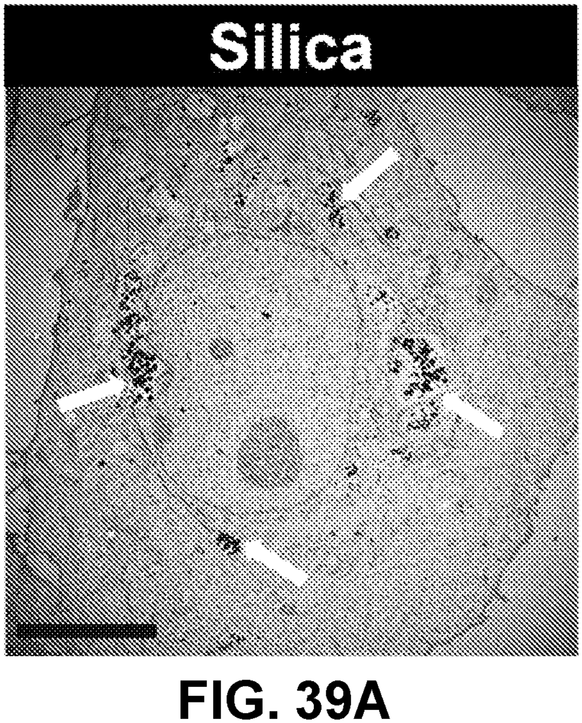
Figure 39B:
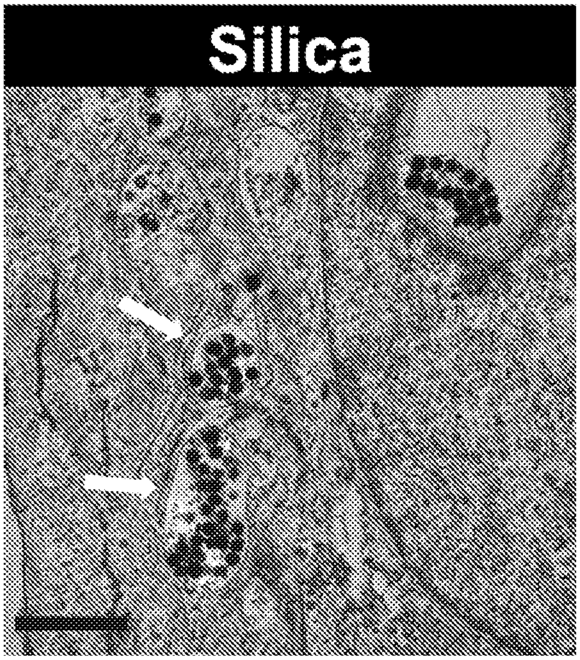

FIG. 39A-39B. STEM micrographs of monolayer NHEK cells treated with 0.04 mg/mL silica nanoparticles for 48 hours, resin-embedded, and sectioned to 60 nm thick. Images were acquired using an HAADF detector and image contrast inverted to simulate traditional bright-field TEM images. (FIG. 39A) scale bar 5 μm, (FIG. 39B) scale bar 1 μm. Arrows point to nanoparticles inside the cell.

Figure 40:
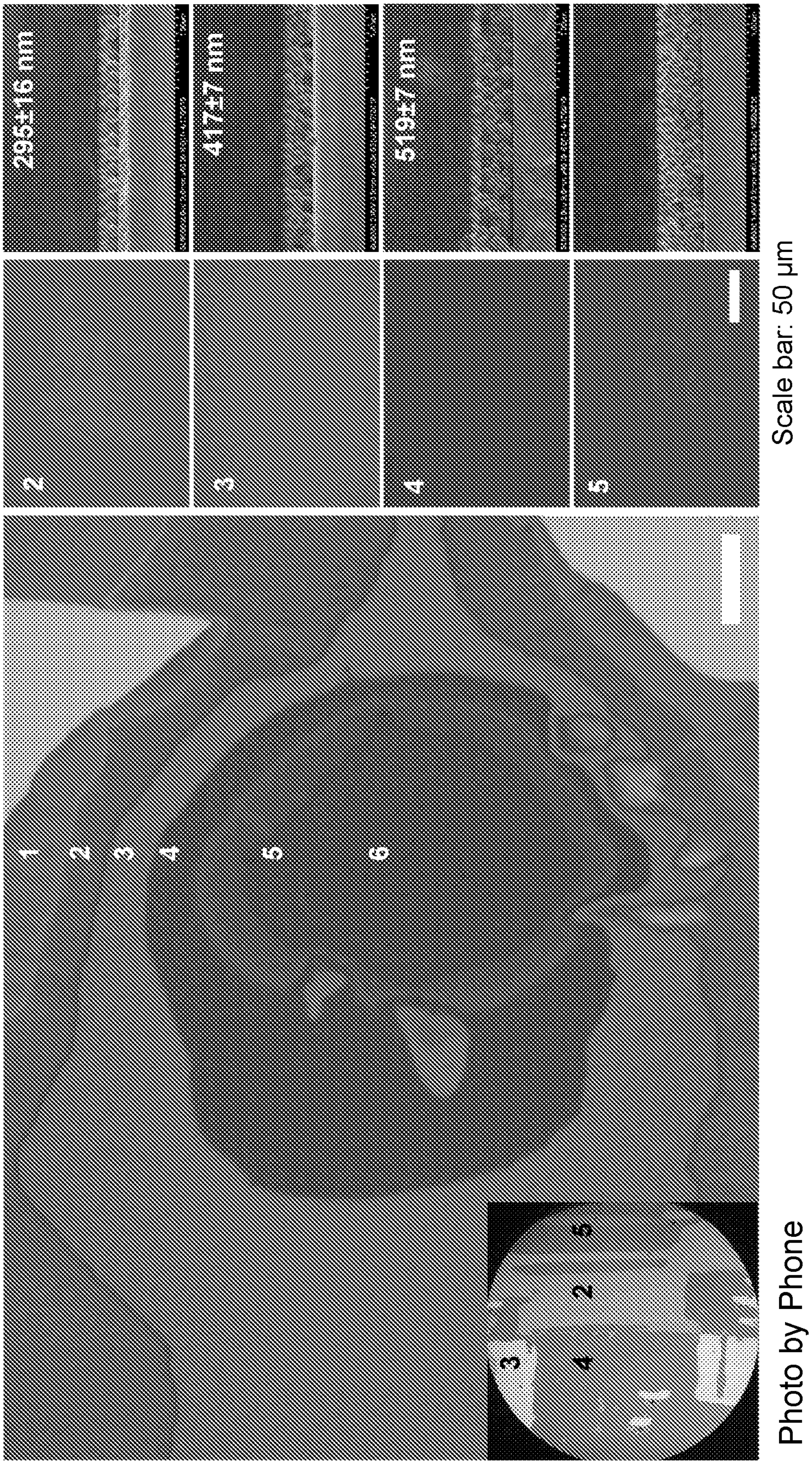
Figure 42:
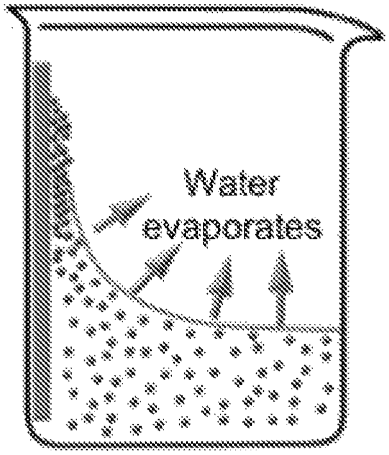

FIG. 40. Photographs and SEM images showing layers of artificial melanin nanoparticles exhibiting structural color. The larger photograph is captured using an optical microscope and the smaller inset photograph is captured using a cellphone camera. A layer of artificial melanin nanoparticles was formed by depositing artificial melanin nanoparticles from a solution and allowing the layer to form during evaporation of the solvent(s), such as illustrated in FIG. 42. The layer is characterized by a plurality of regions, indicated by the number annotations in the photographs, each indicated region having a different thickness. The corresponding SEM images next to the numbered photographs showing a cross-section of the corresponding numbered region of the layer, where each region has a different thickness and a different color due to the effect of structural color, or interference of light with the corresponding region of the layer of artificial melanin nanoparticles. For example: region #2 appears orange in the optical microscope photograph with SEM images showing a layer thickness of 295±16 nm; region #3 appears green in the optical microscope photograph with SEM images showing a layer thickness of 417±7 nm; region #4 appears purple in the optical microscope photograph with SEM images showing a layer thickness of 519±7 nm; and region #5 appears dark green in the optical microscope photograph with SEM images showing a layer thickness of 637±13 nm.

Figure 41:
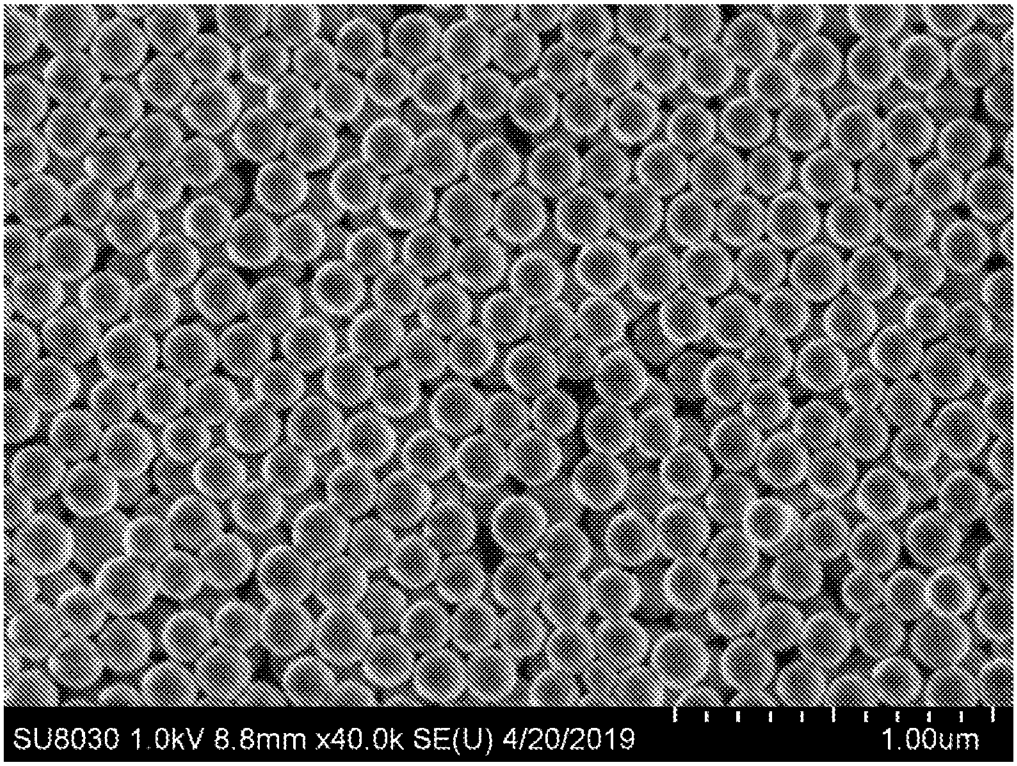

FIG. 41. A top-view of a region of the layer of artificial melanin nanoparticles of FIG. 40.

FIG. 42. An illustration of a method for forming the layer of FIG. 40. The layer is formed by self-assembly via evaporative deposition, where artificial melanin nanoparticles are deposited from a solution and the solvent(s) is allowed to evaporate thereby forming the layer. The layer of FIG. 40 is formed on a silicon wafer substrate having a native silica layer of approximately 2.4 nm thereon. For example, the solution has AMNP-1 artificial melanin nanoparticles at a concentration of 0.5 mg/mL. For example, the particles are approximately 140-170 nm in size. For example, the substrate temperature is approximately 21° C. and the relative humidity of the ambient air is 26% to 33%.

FIGS. 43A-43D. Each panel shows an SEM image and an inset photograph corresponding to a centrifuged pellet of artificial melanin nanoparticles (e.g., AMNP-1), where each different pellet has a different color due to exhibiting the effect of structural color. For example, the pellet of FIG. 43A appears blue in the inset photograph, the pellet of FIG. 43B appears purple in the inset photograph, the pellet of FIG. 43C appears green in the inset photograph, and the pellet of FIG. 43D appears yellow in the inset photograph.

Figure 44:
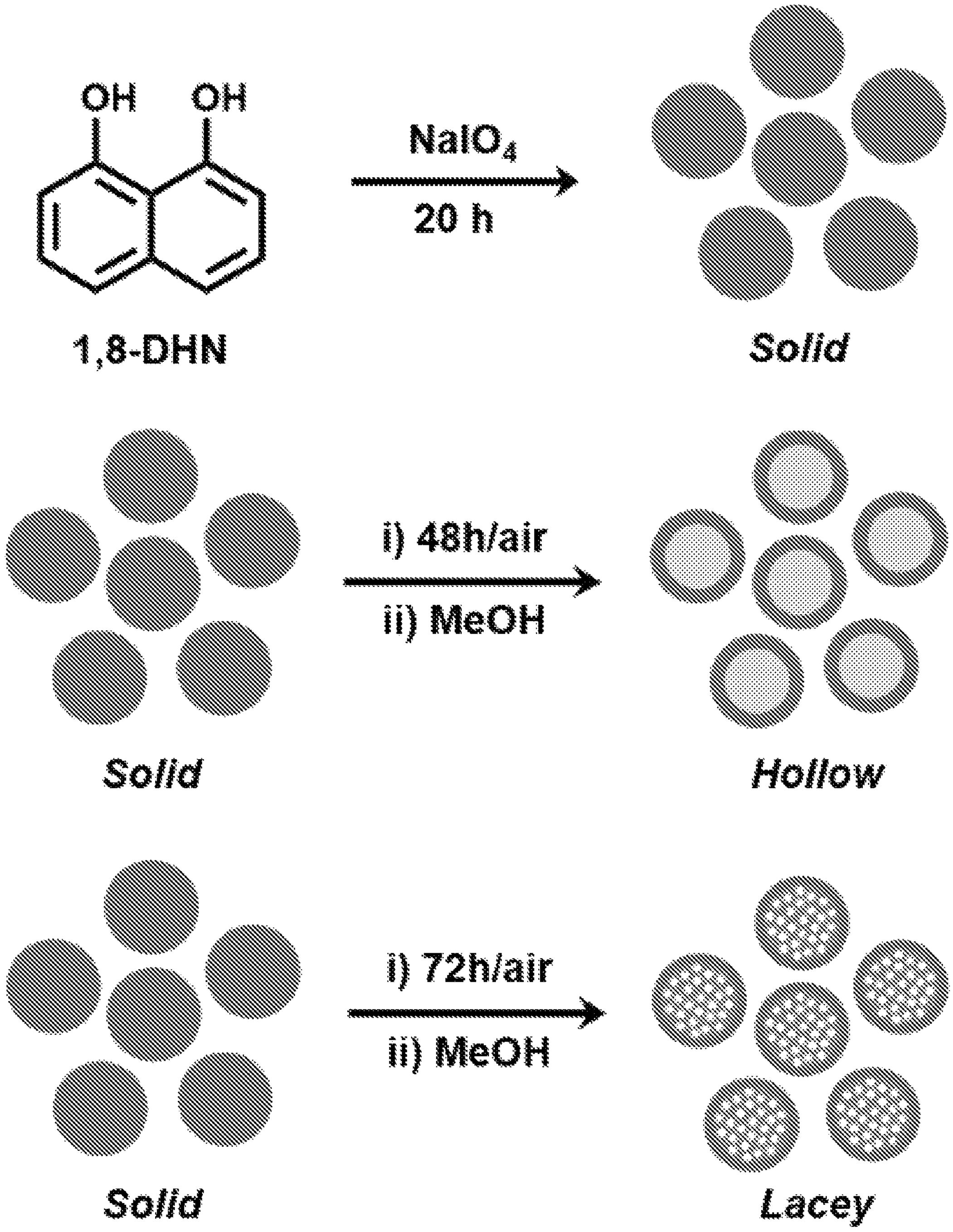

FIG. 44. Schematic of "etching" or partial dissolution process to synthesize lacey and hollow MNPs from solid MNPs. This approach has found to be efficient for creating well-defined structures with the use of MeOH and can be performed using other alcoholic solvents such as isopropanol or ethanol, and/or non-alcoholic solvents such as acetonitrile or acetic acid. The Hollow MNPs are formed at an earlier timepoint where the original solid particle is "fresher" and overall less oxidized and may be less cross-linked, therefore MeOH treatment causes a leaching of more material from the particle core, which is likened to an oxidized "crust" which is still porous enough to allow small oligomers and monomers to leach out. In an embodiment, these particles are incubated with the etching solution for 6 days, therefore no leached material is removed. It re-deposits onto the surface of the particle, increasing the size of the particle by the same amount that leached out. Lacey MNPs are partially dissolved at a later stage (24 hours later), therefore the starting solid particle precursors are more fully oxidized, and less material can leach out upon MeOH treatment. This results in a particle midway between the Solid and Hollow MNPs, and is of an intermediate diameter, as there is less material leaching out that can re-deposit onto the surface. Hollow and Lacey particles are then dialyzed into water after the 6 day incubation with MeOH, where they remain stored in solution.

Figure 45A:
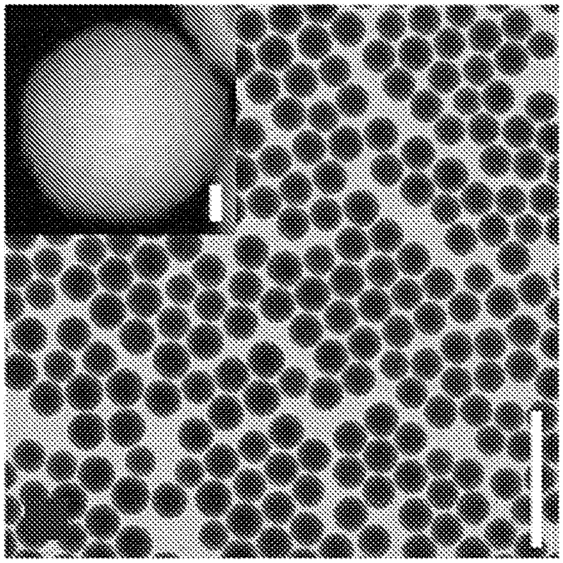
Figure 45B:
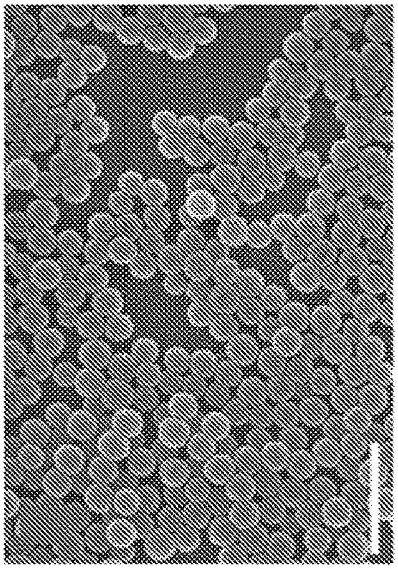
Figure 45C:
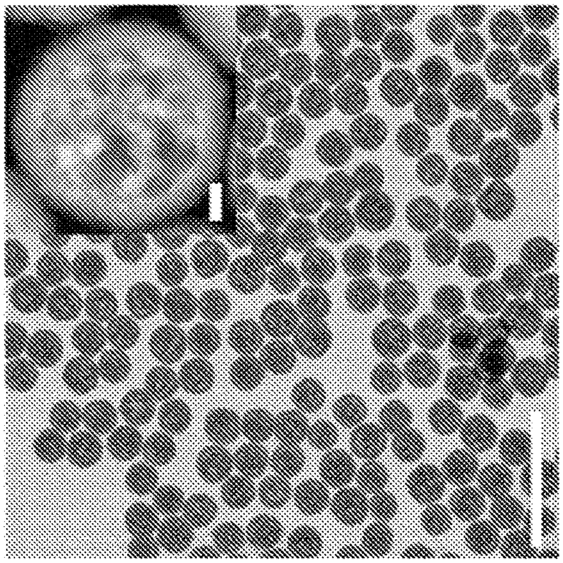
Figure 45D:
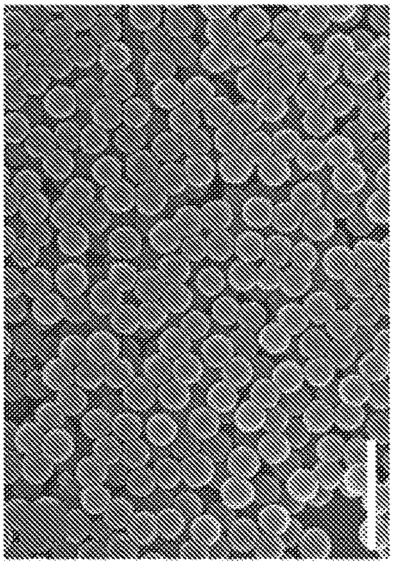
Figure 45E:
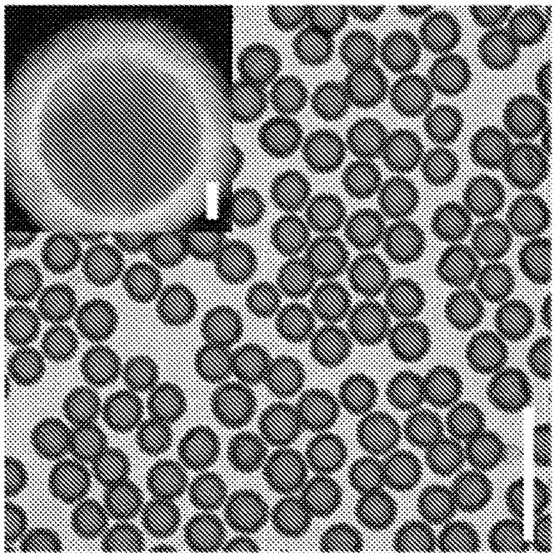
Figure 45F:
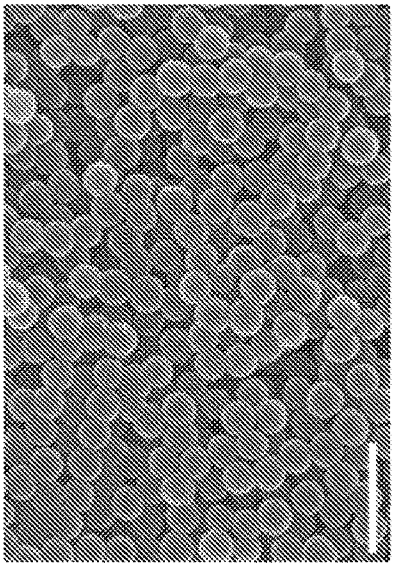

FIGS. 45A-45F. STEM and SEM micrographs of MNPs. Bright-field STEM images of MNPs (top row, with high-angle annular dark-field (HAADF) STEM image insets) and SEM images of MNPs (bottom row) of Solid NMPs (FIGS. 45A-45B), Lacey MNPs (FIGS. 45C-45D), and Hollow MNPs (FIGS. 45E-45F). Scale bars in FIGS. 45A-45F are 500 nm, inset scale bars in FIGS. 45A, 45C and 45E are 20 nm.

Figure 46A:
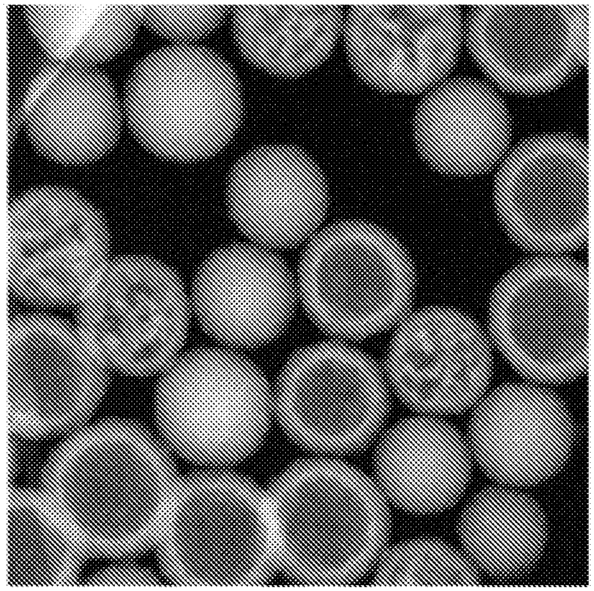
Figure 46B:
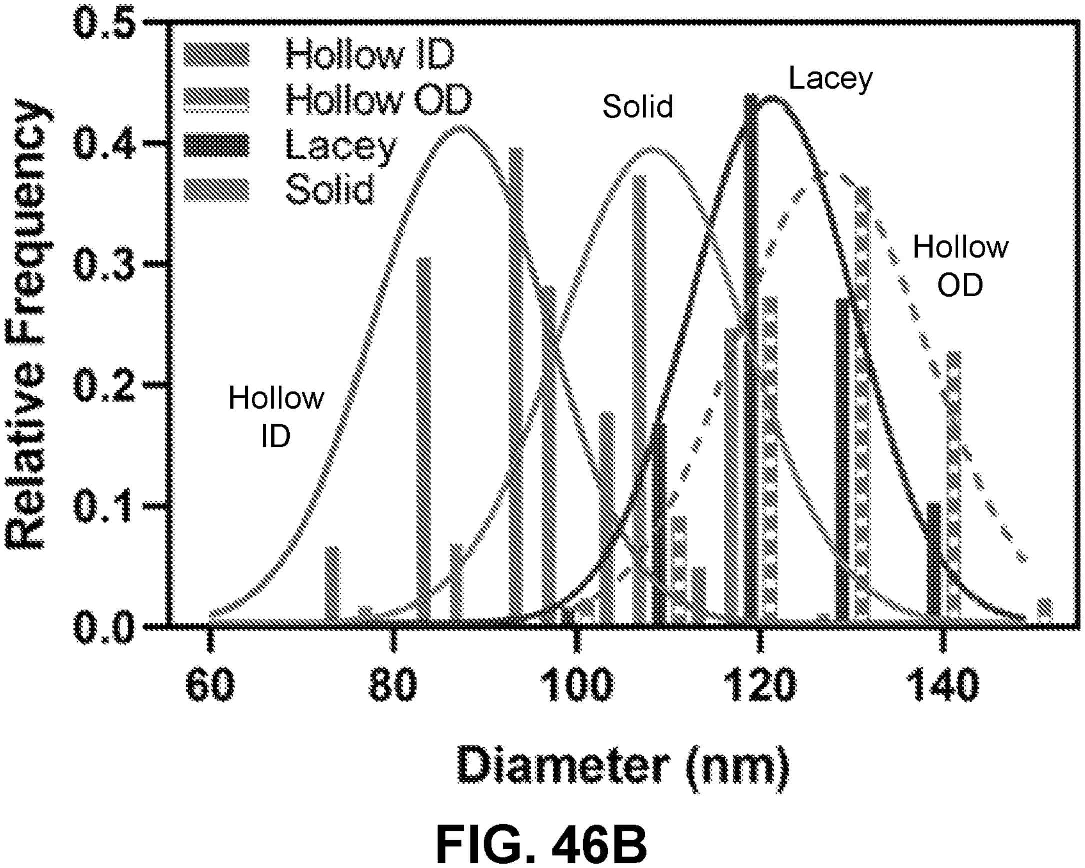
Figure 46C:
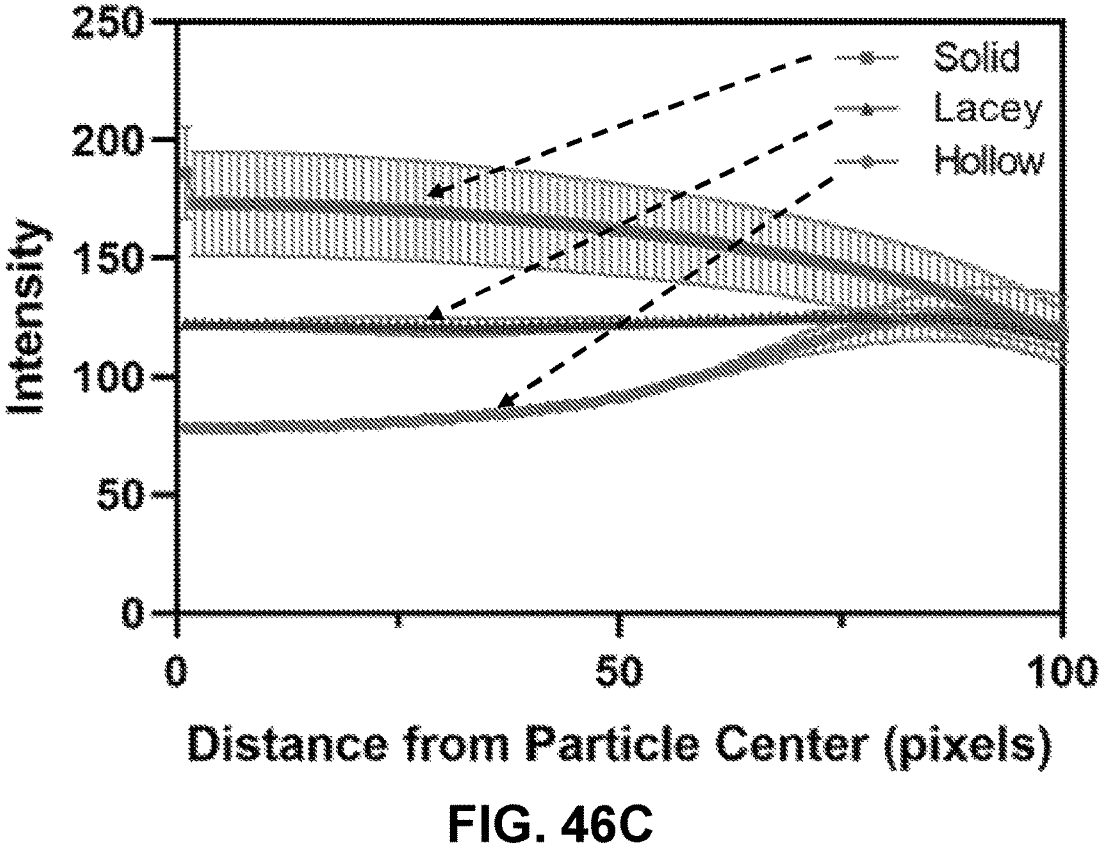
Figure 46D:
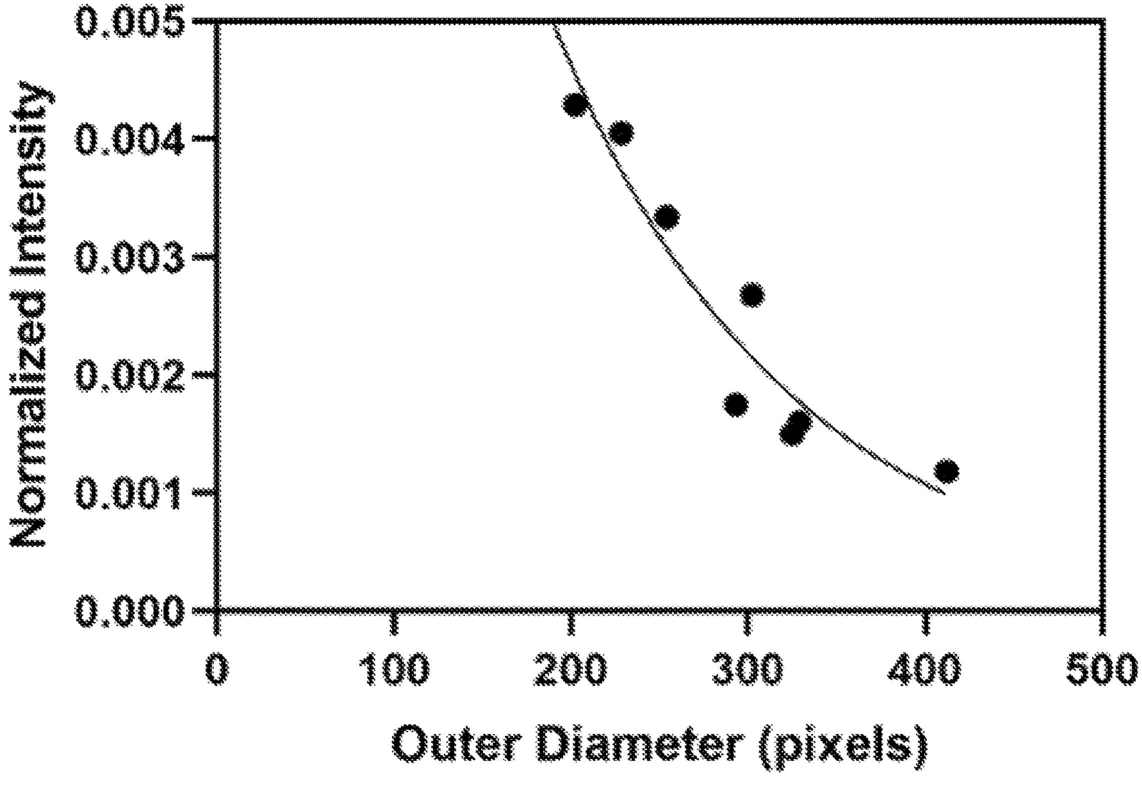

FIGS. 46A-46D. STEM imaging and particle size/growth analysis. FIG. 46A. Representative HAADF STEM micrograph of 1:1:1 Solid:Lacey:Hollow MNPs for analysis. FIG. 46B. Frequency distribution of Solid, Lacey, and Hollow MNP outer diameter (OD) and Hollow MNP inner diameter (ID). FIG. 46C. MNP density analysis. FIG. 46D. Normalized intensity as a function of MNP diameter. These images show that the growth mechanism after partial dissolution of the original solid particles to form "lacey" or "hollow" structures is consistent with a leaching of material, mainly small oligomers, from the center of the particle which are then redeposited onto the outer surface of the particle in a manner that conserves matter. Lacey and Hollow MNPs are slightly larger than their precursor solid particles due to this formation mechanism.

Figure 47:
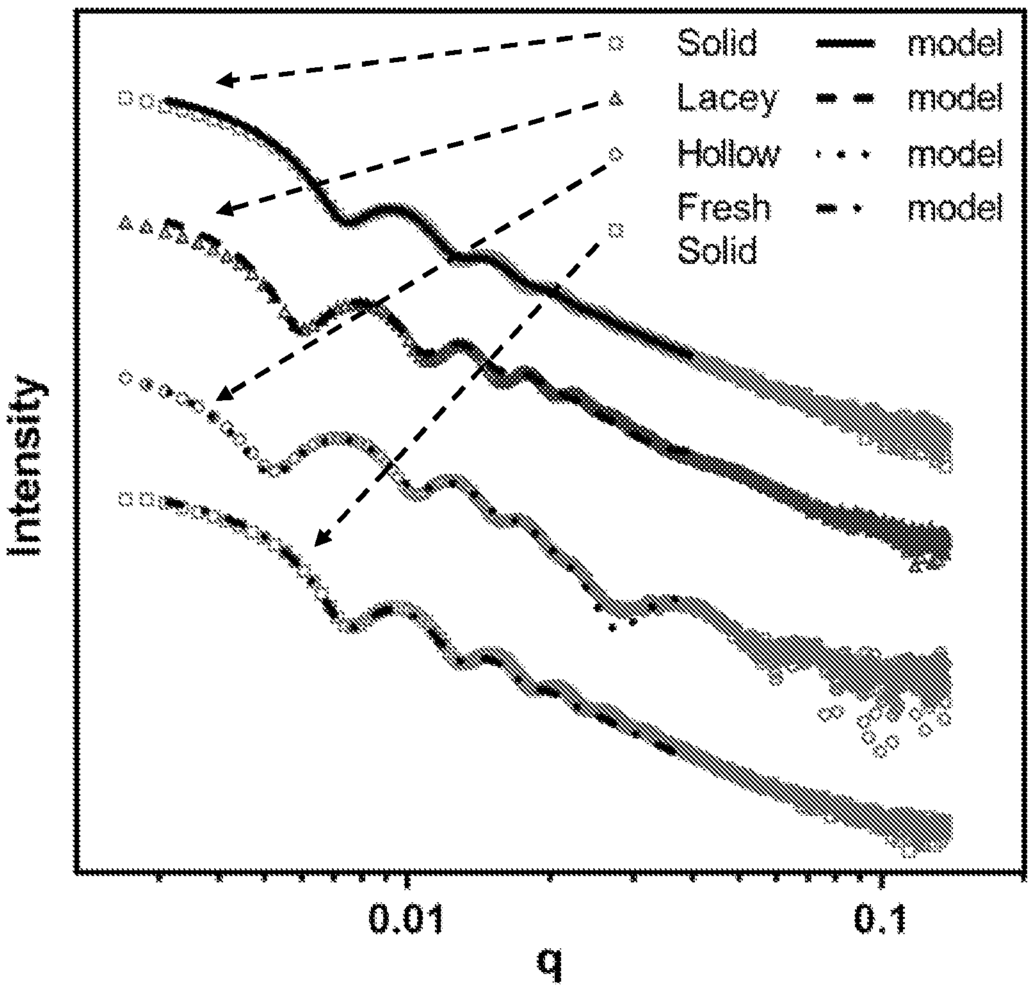

FIG. 47. Small Angle X-Ray Scattering (SAXS) measurements of MNPs (Solid, Lacey, Hollow, and Fresh Solid).

Figure 48A:
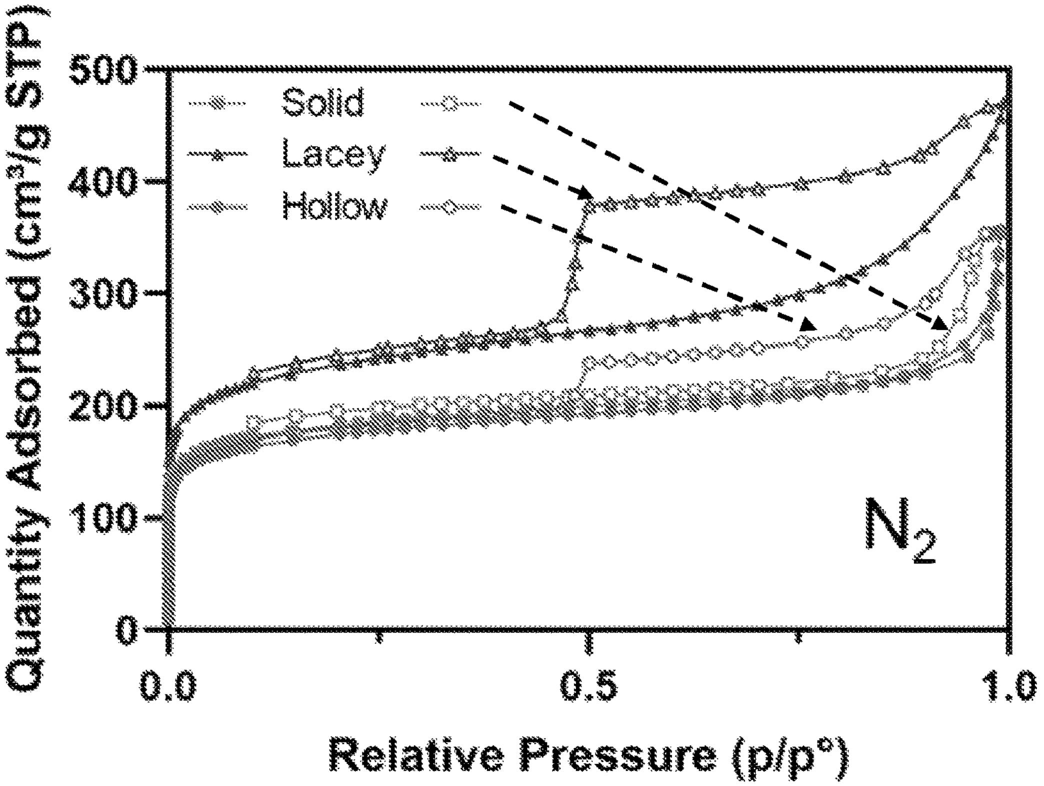
Figure 48B:
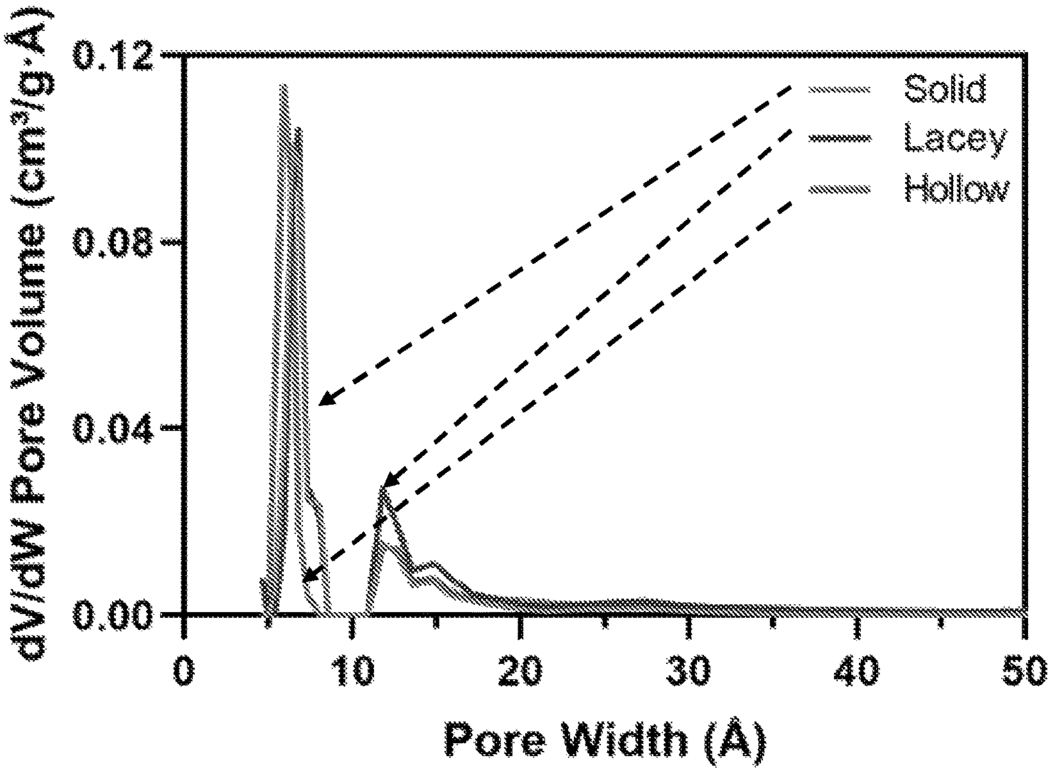

FIGS. 48A-48B. Sorption (closed markers) and desorption (open markers) isotherms for Solid (square marker), Lacey (triangle marker) and Hollow (circle marker) MNPs as well as pore measurements. FIG. 48A. $N_2$ sorption measurements at 77 K. FIG. 48B. Pore size and volume measurements.

Figure 49:
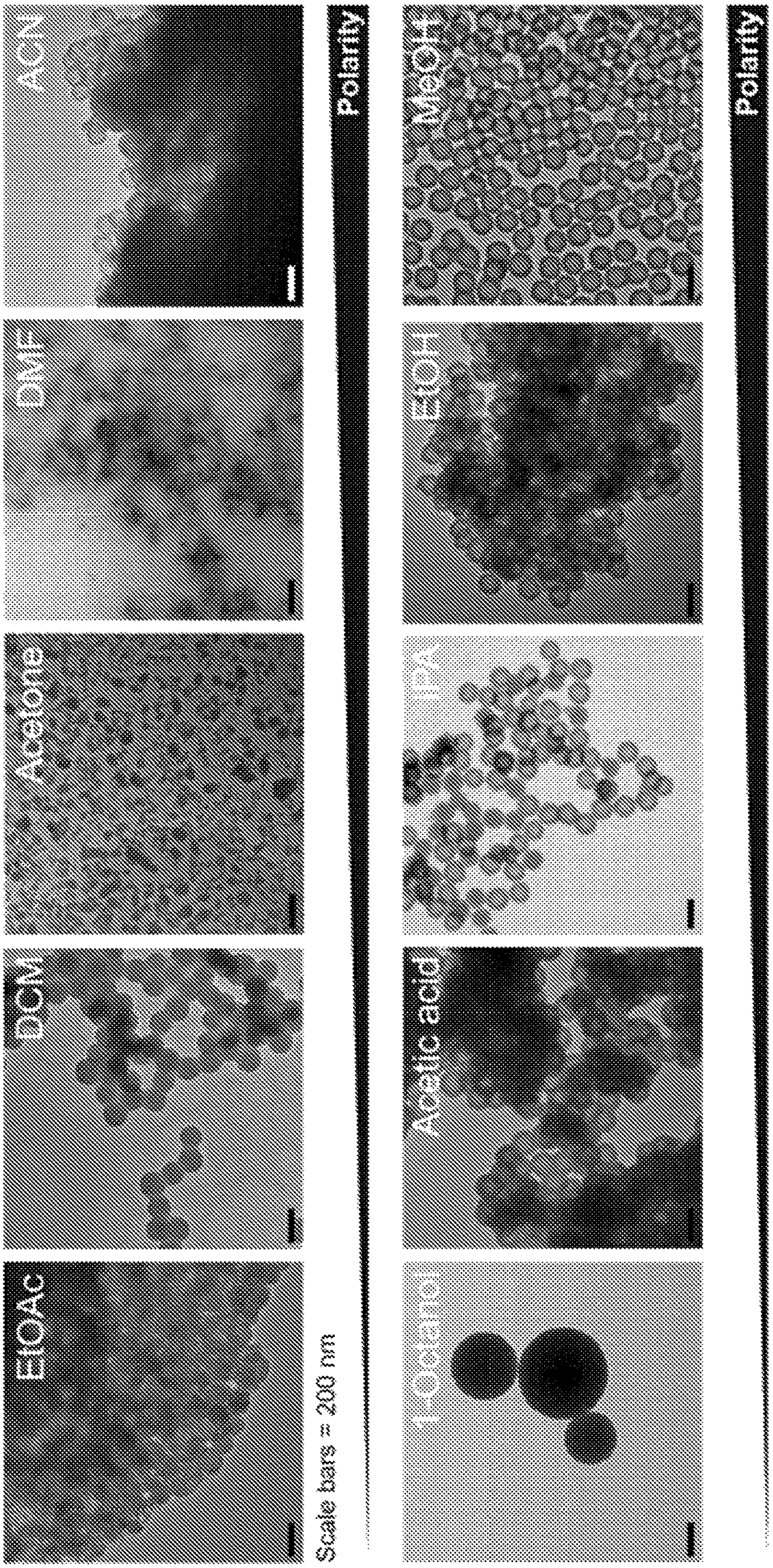

FIG. 49. Solvent screening conditions for formation of hollow MNPs. Acetonitrile (ACN), acetic acid, and alcoholic solvents isopropanol (IPA), ethanol (EtOH) and methanol (MeOH) all etch solid particles to some extent, but MeOH is the most efficient at creating uniform structures. Less polar solvents ethyl acetate (EtOAc), dichloromethane (DCM), acetone, N,N-dimethylformamide (DMF), and 1-octanol do not etch the structures to any appreciable amount.

Figure 50:
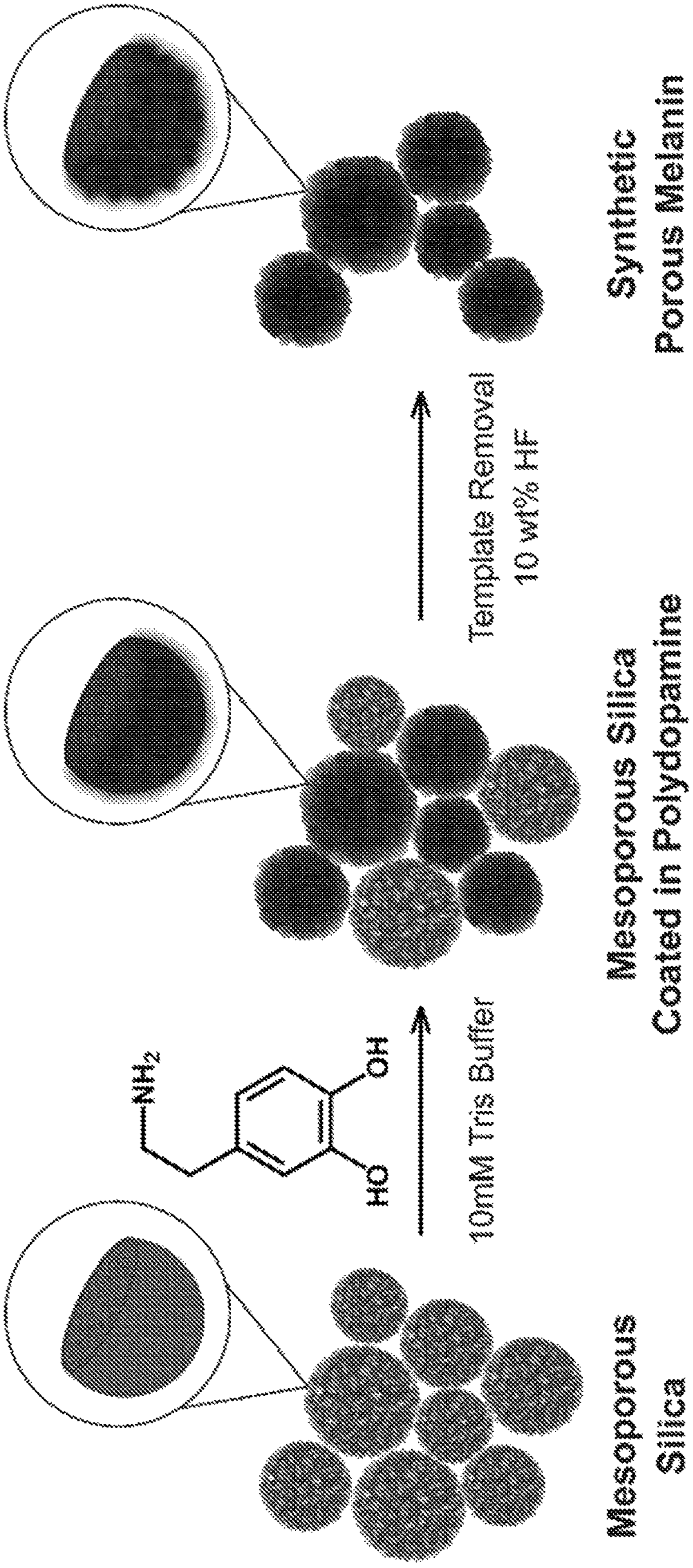

FIG. 50. Schematic of templated synthesis of synthetic porous polydopamine.

Figure 51A:
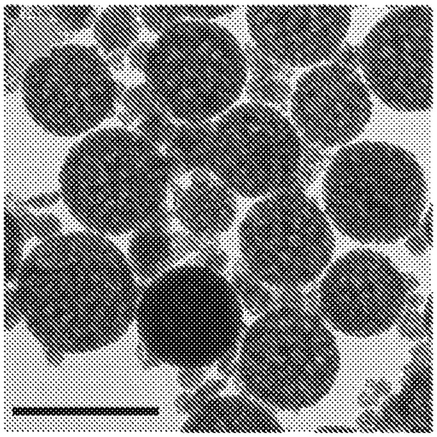
Figure 51B:
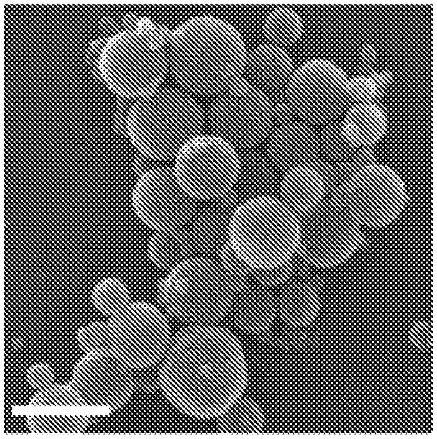
Figure 51C:
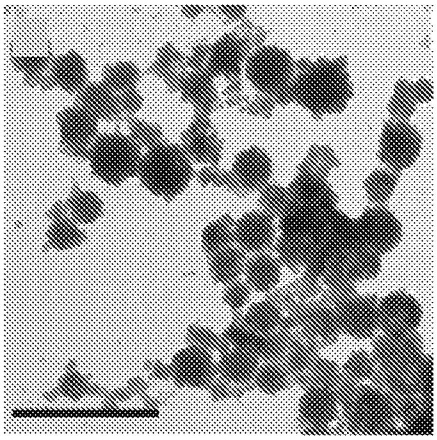
Figure 51D:
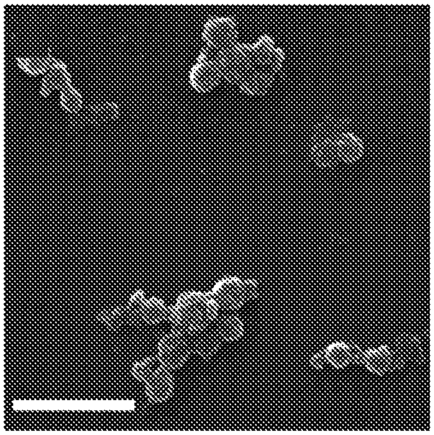
Figure 51E:
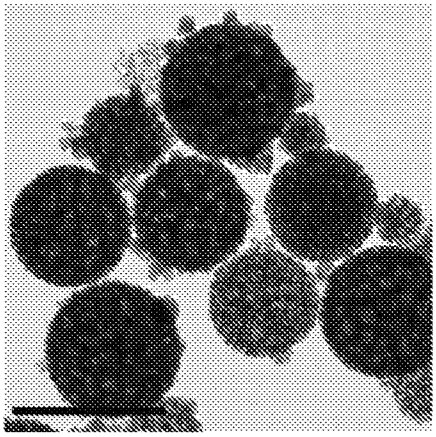
Figure 51F:
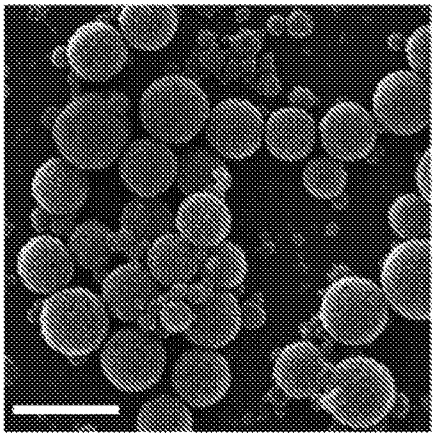
Figure 51G:
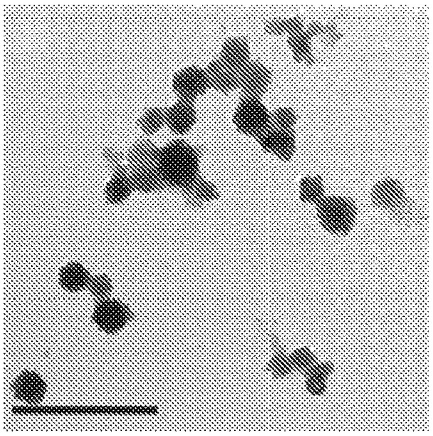
Figure 51H:
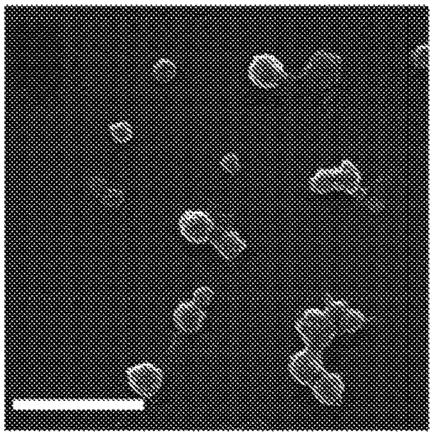
Figure 51I:
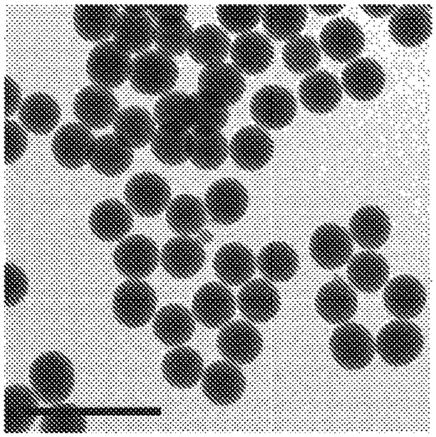
Figure 51J:
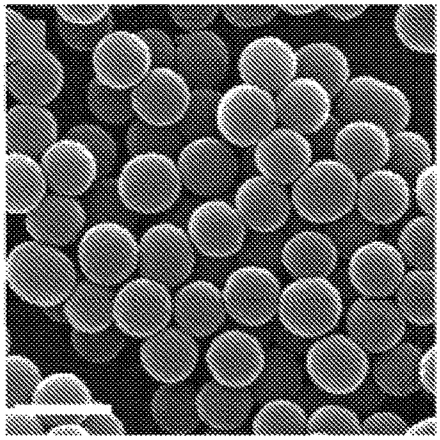

FIGS. 51A-51J. TEM and SEM micrographs of representative oxidatively polymerized polydopamine nanoparticles. Mesoporous silica with 5% loaded polydopamine before etching (FIG. 51A) and (FIG. 51B). Mesoporous silica with 5% loaded polydopamine after etching (5% Loaded SPM) (FIG. 51C) and (FIG. 51D). Mesoporous silica with 25% loaded polydopamine before etching (FIG. 51E) and (FIG. 51F). Mesoporous silica with 25% loaded polydopamine after etching (25% Loaded SPM) (FIG. 51G) and (FIG. 51H). Solid polydopamine nanoparticles (FIG. 51I) and (FIG. 51J). All scale bars 1 micron.

Figure 52A:
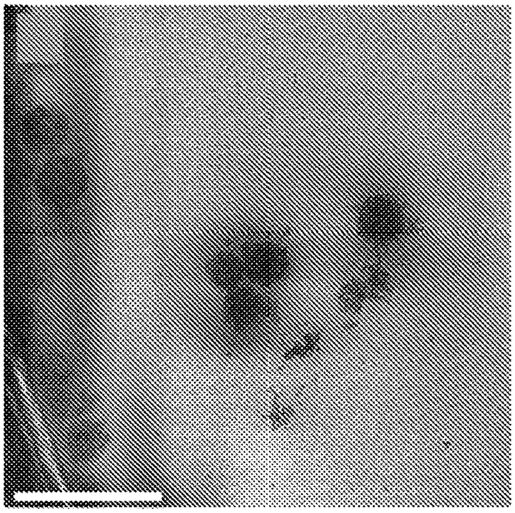
Figure 52B:
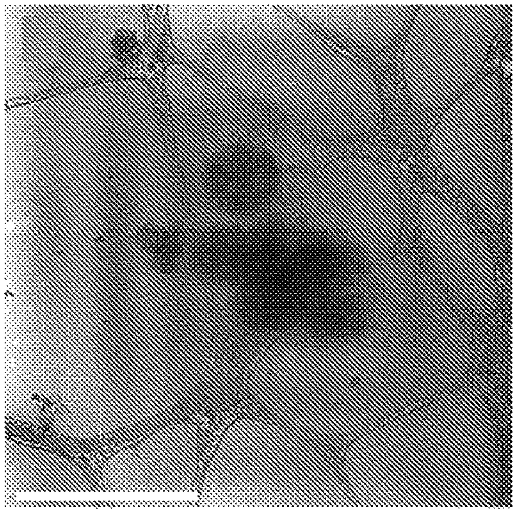

FIGS. 52A-52B. Cryogenic TEM micrographs of SPM. FIG. 52A. 5% Loaded SPM. FIG. 52B. 25% Loaded SPM. All scale bars 1 micron.

Figure 53A:
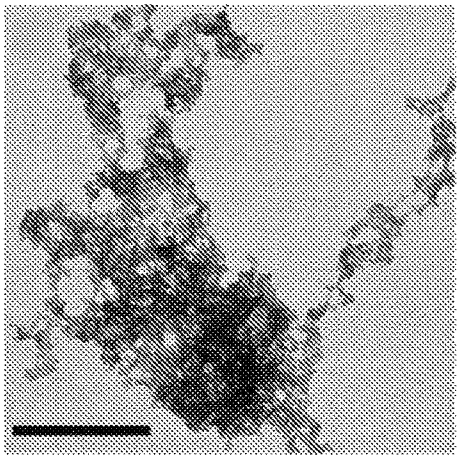
Figure 53B:
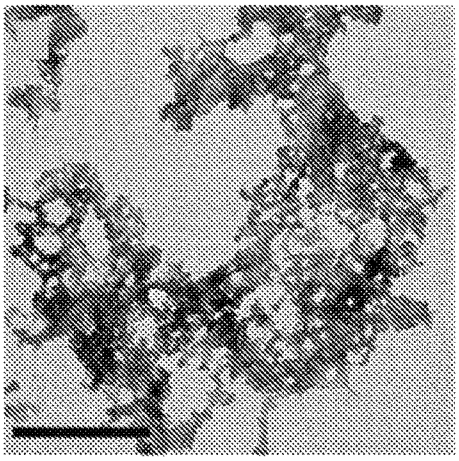
Figure 53C:
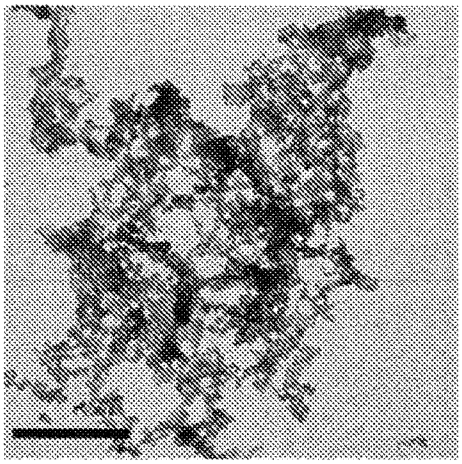
Figure 53D:
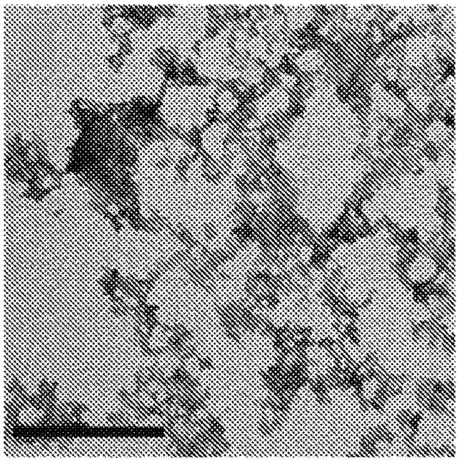
Figure 53E:
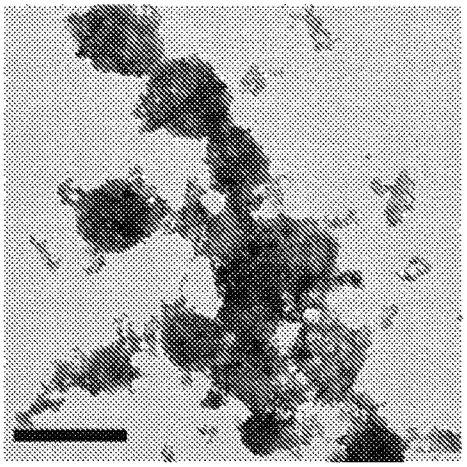
Figure 53F:
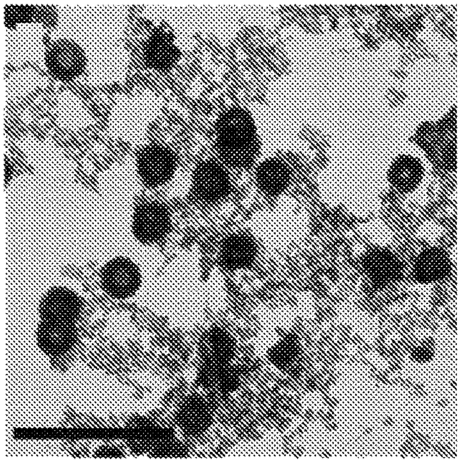

FIGS. 53A-53F. TEM micrographs of 5% Loaded SPM with different ratios of dopamine to mesoporous silica in milligrams. FIG. 53A. 5:10 FIG. 53B. 6:10 FIG. 53C. 7:10 FIG. 53D. 8:10 FIG. 53E. 9:10 FIG. 53F. 10:10. All scale bars 1 micron. Dopamine was polymerized on mesoporous silica for four hours.

Figure 54A:
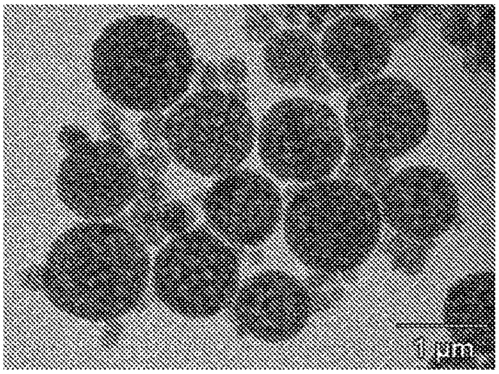
Figure 54B:
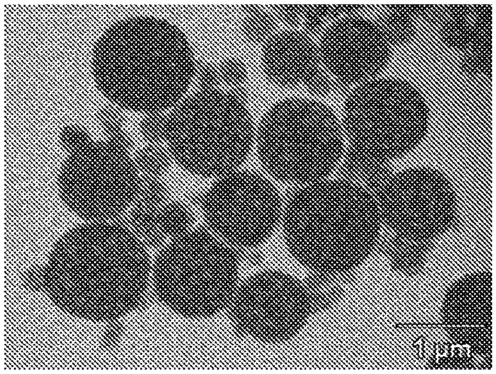
Figure 54C:
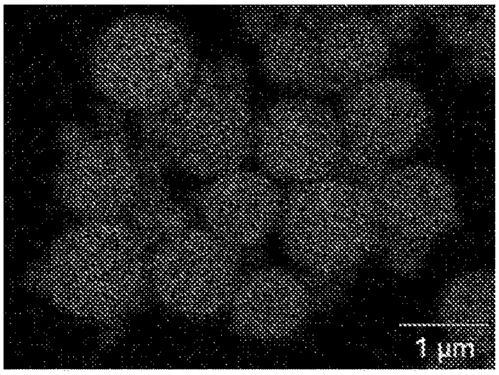
Figure 54D:
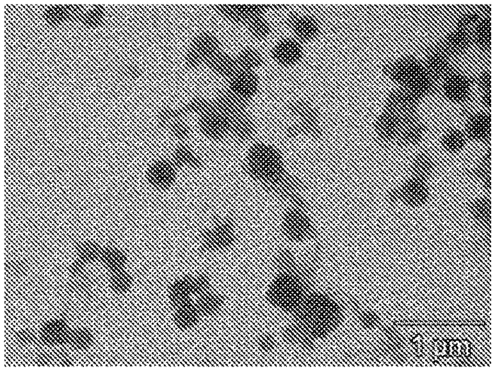
Figure 54E:
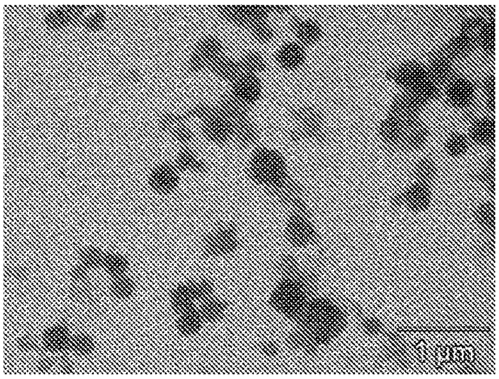
Figure 54F:

FIGS. 54A-54F. Energy-dispersive X-ray spectroscopy (EDS) of 5% Loaded SPM. FIG. 54A. TEM of mesoporous silica coated with dopamine (SPM before etching). FIG. 54B. EDS of silica overlay of SPM before etching. FIG. 54C. EDS of silica of SPM before etching. FIG. 54D. TEM of SPM. FIG. 54E. EDS of silica overlay of SPM. FIG. 54F. EDS of silica of SPM.

Figure 55A:
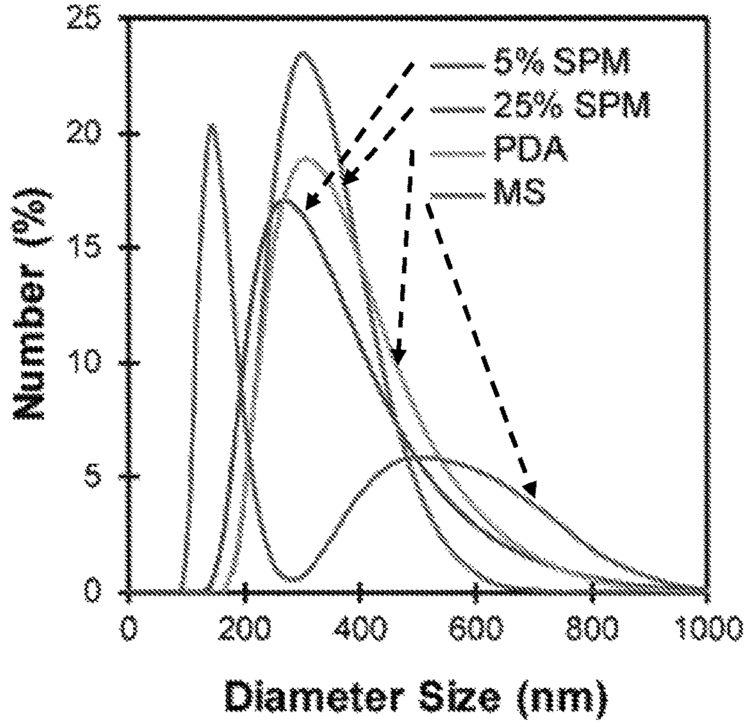
Figure 55B:
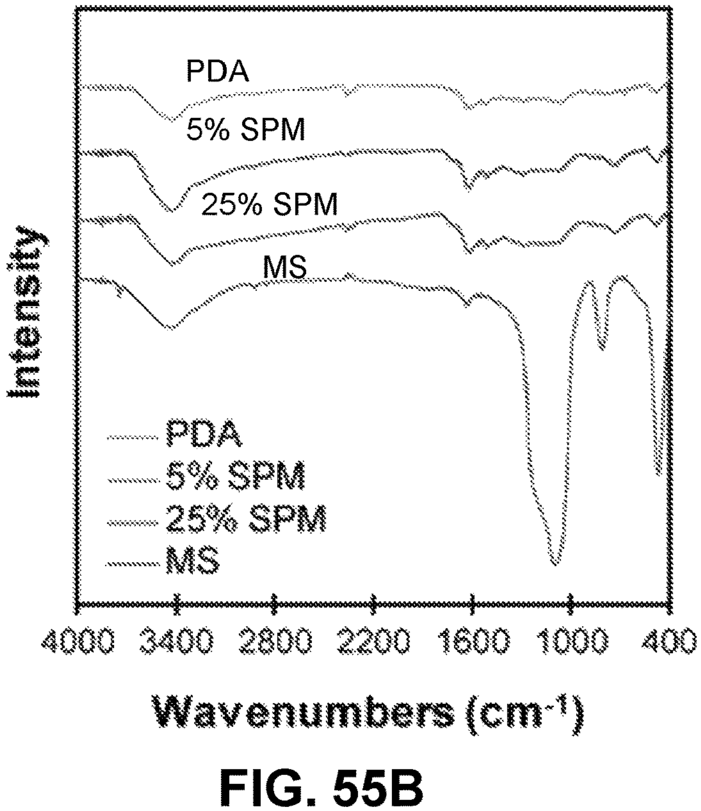
Figure 55C:
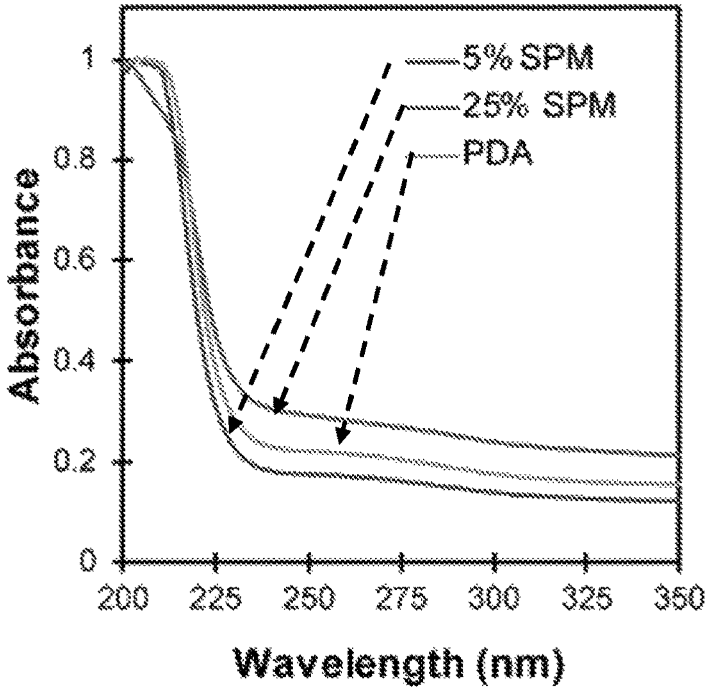
Figure 55D:
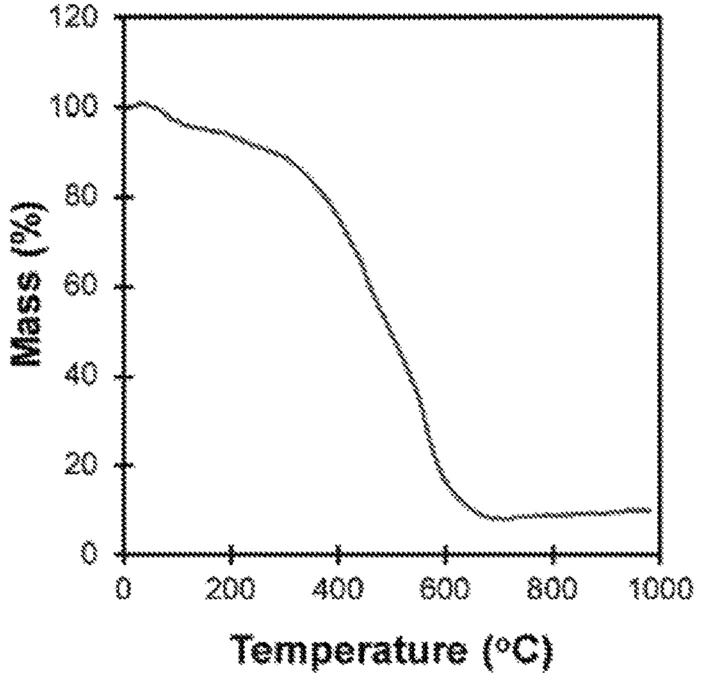

FIGS. 55A-55D. Characterization of 5% Loaded SPM (blue), 25% Loaded SPM (red), PDA (green), and MS (purple). FIG. 55A. Dynamic light scattering. FIG. 55B. Fourier-transform infrared spectroscopy. FIG. 55C. Ultraviolet visible spectroscopy. FIG. 55D. Thermogravimetric analysis.

Figure 56A:
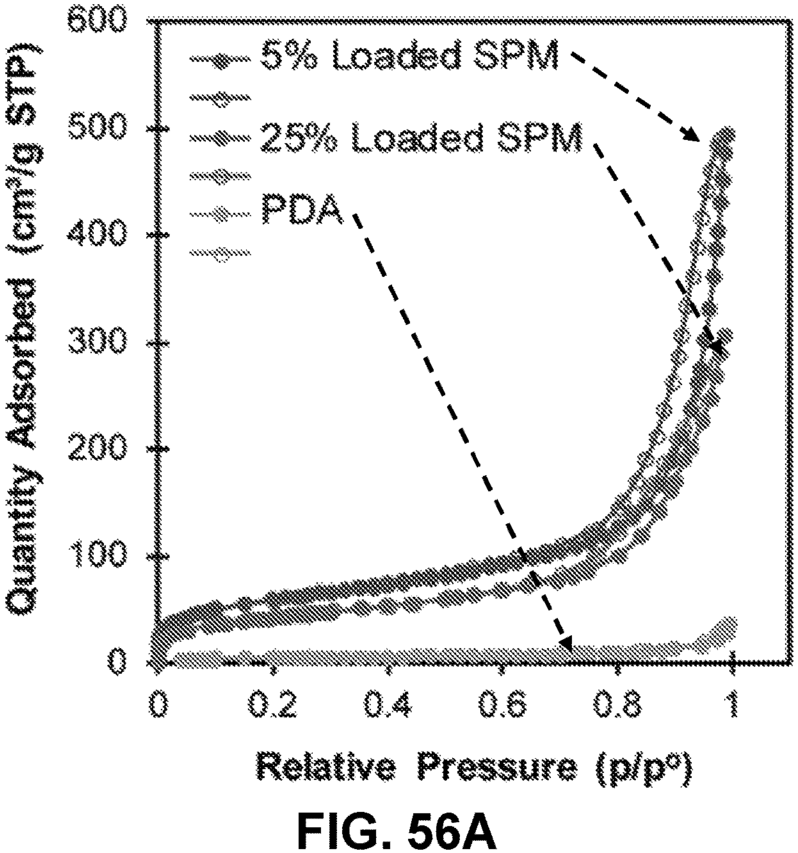
Figure 56B:
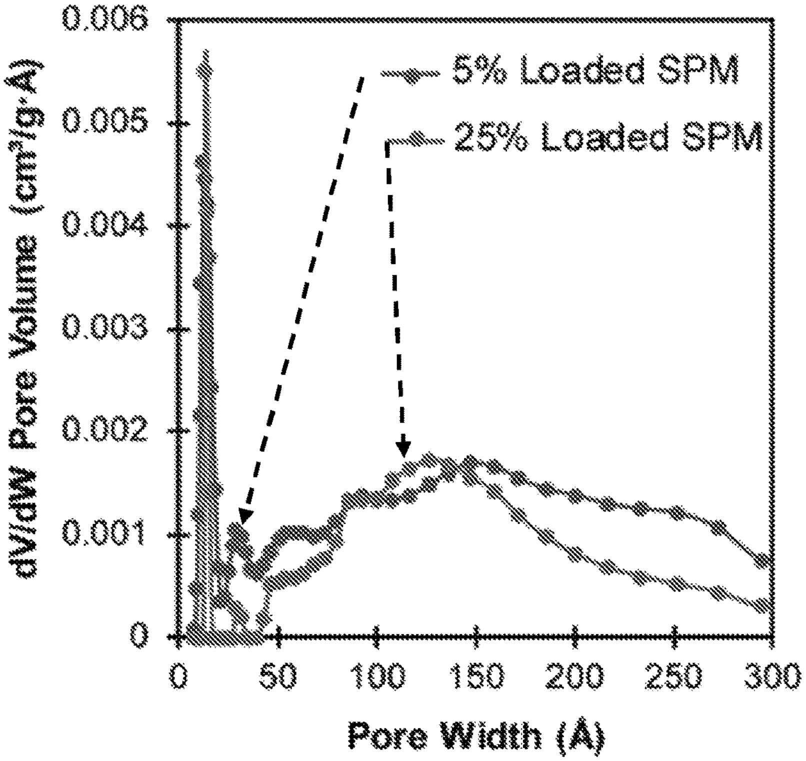

FIGS. 56A-56B. $N_2$ sorption characterization. FIG. 56A. Nitrogen adsorption (solid) and desorption (open) of 5% Loaded SPM (blue), 25% SPM (red), and PDA (green). FIG. 56B. Pore size distribution of 5% (blue) and 25% (red) Loaded SPM determined using DFT.

STATEMENTS REGARDING CHEMICAL COMPOUNDS AND NOMENCLATURE

In general, the terms and phrases used herein have their art-recognized meaning, which can be found by reference to standard texts, journal references and contexts known to those skilled in the art. The following definitions are provided to clarify their specific use in the context of the invention.

The term "melanin" generally refers to one or more compounds or materials that function as a pigment, such as when internalized or taken up by a biological cell, for example. It is also noted that melanin is not necessarily taken up by cells. Melanin can be used for forming cell walls in fungi, for example, such as to provide rigidity, defense mechanisms, and more. In another illustrative example, melanin is used by birds, such as where melanin is organized in a matrix of keratin or similar type of biological material, where it can be organized into monolayers or multilayers to provide structural color, warmth, and more. A melanin compound or material may be, but is not limited to, a melanin monomer, a melanin oligomer, a melanin polymer, or a melanin nanoparticle, for example. For example, melanin nanoparticles internalized by a biological cell function as a pigment in the cell.

The term "artificial melanin" or "synthetic melanin" may refer to one or more melanin compounds or materials, such as melanin monomers, melanin oligomers, or melanin nanoparticles, that are synthesized and are at least partially, or optionally entirely, not derived from or not extracted from a natural source, such as from a biological source or from a living organism. The terms "synthetic melanin nanoparticles" and "artificial melanin nanoparticles" are used interchangeably herein, and are intended to have the same meaning throughout the present disclosure, refer to nanoparticles formed of artificial melanin, such as artificial melanin monomers and/or artificial melanin oligomers. Artificial melanin nanoparticles comprise artificial melanin monomers and/or artificial melanin oligomers. Optionally, in some embodiments, artificial melanin nanoparticles consist of or consist essentially of artificial melanin, such as artificial melanin monomers and/or artificial melanin oligomers. Optionally, artificial melanin nanoparticles, or artificial melanin compounds thereof, are not bound to, conjugated to, attached to, coated by, encompassed by or otherwise associated with a natural or biological proteinaceous lipid. A natural or biological proteinaceous lipid refers to a naturally or biologically derived lipid or a lipid extracted from a natural or biological source, such as a once living organism, said lipid comprising one or more proteins such as the lipid (plasma) membrane of a melanocyte or melanosome). Optionally, artificial melanin nanoparticles, or artificial melanin compounds thereof, are not bound to, conjugated to, attached to, coated by, encompassed by or otherwise associated with a natural or biological lipid (e.g. a lipid bilayer, lipid membrane or phospholipid compound). A natural or biological lipid refers to a naturally or biologically derived lipid or a lipid extracted from a natural or biological source, such as a once living organism. Optionally, artificial melanin nanoparticles, or artificial melanin compounds thereof, are bound to, conjugated to, attached to, coated by, encompassed by, and/or otherwise associated with a synthetic or artificial lipid or with a synthetic or artificial phospholipid. A synthetic or artificial lipid refers to a synthesized lipid that is not derived from or is not extracted from a natural or biological source, such as a once living organism.

The term "aging", when used in reference to artificial melanin nanoparticles herein, refers to a process by which synthesized and isolated artificial melanin nanoparticles oxidize, and optionally further darker, over time during exposure to oxygen, such due to exposure to air. Isolated artificial melanin nanoparticles can be artificial melanin nanoparticles that are purified, such as by centrifugation, and re-dispersed in water, such as ultrapure water, or optionally another solvent or solvent solution. For example, artificial melanin nanoparticles may age if the particles are dispersed in water and are stored in a vial with the vial's top on (closed) and with the top not being opened for some extended period of time, because there is residual oxygen in the container. The aging process can alter certain properties or characteristics of artificial melanin nanoparticles, such as increasing solubility in organic solvent or decreasing toxicity to certain living biological cells. For example, without wishing to be bound by any particular theory, in some embodiments, freshly synthesized artificial melanin nanoparticles can be dynamic and shed monomers or oligomers into a cell when internalized by the cell. For example, without wishing to be bound by any particular theory, in some embodiments, freshly synthesized artificial melanin nanoparticles can be dynamic and have surface chemistry oxidation state that is not optimal for living cells when internalized by cells. For example, without wishing to be bound by any particular theory, in some embodiments, the aging process can lead to more crosslinking or otherwise chemical association between melanin compounds (monomers, oligomers) in the artificial melanin nanoparticles, potentially leading to reduced cytotoxicity, such as due to reduced shedding of melanin compounds into the cell and/or altering or stabilizing of the particles' surface chemistry.

The term "polydispersity" or "dispersity" refers to a measure of heterogeneity of sizes particles. For example, polydispersity can be used to characterize a width of a particle size distribution (e.g., particle size vs. count or frequency), such as a particle size distribution of artificial melanin nanoparticles. For example, polydispersity may characterize heterogeneity of sizes of artificial melanin nanoparticles, such as artificial melanin nanoparticles in a solvent or artificial melanin nanoparticles in a dry state, such as those forming a film or layer. A "polydispersity index" is a measure of polydispersity. A polydispersity index can be measured using Dynamic Light Scattering (DLS), for example. Particles characterized by a polydispersity index of less than 0.1 are typically referred to as "monodisperse". For example, a polydispersity index (PDI) can be calculated as the square of the standard deviation of the particle size distribution divided by its mean:

$$I=\left(\frac{\sigma}{d}\right)^2,$$

where σ is standard deviation of the particle size distribution and d is the mean diameter of the particle size distribution. Polydispersity and polydispersity index, as well as techniques for determining these, are further described in "NanoComposix's Guide to Dynamic Light Scattering Measurement and Analysis" [dated February 2015 (version 1.4), published by nanoComposix of San Diego, CA, and available at nanoComposix_Guidelines_for_DLS_Measurements_and_Analysis (last accessed Jun. 26, 2019)], which is incorporated herein by reference. The polydispersity index can also be calculated from electron microscope (SEM and/or TEM) images where the diameter is measured using software such as ImageJ, followed by calculating a mean size of the distribution, and then using the aforementioned equation to calculate the polydispersity index.

The term "nanoparticle" as used herein, refers to a physical particle whose longest size characteristic or physical dimension is less than 1 μm.

The term "size characteristic" refers to a property, or set of properties, of a particle that directly or indirectly relates to a size attribute. According to some embodiments, a size characteristic corresponds to an empirically-derived size characteristic of a particle(s) being detected, such as a size characteristic based on, determined by, or corresponding to data from any technique or instrument that may be used to determine a particle size, such as electron microscope (e.g., SEM and TEM) or a light scattering technique (e.g., DLS). For example, a size characteristic can correspond to a spherical particle exhibiting similar or substantially same properties, such as aerodynamic, hydrodynamic, optical, and/or electrical properties, as the particle(s) being detected). According to some embodiments, a size characteristic corresponds to a physical dimension, such as a cross-sectional size (e.g., length, width, thickness, or diameter).

The term "particles" refers to small solid objects that may be dispersed and/or suspended in a fluid (e.g., liquid). For example, a slurry, a dispersion, and a suspension each include particles in a fluid. For example, a slurry includes particles dispersed and/or suspended therein. The terms "particle" and "particulate" may be used interchangeably. An exemplary particle is an artificial melanin nanoparticle. A plurality of particles may be associated together to form an agglomerate of particles. Generally, the term "particle", such as "nanoparticle" or "melanin nanoparticle", refers to an individual particle rather than to an agglomerate of such individual particles.

The term "sphericity" may be used to describe a given particle and refers to a ratio of surface area of a sphere (having the same volume as the given particle) to the surface area of the particle. An ideal sphere has a sphericity of 1. For example, an ideal cylinder has a sphericity of approximately 0.874.

The terms "collapsed ellipsoid" optionally refers a structure resembling an ellipsoid that has partially collapsed or imploded, such as a deflated balloon, for example. A collapsed ellipsoid may resemble an ellipsoid having indentations therein. A sphere is an exemplary ellipsoid. A collapsed sphere may resemble, but is not limited to, structures described in Vliegenthart, et al. (G A Vliegenthart and G Gompper, 2011 New J. Phys. 13 045020, DOI 10.1088/1367-2630/13/4/045020). Some walnut-like structures resemble collapsed ellipsoids or ellipsoids having indentations.

The term "dispersed" in regard to solid particles in a fluid refers to a dispersion, or a microscopically homogenous, or uniform, mixture of solid particles in a fluid. A dispersion may be thermodynamically favored remain stably dispersed, or a dispersion may be thermodynamically favored to segregate by sedimentation but wherein sedimentation is kinetically slowed or prevented. Generally, a dispersion is a microscopically homogenous mixture having solid particles therein. One example of a dispersion is a colloid. Particles stably dispersed remain dispersed and do not sediment or precipitate out of the solution for at least 5 hours, optionally at least 12 hours, optionally at least 24 hours, and optionally at least 1 week, under normal temperature and pressure and exposure to air. Particles that are not or cannot be dispersed in a fluid refer to particles that form precipitates or sediments upon being mixed in the fluid.

The term "structural color" refers to the generation of color due to interference of visible light structural features, such as a film or layer or a microstructured surface. A layer of melanin nanoparticles may exhibit color due to interference of visible light with the microstructure of the layer, rather than solely due to pigmentation. Without wishing to be bound by any particular theory, the effect of structural color can enable a spectrum on non-fading, non-photobleaching colors which can be iridescent or non-iridescent. Without wishing to be bound by any particular theory, high refractive index of melanin and synthetic melanin, and its broadband absorption across the visible spectrum allows it to interact with light in such a way that a multitude of colors are produced.

The term "peak size" size refers to the statistical mode, or peak frequency, of a particle size distribution, or the particle size most commonly found in the particle size distribution. A particle size distribution can be measured using dynamic light scattering, for example.

The term "sphere" as used herein, in the usual and customary sense, refers to a round or substantially round geometrical object in three-dimensional space that is substantially the surface of a completely round ball, analogous to a circular object in two dimensions. A sphere may be defined mathematically as the set of points that are all at the same or substantially all at the same distance r from a given point, but in three-dimensional space, where r is the radius of the mathematical ball and the given point is the center or substantially the center of the mathematical ball. In embodiments, the longest straight line through the ball, connecting two points of the sphere, passes through the center and its length is thus twice the radius; it is a diameter of the ball. A nanosphere is a nanoparticle having a radius of less than 1 μm.

The terms "ultraviolet induced damage" and "UV induced damage" as used interchangeably herein refer, in the usual and customary sense, to chemical changes attending irradiation of light of sufficient energy. UV induced damage can include scission of nucleic acids (e.g., DNA or RNA), and breaking of bonds in proteins, lipids, and other physiological molecules. For example, the damage can be damage resulting from reactive oxygen species (ROS).

The terms "reactive oxygen species" and "ROS" as used interchangeably herein refer, in the usual and customary sense, to transient species, typically formed during exposure to radiation (e.g., UV irradiation) capable of inducing oxidative decomposition.

The terms "cell" and "biological cell" are used interchangeably are refer to a cell carrying out metabolic or other function sufficient to preserve or replicate its genomic DNA. A cell can be identified by well-known methods in the art including, for example, presence of an intact membrane, staining by a particular dye, ability to produce progeny or, in the case of a gamete, ability to combine with a second gamete to produce a viable offspring. Cells may include prokaryotic and eukaryotic cells. Prokaryotic cells include but are not limited to bacteria. Eukaryotic cells include but are not limited to yeast cells and cells derived from plants and animals, for example mammalian, insect (e.g., spodoptera) and human cells. A "viable cell" is a living biological cell.

The term "self-assembly" refers to a process in which individual elements assemble into a network or organized structure without external direction. In an embodiment, self-assembly leads to a decrease in entropy of a system. In an embodiment, self-assembly may be induced, or initiated, via contacting or reacting the individual elements, optionally at a certain critical concentration, and/or via temperature and/or via pressure. A "self-assembled structure" is a structure or network formed by self-assembly. In an embodiment, self-assembly is a polymer crystallization process. The Gibbs free energy of the self-assembled structure is lower than of the sum of the individual components in their non-organized arrangement prior to self-assembly under otherwise identical conditions (e.g., temperature and pressure). In an embodiment, entropy of a self-assembled structure is lower than that of the sum of the individual components in their non-organized arrangement prior to self-assembly under otherwise identical conditions (e.g., temperature and pressure). For example, artificial melanin nanoparticles of this disclosure can form by self-assembly of a plurality of oligomers and/or melanin monomers. For example, structures or layers (e.g., films) for artificial melanin nanoparticles may form by self-assembly, such as structures or layers formed of artificial melanin nanoparticles and exhibiting structural color.

The term "substantially" refers to a property, condition, or value that is within 20%, 10%, within 5%, within 1%, optionally within 0.1%, or is equivalent to a reference property, condition, or value. The term "substantially equal", "substantially equivalent", or "substantially unchanged", when used in conjunction with a reference value describing a property or condition, refers to a value that is within 20%, within 10%, optionally within 5%, optionally within 1%, optionally within 0.1%, or optionally is equivalent to the provided reference value. For example, a diameter is substantially equal to 100 nm (or, "is substantially 100 nm") if the value of the diameter is within 20%, optionally within 10%, optionally within 5%, optionally within 1%, within 0.1%, or optionally equal to 100 nm. The term "substantially greater", when used in conjunction with a reference value describing a property or condition, refers to a value that is at least 1%, optionally at least 5%, optionally at least 10%, or optionally at least 20% greater than the provided reference value. The term “substantially less”, when used in conjunction with a reference value describing a property or condition, refers to a value that is at least 1%, optionally at least 5%, optionally at least 10%, or optionally at least 20% less than the provided reference value.

The terms “keratinocyte” and “keratinocytes” as used herein, refer to the predominant cell type in the epidermis, the outermost layer of the skin, constituting the majority (e.g., 90%-95%) of the cells found there. Keratinocytes are found in the deepest basal layer of the stratified epithelium that comprises the epidermis, and are sometimes referred to as basal cells or basal keratinocytes. Keratinocytes are maintained at various stages of differentiation in the epidermis and are responsible for forming tight junctions with the nerves of the skin. They also keep Langerhans cells of the epidermis and lymphocytes of the dermis in place. Keratinocytes contribute to protecting the body from UV radiation by taking up melanosomes. Keratinocytes contribute to protecting the body from UV radiation by taking up melanosomes, vesicles containing the endogenous photoprotectant melanin, from epidermal melanocytes. Each melanocyte in the epidermis has several dendrites that stretch out to connect it with many keratinocytes. The melanin is then stored within keratinocytes and melanocytes in the perinuclear area as “supranuclear caps”, where it protects the DNA from UV-induced damage. In addition to their structural role, keratinocytes play a role in immune system function. The skin is the first line of defense and keratinocytes serve as a barrier between an organism and its environment. In addition to preventing toxins and pathogens from entering an organisms body, they prevent the loss of moisture, heat and other important constituents of the body. In addition to their physical role, keratinocytes serve a chemical immune role as immunomodulaters, responsible for secreting inhibitory cytokines in the absence of injury and stimulating inflammation and activating Langerhans cells in response to injury. Langerhans cells serve as antigen-presenting cells when there is a skin infection and are the first cells to process microbial antigens entering the body from a skin breach.

The terms “under conditions suitable to afford uptake”, “taken up” and “take up” as used herein, refer, in the usual and customary sense, to experimental conditions well known in the art which allow uptake (e.g., endocytosis) of a species into a cell. In some embodiments, the term “internalized” when referring to particles internalized in or by a biological cell, refers to particles taken up by the biological cell, such as by, but not limited to, formation of perinuclear caps.

The term “endocytosis” as used herein, refers to a form of active transport in which a cell transports molecules (such as proteins) into the cell by engulfing them in an energy-using process. Endocytosis includes pinocytosis and phagocytosis. Pinocytosis is a mode of endocytosis in which small particles are brought into the cell, forming an invagination, and then suspended within small vesicles. These pinocytotic vesicles subsequently fuse with lysosomes to hydrolyze (break down) the particles. Phagocytosis is the process by which a cell engulfs a solid particle to form an internal compartment known as a phagosome.

The terms “treating” or “treatment” as used herein, refers to any indicia of success in the treatment or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient’s physical or mental well-being. The treatment or amelioration of symptoms can be based on objective or subjective parameters; including the results of a physical examination, neuropsychiatric exams, and/or a psychiatric evaluation. The term “treating,” and conjugations thereof, include prevention of an injury, pathology, condition, or disease.

The term “effective amount” as used herein, refers to an amount sufficient to accomplish a stated purpose (e.g. Achieve the effect for which it is administered, treat a disease, reduce one or more symptoms of a disease or condition, and the like). An example of an “effective amount” is an amount sufficient to contribute to the treatment, prevention, or reduction of a symptom or symptoms of a disease, which could also be referred to as a “therapeutically effective amount.” A “reduction” of a symptom or symptoms (and grammatical equivalents of this phrase) means decreasing of the severity or frequency of the symptom(s), or elimination of the symptom(s). A “prophylactically effective amount” of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. The exact amounts will depend on the purpose of the treatment, and will be ascertainable by one skilled in the art using known techniques (see, e.g., Lieberman, Pharmaceutical Dosage Forms (vols. 1-3, 1992); Lloyd, The Art, Science and Technology of Pharmaceutical Compounding (1999); Pickar, Dosage Calculations (1999); and Remington: The Science and Practice of Pharmacy, 20th Edition, 2003, Gennaro, Ed., Lippincott, Williams & Wilkins).

The term “administering” as used herein, refers to oral administration, administration as an inhaled aerosol or as an inhaled dry powder, suppository, topical contact, intravenous, parenteral, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. By “co-administer” it is meant that a composition described herein is administered at the same time, just prior to, or just after the administration of one or more additional therapies, for example cancer therapies such as chemotherapy, hormonal therapy, radiotherapy, or immunotherapy. The compound of the invention can be administered alone or can be co-administered to the patient. Co-administration is meant to include simultaneous or sequential administration of the compound individually or in combination (more than one compound or agent). The compositions of the present invention can be delivered transdermally, by a topical route, formulated as applicator sticks, solutions, suspensions, emulsions, gels, creams, ointments, pastes, jellies, paints, powders, and aerosols. Oral preparations include tablets, pills, powder, dragees, capsules, liquids, lozenges, cachets, gels, syrups, slurries, suspensions, etc., suitable for ingestion by the patient. Solid form preparations include powders, tablets, pills, capsules, cachets, suppositories, and dispersible granules. Liquid form preparations include solutions, suspensions, and emulsions, for example, water or water/propylene glycol solutions. The compositions of the present invention may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes. The compositions of the present invention can also be delivered as microspheres for slow release in the body. For example, microspheres can be administered via intradermal injection of drug-containing microspheres, which slowly release subcutaneously (see Rao, J Biomater Sci. Polym. Ed. 7:623-645, 1995; as biodegradable and injectable gel formulations (see, e.g., Gao Pharm. Res. 12:857-863, 1995); or, as microspheres for oral administration (see, e.g., Eyles, J Pharm. Pharmacol. 49:669-674, 1997). In another embodiment, the formulations of the compositions of the present invention can be delivered by the use of liposomes which fuse with the cellular membrane or are endocytosed, i.e., by employing receptor ligands attached to the liposome, that bind to surface membrane protein receptors of the cell resulting in endocytosis. By using liposomes, particularly where the liposome surface carries receptor ligands specific for target cells, or are otherwise preferentially directed to a specific organ, one can focus the delivery of the compositions of the present invention into the target cells in vivo. (See, e.g., Al-Muhammed, J. Microencapsul. 13:293306, 1996; Chonn, Curr. Opin. Biotechnol. 6:698-708, 1995; Qstio, Am. J Hasp. Pharm. 46: 1576-1587, 1989).

The term “contacting” may include allowing two species to react, interact, or physically touch, wherein the two species may be, for example, a pharmaceutical composition as provided herein and a cell. In embodiments contacting includes, for example, allowing a pharmaceutical composition as described herein to interact with a cell or a patient.

The terms “analog” and “analogue” are used interchangeably and are used in accordance with their plain ordinary meaning within Chemistry and Biology and refers to a chemical compound that is structurally similar to another compound (i.e., a so-called “reference” compound) but differs in composition, e.g., in the replacement of one atom by an atom of a different element, or in the presence of a particular functional group, or the replacement of one functional group by another functional group, or the absolute stereochemistry of one or more chiral centers of the reference compound, including isomers thereof. Accordingly, an analog is a compound that is similar or comparable in function and appearance but not in structure or origin to a reference compound.

Except where otherwise specified, the term “molecular weight” refers to an average molecular weight. Except where otherwise specified, the term “average molecular weight,” refers to number-average molecular weight. Number average molecular weight is defined as the total weight of a sample volume divided by the number of molecules within the sample. As is customary and well known in the art, peak average molecular weight and weight average molecular weight may also be used to characterize the molecular weight of the distribution of polymers within a sample.

The term “weight-average molecular weight” ($M_w$) refers to the average molecular weight defined as the sum of the products of the molecular weight of each polymer molecule ($M_i$) multiplied by its weight fraction ($w_i$): $M_w=\Sigma w_i M_i$. As is customary and well known in the art, peak average molecular weight and number average molecular weight may also be used to characterize the molecular weight of the distribution of polymers within a sample.

The term “oligomerization” refers to a chemical process of converting a monomer or a mixture of monomers into an oligomer. The term “oxidative oligomerization” refers to a chemical process of oligomerization that includes chemical oxidation of one or more monomers to form an oligomer.

As used herein, the term “polymer” refers to a molecule composed of repeating structural units connected by covalent chemical bonds often characterized by a substantial number of repeating units, also referred to as base units, (e.g., equal to or greater than 3 repeating units, optionally, in some embodiments equal to or greater than 10 repeating units, in some embodiments greater or equal to 30 repeating units) and a high molecular weight (e.g. greater than or equal to 10,000 Da, in some embodiments greater than or equal to 50,000 Da or greater than or equal to 100,000 Da). Polymers are commonly the polymerization product of one or more monomer precursors. The term polymer includes homopolymers, or polymers consisting essentially of a single repeating monomer subunit. The term polymer also includes copolymers which are formed when two or more different types of monomers are linked in the same polymer. Copolymers may comprise two or more monomer subunits, and include random, block, brush, brush block, alternating, segmented, grafted, tapered and other architectures. Useful polymers include organic polymers or inorganic polymers that may be in amorphous, semi-amorphous, crystalline or semi-crystalline states. Polymer side chains capable of cross linking polymers (e.g., physical cross linking) may be useful for some applications.

An “oligomer” refers to a molecule composed of repeating structural units, also referred to as base units, connected by covalent chemical bonds often characterized by a number of repeating units less than that of a polymer (e.g., equal to or less than 100 repeating units) and a lower molecular weights (e.g. less than or equal to 10,000 Da) than polymers. Oligomers may be the polymerization product of one or more monomer precursors. Polymerization of one or more monomers, or monomer precursors, resulting in formation of an oligomer may be referred to as oligomerization. An oligomer optionally includes 100 or less, 50 or less, 15 or less, 12 or less, 10 or less, or 5 or less repeating units (or, “base units”). An oligomer may be characterized has having a molecular weight of 10,000 Da or less, 5,000 Da or less, 1,000 Da or less, 500 Da or less, or 200 Da or less. A dimer, a trimer, a tetramer, or a pentamer is an oligomer having two, three, four, or five, respectively, repeating units, or base units.

The term “internal structure” refers to the internal geometry or internal configuration in a material (e.g., within the external boundaries (e.g., external surfaces) of the material). The term internal structure does not refer to structure on an atomic length scale of a material, such as the characterization of crystallographic structure. An internal structure comprising pores (e.g voids) can be characterized as a “porous internal structure.”

The term "porous", as used herein, refers to a material or structure within which pores are present, organized and/or arranged in the material. Thus, for instance, in a porous material, the pores are volumes within the body of the material where there is no material (e.g. voids). Pores in a material are not intended to include the space occupied by atoms, ions and/or molecules of a materials including monomers, oligomers and polymers, for example, of a melanin material. In some embodiments, porous materials and pores may be characterized by a "pore characteristic" including, but not limited to, a size characteristic, size distribution, spatial distribution (e.g., uniform or random), pore type, directionality and/or composition. In some embodiments a size characteristic is a geometrical parameter such as a size dimension or average size dimension, including one or more cross sectional dimensions (e.g., diameter, effective diameter thickness, cross sectional length or width, etc.) and/or one or more longitudinal dimensions (e.g. channel or cavity length, channel or cavity pathway, etc.). Additional pore characteristics including a pore-type, directionality, being a continuous through-pore, a pore distribution and any combinations of these. Geometrical parameters of a pore may be exemplary size characteristics, including average size characteristics of the pores of a material. In an embodiment, for example, a size dimension is one or more, optional all of, cross sectional dimensions or an average cross sectional dimension. In an embodiment, a material is characterized by a uniform spatial distribution or random spatial distribution of pores throughout the material, for example, in contrast to a hollow pore configuration having a central pore.

The term porosity refers to a characteristic of a porous material or structure. In some embodiments, porosity is a measure of the void (i.e. "empty") spaces, such as pores, in a material. Porosity may be expressed as the fraction of the volume of voids over the total volume, between 0 and 1, or as a percentage between 0% and 100%. "Pore volume per mass" refers to a characteristic of a porous material or porous structure corresponding to the ratio of the volume of pores (e.g., voids) to the mass of a material, for example, the ratio of the volume of pores in a sample of material to the mass of the sample. Pore volume per mass of material may be determined by a range of techniques known in the art including gas sorption measurements, Brunauer-Emmett-Teller (BET) surface measurements, optical measurements, gravimetric measurements, imbibition methods, thermoporosimetry methods and the like. The pores of a porous artificial melanin material may also be characterized by nitrogen isotherms, Brunauer-Emmett-Teller theory analysis, and Density Functional Theory analysis.

The invention provides compositions and related synthetic methods including different categories of porous melanin particles corresponding to different structurally properties such as pore size, pore type and spatial distribution of pores. In some embodiments, for example, the invention provides solid porous melanin particles, lacey porous melanin particles and hollow porous melanin particles, in each case the particles are porous wherein: (i) the lacey porous melanin particles have larger voids interspersed throughout, (ii) the hollow porous melanin particles have a single spherical void, for example, in the center and (iii) the solid porous melanin particles have a uniform distribution or random distribution of material throughout.

The following references provide description of pore types including cylindrical pores, channel-like pores, slit-shape pores and ink-bottle pores, for example, including pore types that are typically characterized by nitrogen isotherms: (i) Bardestani, R.; Patience, G. S.; Kaliaguine, S., Experimental methods in chemical engineering: specific surface area and pore size distribution measurements-BET, BJH, and DFT. The Canadian Journal of Chemical Engineering 2019, 97 (11), 2781-2791. DOI: 10.1002/cjce.23632; (ii) Sing, K. S. W.; Everett, D. H.; Haul, R. A. W.; Moscou, L.; Pierotti, R. A.; Rouquerol, J.; Siemieniewska, T., Reporting physisorption data for gas/solid systems with special reference to the determination of surface area and porosity. Pure Appl. Chem. 1985, 57 (4), 603-619. DOI: 10.1351/pac198557040603

"Microporous" refers to a material containing pores having at least one size dimension, such as a cross sectional dimension (e.g, effective diameter), less than 2 nm. "Mesoporous" refers to a material containing pores having at least one cross sectional dimension (e.g., effective diameter), greater than 2 nm and less than 50 nm.

As used herein, the term "group" may refer to a functional group of a chemical compound. Groups of the present compounds refer to an atom or a collection of atoms that are a part of the compound. Groups of the present invention may be attached to other atoms of the compound via one or more covalent bonds. Groups may also be characterized with respect to their valence state. The present invention includes groups characterized as monovalent, divalent, trivalent, etc. valence states.

As used herein, the term "substituted" refers to a compound wherein a hydrogen is replaced by another functional group, including, but not limited to: a halogen or halide, an alkyl, a cycloalkyl, an aryl, a heteroaryl, an acyl, an alkoxy, an alkenyl, an alkynyl, an alkylaryl, an arylene, a heteroarylene, an alkenylene, a cycloalkenylene, an alkynylene, a hydroxyl (—OH), a carbonyl (RCOR'), a sulfide (e.g., RSR'), a phosphate ($ROP(=O)(OH)_2$), an azo (RNNR'), a cyanate (ROCN), an amine (e.g., primary, secondary, or tertiary), an imine (RC(=NH)R'), a nitrile (RCN), a pyridinyl (or pyridyl), a diamine, a triamine, an azide, a diimine, a triimine, an amide, a diimide, or an ether (ROR'); where each of R and R' is independently a hydrogen or a substituted or unsubstituted alkyl group, aryl group, alkenyl group, or a combination of these. Optional substituent functional groups are also described below. In some embodiments, the term substituted refers to a compound wherein more than one hydrogen is replaced by another functional group, such as a halogen group.

As is customary and well known in the art, hydrogen atoms in formulas, such as in formula FX1, are not always explicitly shown, for example, hydrogen atoms bonded to the carbon atoms of aromatic, heteroaromatic, and alicyclic rings are not always explicitly shown. The structures provided herein, for example in the context of the description of formula (FX1) and schematics and structures in the drawings, are intended to convey to one of reasonable skill in the art the chemical composition of compounds of the methods and compositions of the invention, and as will be understood by one of skill in the art, the structures provided do not indicate the specific positions and/or orientations of atoms and the corresponding bond angles between atoms of these compounds.

As used herein, the terms "alkylene" and "alkylene group" are used synonymously and refer to a divalent group derived from an alkyl group as defined herein. The invention includes compounds having one or more alkylene groups. Alkylene groups in some compounds function as linking and/or spacer groups. Compounds of the invention may have substituted and/or unsubstituted $C_1$-$C_{20}$ alkylene, $C_1$-$C_{10}$ alkylene and $C_1$-$C_5$ alkylene groups, for example, as one or more linking groups (e.g. $L^1$-$L^6$).

As used herein, the terms "cycloalkenylene" and "cycloalkenylene group" are used synonymously and refer to a divalent group derived from a cycloalkenyl group as defined herein. The invention includes compounds having one or more cycloalkenylene groups. Cycloalkenylene groups in some compounds function as linking and/or spacer groups. Compounds of the invention may have substituted and/or unsubstituted $C_3$-$C_{20}$ cycloalkenylene, $C_3$-$C_{10}$ cycloalkenylene and $C_3$-$C_5$ cycloalkenylene groups, for example, as one or more linking groups (e.g. $L^1$-$L^6$).

As used herein, the terms "arylene" and "arylene group" are used synonymously and refer to a divalent group derived from an aryl group as defined herein. The invention includes compounds having one or more arylene groups. In some embodiments, an arylene is a divalent group derived from an aryl group by removal of hydrogen atoms from two intra-ring carbon atoms of an aromatic ring of the aryl group. Arylene groups in some compounds function as linking and/or spacer groups. Arylene groups in some compounds function as chromophore, fluorophore, aromatic antenna, dye and/or imaging groups. Compounds of the invention include substituted and/or unsubstituted $C_3$-$C_{30}$ arylene, $C_3$-$C_{20}$ arylene, $C_3$-$C_{10}$ arylene and $C_1$-$C_5$ arylene groups, for example, as one or more linking groups (e.g. $L^1$-$L^6$).

As used herein, the terms "heteroarylene" and "heteroarylene group" are used synonymously and refer to a divalent group derived from a heteroaryl group as defined herein. The invention includes compounds having one or more heteroarylene groups. In an embodiment, a heteroarylene is a divalent group derived from a heteroaryl group by removal of hydrogen atoms from two intra-ring carbon atoms or intra-ring nitrogen atoms of a heteroaromatic or aromatic ring of the heteroaryl group. Heteroarylene groups in some compounds function as linking and/or spacer groups. Heteroarylene groups in some compounds function as chromophore, aromatic antenna, fluorophore, dye and/or imaging groups. Compounds of the invention include substituted and/or unsubstituted $C_3$-$C_{30}$ heteroarylene, $C_3$-$C_{20}$ heteroarylene, $C_1$-$C_{10}$ heteroarylene and $C_3$-$C_5$ heteroarylene groups, for example, as one or more linking groups (e.g. $L^1$-$L^6$).

As used herein, the terms "alkenylene" and "alkenylene group" are used synonymously and refer to a divalent group derived from an alkenyl group as defined herein. The invention includes compounds having one or more alkenylene groups. Alkenylene groups in some compounds function as linking and/or spacer groups. Compounds of the invention include substituted and/or unsubstituted $C_2$-$C_{20}$ alkenylene, $C_2$-$C_{10}$ alkenylene and $C_2$-$C_5$ alkenylene groups, for example, as one or more linking groups (e.g. $L^1$-$L^6$).

As used herein, the terms "cylcoalkenylene" and "cylcoalkenylene group" are used synonymously and refer to a divalent group derived from a cylcoalkenyl group as defined herein. The invention includes compounds having one or more cylcoalkenylene groups. Cycloalkenylene groups in some compounds function as linking and/or spacer groups. Compounds of the invention include substituted and/or unsubstituted $C_3$-$C_{20}$ cylcoalkenylene, $C_3$-$C_{10}$ cylcoalkenylene and $C_3$-$C_5$ cylcoalkenylene groups, for example, as one or more linking groups (e.g. $L^1$-$L^6$).

As used herein, the terms "alkynylene" and "alkynylene group" are used synonymously and refer to a divalent group derived from an alkynyl group as defined herein. The invention includes compounds having one or more alkynylene groups. Alkynylene groups in some compounds function as linking and/or spacer groups. Compounds of the invention include substituted and/or unsubstituted $C_2$-$C_{20}$ alkynylene, $C_2$-$C_{10}$ alkynylene and $C_2$-$C_5$ alkynylene groups, for example, as one or more linking groups (e.g. $L^1$-$L^6$).

As used herein, the term "halo" refers to a halogen group such as a fluoro (—F), chloro (—Cl), bromo (—Br), iodo (—I) or astato (—At).

The term "heterocyclic" refers to ring structures containing at least one other kind of atom, in addition to carbon, in the ring. Examples of such heteroatoms include nitrogen, oxygen and sulfur. Heterocyclic rings include heterocyclic alicyclic rings and heterocyclic aromatic rings. Examples of heterocyclic rings include, but are not limited to, pyrrolidinyl, piperidyl, imidazolidinyl, tetrahydrofuryl, tetrahydrothienyl, furyl, thienyl, pyridyl, quinolyl, isoquinolyl, pyridazinyl, pyrazinyl, indolyl, imidazolyl, oxazolyl, thiazolyl, pyrazolyl, pyridinyl, benzoxadiazolyl, benzothiadiazolyl, triazolyl and tetrazolyl groups. Atoms of heterocyclic rings can be bonded to a wide range of other atoms and functional groups, for example, provided as substituents.

The term "carbocyclic" refers to ring structures containing only carbon atoms in the ring. Carbon atoms of carbocyclic rings can be bonded to a wide range of other atoms and functional groups, for example, provided as substituents.

The term "alicyclic ring" refers to a ring, or plurality of fused rings, that is not an aromatic ring. Alicyclic rings include both carbocyclic and heterocyclic rings.

The term "aromatic ring" refers to a ring, or a plurality of fused rings, that includes at least one aromatic ring group. The term aromatic ring includes aromatic rings comprising carbon, hydrogen and heteroatoms. Aromatic ring includes carbocyclic and heterocyclic aromatic rings. Aromatic rings are components of aryl groups.

The term "fused ring" or "fused ring structure" refers to a plurality of alicyclic and/or aromatic rings provided in a fused ring configuration, such as fused rings that share at least two intra ring carbon atoms and/or heteroatoms.

As used herein, the term "alkoxyalkyl" refers to a substituent of the formula alkyl-O-alkyl.

As used herein, the term "polyhydroxyalkyl" refers to a substituent having from 2 to 12 carbon atoms and from 2 to 5 hydroxyl groups, such as the 2,3-dihydroxypropyl, 2,3,4-trihydroxybutyl or 2,3,4,5-tetrahydroxypentyl residue.

As used herein, the term "polyalkoxyalkyl" refers to a substituent of the formula alkyl-(alkoxy)$_n$-alkoxy wherein n is an integer from 1 to 10, preferably 1 to 4, and more preferably for some embodiments 1 to 3.

Amino acids include glycine, alanine, valine, leucine, isoleucine, methionine, proline, phenylalanine, tryptophan, asparagine, glutamine, glycine, serine, threonine, serine, threonine, asparagine, glutamine, tyrosine, cysteine, lysine, arginine, histidine, aspartic acid and glutamic acid. As used herein, reference to "a side chain residue of a natural α-amino acid" specifically includes the side chains of the above-referenced amino acids. Peptides are comprised of two or more amino-acid connected via peptide bonds.

Alkyl groups include straight-chain, branched and cyclic alkyl groups. Alkyl groups include those having from 1 to 30 carbon atoms. Alkyl groups include small alkyl groups having 1 to 3 carbon atoms. Alkyl groups include medium length alkyl groups having from 4-10 carbon atoms. Alkyl groups include long alkyl groups having more than 10 carbon atoms, particularly those having 10-30 carbon atoms. The term cycloalkyl specifically refers to an alky group having a ring structure such as ring structure comprising 3-30 carbon atoms, optionally 3-20 carbon atoms and optionally 2-10 carbon atoms, including an alkyl group having one or more rings. Cycloalkyl groups include those having a 3-, 4-, 5-, 6-, 7-, 8-, 9- or 10-member carbon ring(s) and particularly those having a 3-, 4-, 5-, 6-, 7-, or 8-member ring(s). The carbon rings in cycloalkyl groups can also carry alkyl groups. Cycloalkyl groups can include bicyclic and tricycloalkyl groups. Alkyl groups are optionally substituted. Substituted alkyl groups include among others those which are substituted with aryl groups, which in turn can be optionally substituted. Specific alkyl groups include methyl, ethyl, n-propyl, iso-propyl, cyclopropyl, n-butyl, s-butyl, t-butyl, cyclobutyl, n-pentyl, branched-pentyl, cyclopentyl, n-hexyl, branched hexyl, and cyclohexyl groups, all of which are optionally substituted. Substituted alkyl groups include fully halogenated or semihalogenated alkyl groups, such as alkyl groups having one or more hydrogens replaced with one or more fluorine atoms, chlorine atoms, bromine atoms and/or iodine atoms. Substituted alkyl groups include fully fluorinated or semifluorinated alkyl groups, such as alkyl groups having one or more hydrogens replaced with one or more fluorine atoms. An alkoxy group is an alkyl group that has been modified by linkage to oxygen and can be represented by the formula R—O and can also be referred to as an alkyl ether group. Examples of alkoxy groups include, but are not limited to, methoxy, ethoxy, propoxy, butoxy and heptoxy. Alkoxy groups include substituted alkoxy groups wherein the alky portion of the groups is substituted as provided herein in connection with the description of alkyl groups. As used herein MeO— refers to $CH_3O$—. Compositions of some embodiments of the invention comprise alkyl groups as terminating groups, such as polymer backbone terminating groups and/or polymer side chain terminating groups. Substituted alkyl groups may include substitution to incorporate one or more silyl groups, for example wherein one or more carbons are replaced by Si.

Alkenyl groups include straight-chain, branched and cyclic alkenyl groups. Alkenyl groups include those having 1, 2 or more double bonds and those in which two or more of the double bonds are conjugated double bonds. Alkenyl groups include those having from 2 to 20 carbon atoms. Alkenyl groups include small alkenyl groups having 2 to 3 carbon atoms. Alkenyl groups include medium length alkenyl groups having from 4-10 carbon atoms. Alkenyl groups include long alkenyl groups having more than 10 carbon atoms, particularly those having 10-20 carbon atoms. Cycloalkenyl groups include those in which a double bond is in the ring or in an alkenyl group attached to a ring. The term cycloalkenyl specifically refers to an alkenyl group having a ring structure, including an alkenyl group having a 3-, 4-, 5-, 6-, 7-, 8-, 9- or 10-member carbon ring(s) and particularly those having a 3-, 4-, 5-, 6- or 7-member ring(s). The carbon rings in cycloalkenyl groups can also carry alkyl groups. Cycloalkenyl groups can include bicyclic and tricyclic alkenyl groups. Alkenyl groups are optionally substituted. Substituted alkenyl groups include among others those which are substituted with alkyl or aryl groups, which groups in turn can be optionally substituted. Specific alkenyl groups include ethenyl, prop-1-enyl, prop-2-enyl, cycloprop-1-enyl, but-1-enyl, but-2-enyl, cyclobut-1-enyl, cyclobut-2-enyl, pent-1-enyl, pent-2-enyl, branched pentenyl, cyclopent-1-enyl, hex-1-enyl, branched hexenyl, cyclohexenyl, all of which are optionally substituted. Substituted alkenyl groups include fully halogenated or semihalogenated alkenyl groups, such as alkenyl groups having one or more hydrogens replaced with one or more fluorine atoms, chlorine atoms, bromine atoms and/or iodine atoms. Substituted alkenyl groups include fully fluorinated or semifluorinated alkenyl groups, such as alkenyl groups having one or more hydrogen atoms replaced with one or more fluorine atoms. Compositions of some embodiments of the invention comprise alkenyl groups as terminating groups, such as polymer backbone terminating groups and/or polymer side chain terminating groups.

Aryl groups include groups having one or more 5-, 6-7-, or 8-member aromatic rings, including heterocyclic aromatic rings. The term heteroaryl specifically refers to aryl groups having at least one 5-, 6-7-, or 8-member heterocyclic aromatic rings. Aryl groups can contain one or more fused aromatic rings, including one or more fused heteroaromatic rings, and/or a combination of one or more aromatic rings and one or more nonaromatic rings that may be fused or linked via covalent bonds. Heterocyclic aromatic rings can include one or more N, O, or S atoms in the ring. Heterocyclic aromatic rings can include those with one, two or three N atoms, those with one or two O atoms, and those with one or two S atoms, or combinations of one or two or three N, O or S atoms. Aryl groups are optionally substituted. Substituted aryl groups include among others those that are substituted with alkyl or alkenyl groups, which groups in turn can be optionally substituted. Specific aryl groups include phenyl, biphenyl groups, pyrrolidinyl, imidazolidinyl, tetrahydrofuryl, tetrahydrothienyl, furyl, thienyl, pyridyl, quinolyl, isoquinolyl, pyridazinyl, pyrazinyl, indolyl, imidazolyl, oxazolyl, thiazolyl, pyrazolyl, pyridinyl, benzoxadiazolyl, benzothiadiazolyl, and naphthyl groups, all of which are optionally substituted. Substituted aryl groups include fully halogenated or semihalogenated aryl groups, such as aryl groups having one or more hydrogens replaced with one or more fluorine atoms, chlorine atoms, bromine atoms and/or iodine atoms. Substituted aryl groups include fully fluorinated or semifluorinated aryl groups, such as aryl groups having one or more hydrogens replaced with one or more fluorine atoms. Aryl groups include, but are not limited to, aromatic group-containing or heterocylic aromatic group-containing groups corresponding to any one of the following: benzene, naphthalene, naphthoquinone, diphenylmethane, fluorene, anthracene, anthraquinone, phenanthrene, tetracene, tetracenedione, pyridine, quinoline, isoquinoline, indoles, isoindole, pyrrole, imidazole, oxazole, thiazole, pyrazole, pyrazine, pyrimidine, purine, benzimidazole, furans, benzofuran, dibenzofuran, carbazole, acridine, acridone, phenanthridine, thiophene, benzothiophene, dibenzothiophene, xanthene, xanthone, flavone, coumarin, azulene or anthracycline. As used herein, a group corresponding to the groups listed above expressly includes an aromatic or heterocyclic aromatic group, including monovalent, divalent and polyvalent groups, of the aromatic and heterocyclic aromatic groups listed herein are provided in a covalently bonded configuration in the compounds of the invention at any suitable point of attachment. In embodiments, aryl groups contain between 5 and 30 carbon atoms. In embodiments, aryl groups contain one aromatic or heteroaromatic six-member ring and one or more additional five- or six-member aromatic or heteroaromatic ring. In embodiments, aryl groups contain between five and eighteen carbon atoms in the rings. Aryl groups optionally have one or more aromatic rings or heterocyclic aromatic rings having one or more electron donating groups, electron withdrawing groups and/or targeting ligands provided as substituents. Compositions of some embodiments of the invention comprise aryl groups as terminating groups, such as polymer backbone terminating groups and/or polymer side chain terminating groups.

Arylalkyl groups are alkyl groups substituted with one or more aryl groups wherein the alkyl groups optionally carry additional substituents and the aryl groups are optionally substituted. Specific alkylaryl groups are phenyl-substituted alkyl groups, e.g., phenylmethyl groups. Alkylaryl groups are alternatively described as aryl groups substituted with one or more alkyl groups wherein the alkyl groups optionally carry additional substituents and the aryl groups are optionally substituted. Specific alkylaryl groups are alkyl-substituted phenyl groups such as methylphenyl. Substituted arylalkyl groups include fully halogenated or semihalogenated arylalkyl groups, such as arylalkyl groups having one or more alkyl and/or aryl groups having one or more hydrogens replaced with one or more fluorine atoms, chlorine atoms, bromine atoms and/or iodine atoms. Compositions of some embodiments of the invention comprise arylalkyl groups as terminating groups, such as polymer backbone terminating groups and/or polymer side chain terminating groups.

As to any of the groups described herein which contain one or more substituents, it is understood that such groups do not contain any substitution or substitution patterns which are sterically impractical and/or synthetically non-feasible. In addition, the compounds of this invention include all stereochemical isomers arising from the substitution of these compounds. Optional substitution of alkyl groups includes substitution with one or more alkenyl groups, aryl groups or both, wherein the alkenyl groups or aryl groups are optionally substituted. Optional substitution of alkenyl groups includes substitution with one or more alkyl groups, aryl groups, or both, wherein the alkyl groups or aryl groups are optionally substituted. Optional substitution of aryl groups includes substitution of the aryl ring with one or more alkyl groups, alkenyl groups, or both, wherein the alkyl groups or alkenyl groups are optionally substituted.

Optional substituents for any alkyl, alkenyl and aryl group includes substitution with one or more of the following substituents, among others:

halogen, including fluorine, chlorine, bromine or iodine;

pseudohalides, including —CN;

—COOR where R is a hydrogen or an alkyl group or an aryl group and more specifically where R is a methyl, ethyl, propyl, butyl, or phenyl group all of which groups are optionally substituted;

—COR where R is a hydrogen or an alkyl group or an aryl group and more specifically where R is a methyl, ethyl, propyl, butyl, or phenyl group all of which groups are optionally substituted;

—$CON(R)_2$ where each R, independently of each other R, is a hydrogen or an alkyl group or an aryl group and more specifically where R is a methyl, ethyl, propyl, butyl, or phenyl group all of which groups are optionally substituted; and where R and R can form a ring which can contain one or more double bonds and can contain one or more additional carbon atoms;

—$OCON(R)_2$ where each R, independently of each other R, is a hydrogen or an alkyl group or an aryl group and more specifically where R is a methyl, ethyl, propyl, butyl, or phenyl group all of which groups are optionally substituted; and where R and R can form a ring which can contain one or more double bonds and can contain one or more additional carbon atoms;

—$N(R)_2$ where each R, independently of each other R, is a hydrogen, or an alkyl group, or an acyl group or an aryl group and more specifically where R is a methyl, ethyl, propyl, butyl, phenyl or acetyl group, all of which are optionally substituted; and where R and R can form a ring which can contain one or more double bonds and can contain one or more additional carbon atoms;

—SR, where R is hydrogen or an alkyl group or an aryl group and more specifically where R is hydrogen, methyl, ethyl, propyl, butyl, or a phenyl group, which are optionally substituted;

—$SO_2R$, or —SOR where R is an alkyl group or an aryl group and more specifically where R is a methyl, ethyl, propyl, butyl, or phenyl group, all of which are optionally substituted;

—OCOOR where R is an alkyl group or an aryl group;

—$SO_2N(R)_2$ where each R, independently of each other R, is a hydrogen, or an alkyl group, or an aryl group all of which are optionally substituted and wherein R and R can form a ring which can contain one or more double bonds and can contain one or more additional carbon atoms; and —OR where R is H, an alkyl group, an aryl group, or an acyl group all of which are optionally substituted. In a particular example R can be an acyl yielding —OCOR" where R" is a hydrogen or an alkyl group or an aryl group and more specifically where R" is methyl, ethyl, propyl, butyl, or phenyl groups all of which groups are optionally substituted.

Specific substituted alkyl groups include haloalkyl groups, particularly trihalomethyl groups and specifically trifluoromethyl groups. Specific substituted aryl groups include mono-, di-, tri, tetra- and pentahalo-substituted phenyl groups; mono-, di-, tri-, tetra-, penta-, hexa-, and hepta-halo-substituted naphthalene groups; 3- or 4-halo-substituted phenyl groups, 3- or 4-alkyl-substituted phenyl groups, 3- or 4-alkoxy-substituted phenyl groups, 3- or 4-RCO-substituted phenyl, 5- or 6-halo-substituted naphthalene groups. More specifically, substituted aryl groups include acetylphenyl groups, particularly 4-acetylphenyl groups; fluorophenyl groups, particularly 3-fluorophenyl and 4-fluorophenyl groups; chlorophenyl groups, particularly 3-chlorophenyl and 4-chlorophenyl groups; methylphenyl groups, particularly 4-methylphenyl groups; and methoxyphenyl groups, particularly 4-methoxyphenyl groups.

As to any of the above groups which contain one or more substituents, it is understood that such groups do not contain any substitution or substitution patterns which are sterically impractical and/or synthetically non-feasible.

Many of the molecules disclosed herein contain one or more ionizable groups. Ionizable groups include groups from which a proton can be removed (e.g., —COOH) or added (e.g., amines) and groups that can be quaternized (e.g., amines). All possible ionic forms of such molecules and salts thereof are intended to be included individually in the disclosure herein. With regard to salts of the compounds herein, one of ordinary skill in the art can select from among a wide variety of available counterions that are appropriate for preparation of salts of this invention for a given application. In specific applications, the selection of a given anion or cation for preparation of a salt can result in increased or decreased solubility of that salt.

The compounds of this invention can contain one or more chiral centers. Accordingly, this invention is intended to include racemic mixtures, diastereomers, enantiomers, tautomers and mixtures enriched in one or more stereoisomer. The scope of the invention as described and claimed encompasses the racemic forms of the compounds as well as the individual enantiomers and non-racemic mixtures thereof.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

Where substituent groups are specified by their conventional chemical formulae, written from left to right, they equally encompass the chemically identical substituents that would result from writing the structure from right to left, e.g., $—CH_2O—$ is equivalent to $—OCH_2—$.

In an embodiment, a composition or compound of the invention, such as an alloy or precursor to an alloy, is isolated or substantially purified. In an embodiment, an isolated or purified compound is at least partially isolated or substantially purified as would be understood in the art. In an embodiment, a substantially purified composition, compound or formulation of the invention has a chemical purity of 95%, optionally for some applications 99%, optionally for some applications 99.9%, optionally for some applications 99.99%, and optionally for some applications 99.999% pure.

DETAILED DESCRIPTION OF THE INVENTION

In the following description, numerous specific details of the devices, device components and methods of the present invention are set forth in order to provide a thorough explanation of the precise nature of the invention. It will be apparent, however, to those of skill in the art that the invention can be practiced without these specific details.

Synthetic mimics of allomelanin offer key properties found in natural sources, and can be manufactured reproducibly and with low cost materials. The facile one-pot synthesis in aqueous solution avoids the use of highly toxic reagents and allows for the production of scalable materials in an environmentally friendly manner.

Applications for the artificial melanin nanoparticles disclosed herein include, but are not limited to, radioprotection, antioxidant capability, skin pigmentations, a variety of medical and pharmaceutical applications, and structural color.

These methods provide a new synthesis of synthetic allomelanin, provide well-defined chemical composition, are scalable, provide uniform and ordered morphologies, provide size-tunability, and include a new method for producing structural color.

Dihydroxynaphthalene-based melanin (DHN-melanin) is one type of allomelanin most commonly found in fungi. Studies show that DHN-melanin can protect fungi from many types of environmental stresses, such as UV radiation, oxidizing agents, high salinity, and heavy metal exposure. Several interesting properties such as radioprotection and antioxidant capability allow DHN-melanin the potential for useful applications, however, extraction of DHN-melanin from natural sources can be problematic and time-consuming. Therefore, finding an efficient synthetic method is necessary. DHN-melanin can be synthesized using an enzymatic oxidation method according to previous reports. To the best of our knowledge, there are no reports using chemical methods to synthesize DHN-melanin.

In methods included herein, synthetic DHN-melanin is synthesized by oxidizing the monomer 1,8-dihydroxynaphthalene (1,8-DHN) using the chemical oxidizing agents $KMnO_4$ and $NaIO_4$. The resulting DHN-melanin product is a spherically structured particle on the order of the nanoscale. Several methods, including transmission electron microscopy (TEM), scanning electron microscopy (SEM), dynamic light scattering (DLS), Fourier transform infrared spectrometry (FTIR), UV-vis spectrometry, X-ray photoelectron spectroscopy (XPS), electrospray ionization mass spectrometry (ESI-MS) and solid-state NMR (ssNMR) are utilized to characterize the chemical composition and structure of these materials.

In addition to the novel chemical synthesis, DHN-melanin particles are internalized by neonatal human epidermal keratinocyte (NHEK) cells, which are the predominant cells of the epidermis. The particles are arranged around the nuclei of the cells, forming perinuclear caps, otherwise known as microparasols or supranuclear caps. The treated cells showed a lower ROS response as compared to vehicle treated control cells. We are currently examining the UV- and x-ray-protective capabilities of these materials in NHEK cells.

The invention can be further understood by the following non-limiting examples.

Example 1: Artificial Allomelanin Nanoparticles

Abstract: Allomelanin is a type of nitrogen-free melanin most commonly found in fungi. Its existence enhances resistance of the organisms to environmental damage and helps fungi survive harsh radiation conditions such as those found on spacecraft and inside contaminated nuclear power plants. We report the preparation and characterization of artificial allomelanin nanoparticles (AMNPs) via oxidative oligomerization of 1,8-dihydroxynaphthalene (1,8-DHN). We describe the resulting morphological and size control of AMNPs and demonstrate that they are radical scavengers. Finally, we show AMNPs are taken up by neonatal human epidermal keratinocytes and packaged into perinuclear caps where they quench reactive oxygen species generated following UV exposure.

Melanins are a group of natural pigments found in numerous organisms such as animals, plants and microorganisms.[1] They are best known for their role in human skin coloring, however they are also involved in various biological activities, such as sequestering metal ions,[2-4] quenching free radicals,[5-7] photoprotection[8-10] and neuroprotection.[11,12] On the basis of the structure, melanins can be classified into five types: eumelanin,[13] pheomelanin,[14] neuromelanin,[15] pyomelanin[16] and allomelanin.[17,18] In nature, eumelanin, pheomelanin and neuromelanin share chemical composition similarities originating from their formation from a 3,4-dihydroxyphenylalanine precursor. Most commonly, synthetic mimics of eumelanin have most commonly involved preparation of materials by oxidative polymerization of dopamine.[19-23] In last decade, polydopamine nanoparticles have rapidly expanded to many important applications, such as radiation protection,[24,25] surface coating,[26] biological imaging[27,28] and structural color.[29]

Allomelanin refers to a group of melanins that consist of nitrogen-free precursors such as catechol and 1,8-dihydroxynaphthalene (1,8-DHN). Typically, allomelanins found in fungi utilize 1,8-DHN as the precursor, thus referred to as DHN-melanin. In fungi, both eumelanin and DHN-melanin aid in survival in hostile environments[30,31] by acting as essential components of the cell wall by increasing its rigidity, hydrophobicity, negative charge and reducing porosity.[32,33] Furthermore, fungal melanins can protect these organisms from high doses of radiation, and in some cases gamma radiation has been shown to be beneficial to melanized fungi[34] with some species found in spacecraft and within the reactor at Chernobyl.[34-37] Given the myriad functions of natural melanins and the inherent complexity of their chemical nature, synthetic efforts to generate mimics of each type provide promising routes for structure and function analysis of melanins. In many organisms, and organ systems (e.g. in the human brain versus skin), mixtures of melanins with subtle variations in chemistry are found. Hence, in this paper, we describe reliable chemical synthetic routes to allomelanin as a first step, and describe how the resulting artificial allomelanin nanoparticles function as radiation protection agents in human skin cells via radical scavenging.

Despite the potential of allomelanin in biomedical applications where radiation resistance is desirable including as radiation protection agents used in tandem with gamma radiation treatments,[38] very little is known about the chemical structure. Some insight is now available given a recent study where synthetic DHN-melanin was prepared via a chemoenzymatic route.[39,40] These initial studies described dimers, trimers, and tetramers through C—C bond formation analyzed by liquid chromatography mass spectrometry (LCMS). For study in biological systems, and to explore radical scavenging ability, we utilized a strategy for formulating uniform allomelanin nanoparticles (AMNPs). Here, we describe synthetic routes via oxidative oligomerization of 1,8-DHN using the chemical oxidizing agents $KMnO_4$ or $NaIO_4$ to access 100-300 nm AMNPs. Notably, these AMNPs perform reversible redox activity and show similar free radical scavenging activity to ascorbic acid, a known antioxidant, with much higher activity than that of size-matched polydopamine-based synthetic melanin nanoparticles (PDA-NPs). The polydopamine-based synthetic melanin nanoparticles (PDA-NPs) are, for example, those disclosed in International Pat. Pub. No. WO 2018/013609 A2 (Gianneschi, et al., filed Jul. 11, 2017), which is incorporated herein by reference in its entirety to the extent not inconsistent herewith. Polydopamine-based synthetic melanin nanoparticles (PDA-NPs) also can be synthesized as described below (see "Synthesis of Polydopamine Nanoparticles (PDA-NPs)" below). In addition, we demonstrate that AMNPs are non-toxic, and can be internalized by neonatal human epidermal keratinocytes (NHEK) resulting in the formation of microparasols, the protective perinuclear caps found in melanized human keratinocytes.[24] Artificial, synthetic allomelanin-based microparasols protect NHEK cells upon UV irradiation as detected by a quenching effect of reactive oxygen species (ROS) in cell culture.

Results and Discussion

Synthesis and Characterization of DHN-based Allomelanin Nanoparticles (AMNPs). AMNPs were synthesized via oxidative oligomerization of 1,8-DHN in aqueous solution at room temperature. Two oxidizing agents, $NaIO_4$ and $KMnO_4$, were applied (FIG. 1).[19] Briefly, 1,8-DHN (1.0 mg/mL) was dissolved in a mixture of acetonitrile and ultrapure water, followed by injection of a 1 N $NaIO_4$ solution. The ultrapure water was exchanged for acetate buffer (0.1 M, pH=3.7) when using $KMnO_4$ as the oxidizing agent to ensure the oxidative capability of $KMnO_4$. As soon as the $NaIO_4$ or $KMnO_4$ solutions were injected under vigorous stirring, the colorless solution rapidly turned yellow, then gradually to dark grey. After 12 h, the resulting nanoparticles were purified through five centrifugation/redispersion processes in ultrapure water. Chemoenzymatic AMNPs were synthesized by laccase-mediated oxidation of 1,8-DHN.[39] AMNPs synthesized using $NaIO_4$, $KMnO_4$, and laccase were named AMNP-1, AMNP-2, and AMNP-3, respectively.

AMNPs were characterized by transmission electron microscopy (TEM) and scanning electron microscopy (SEM) (FIGS. 2A-2F). AMNP-1, synthesized using $NaIO_4$, resulted in monodisperse spheres with an average diameter of 140±10 nm calculated from TEM micrographs. The hydrodynamic diameter of AMNPs was measured using dynamic light scattering (DLS) (FIG. 17), showing a diameter of 194 nm with a polydispersity index of 0.08 for AMNP-1. AMNP-2, synthesized using $KMnO_4$, resulted in higher dispersity spherical nanostructures with diameters between 100 nm and 300 nm by TEM and 227 nm with a polydispersity index of 0.09 by DLS. TEM images reveal the poorly defined morphology of chemoenzymatically prepared AMNP-3 with DLS showing a similar range in sizes with a peak at 970 nm with a polydispersity index of 0.36. The zeta potentials for synthetic AMNPs show peaks at −31 mV, −33 mV and −27 mV for AMNP-1, AMNP-2, and AMNP-3, respectively, indicating high colloidal stability (FIG. 17).

In addition, by changing the molar ratio of $NaIO_4$ to 1,8-DHN monomer, AMNP-1 morphology was altered (FIGS. 3A-3H). TEM and SEM images show spherical or "walnut-like" structures when $NaIO_4$ to 1,8-DHN molar ratios were changed from 0.2 to 1.5. The sizes of each AMNP-1 in FIGS. 3A-3D were 128±11 nm, 139±10 nm, 140±15 nm and 105±13 nm, respectively, calculated from TEM micrographs.

Figure 4:
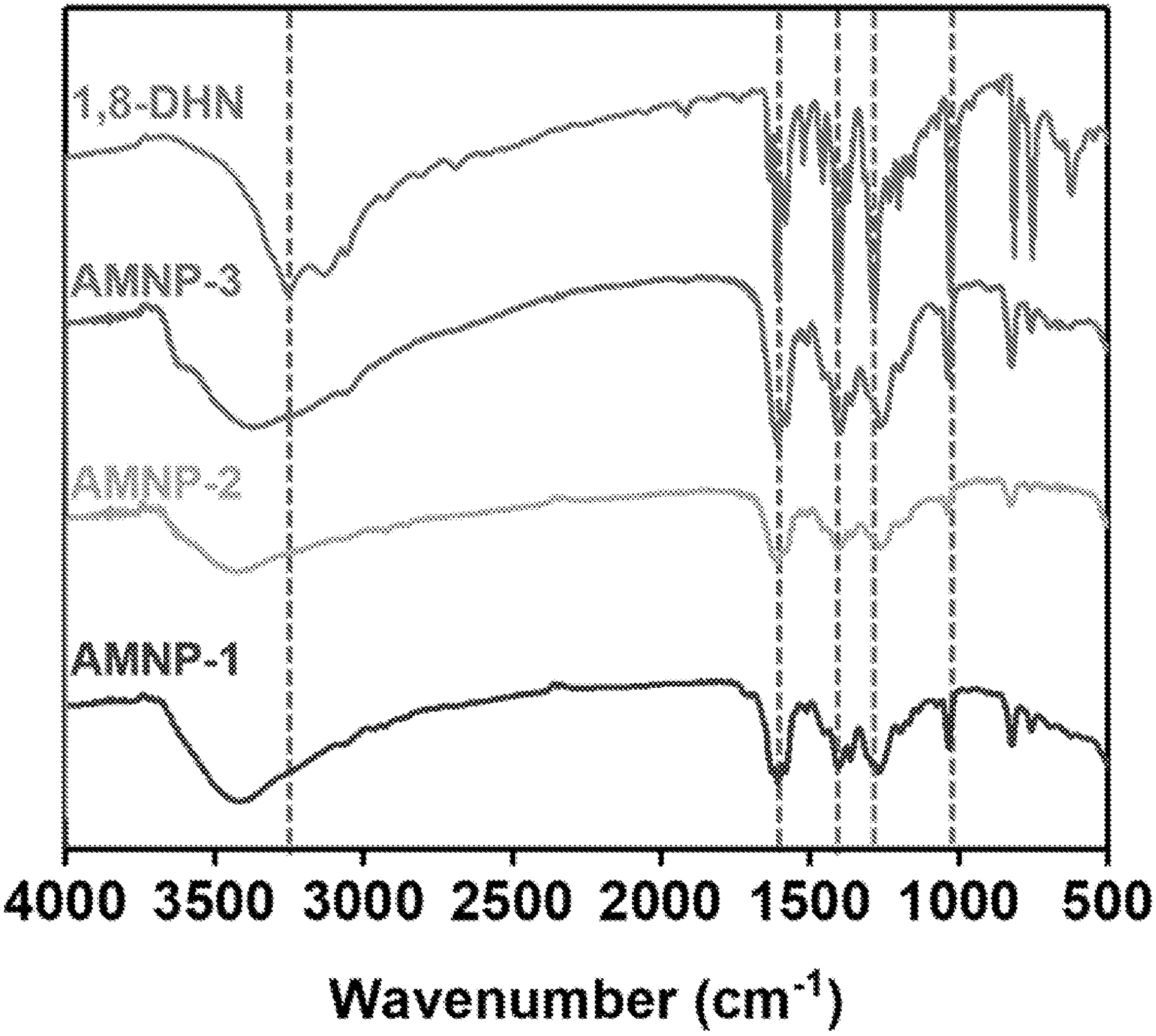
FIG. 4. FTIR spectra of AMNP-1, AMNP-2, AMNP-3 and 1,8-DHN monomer.
Figure 5A:
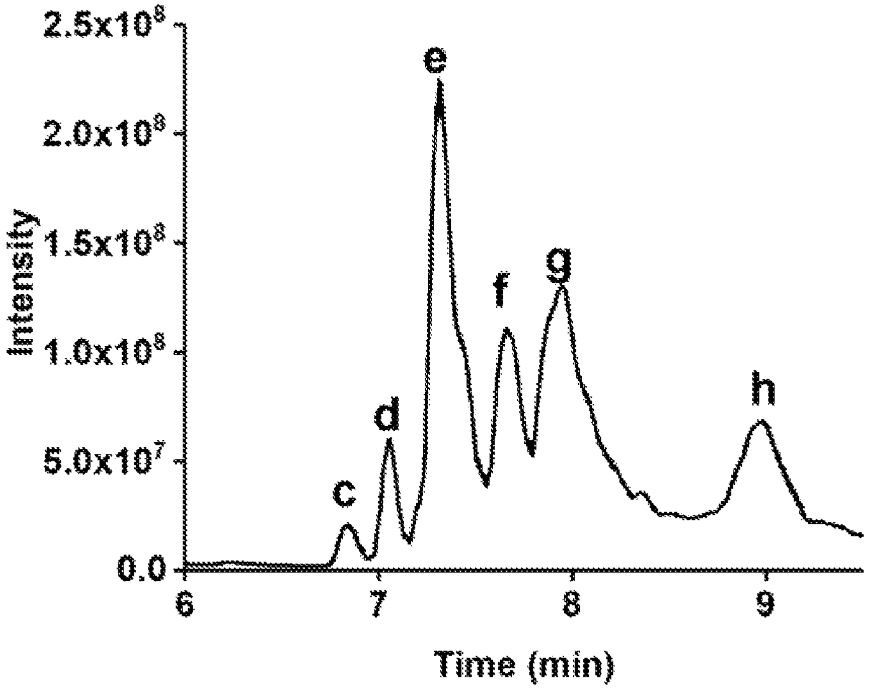
FIG. 5A. LC spectrum of AMNP-1 with a 0.5 molar ratio of $NaIO_4$ to DHN; ESI-MS spectra of (FIG. 5B) AMNP-1 in negative mode.
Figure 5B:
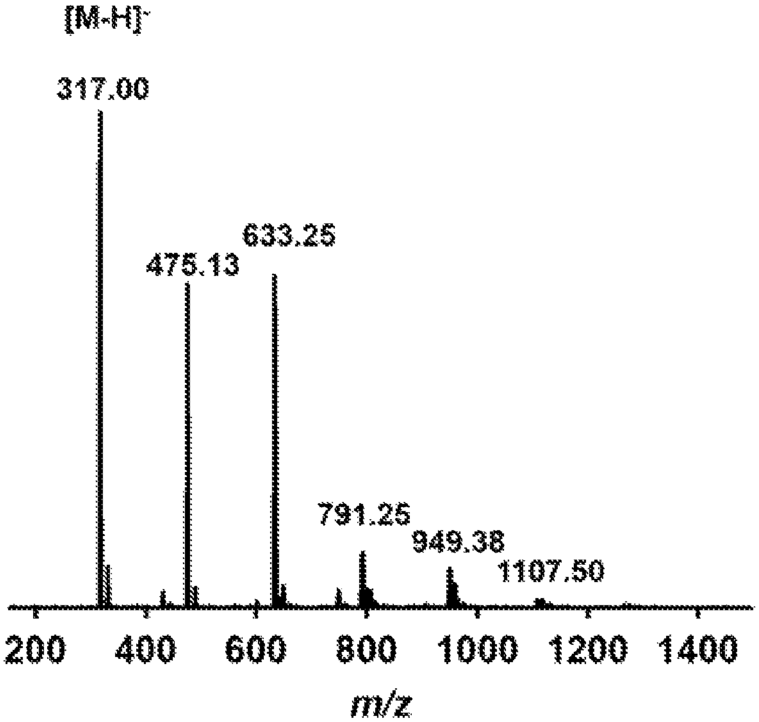
(FIG. 5C) monomer, t=6.83 min.
(FIG. 5D) dimer, t=7.05 min.
(FIG. 5E) dimer, t=7.31 min.
(FIG. 5F) trimer, t=7.66 min.
(FIG. 5G) tetramer, t=7.96 min.
(FIG. 5H) pentamer, t=8.98 min.
Figure 5C:
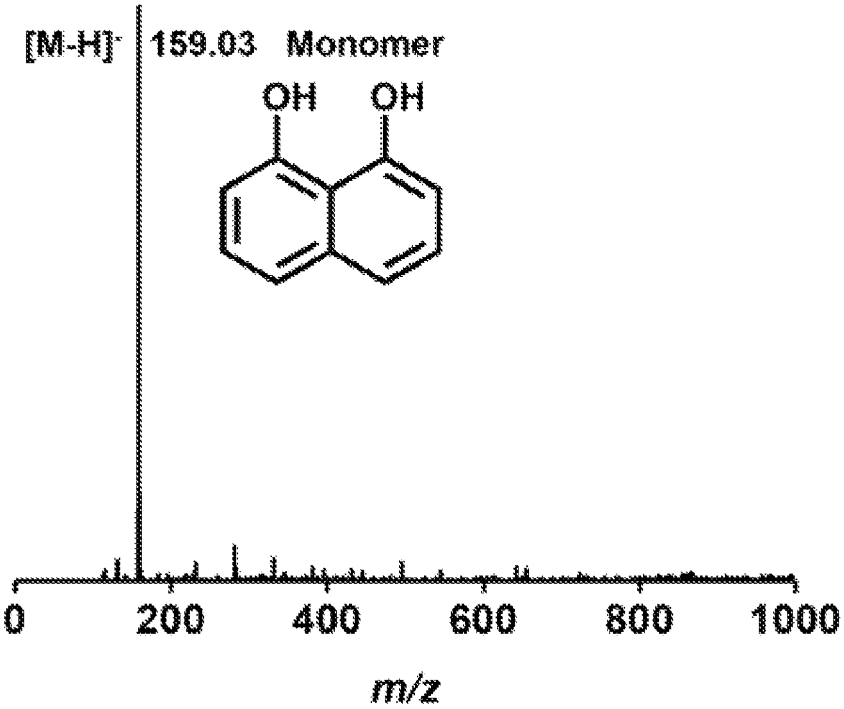
Figure 5D:
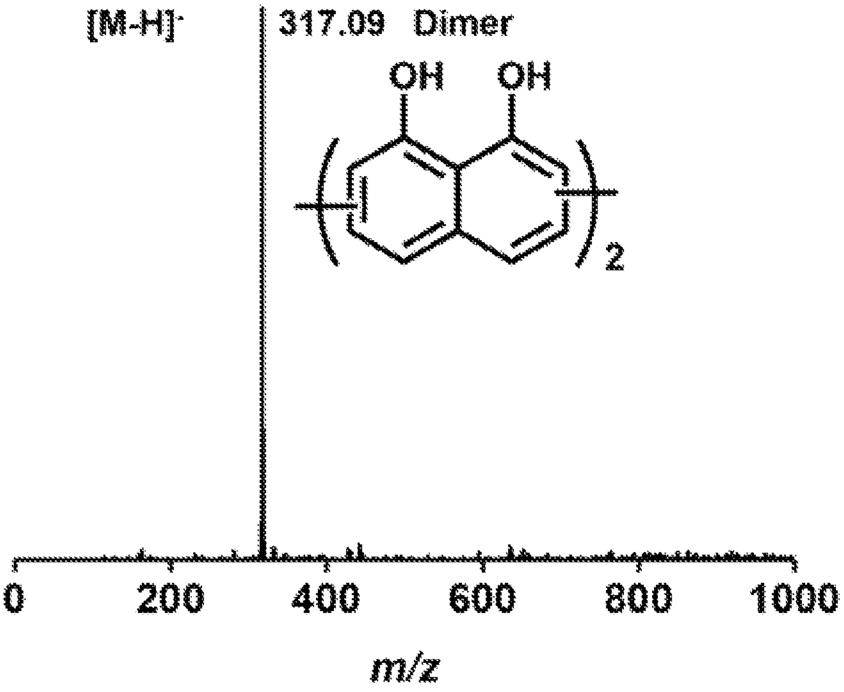
Figure 5E:
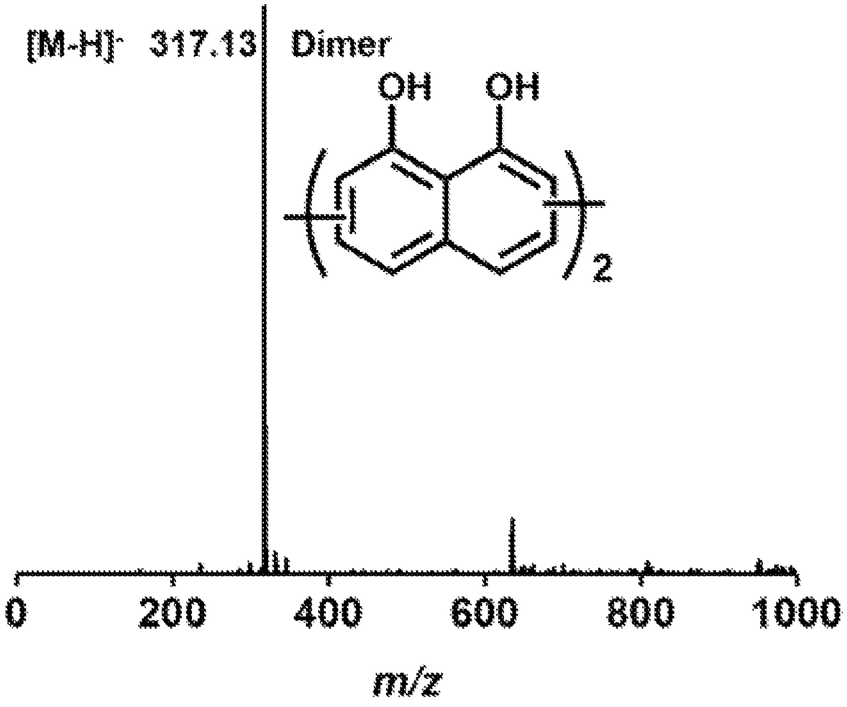
Figure 5F:
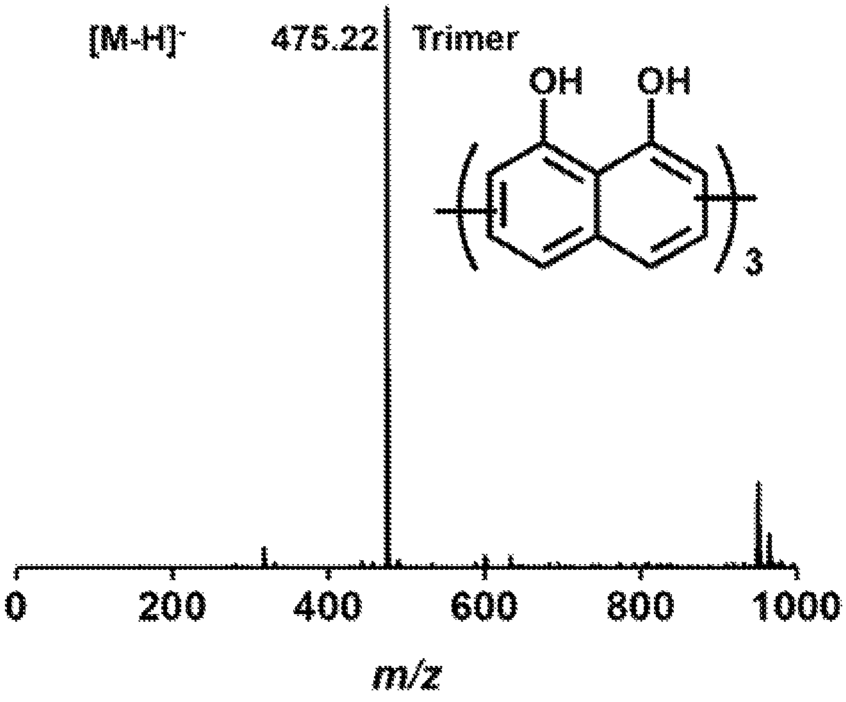
Figure 5G:
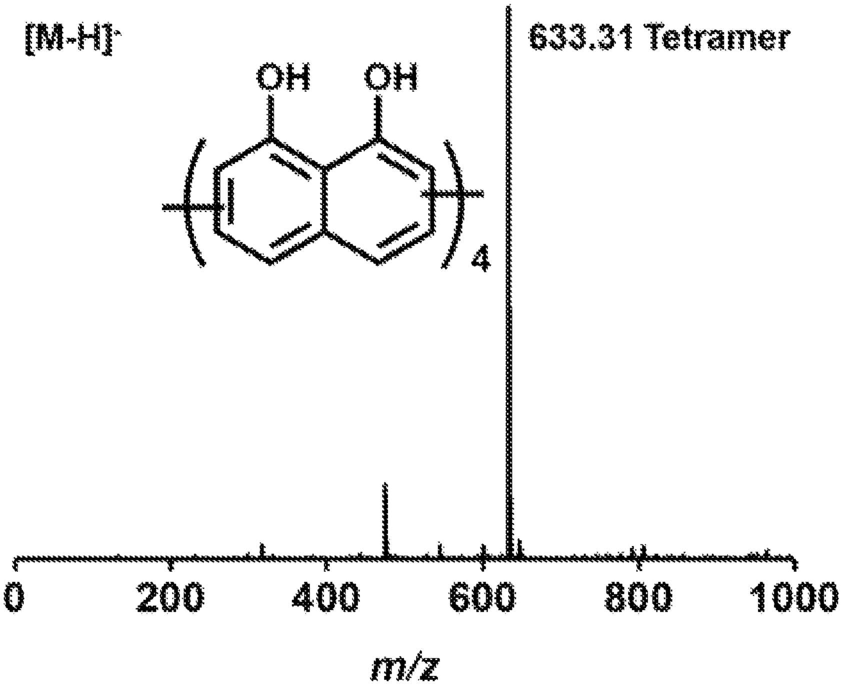
Figure 5H:
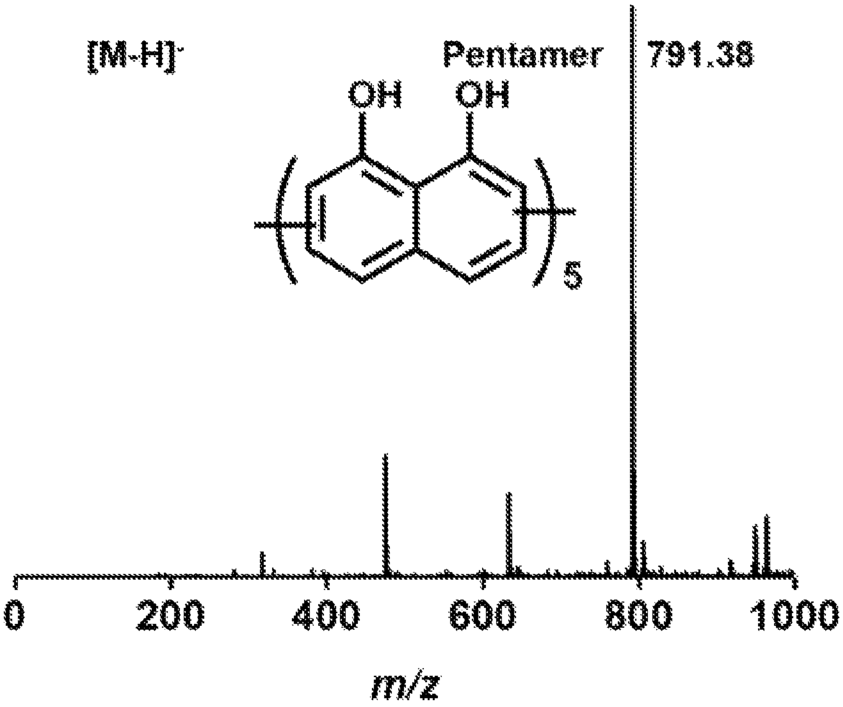

Fourier transform infrared spectroscopy (FTIR) was performed to investigate the chemical structure of AMNPs (FIG. 4). All three AMNP samples share the same characteristic peaks observed for the 1,8-DHN monomer. The sharp peaks at 3120 $cm^{-1}$, 1611 $cm^{-1}$, 1402 $cm^{-1}$, 1284 $cm^{-1}$, and 1038 $cm^{-1}$ correspond to aromatic C—H stretching, aromatic C═C stretching, C—OH bending, C—OH stretching, and aromatic C—H bending, respectively. The broad peaks in the 3200-3400 $cm^{-1}$ range are attributed to the stretching of —OH groups on the naphthalene ring. After formation of AMNPs, the aromatic C—H bending peak at 753 $cm^{-1}$ is strongly suppressed due to intermolecular cross-linking of the naphthalene rings.

Figure 18:
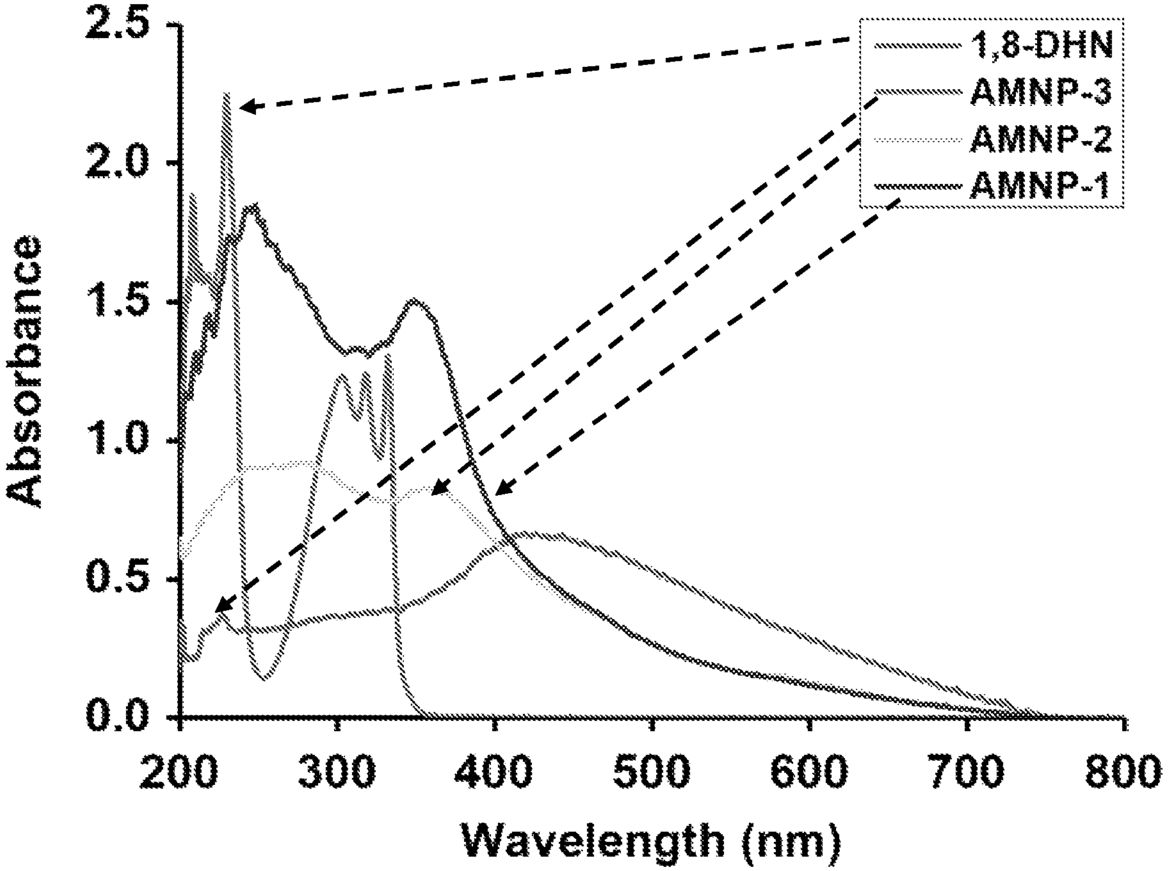
FIG. 18. UV-Vis spectra of AMNPs and 1,8-DHN monomer.
Figure 19A:
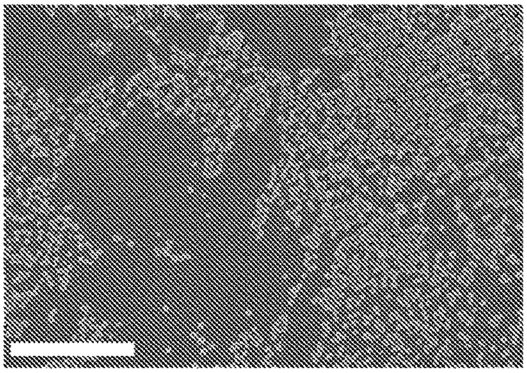
FIGS. 19A-19E. SEM images of AMNP-1 with 0.5 molar ratio of $NaIO_4$ to 1,8-DHN in different solvents, (FIG. 19A) Water.
Figure 19B:
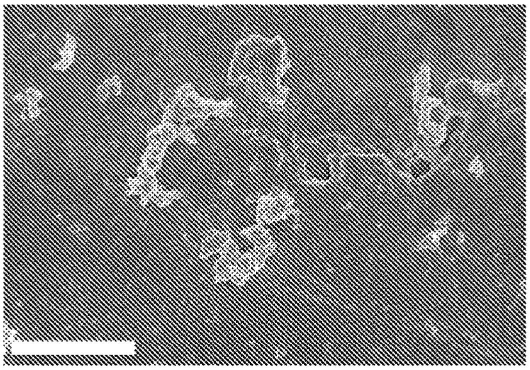
Figure 19C:
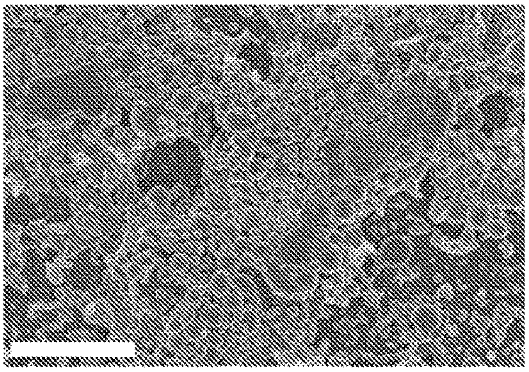
Figure 19D:
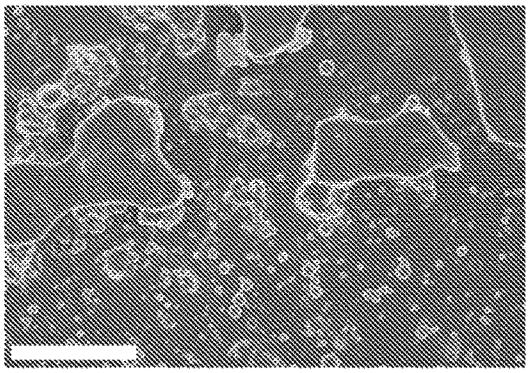
Figure 19E:
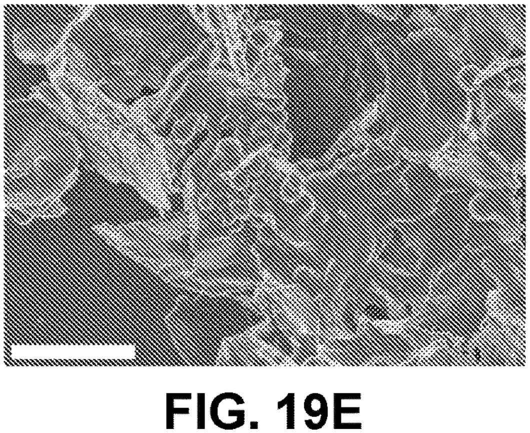
Figure 20A:
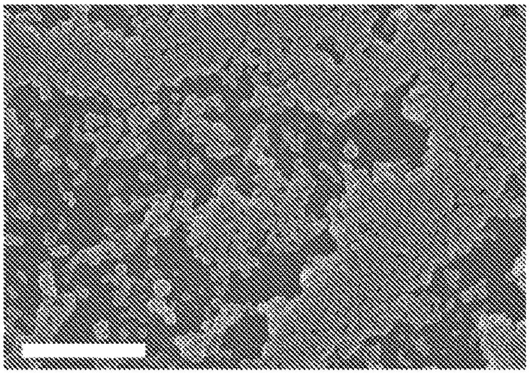
FIGS. 20A-20E. SEM images of AMNP-2 with 0.2 molar ratio of $KMnO_4$ to 1,8-DHN in different solvents, (FIG. 20A) Water.
Figure 20B:
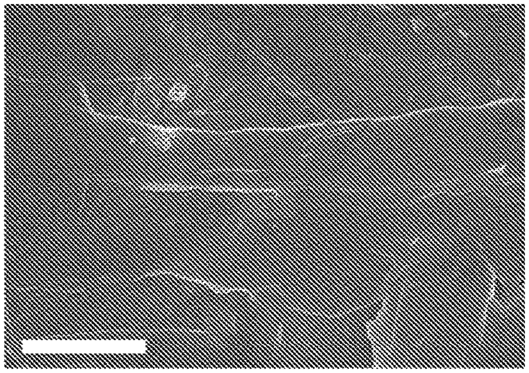
Figure 20C:
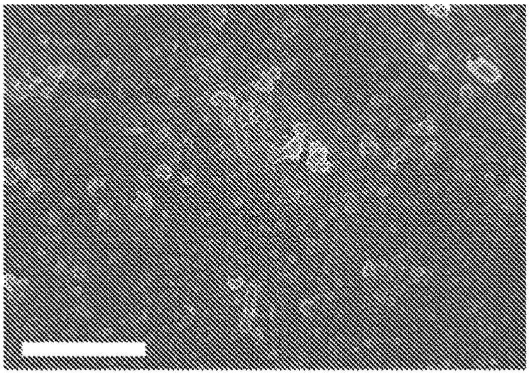
Figure 20D:
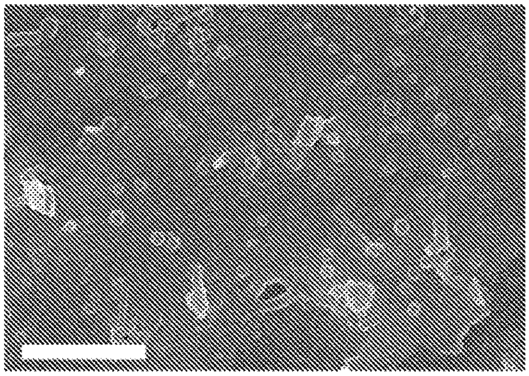
Figure 20E:
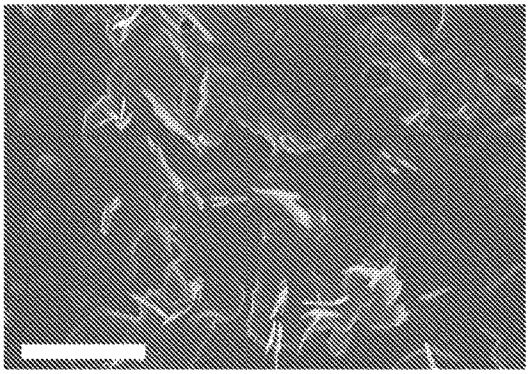

AMNP-1 and AMNP-2 show a broad absorption in the UV, peaking at ~350 nm, while AMNP-3 shows a broader, red-shifted absorption, with a maximum at approximately 430 nm (FIG. 18). Compared to the absorption of the 1,8-DHN monomer, all three types of AMNPs show a bathochromic shift which may indicate an expansion of the conjugated system due to the oxidative coupling as well as strong π-π-stacking interactions between the molecules.[41]

Figure 21A:
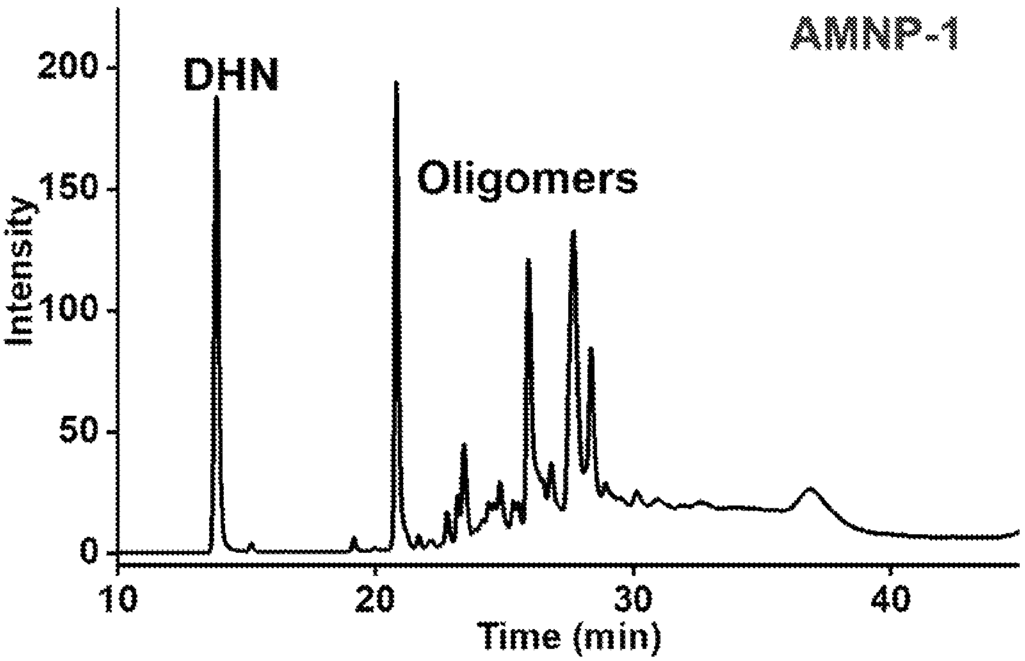
FIGS. 21A-21B. HPLC spectrum of (FIG. 21A) AMNP-1 with 0.5 molar ratio of $NaIO_4$ to DHN (retention time at 14.0 min corresponds to DHN monomer)
Figure 21B:
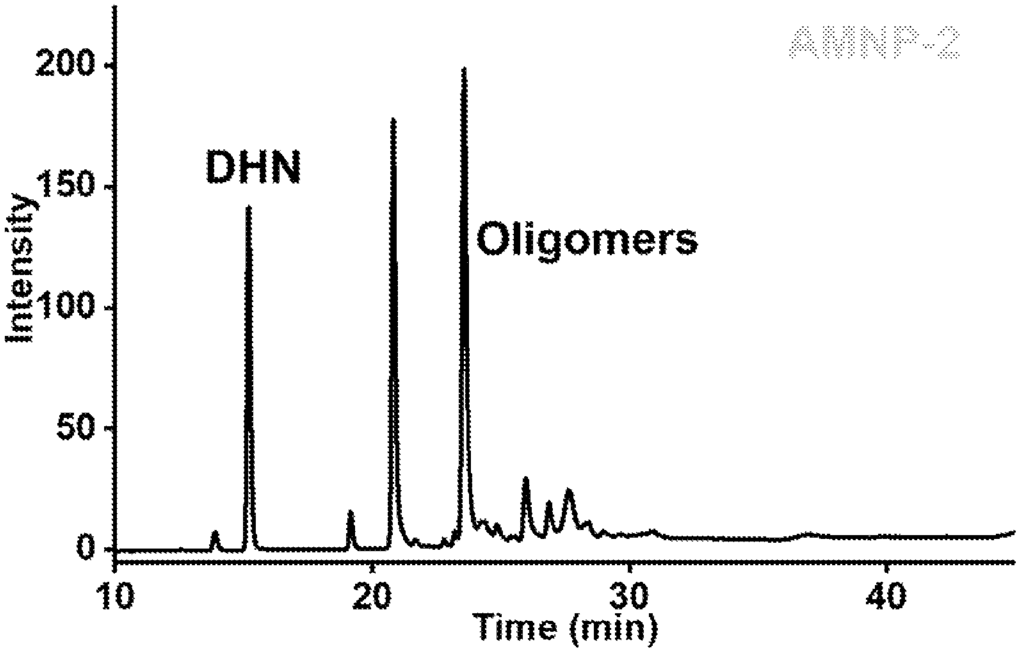

We endeavored to examine the chemical structure of the components of the AMNPs. Given their stability in water, we tested whether they could be broken up and dispersed in organic solvents. AMNP-1 (FIG. 19) and AMNP-2 (FIG. 20) broke apart in organic solvents including acetonitrile, methanol, ethanol, and dimethylformamide (DMF) immediately following synthesis. AMNP-3 could not be dispersed in any of the organic solvents tested, possibly explained by it consisting mostly of higher molecular weight polymers. High-performance liquid chromatography (HPLC) of AMNP-1 could be obtained after dissolving in acetonitrile and running an acetonitrile/water gradient (FIG. 21). Electrospray ionization mass spectrometry (ESI-MS) and LCMS revealed that monomer and oligomers could be separated and assigned, with the most abundant oligomer being a dimer at m/z 317, with pentamers detectable (FIGS. 5A-5H).

Figure 22A:
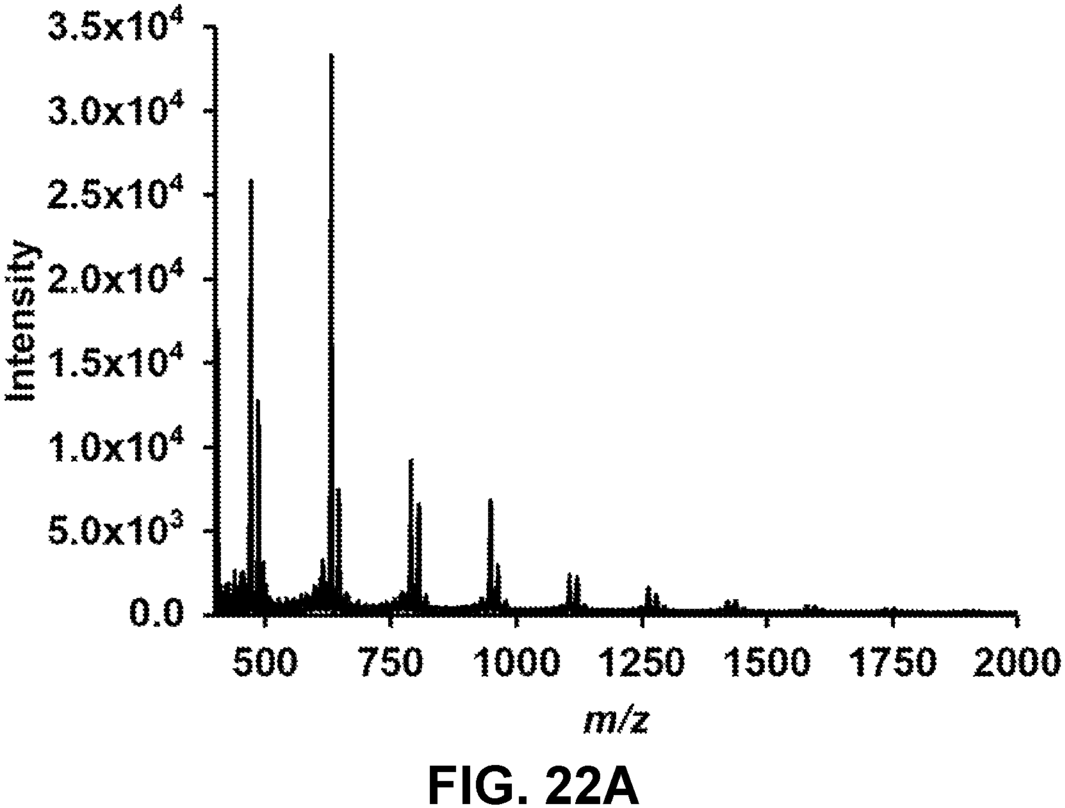
FIGS. 22A-22C. MALDI-TOF spectra of (FIG. 22A) AMNP-1, (FIG. 22B) AMNP-2, (FIG. 22C) AMNP-3 in reflectron, negative mode.
Figure 22B:
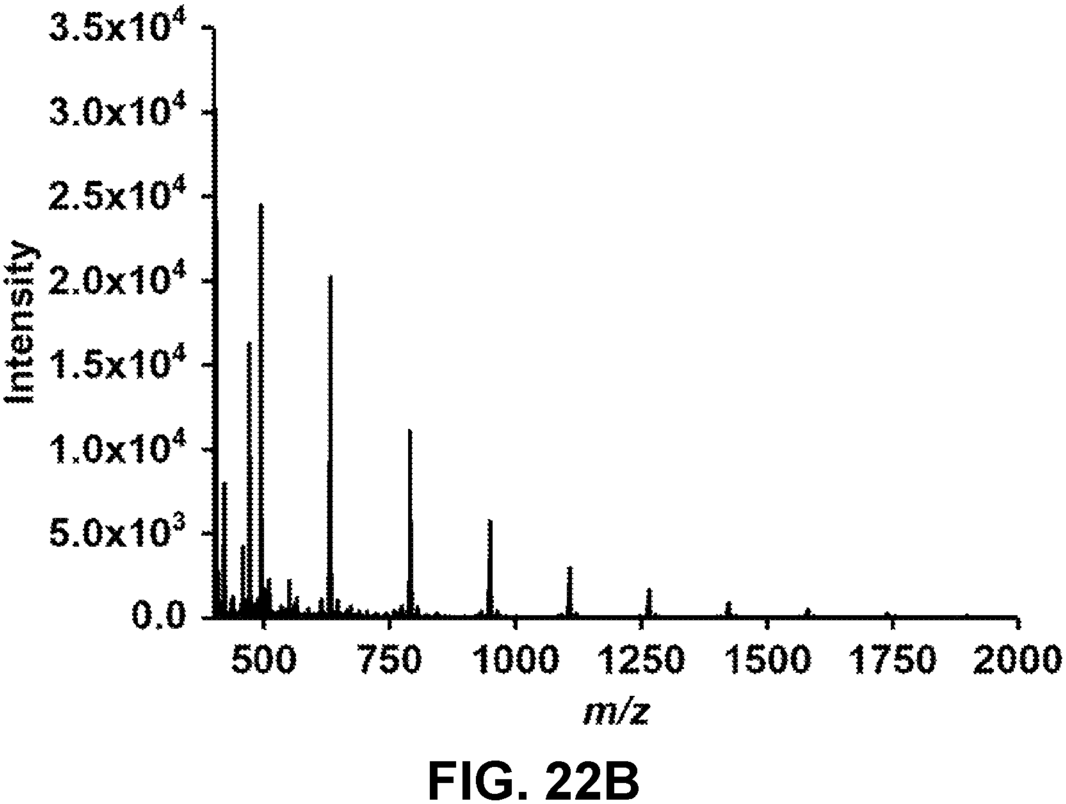
Figure 22C:
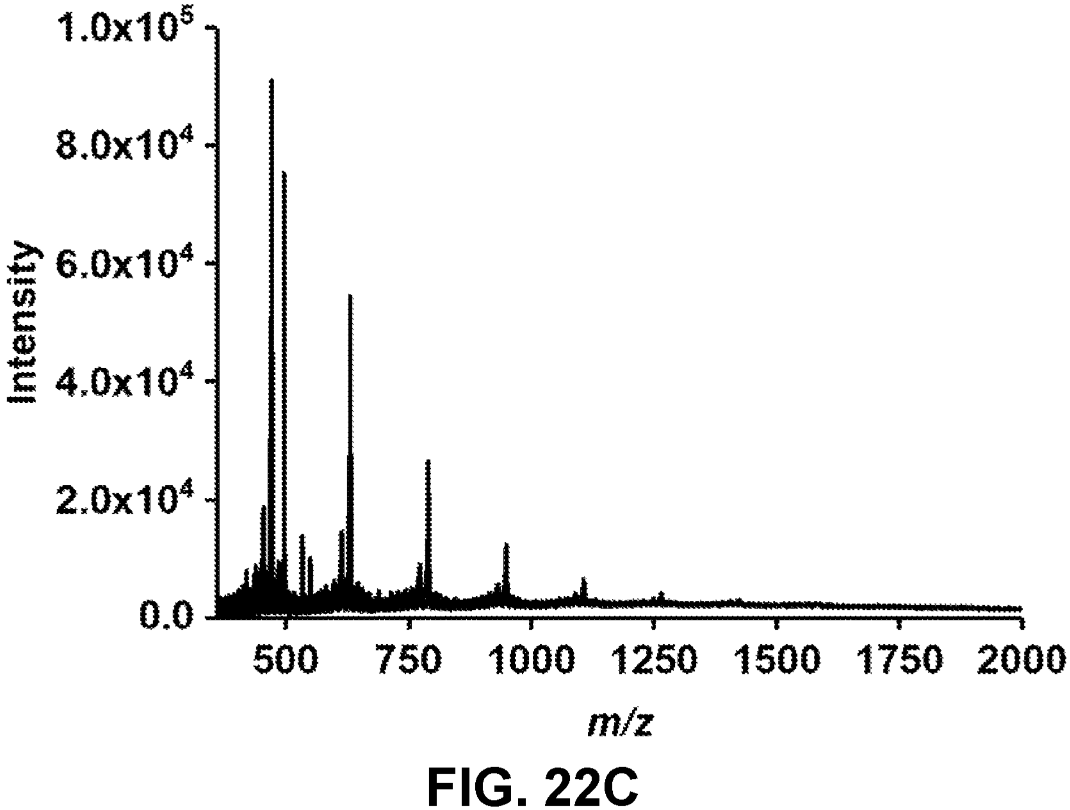
Figure 23A:
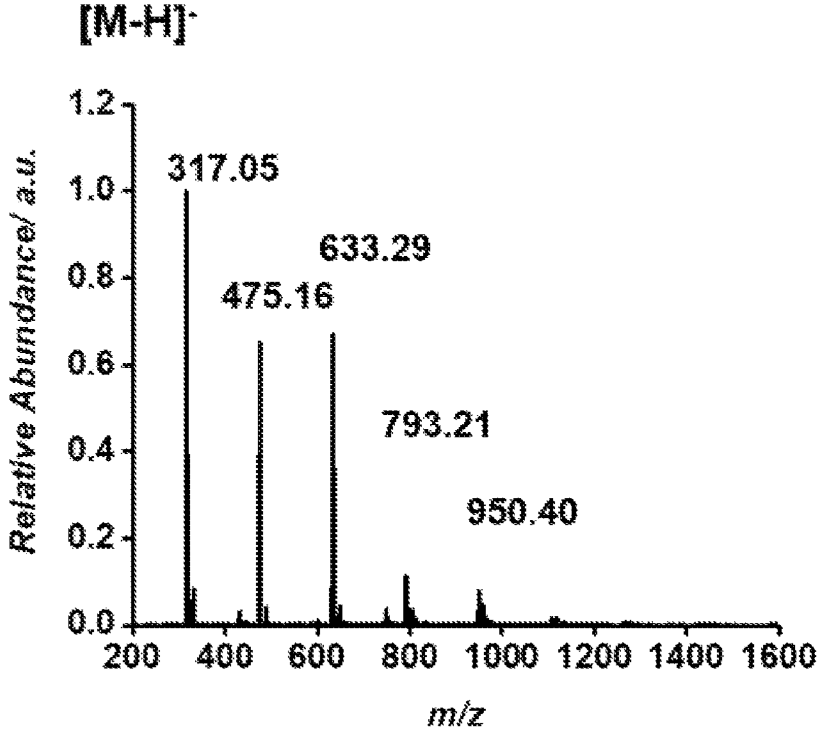
FIGS. 23A-23D. ESI-MS spectra of AMNP-1 with different molar ratios of $NaIO_4$ to 1,8-DHN monomer at (FIG. 23A) 0.2:1.0.
Figure 23B:
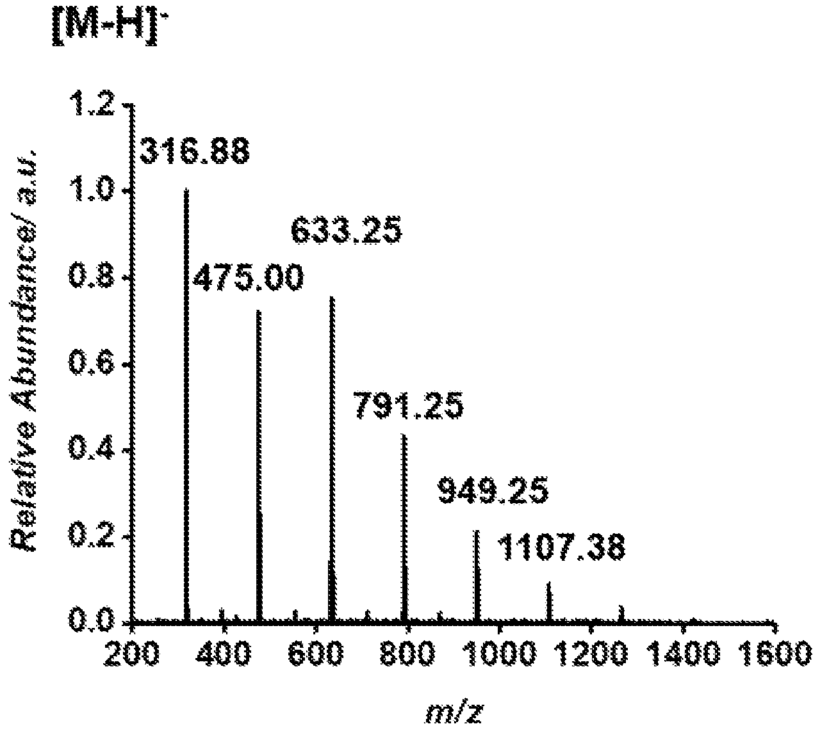
Figure 23C:
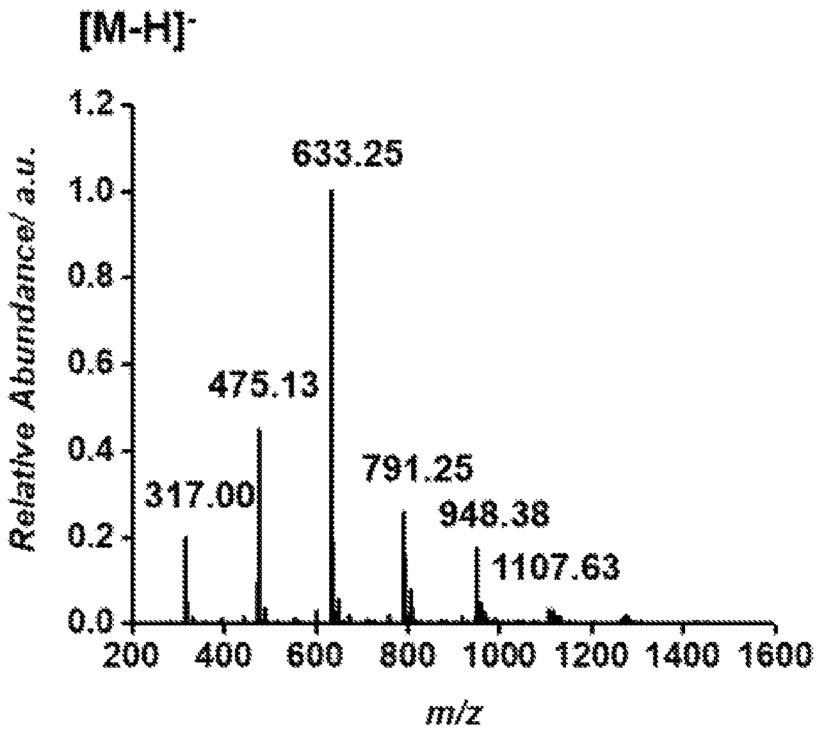
Figure 23D:
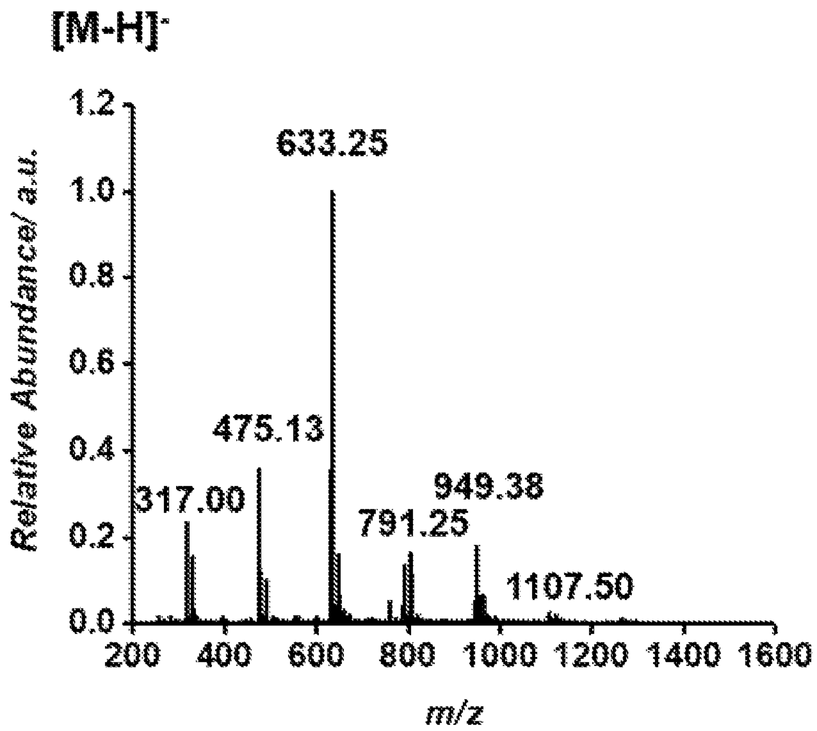

In a complementary mass spectrometry study, matrix assisted laser desorption ionization-time of flight (MALDI-TOF) mass spectra of AMNPs were obtained. These display a distribution of oligomers that are separated by 158 Da, corresponding to the "in-chain" DHN unit (FIG. 22). Oligomers with repeating units up to 12 can be observed for AMNP-1 and AMNP-2. For AMNP-3, either low molecular weight oligomers or the fragments of high molecular weight oligomers could be observed (FIG. 22*c*). ESI-MS spectra of AMNP-1 with different molar ratios of $NaIO_4$ to 1,8-DHN monomer showed that higher ratios of $NaIO_4$/DHN can generate oligomers with higher molecular weights (FIG. 23).

Figure 24:
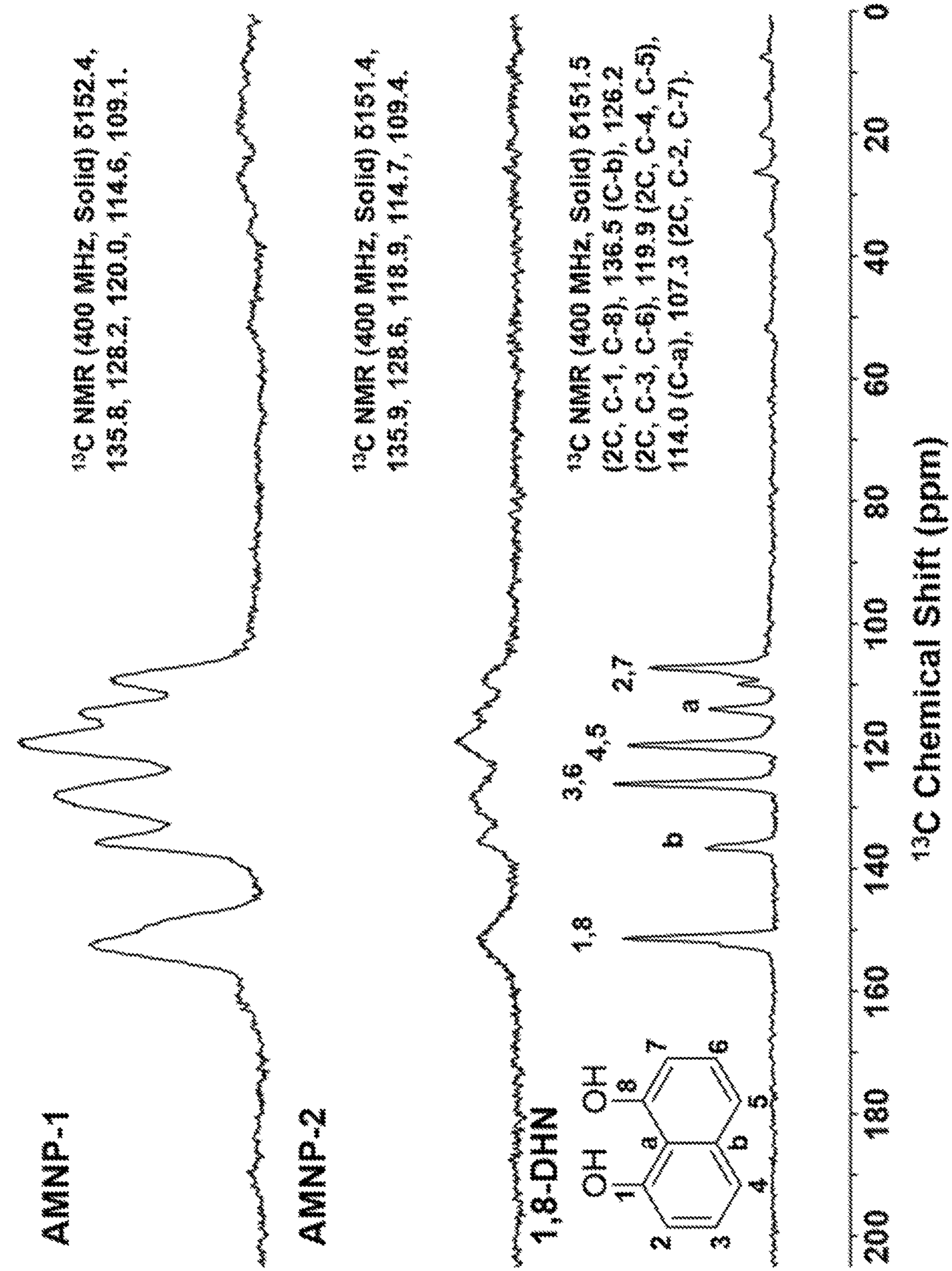
FIG. 24. $^{13}C$ solid-state NMR spectra of AMNP-1, AMNP-2, and 1,8-DHN monomer.
Figure 25A:
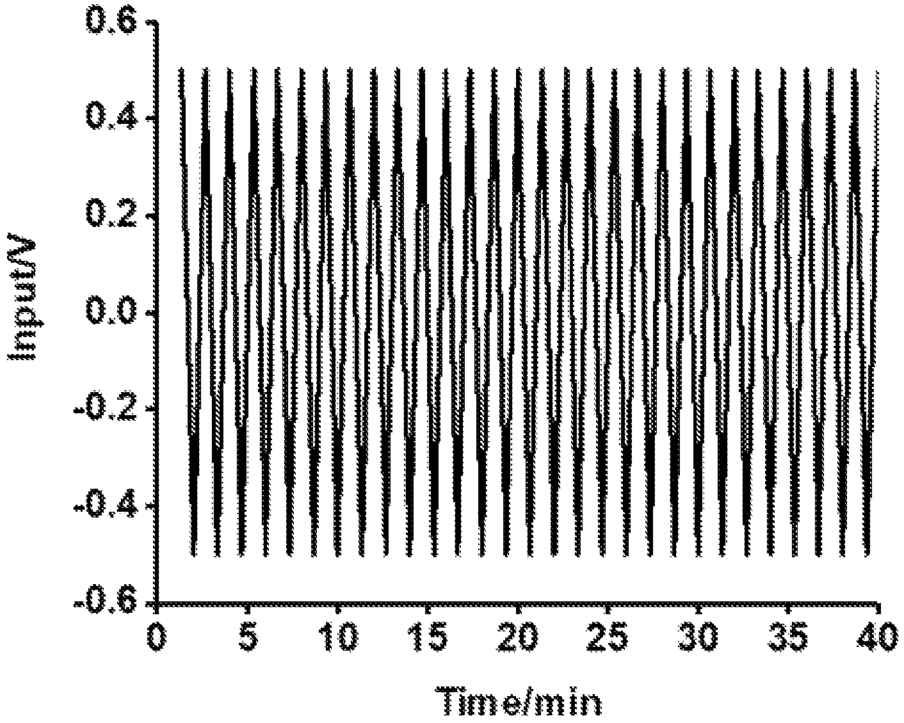
FIGS. 25A-25D. Mediated electrochemical probing (MEP) to characterize redox properties of AMNP-2. Chitosan was applied as a control.
Figure 25B:
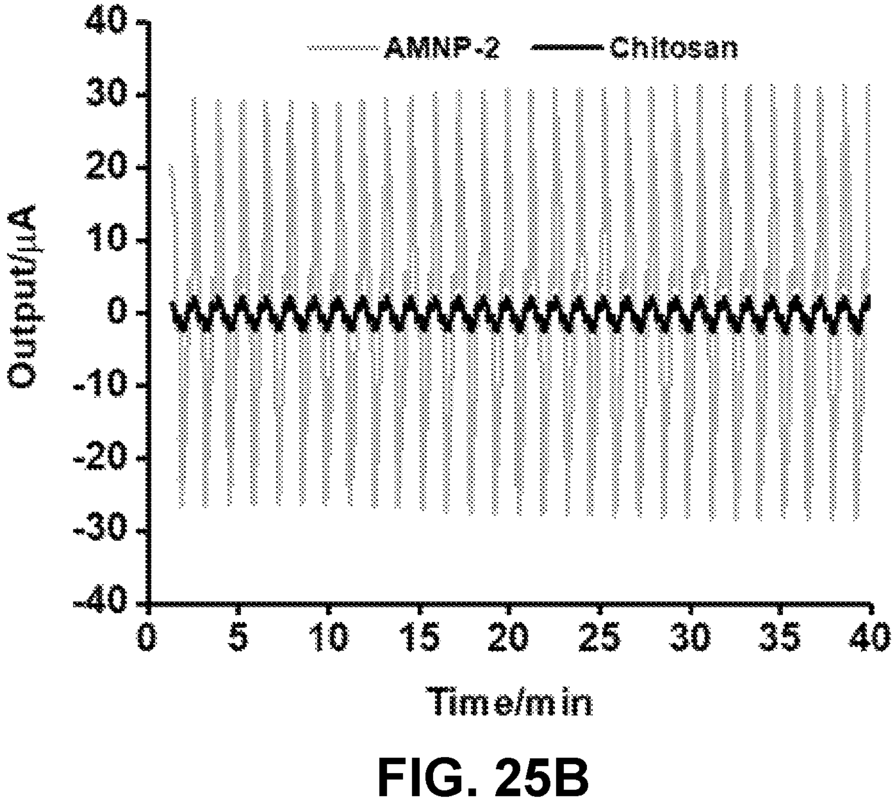
Figure 25C:
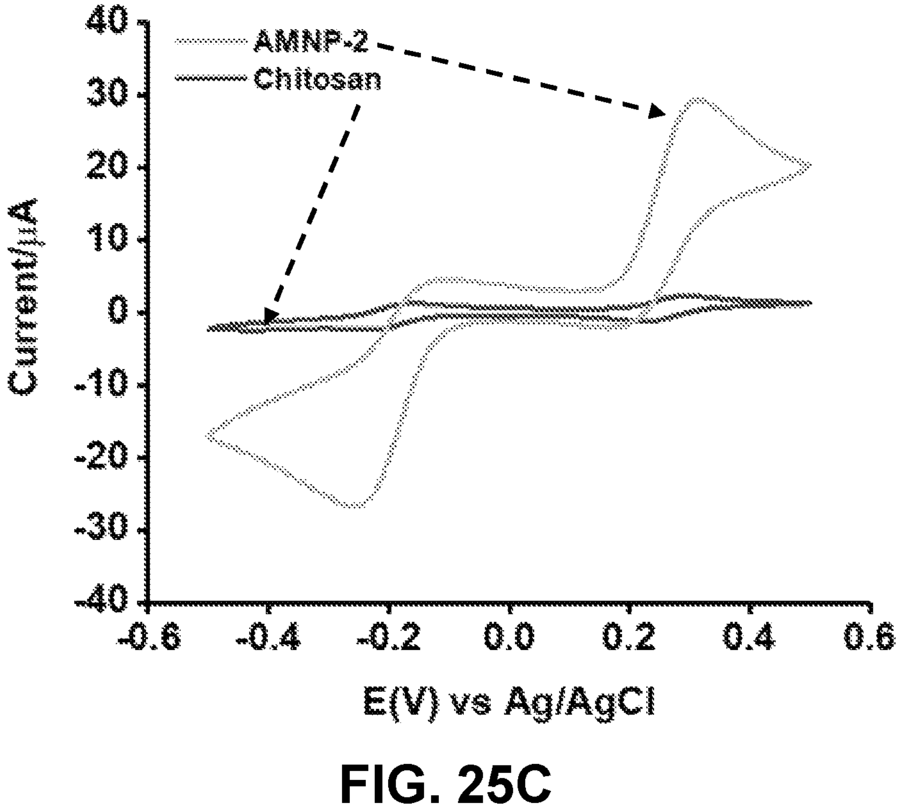
Figure 25D:
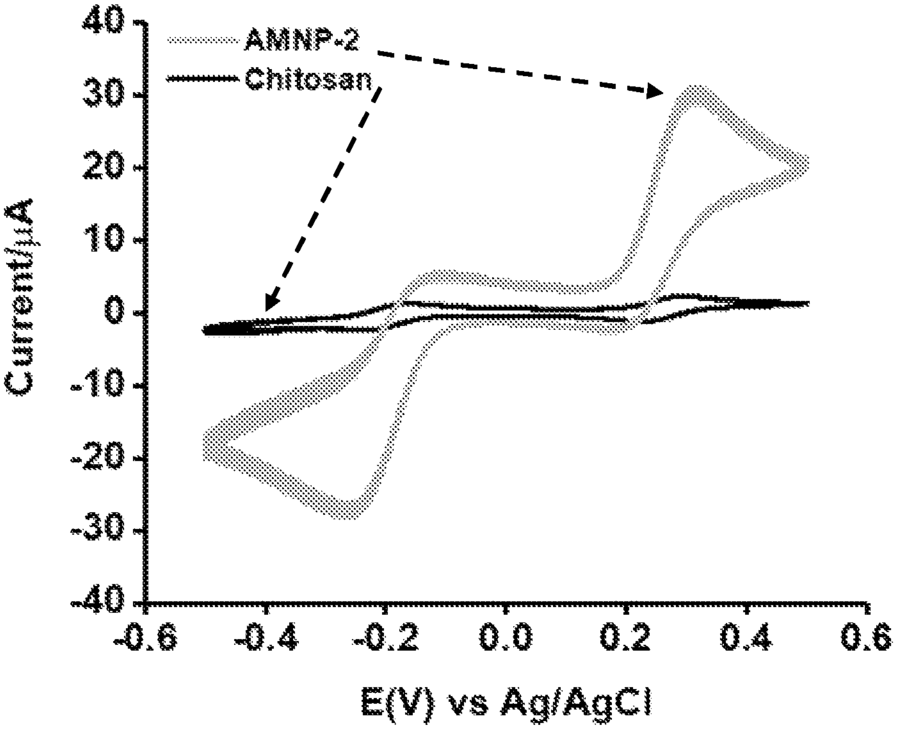
Figure 26A:
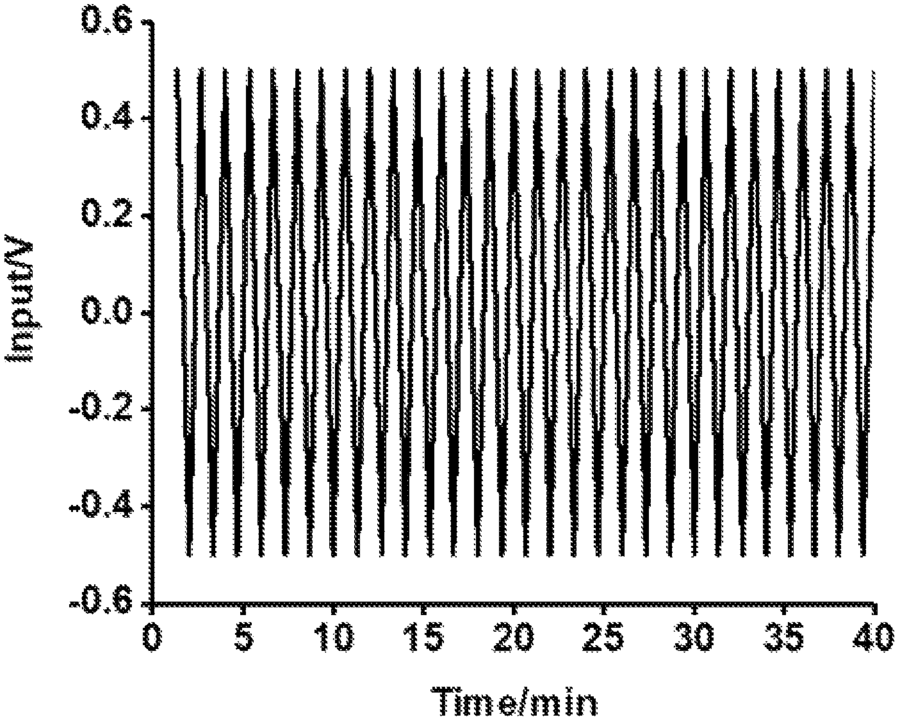
FIGS. 26A-26D. Mediated electrochemical probing (MEP) to characterize redox properties of AMNP-3. Chitosan was applied as a control.
Figure 26B:
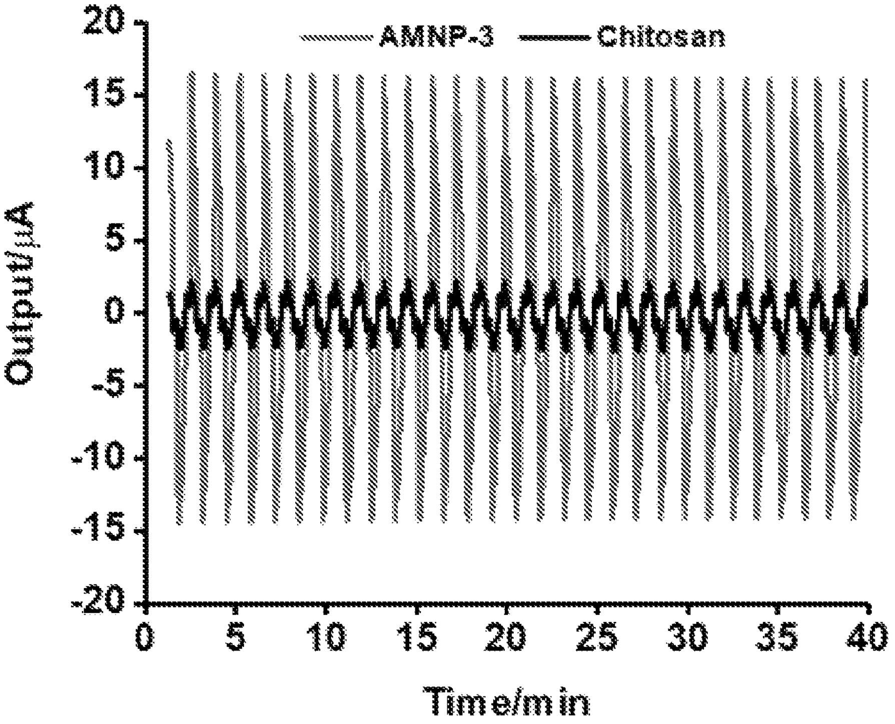
Figure 26C:
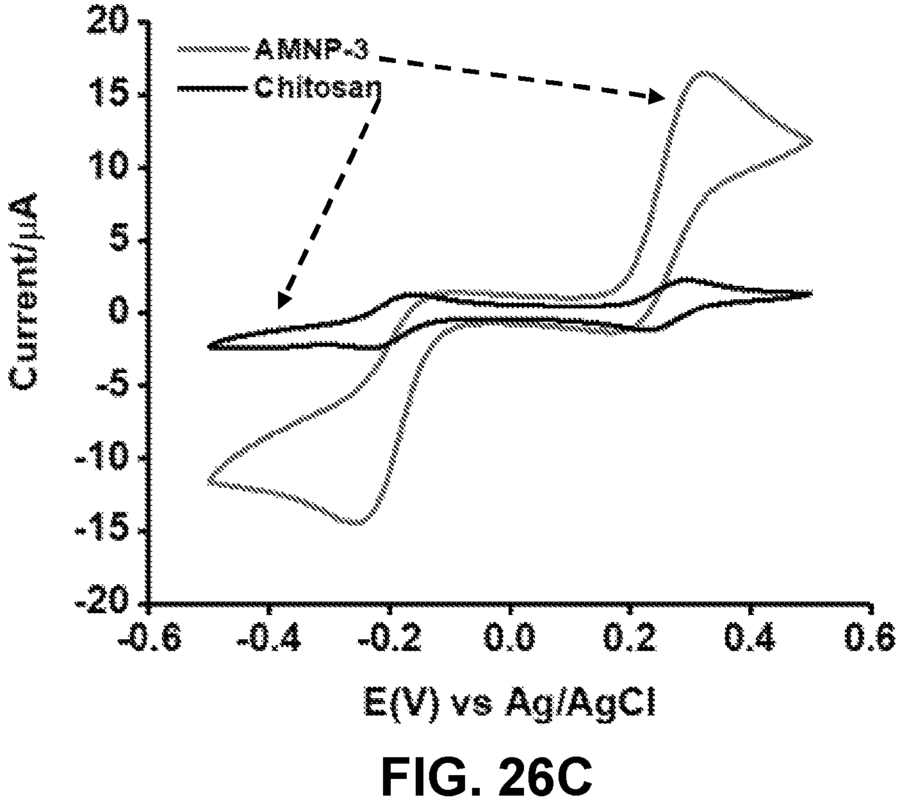
Figure 26D:
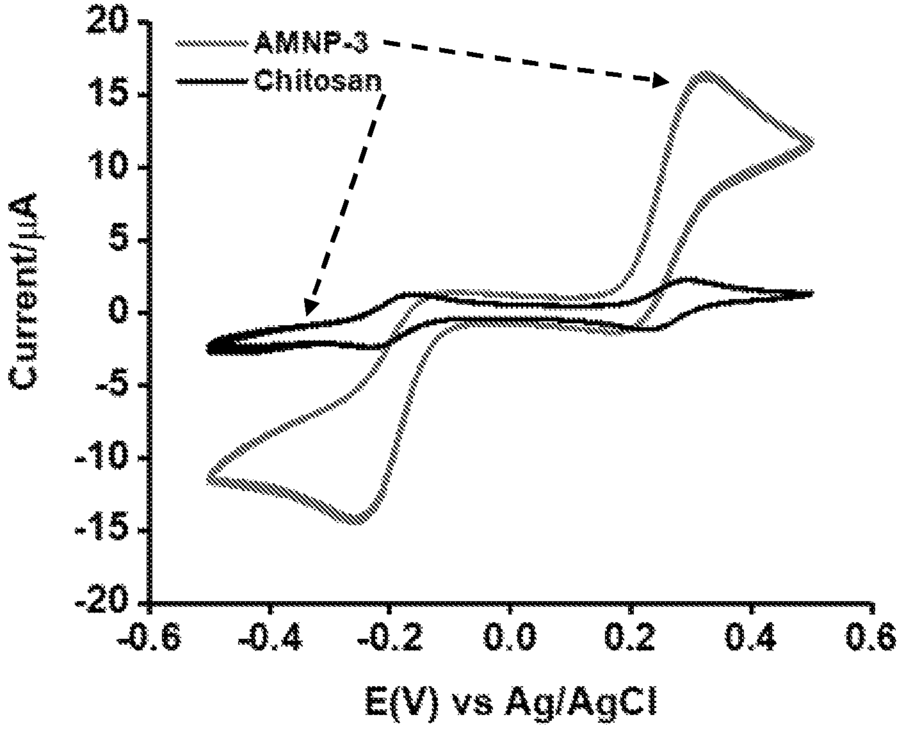

To further explore their structures, solid-state NMR (ssNMR) of 1,8-DHN and AMNPs was performed. The resonances attributed to phenoxy C atoms (C1 and C8, 152.4 ppm), ortho C atoms (C2 and C7, 109.1 ppm), meta C atoms (C3 and C6, 128.2 ppm), para C atoms (C4 and C5, 120.0 ppm), Ca (114.6 ppm) and Cb (135.8 ppm) are in agreement with the 1,8-DHN monomer (FIG. 24).

Figure 1:
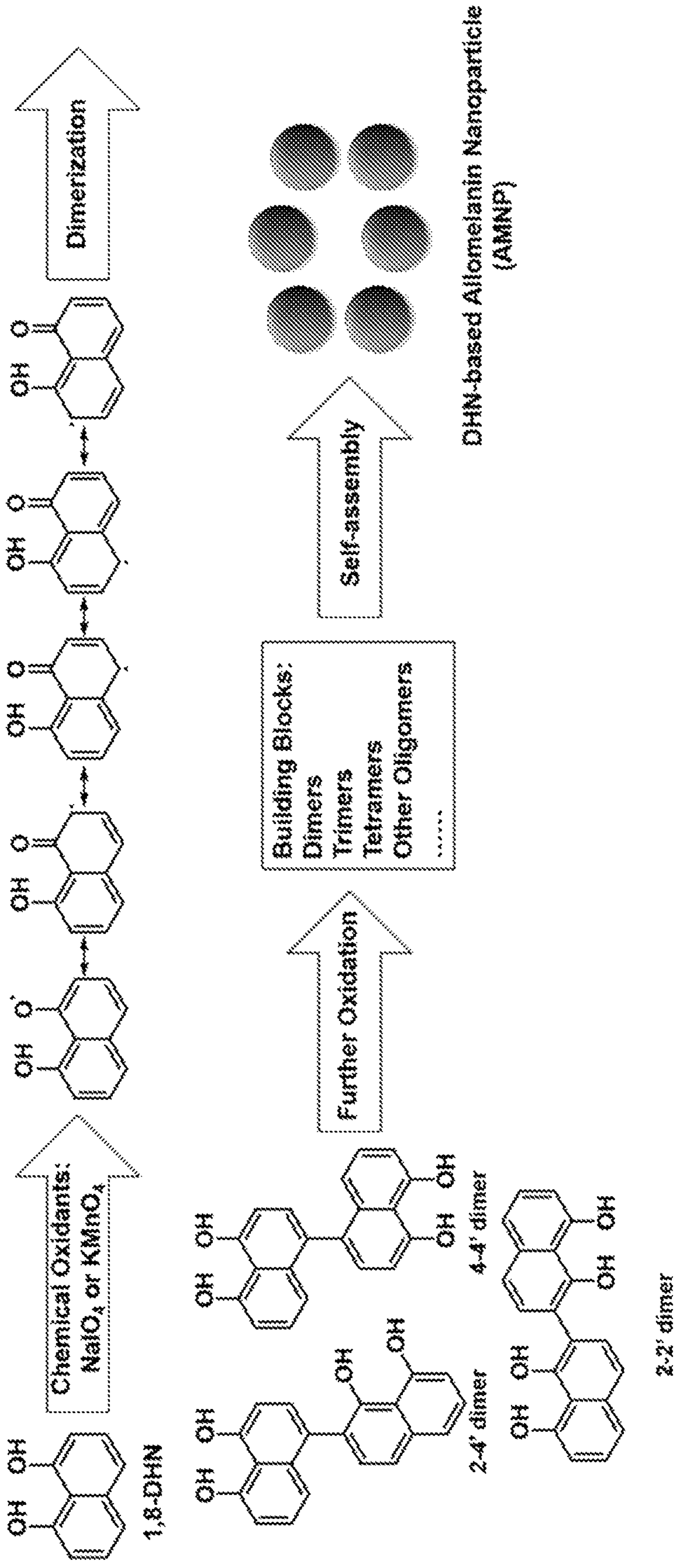
FIG. 1. Synthesis of AMNPs. Oxidative oligomerization of 1,8-DHN was achieved using oxidizing agents $NaIO_4$ or $KMnO_4$. Resulting oligomers and polymers self-assemble to form AMNPs.
Figure 2A:
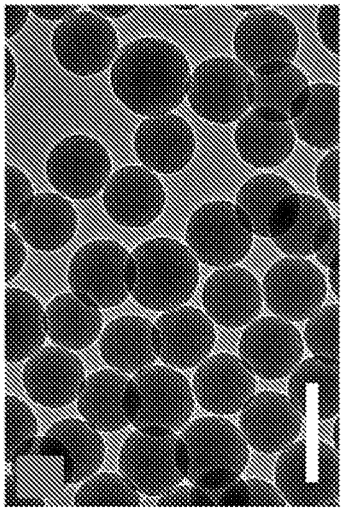
FIGS. 2A-2F. Morphology and size characterization of AMNPs by (FIGS. 2A-2C) TEM, scale bars 200 nm, and (FIGS. 2D-2F) SEM, scale bars 400 nm. Electron micrographs of (FIGS. 2A and 2D) AMNP-1, (FIGS. 2B and 2E) AMNP-2, and (FIGS. 2C and 2F) AMNP-3.
Figure 2B:
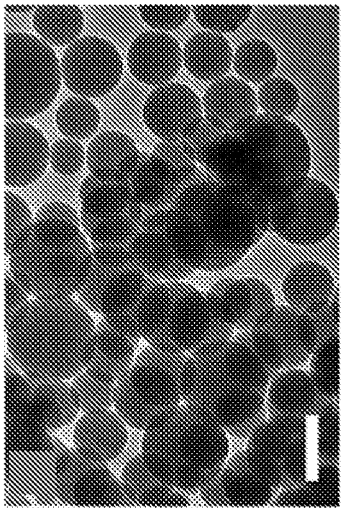
Figure 2C:
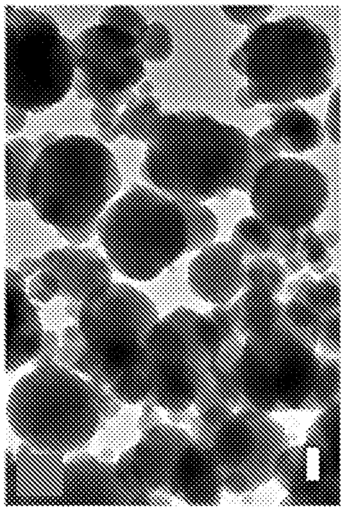
Figure 2D:
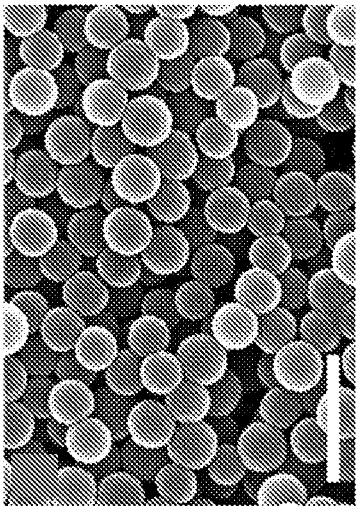
Figure 2E:
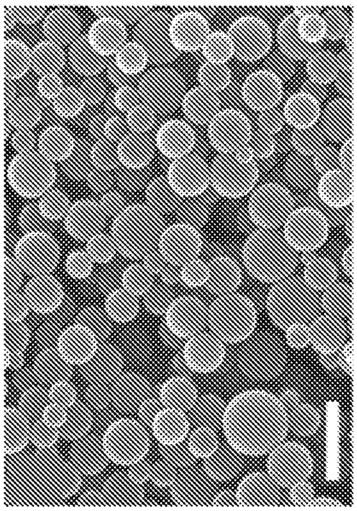
Figure 2F:
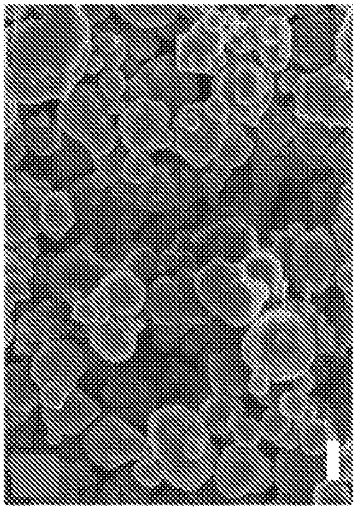

The above analyses suggest that oligomerization of AMNPs involves intermolecular C—C coupling, further oxidation to form oligomers, and non-covalent self-assembly to form nanoparticles.[39] Therefore, the 1,8-DHN monomer was first oxidized to form a 1,8-DHN radical. This radical has several resonance structures leading to coupling through C—C bonds to form appropriate dimers. Considering the resonance structures, the coupling reaction happens mainly between C2, C7, C4, and C5 to form three types of dimers: 2-2', 4-4', and 4-2' dimers. Further oxidation and oligomerization of these dimers results in oligomers of the 1,8-DHN monomer which self-assemble to form spherical nanoparticles through the hydrogen bonding of —OH groups and π-π stacking of naphthalene rings (FIG. 1).

Figure 16A:
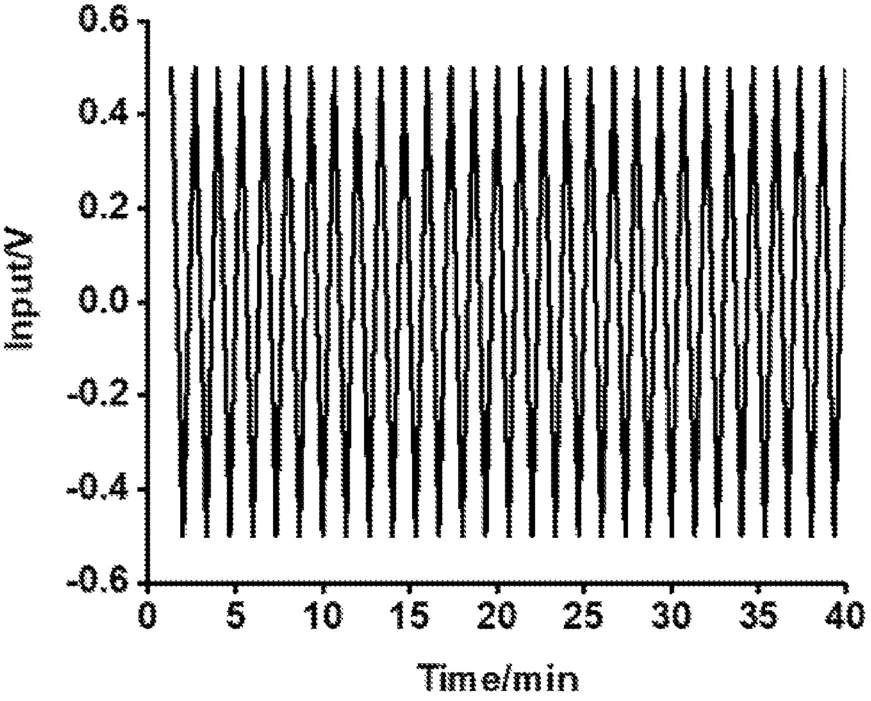
FIGS. 16A-16D. Mediated electrochemical probing (MEP) to characterize redox properties of AMNP-1. Chitosan was applied as a control.
Figure 16B:
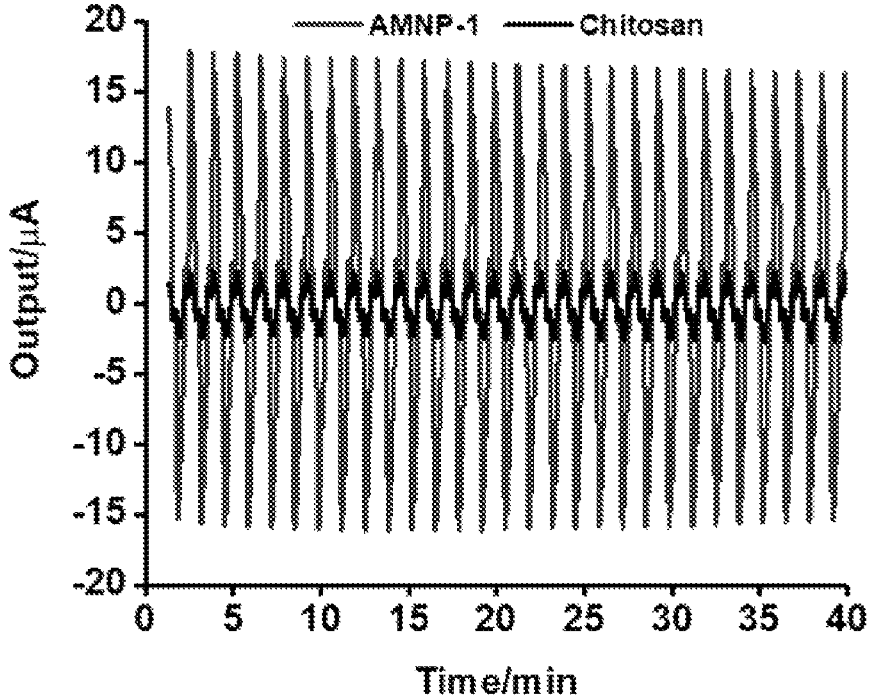
Figure 16C:
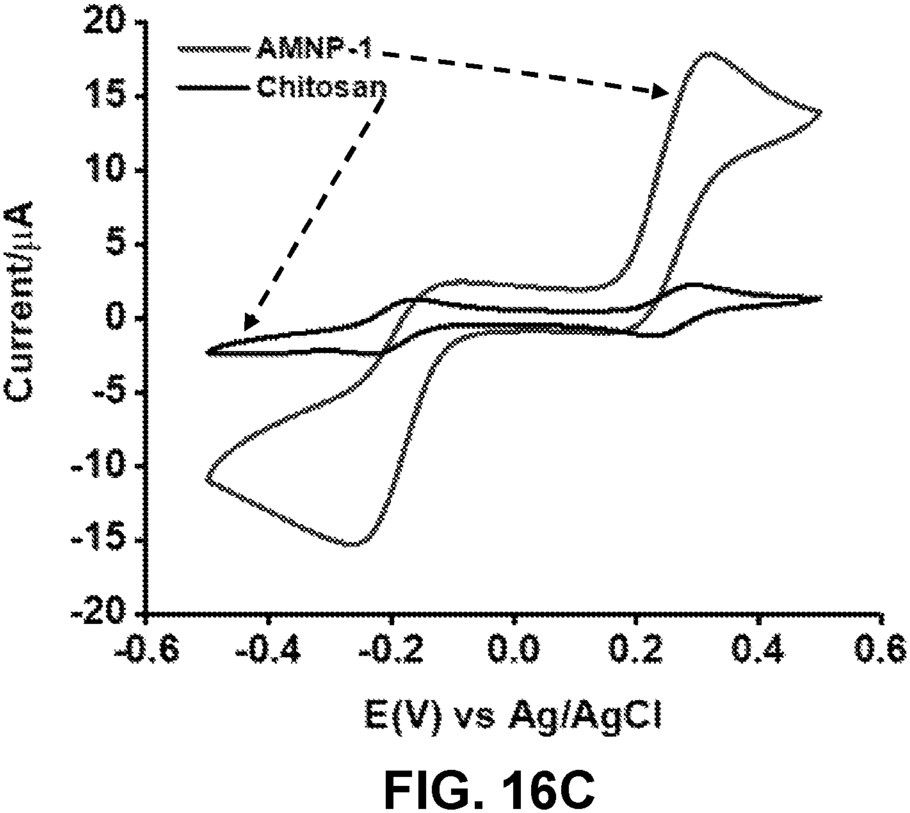
Figure 16D:
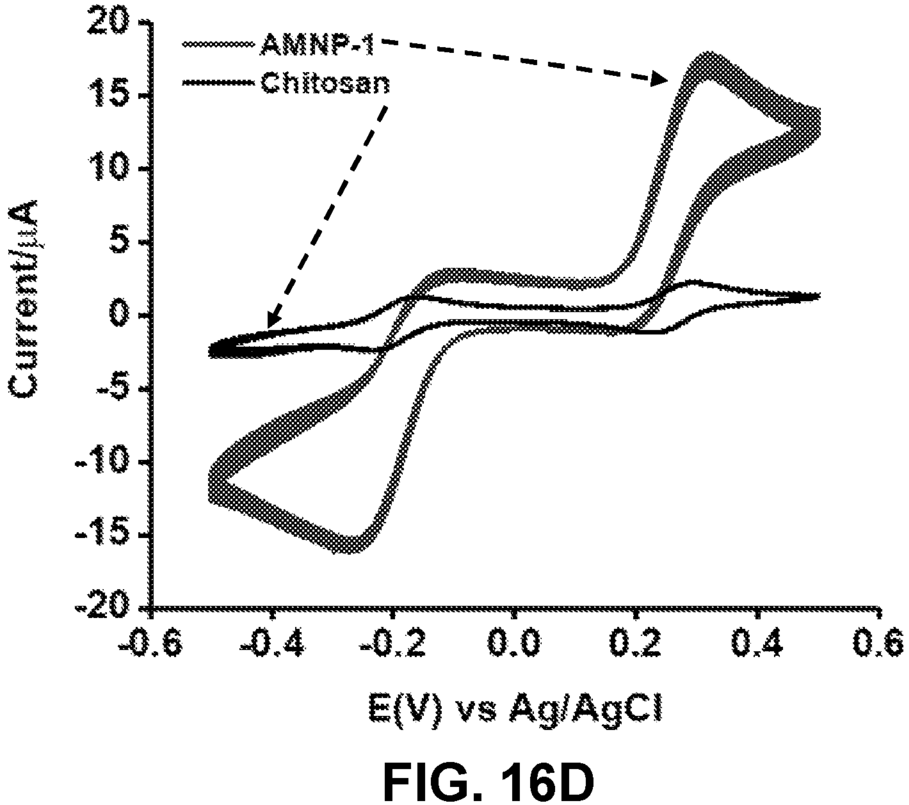
Figure 17A:
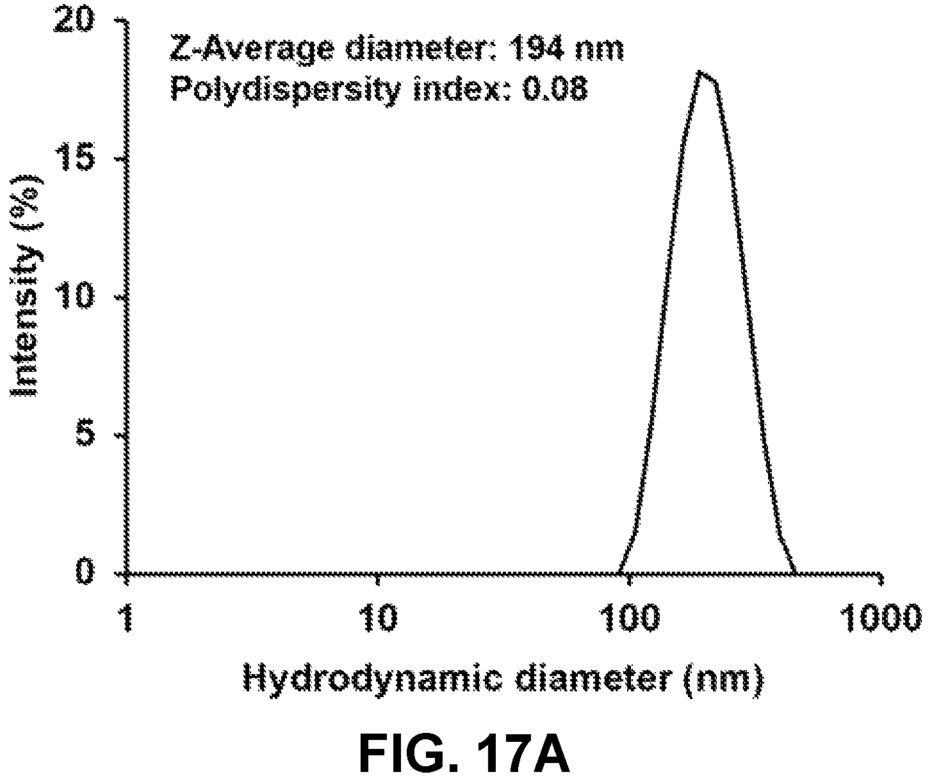
FIGS. 17A-17F. Average size of AMNPs was determined via dynamic light scattering in ultrapure water to be (FIG. 17A) 194 nm with a polydispersity index of 0.08 for AMNP-1.
Figure 17B:
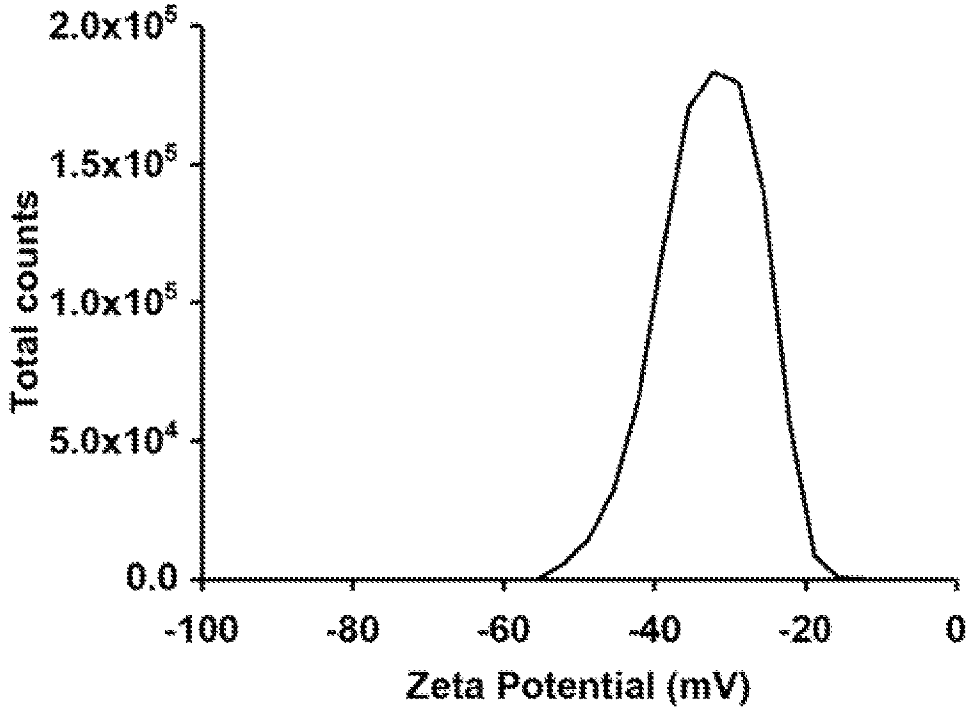
Figure 17C:
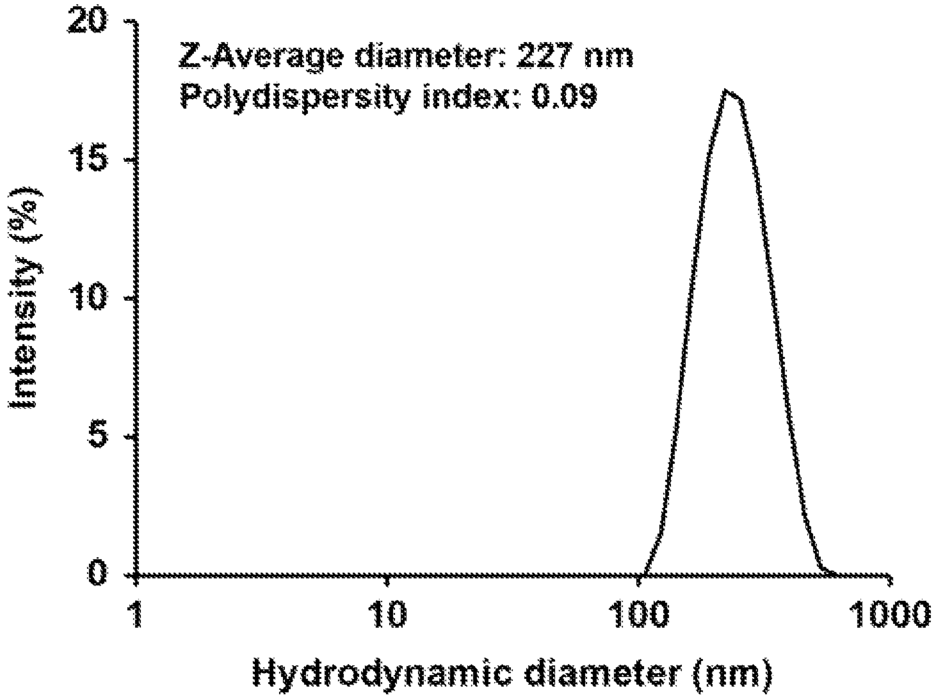
Figure 17D:
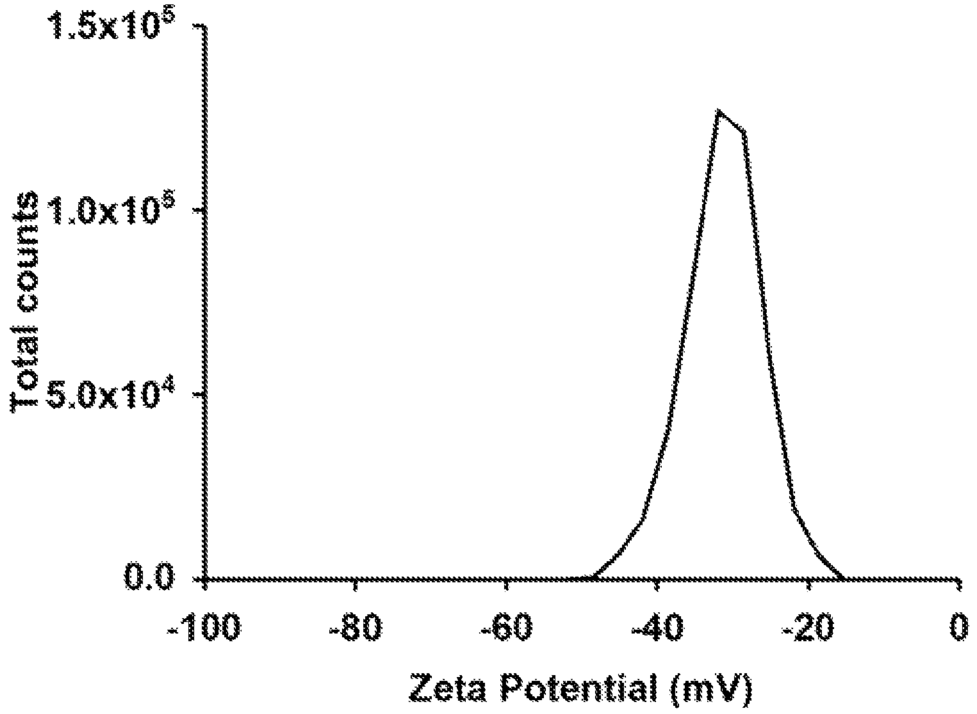
Figure 17E:
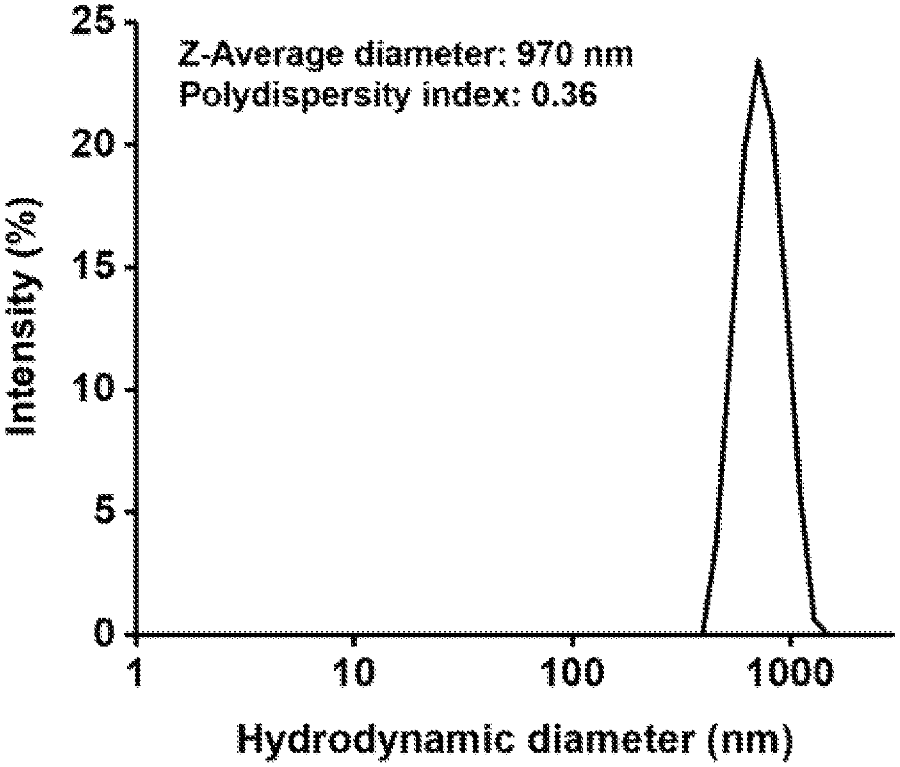
Figure 17F:
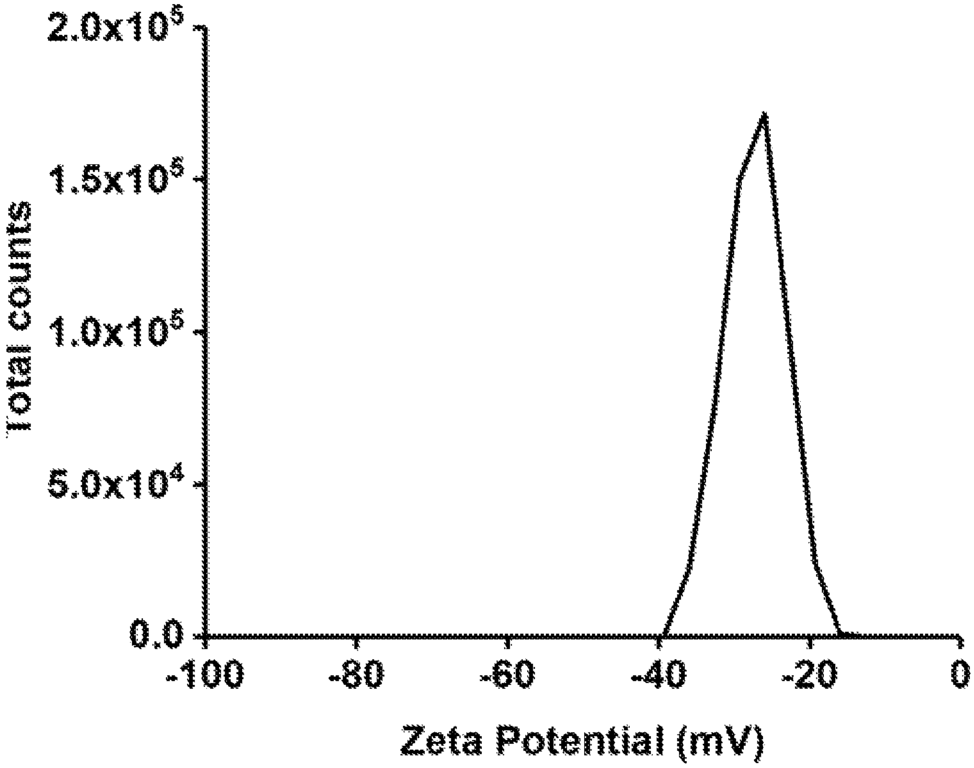
Figure 27:
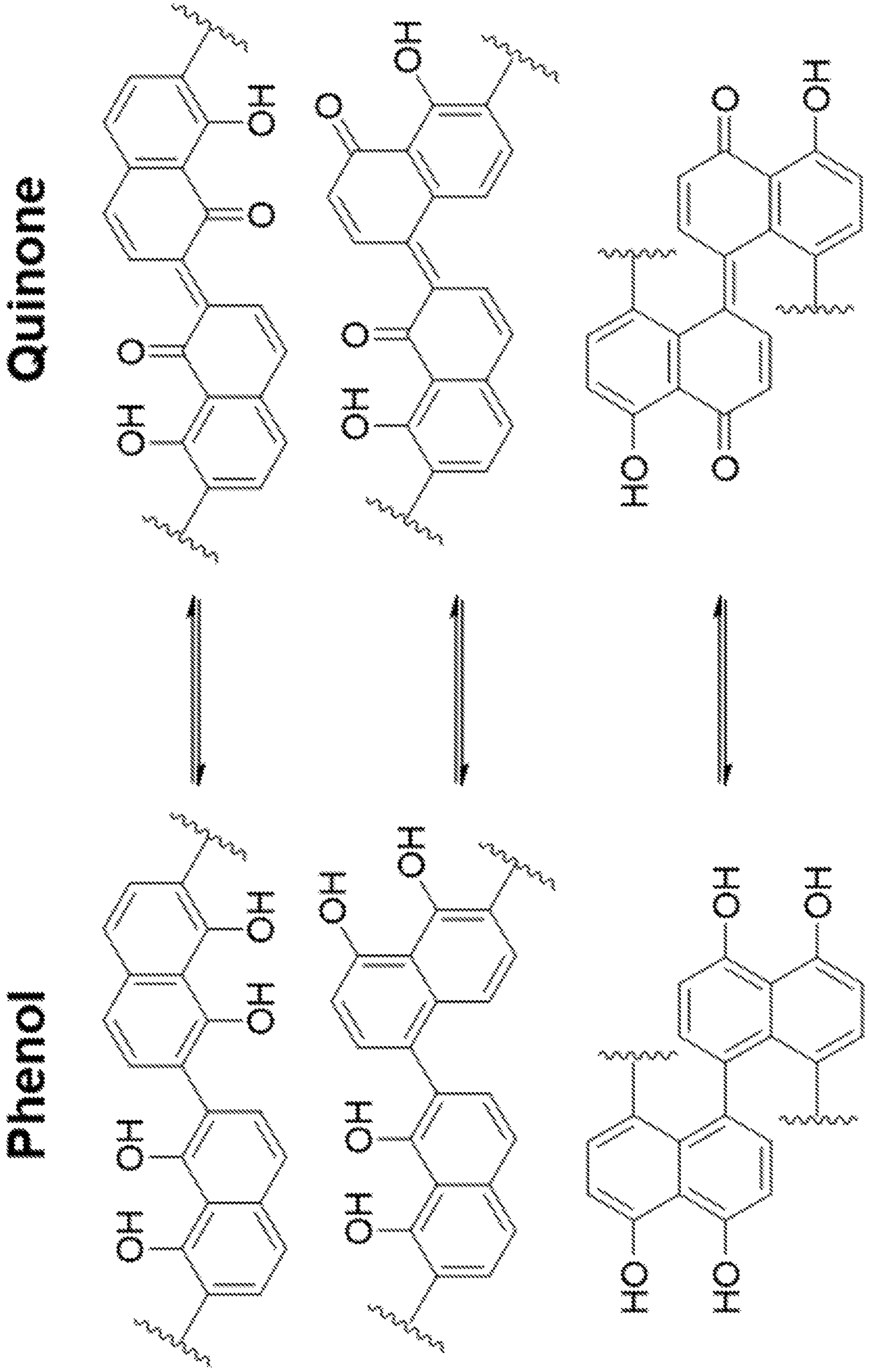
FIG. 27. Phenol/quinone structures in AMNPs.

Reversible Redox Activity of AMNPs. Natural melanins have been found to have reversible redox activities investigated using a method called mediated electrochemical probing (MEP).[42, 43] Here, we applied the same method to reveal the redox properties of AMNPs. First, AMNPs were entrapped within a chitosan hydrogel on a glassy carbon electrode surface. AMNPs were probed using two mediators, one oxidative mediator (300 M ferrocene dimethanol, Fc, $E^0$=+0.25 V vs Ag/AgCl) and one reductive mediator (300 M $Ru(NH_3)_6Cl_3$, $Ru^{3+}$, $E^0$=−0.20 V vs Ag/AgCl). A cyclic potential was applied to the electrodes (between −0.5 V and +0.5 V, 30 cycles, scan rate of 25 mV/s). The resulting cyclic voltammograms (CVs) showed significant amplification of both $Ru^{3+}$-reduction and Fc-oxidation currents as compared to the chitosan control (AMNP-1 FIG. 16, AMNP-2 FIG. 25, AMNP-3 FIG. 26), which are the characteristic feature of redox activity. In addition, AMNPs showed steady electrical output over 30 repeated cycles that provide evidence for reversible redox activity (FIGS. 16*b* and 16*d*). These studies reveal that AMNPs have reversible redox activities, and they can repeatedly donate and accept electrons with mediators. AMNPs have a redox potential that is between the two mediators (−0.20 V and +0.25V), corresponding to the redox potential for a phenol/quinone redox couple (FIG. 27) (i.e. the redox potential for a catechol/quinone redox couple is $E^0$=+0.20 V.[44, 45]).

Figure 6A:
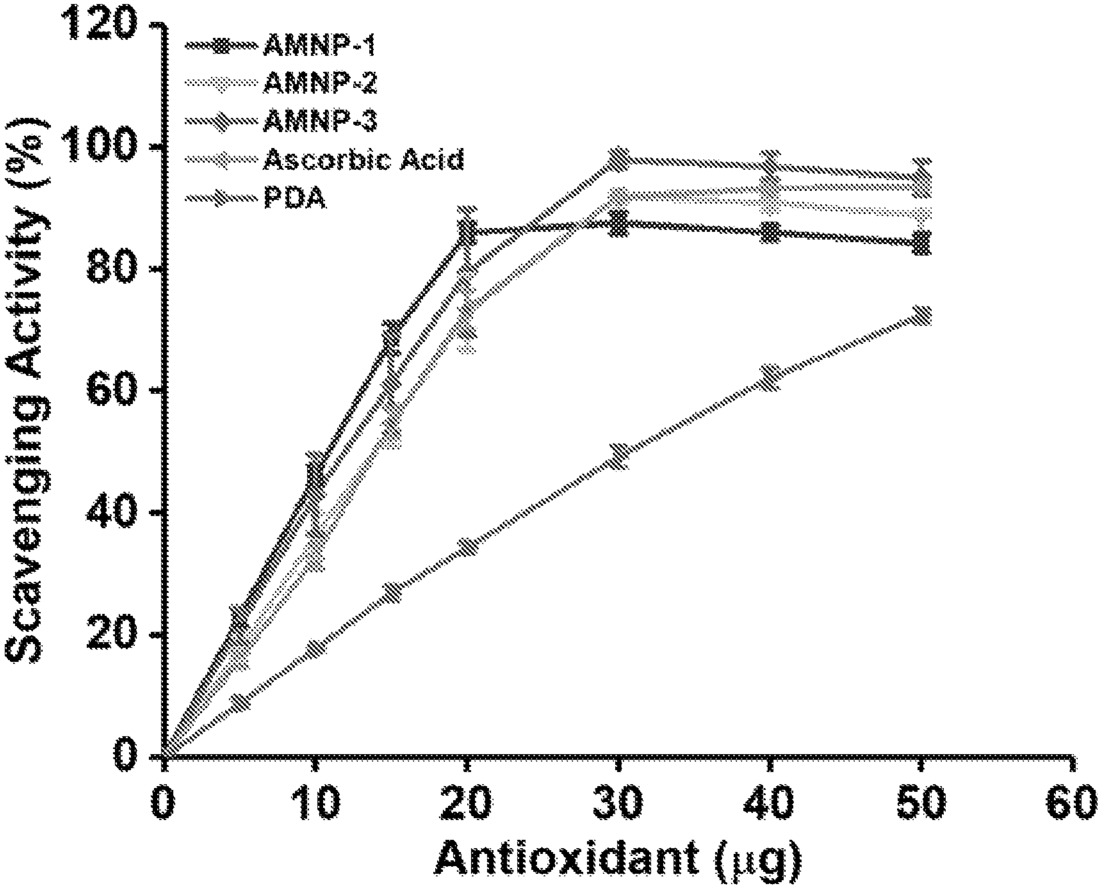
FIGS. 6A-6B. Radical scavenging by AMNPs compared to PDA-NPs and ascorbic acid.
Figure 6B:
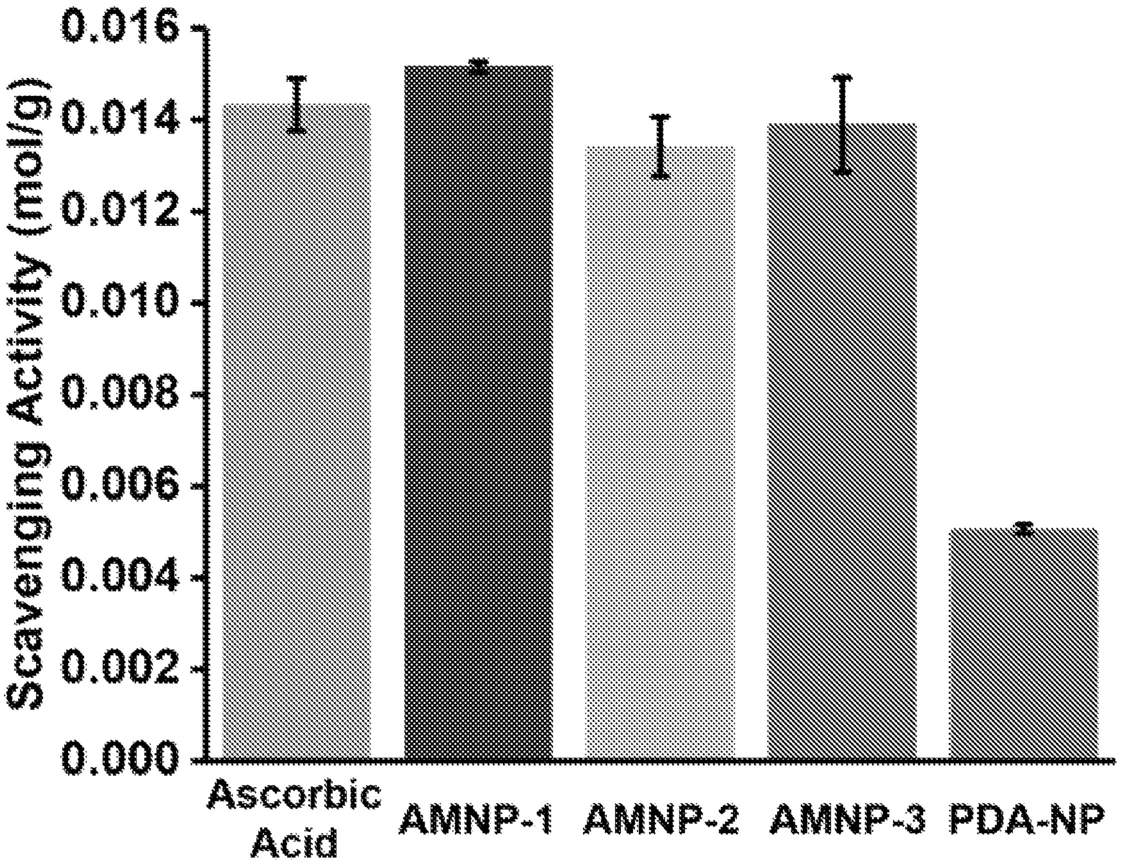
Figure 28A:
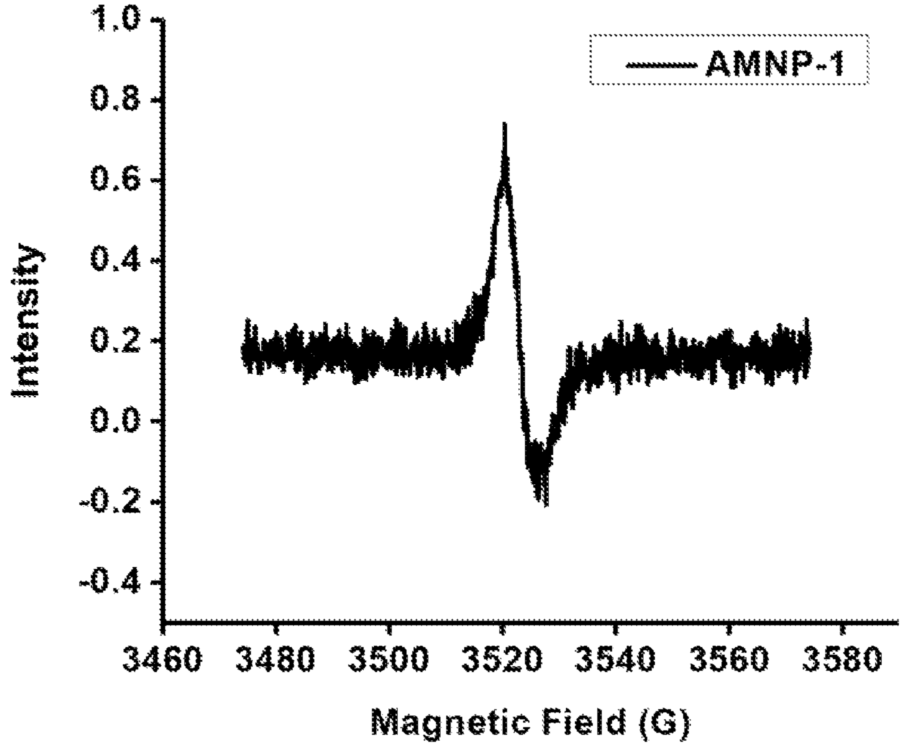
FIGS. 28A-28C. Electron paramagnetic resonance (EPR) spectrum of AMNPs.
Figure 28B:
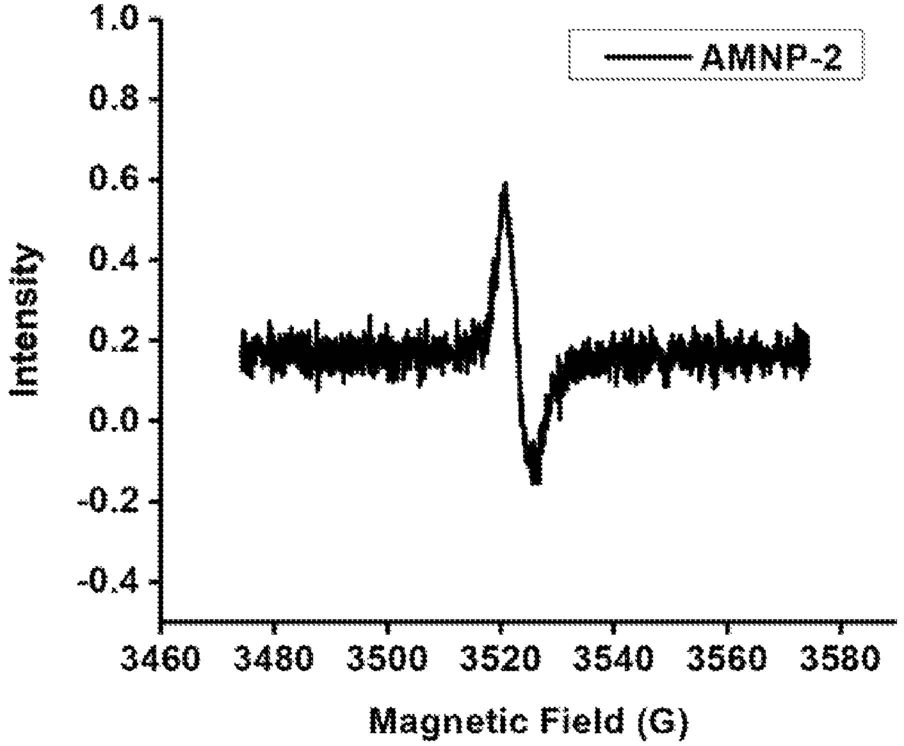
Figure 28C:
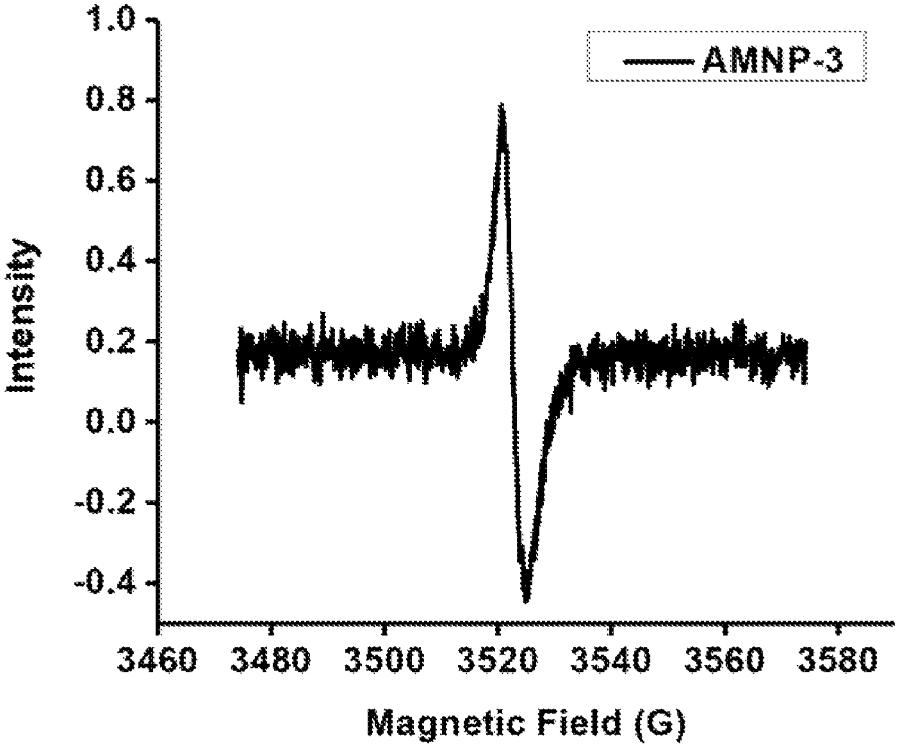
Figure 29A:
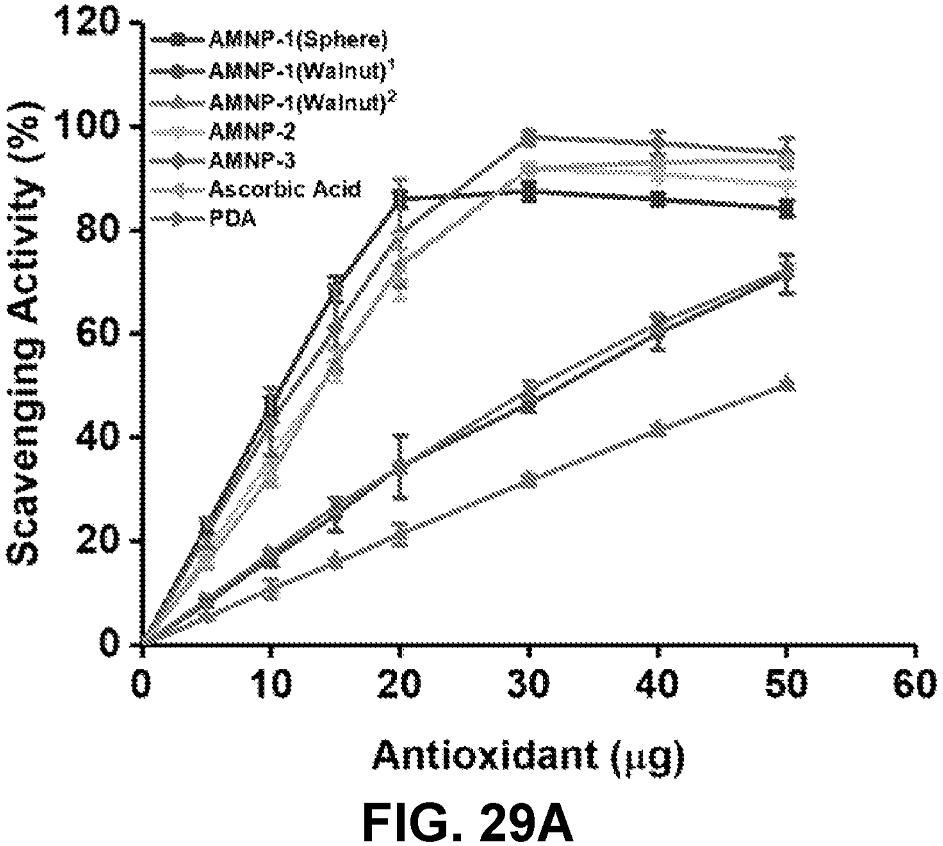
FIGS. 29A-29B. Radical scavenging by AMNPs compared to PDA-NPs and ascorbic acid.
Figure 29B:
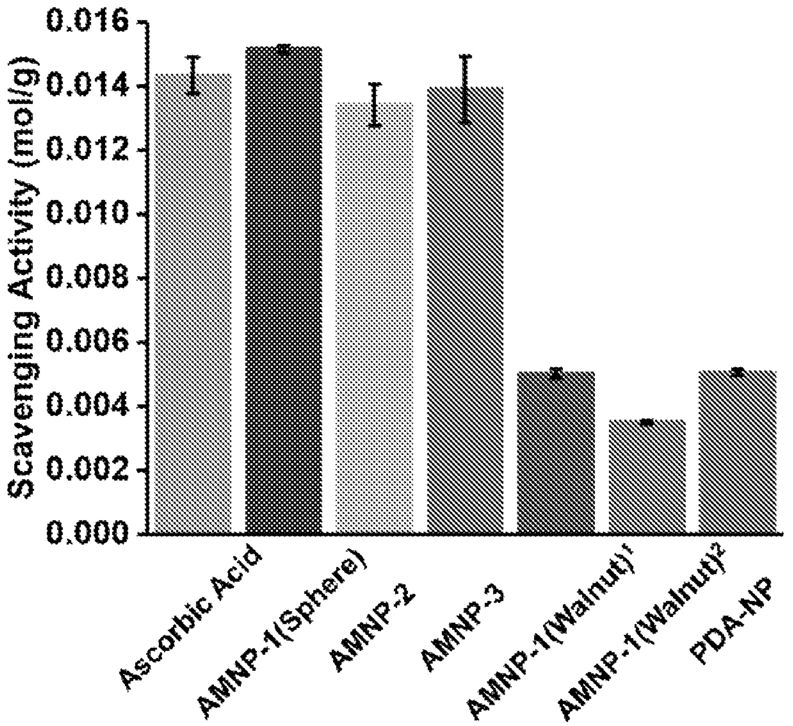

Radical Scavenging Activity of AMNPs. Melanin pigments extracted from several species of fungi have shown the ability to perform as natural antioxidants which can scavenge free-radicals (reactive nitrogen and oxygen species).[46] AMNPs were initially characterized by EPR to confirm the existence of free-radicals (FIG. 28). Next, the antioxidant properties of AMNPs were investigated using the 2,2-diphenyl-1-(2,4,6-trinitrophenyl) hydrazyl (DPPH) assay (FIGS. 6A-6B).[46] The scavenging activity was determined by monitoring the decrease in absorbance at 516 nm, indicative of the free radical DPPH. DPPH is reduced through an electron transfer from the antioxidant material, and the radical scavenging activity can be evaluated using UV-Vis spectroscopy. Free-radical scavenging activity of PDA-NPs and ascorbic acid, a known antioxidant, were included for comparison to that of the AMNPs (FIG. 6A). Scavenging activity for all three types of AMNPs was significantly higher than for PDA-NPs per gram of material (FIG. 6B). Based on these results, AMNPs show a much higher antioxidant activity than that of PDA-NPs, with similar activity to ascorbic acid. Radical scavenging activity of walnut-like AMNP-1 was also tested (FIG. 29), observing a trend of decreasing radical scavenging activity corresponding to increasing amount of NalO4 in AMNP-1, which could be attributed to a higher degree of oligomerization from over-oxidation of the particles.

Figure 7:
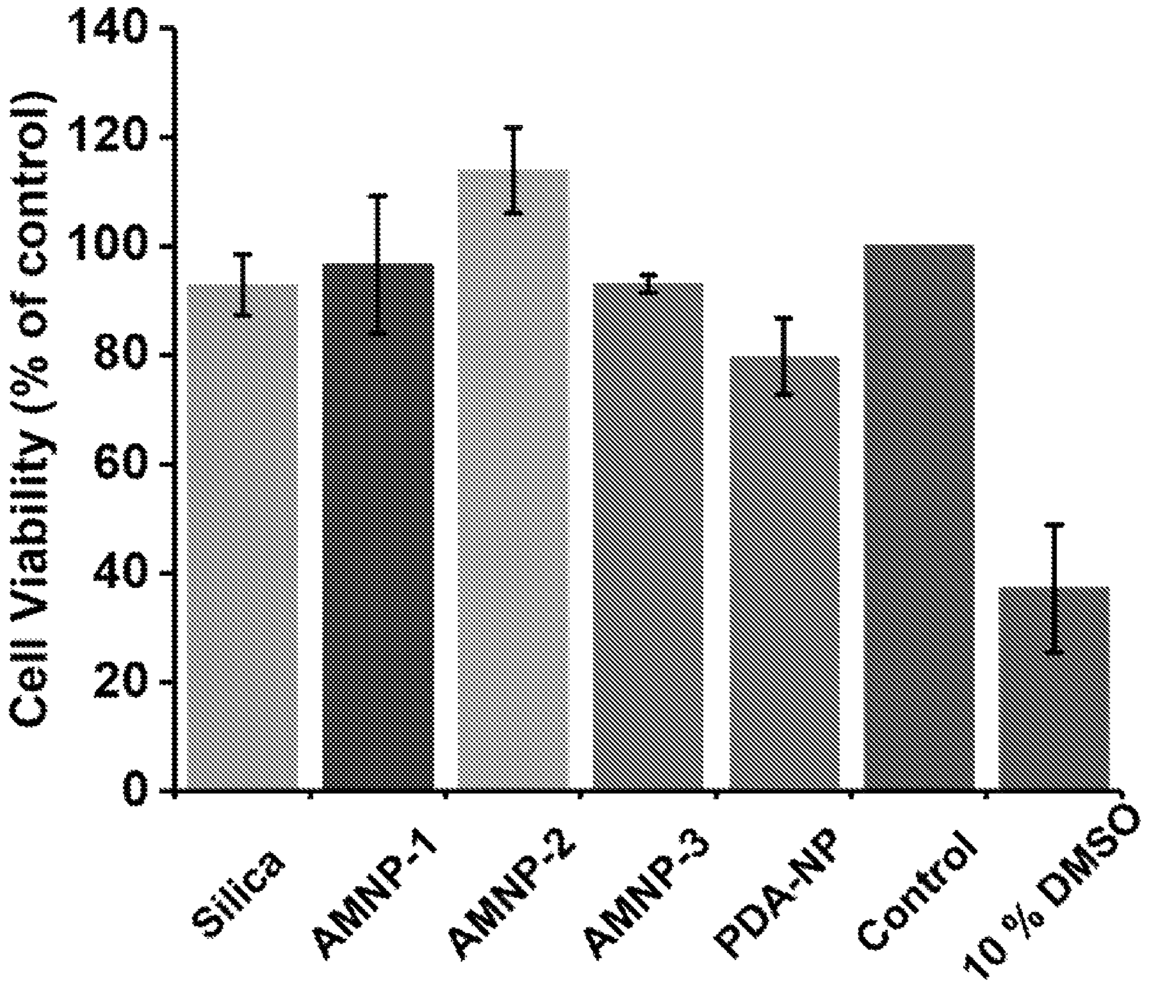
FIG. 7. Cell viability of NHEK cells incubated for 24 hours with 0.04 mg/mL of AMNPs, PDA-NPs, silica nanoparticles, or the vehicle (water) as a control, and assessed using the MTT assay. All values are relative to the control, normalized to 100%.

Cellular Uptake of AMNPs. Cell studies were performed to understand and probe the cellular compatibility and protective nature of AMNPs. PDA-NPs have been shown to serve as melanin mimics that are internalized by primary adult human keratinocytes to form perinuclear structures which serve as protective agents for the cells.[24] Here, we utilized primary neonatal human epidermal keratinocyte (NHEK) cells. Our ability to acquire a steady source of fresh tissue to isolate primary cells enabled us to obtain cells from different donors, increasing our sample size, thereby allowing for more rigor in our experiments. Furthermore, the NHEK cells were readily amenable to differentiation, which allowed for assessment of the penetration of AMNPs into more complex and developed cell monolayers. In initial uptake studies, undifferentiated NHEK cells were incubated with AMNPs, PDA-NPs (for PDA-NP SEM, TEM, DLS, and zeta potential analysis, see FIG. 30), or silica nanoparticles (for silica nanoparticle SEM, TEM, DLS, and zeta potential analysis, see FIG. 31). The PDA-NPs were used for comparison to previous studies, and the silica nanoparticles served as a non-toxic, non-melanin-based control particle of similar size and zeta potential to AMNPs. We also performed cryogenic TEM (cryo-TEM) on AMNPs to ascertain the stability of the particles in cell media (FIG. 32). The particles remain as discrete objects after incubation with cell media at 0.04 mg/mL for 48 hours, avoiding aggregation issues seen with some nanoparticle systems. After treatment of NHEK cells with 0.04 mg/mL of silica, AMNP, or PDA nanoparticles for 24 hours, we observed no appreciable cytotoxicity as compared to the vehicle-treated control (FIG. 7). This concentration was chosen as the near maximum amount that the cells can internalize before becoming coated on their surfaces.

Figure 8:
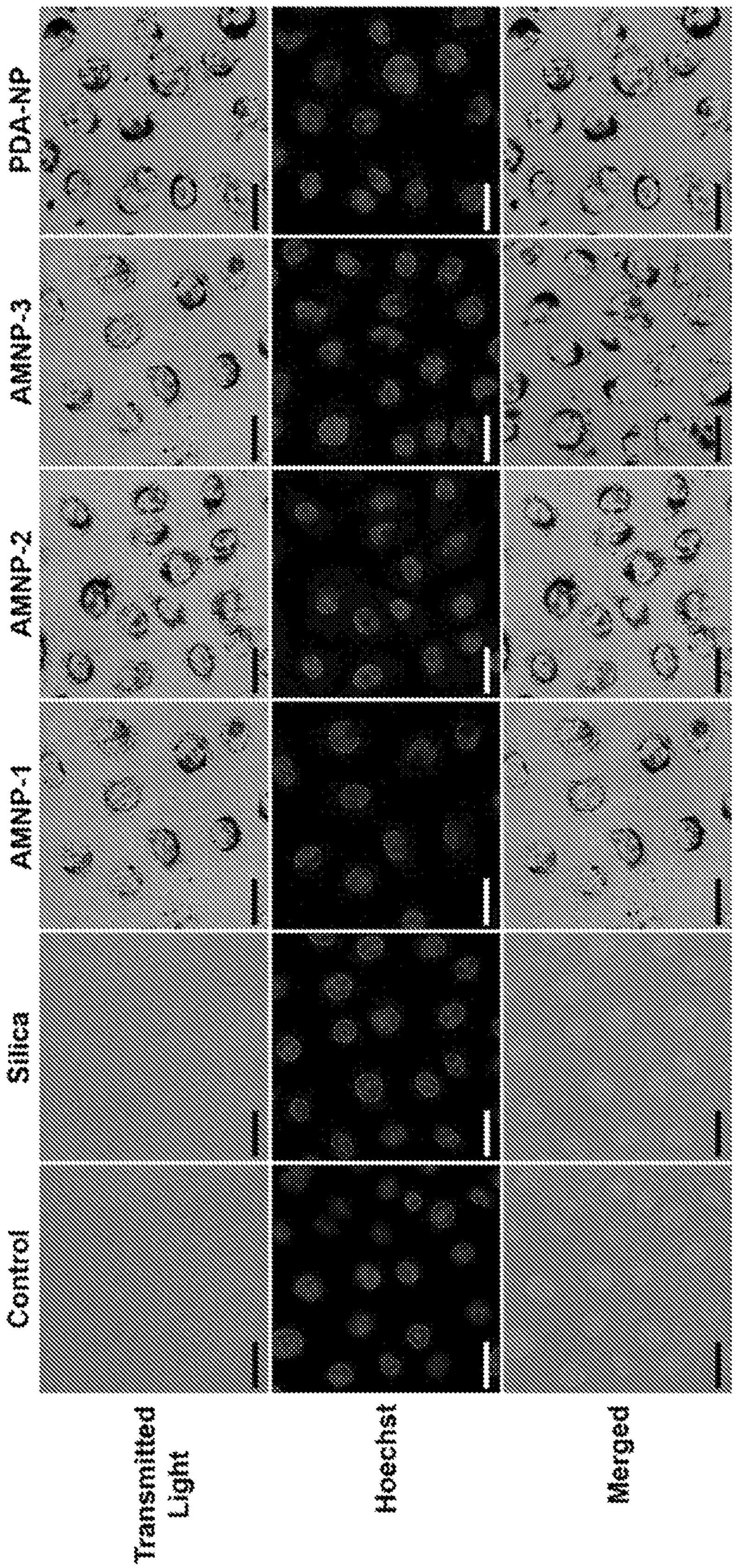
FIG. 8. Confocal microscopy of NHEK cells incubated with 0.04 mg/mL of particles for 48 hours. Microparasol formation is apparent as black crescents in the perinuclear region of each cell in the transmitted light images. Nuclei are labeled with Hoechst (blue). Scale bars 25 μm.

Cellular uptake of AMNPs resulted in trafficking of particles to the perinuclear region to form cap-like structures (also called microparasols), which are visibly similar to those formed after incubation with PDA-NPs (FIG. 8). This result is unexpected given the differences in chemistry between dopamine and 1,8-DHN precursors, and the lack of nitrogen in AMNPs, but suggests that the surface chemistry is perhaps sufficient to be recognized as melanin. The perinuclear structures are most apparent in transmitted light images where the caps appear black. They can be seen forming condensed structures around the nuclei in bright field and fluorescence merged images. At higher concentrations, caps begin to form 360° around the nucleus, however, at concentrations below 0.04 mg/mL they are commonly asymmetric and localized to one side of the nucleus, as in naturally melanized human keratinocytes.[47,48]

Figures 9A, 9B, 9C, 9D, 9E, 9F, 9G, 9H, 9I, 9J, 9K, 9L:
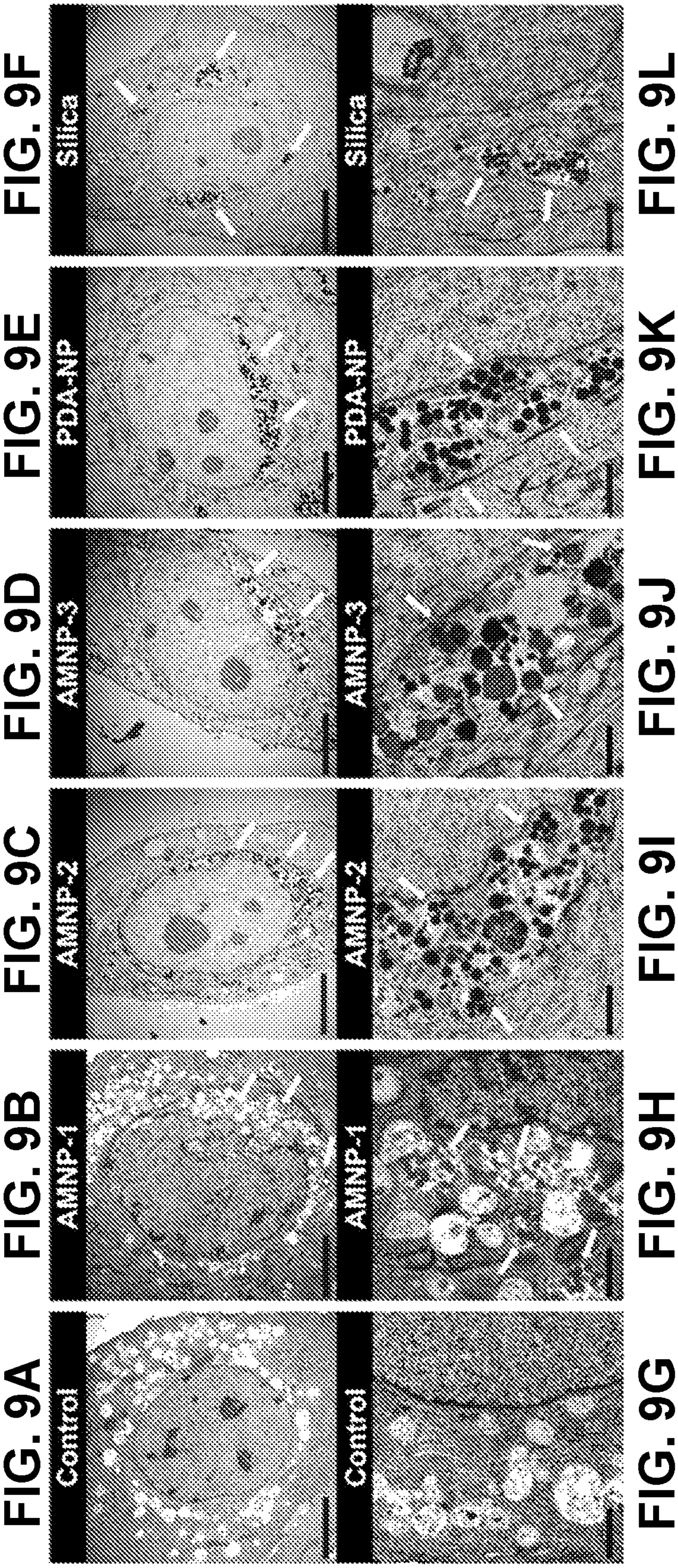
FIGS. 9A-9L. STEM micrographs of monolayer NHEK cells treated with the vehicle or 0.04 mg/mL AMNPs, PDA-NPs, or silica nanoparticles for 48 hours, resin-embedded, and sectioned to 60 nm thick. Images were acquired using an HAADF detector and the image contrast inverted to simulate traditional bright-field TEM images. Scale bars are 5 μm (FIGS. 9A-9F) and 1 μm (FIGS. 9G-9L). Arrows point to nanoparticles inside the cells.

NHEK cells in confluent monolayers were also exposed to high calcium media (1.2 mM) for 24 hours to partially induce epidermal differentiation (FIG. 33).[49] As in the non-differentiated cells, perinuclear caps are formed in these cells. To visualize the structures formed around the nuclei at high magnification and resolution, undifferentiated cells were grown in a monolayer, treated with nanoparticles, embedded in resin, and sectioned for scanning TEM (STEM) imaging (FIGS. 9A-9L, FIGS. 34-39). Images were acquired using a high-angle annular dark field (HAADF) detector and the contrast inverted to maintain the appearance of conventional bright-field TEM. All AMNPs form perinuclear caps, visible at lower magnification (FIGS. 9B-9D), and more detailed at higher magnification (FIGS. 9H-9J), in a similar fashion to PDA-NPs (FIGS. 9E and 9K). After treatment with silica nanoparticles, we observe a distribution of particles packaged in vesicles throughout the cell (FIGS. 9F and 9L).

Figure 10:
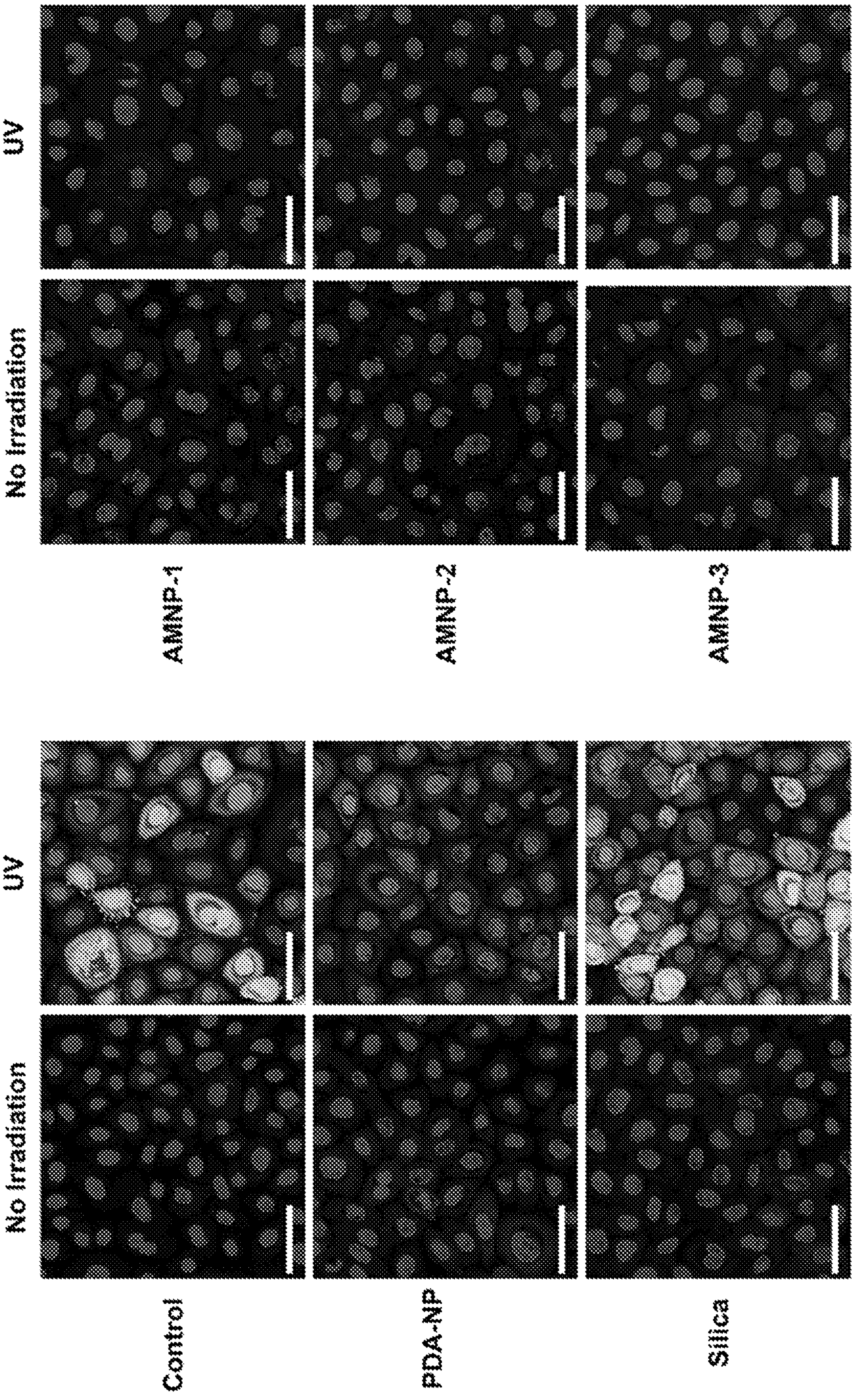
FIG. 10. Oxidative stress was assessed via the ROS-activated CM-$H_2$DCFDA dye (green). NHEK cells were incubated for 3 days with 0.02 mg/mL of AMNP-1, -2 and -3, PDA-NPs, silica nanoparticles, or the vehicle (water), treated with the dye, subjected to UV irradiation, and imaged live. Nuclei were stained with Hoechst (blue).
Figure 11:
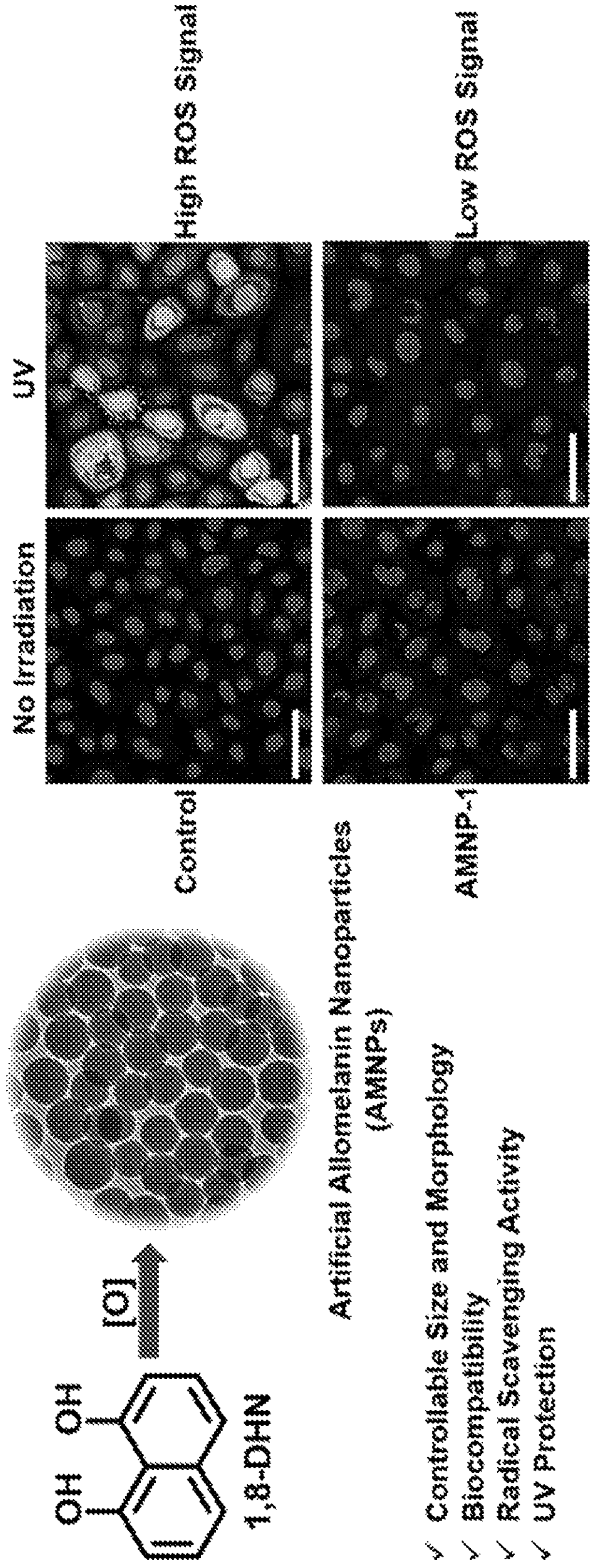
FIG. 11. A schematic illustrating some embodiments of the artificial melanin particles disclosed herein and their benefits.
Figure 12:
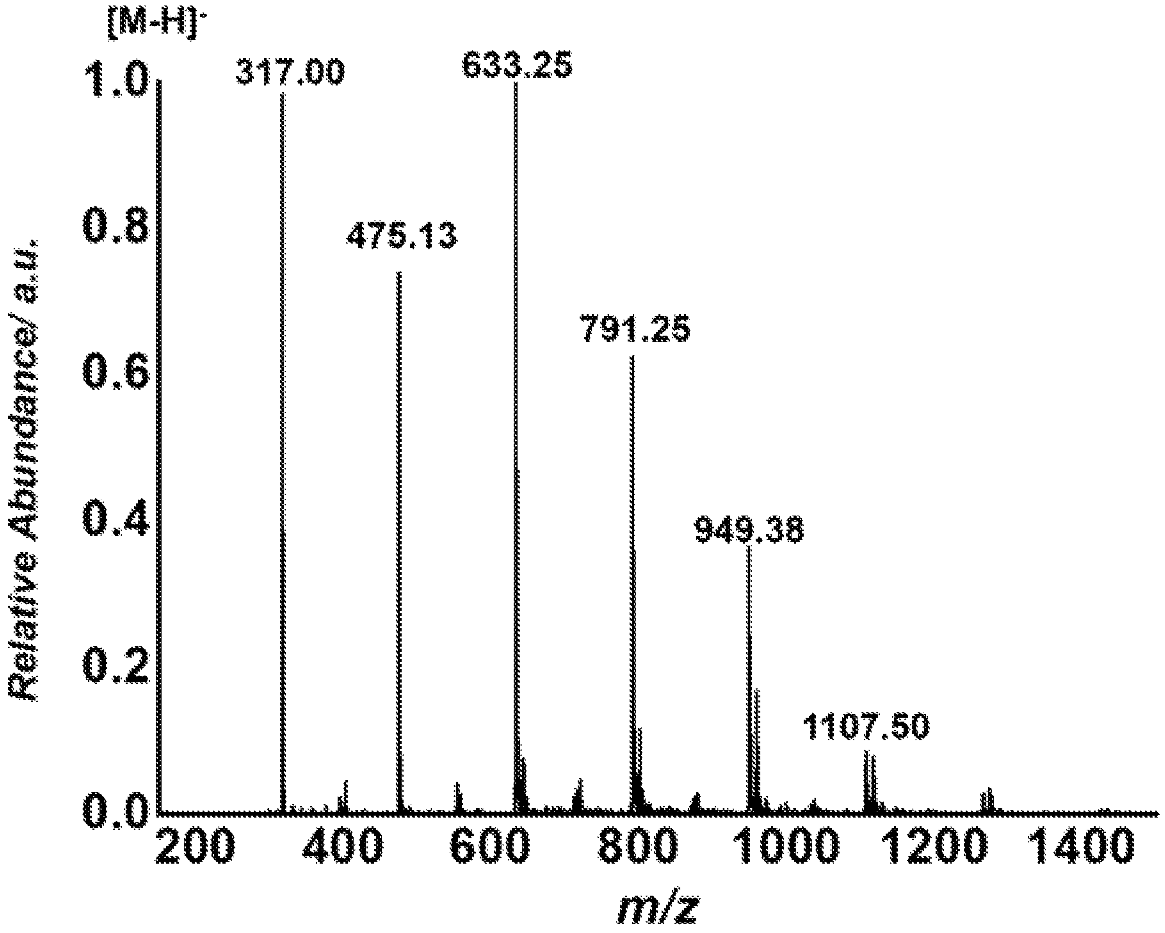
FIG. 12. ESI mass spectra of chemical synthetic DHN-melanin with the oxidizing agent $KMnO_4$.
Figure 13:
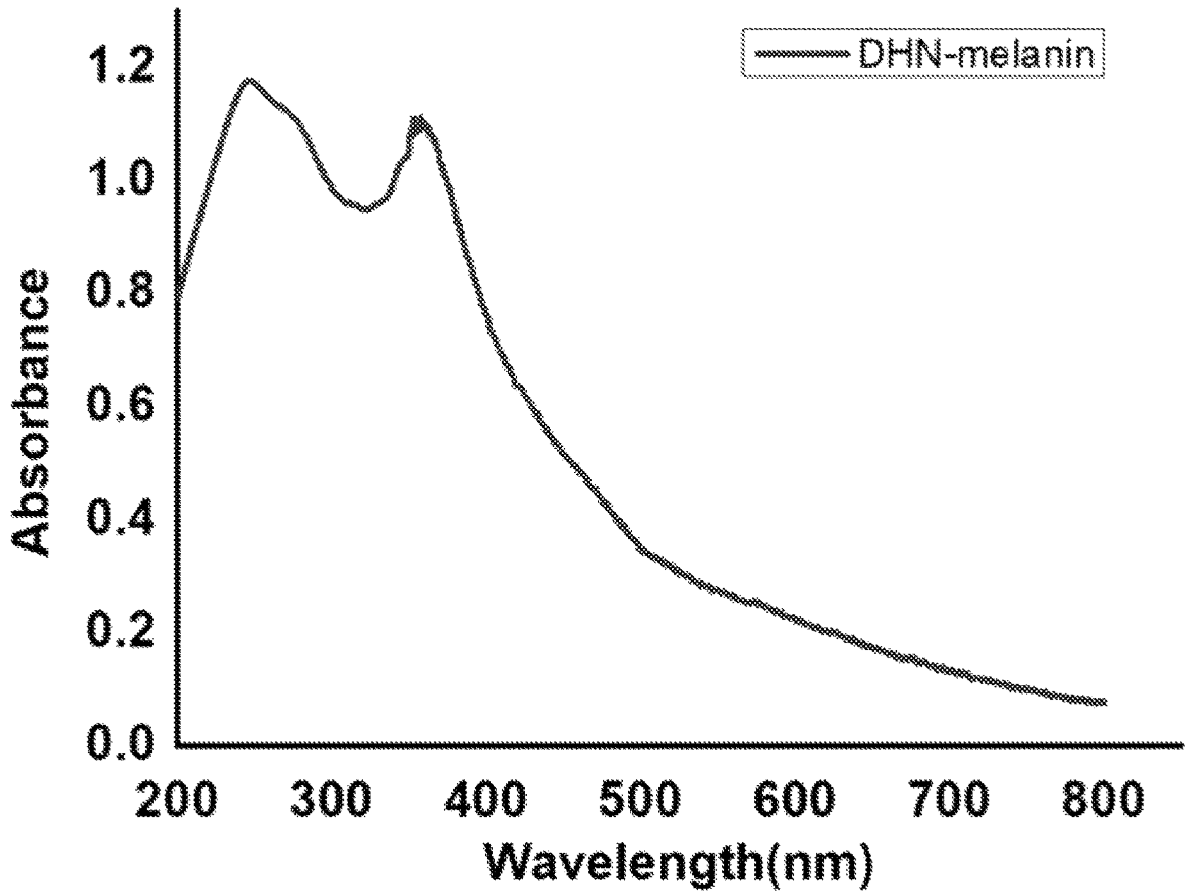
FIG. 13. UV-vis spectrum of chemical synthetic DHN-melanin using $NaIO_4$.
Figure 14:
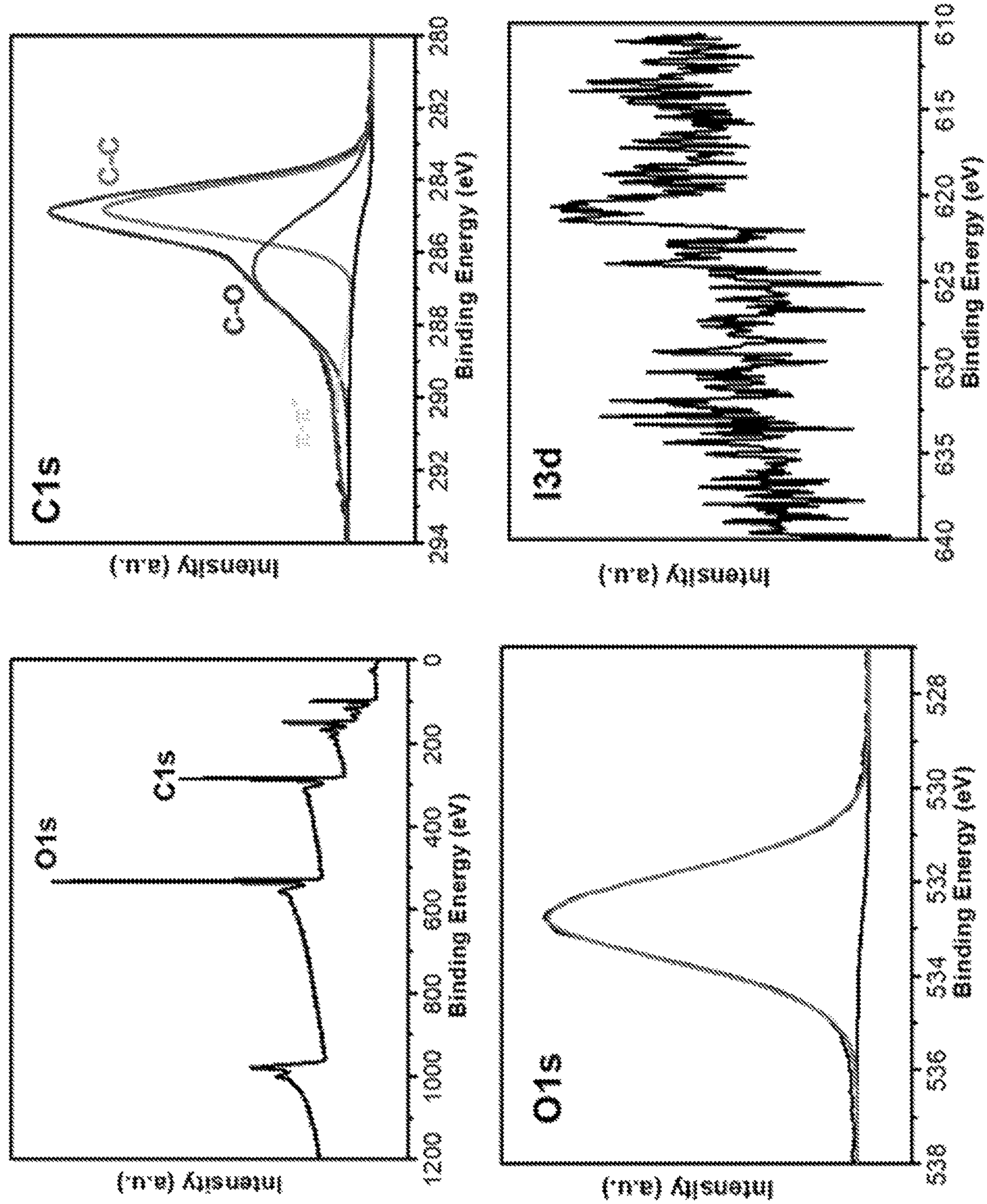
FIG. 14. XPS spectra of chemical synthetic DHN-melanin using $NaIO_4$.
Figure 15:
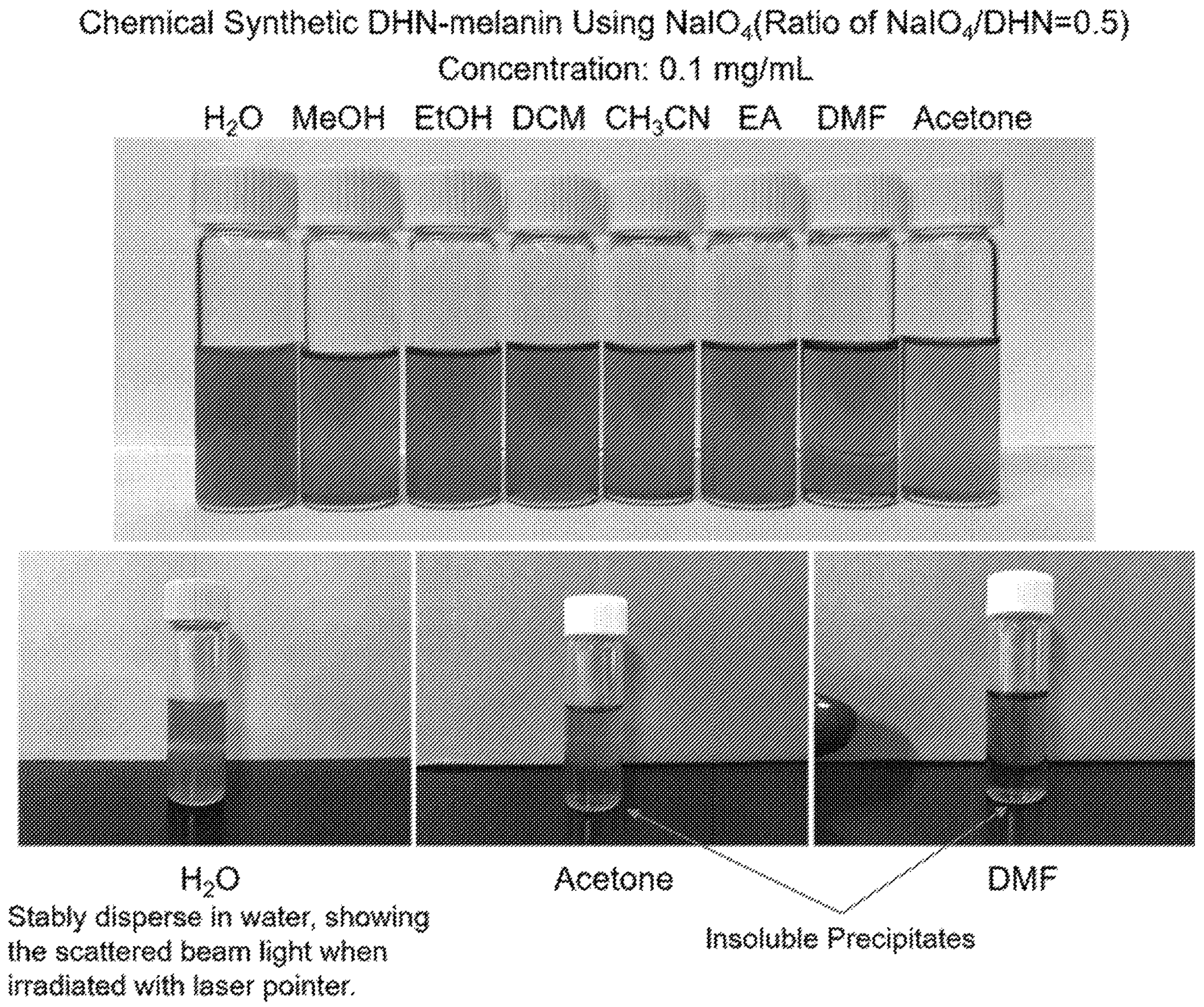
FIG. 15. Solubility of chemical synthetic DHN-melanin using $NaIO_4$ in different solvents.

Radiation Protection of AMNPs. To assess cellular protection ability, cells were treated for 3 days with either the vehicle or 0.02 mg/mL AMNPs, PDA-NPs or silica nanoparticles. They were subsequently incubated with 5/6-chloromethyl-2',7'-dichlorodihydrofluorescein diacetate (CM-$H_2$DCFDA), a pro-fluorescent dye that is ROS-responsive, and then directly exposed to 365 nm UV light for 2 minutes (FIG. 10). The control (vehicle-treated) and silica-treated cells showed a higher signal in the CM-$H_2$DCFDA channel than the AMNP- or PDA-NP-treated cells, indicating that AMNPs serve as effective antioxidants inside the cells.

Conclusion

In summary, we have developed methods for synthesizing artificial AMNPs from the precursor 1,8-DHN by oxidative oligomerization. We demonstrated the ability to access different morphologies of AMNPs by tuning the type and amount of oxidizing agent. For example, we could obtain uniform spherical and "walnut-like" AMNPs using $NaIO_4$. AMNPs were characterized by UV-Vis, FTIR, mass spectrometry, solid state NMR, and EPR, showing similar chemical makeup for each type of oxidant used. We observed from LCMS that the formation of AMNPs involves covalent coupling to form oligomers. This is then followed by the non-covalent self-assembly of oligomers to form AMNPs, observable by SEM, TEM and DLS. Furthermore, AMNPs were found to exhibit good radical scavenging abilities compared to PDA-NPs. In addition, these nitrogen-free melanins, not naturally found in humans, are not only biocompatible but are recognized, internalized, and packaged by NHEK cells as protective microparasol structures. Cells treated with AMNPs and subsequently exposed to UV irradiation show a decreased signal from an ROS-activated fluorophore, indicating that AMNPs are effective radical quenchers not only by themselves, but also in vitro in human cells. With a synthetic route in hand, and initially promising in vitro data showing radical scavenging and radiation protection, we propose AMNPs as of potential utility in sunscreens and in protective coatings.

Experimental Section

Synthesis of Artificial DHN-based Allomelanin Nanoparticles (AMNP-1 and AMNP-2). AMNP were prepared by oxidative oligomerization of 1,8-DHN in a solution containing sodium periodate ($NaIO_4$) or potassium permanganate ($KMnO_4$) at room temperature, open to ambient air.

For AMNP-1, 20 mg of 1,8-DHN was dissolved in 19.00 mL of ultrapure water and 1.00 mL acetonitrile. 124.9 μL of 1 N $NaIO_4$ was added to the mixture. After 12 h, AMNPs were retrieved by centrifugation (11,000 rpm, 10 min) and washed with ultrapure water five times.

For AMNP-2, 20 mg of 1,8-DHN was dissolved in 12.06 mL of 0.1 M HOAc—NaOAc buffer solution (pH=3.7) and 1.27 mL acetonitrile. 106.6 μL of 1 N $KMnO_4$ was added to the mixture. After 12 h, AMNPs were retrieved by centrifugation (11,000 rpm, 10 min) and washed with ultrapure water five times.

Synthesis of Laccase-mediated Chemoenzymatic DHN-based Allomelanin Nanoparticles (AMNP-3). AMNP-3 was prepared by laccase-mediated oligomerization of 1,8-DHN under acetate buffer solution at room temperature.[39] Briefly, 30 mg 1,8-DHN was dissolved in 17.10 mL of 0.1 M HOAc—NaOAc buffer solution (pH=5.0) and 1.90 mL acetonitrile. Laccase from *Trimetes versicolor*(0.66 EU $mg^{-1}$) dissolved in 1.00 mL of 0.1 M HOAc—NaOAc buffer was added to the mixture. Ambient air was bubbled into the solution for the first 5 min of the reaction, and then the reaction was completed open to ambient air over a period of 24 h. The reaction was quenched by 60 μL of a saturated sodium dithionite solution. AMNPs were retrieved by centrifugation (11,000 rpm, 10 min) and washed with ultrapure water five times.

Synthesis of Polydopamine Nanoparticles (PDA-NPs). PDA-NPs were synthesized through the oxidation and self-polymerization of dopamine in a solution consisting of water and sodium hydroxide at room temperature.[24] Typically, 150 mL of ultrapure water was fully mixed with 300 mg dopamine hydrochloride under stirring at room temperature for about 15 mins. Subsequently, 1.45 mL of 1 M NaOH was quickly injected into this solution. It was observed that the solution color turned to pale yellow immediately and then gradually changed to black. After 24 h, the targeted PDA-NPs were separated by centrifugation (10,000 rpm, 10 min) and washed with ultrapure water three times.

Synthesis of Silica Nanoparticles.[50] Silica nanoparticles were synthesized using the modified Stöber method, which utilizes a stepwise silica seed and growth synthesis. Specifically, the silica precursor, tetraethyl orthosilicate (TEOS, 0.48 ml) was mixed with ethanol (8 ml) while stirring for 10 min. Then, a mixture consisting of an ammonium hydroxide solution (28-30%, 0.7 ml), ethanol (8 ml) and ultrapure water (1.2 ml), was continuously added dropwise into the above precursor solution. The silica seeds grew at room temperature under constant stirring for six hours, were collected by centrifugation (12,000 rpm, 10 min), and were washed with ultrapure water four times. The as-prepared silica seeds (12.6 mg) were dispersed in water (0.6 ml) by sonication, and then mixed with ethanol (4 ml) and ammonium hydroxide (28-30%, 0.4 ml). A solution mixture containing TEOS (0.24 ml) and ethanol (4 ml) was added into the above silica seed solution and reacted under constant stirring for another 85 min. The resulting silica nanoparticles were collected using centrifugation (10,000 rpm, 7 min), and washed with ultrapure water four times.

DPPH Assay for Antioxidant Activity of AMNPs. DPPH radical scavenging activity of AMNPs was measured according to the literature.[46] Briefly, 0.2 mM of DPPH solution in 95% ethanol was prepared before use, and then 100 μL of AMNPs dispersed in water was mixed with 1.8 mL of the DPPH solution. The total amount of AMNPs was varied from 5 to 50 μg in each solution. The scavenging activity was evaluated by monitoring the absorbance decrease at 516 nm after it remained in the dark for 20 min.

DPPH radical scavenging activity was calculated as I=[1−(Ai−Aj)/Ac]*100%, where Ac is the absorbance of DPPH solution without AMNPs samples, Ai is the absorbance of the samples of AMNPs mixed with DPPH solution, and Aj is the absorbance of the samples of AMNPs themselves without DPPH solution. PDA-NPs were used for comparison and ascorbic acid was used as a positive control. The amount of quenched DPPH per gram of antioxidant was calculated by first obtaining the slope from a linear fit of the scavenging activity. The absolute value of this slope represents the absorbance of quenched DPPH per gram of antioxidant. After making a standard curve of DPPH to convert absorbance to moles, the scavenging activity (mol/g) was obtained for each antioxidant.

Cell Culture. Primary neonatal epidermal keratinocyte (NHEK) cells were isolated from freshly excised neonatal foreskins and gifted by the Perez-White lab at Northwestern Feinberg School of Medicine. To isolate the cells, the tissue was treated overnight with dispase and then incubated with 0.25% trypsin with 1 mM EDTA for 10 min at 37° C. The trypsin was neutralized with FBS, the cells suspended in PBS, filtered through a 40 μm sieve, and then centrifuged at 1,000 rpm for 5 minutes. The cell pellets were resuspended in, and subsequently maintained in, M154 medium supplemented with human keratinocyte growth supplement (HKGS), 10 μg/mL gentamicin, 0.25 μg/mL amphotericin B, and 0.07 mM $CaCl_2$, and maintained at 37° C. with 5% $CO_2$. For differentiation, the cells were plated to confluency in complete media with 0.07 mM $CaCl_2$) for 24 hours, switched to complete media with 0.03 mM $CaCl_2$) for 24 hours, and then switched to media with 1.2 mM $CaCl_2$) (without HKGS) for 24 hours before incubation of the nanoparticles.

Cell Viability Assay. NHEK cells were maintained at 37° C. with 5% $CO_2$. They were incubated with AMNPs, PDA-NPs, or silica nanoparticles at a final concentration of 0.04 mg/mL, the vehicle (sterile water, 2 μL), or 10% DMSO for 24 hours. After 24 hours, they were rinsed with DPBS and then incubated with thiazolyl blue tetrazolium bromide (MTT) at a final concentration of 0.5 mg/mL for 4 hours. The solution was carefully removed and the MTT crystals were dissolved in DMSO and incubated for 15 minutes at 37° C. Absorbance at 590 nm was recorded and all treatment values were calculated as a percentage of the controls, which were normalized to 100%.

Live Cell Confocal Microscopy. Microparasol formation and the ROS assay (FIG. 8 and FIG. 10, respectively) were imaged using live cells in a humidity controlled chamber maintained at 37° C. and supplemented with 5% $CO_2$.

ROS Assay. NHEK cells were incubated with 0.02 mg/mL AMNPs, PDA-NPs, or silica nanoparticles for 3 days, rinsed with DPBS, and then incubated with 4 μM CM-$H_2$DCFDA in DPBS for 45 minutes at 37° C. The cells were rinsed with DPBS and then allowed a 10-minute recovery time in complete growth medium at 37° C. The cells were then subjected to irradiation by a 365 nm, 8 W lamp with an irradiance of 2.25 mW/$cm^2$ for 2 minutes at a height of 18 mm. Hoechst 33342 was added to each well, incubated for 15 minutes at room temperature, and then the cells were imaged live. A Thorlabs S120VC standard photodiode power sensor was used to determine the irradiance of the lamp.

Preparation of Cells for TEM Imaging. NHEK cells were grown on 13 mm Thermanox™ coverslips and fixed in 0.1 M sodium phosphate or PIPES buffer with 2.5% glutaraldehyde and 2% paraformaldehyde. After a fresh exchange of fixative, the cells were microwave processed using a Pelco Biowave. The samples were post-fixed with 1% $OsO_4$ in water or 1% $OsO_4$ in imidazole followed by 1% uranyl acetate. Dehydration occurred with a graded series of ethanol and acetone prior to infiltration with EMBed812 epoxy resin. The cells were embedded flat in upturned BEEM® capsules and the resin polymerized at 60° C. for 48 hours prior to ultramicrotomy in a Leica EM UC7 Ultramicrotome. Ultra-thin sections (60 nm) were post-stained with uranyl acetate and Reynolds lead citrate. Image data was gathered on a Hitachi HD2300 cFEG STEM with an HAADF detector at 80 kV. Finally, image contrast was inverted to simulate traditional bright-field TEM images.

Supplemental Information for Example 1

Materials and Methods

Materials 1,8-Dihydroxynaphthalene (1,8-DHN) (95+%) was purchased from Matrix Scientific. Dopamine hydrochloride (99%) was purchased from Alfa Aesar. Tetraethyl orthosilicate (TEOS) (98%) and sodium phosphate monobasic dihydrate (98%) were purchased from Acros Organics. Laccase from *Trimetes versicolor* (0.5 U/mg), 2,2-Diphenyl-1-(2,4,6-trinitrophenyl) hydrazyl (DPPH), ammonium hydroxide solution (28-30%), sodium phosphate dibasic (99.0%), chitosan (molecular weight, 50,000-190,000 Da), 1,1'-ferrocenedimethanol (Fc) (97%) and hexaammineruthenium(II) chloride ($Ru(NH_3)_6Cl_3$) (99.9%) were purchased from Sigma-Aldrich. Sodium hydroxide (NaOH) (extra pure), potassium permanganate ($KMnO_4$) (99%), sodium periodate ($NaIO_4$) (99.8%), HPLC-grade acetonitrile ($CH_3CN$) (≥99.99%), acetic acid (HOAc) (99.7%), sodium acetate trihydrate ($NaOAc.3H_2O$) (99%), sodium dithionite (laboratory grade), and all other chemical reagents were purchased from ThermoFisher Scientific unless otherwise noted. Ethanol (200 proof) was purchased from Flinn Scientific. All chemicals were used as received. Ultrapure water was purified using a Branstead GenPure xCAD Plus system from ThermoFisher Scientific and used in all experiments. All grids for transmission electron microscopy (TEM) and scanning electron microscopy (SEM) were purchased from Electron Microscopy Sciences (EMS) unless otherwise noted. Cryogenic TEM (cryoTEM) was performed on QUANTIFOIL® Q250-CR2 holey carbon copper grids. Cell sections were imaged on 1-2 mm slotted copper formvar/carbon grids. Lacey carbon, 300 mesh, copper grids were purchased from Ted Pella. Grids were surface plasma treated using a PELCO easiGlow glow discharge cleaning system. Cell viability was performed using the thiazolyl blue tetrazolium bromide (MTT) reagent (98%) from Sigma Aldrich. Neonatal human epidermal keratinocyte (NHEK) cells were donated by the Bethany Perez-White Lab at Northwestern University Feinberg School of Medicine. All other cell culture reagents were acquired from ThermoFisher Scientific.

Instrumentation

SEM images were acquired on a Hitachi S4800-II cFEG SEM and a Hitachi SU8030. Dry state TEM of nanoparticles was conducted on a Hitachi HT-7700 biological TEM at an acceleration voltage of 120 kV. CryoTEM experiments were performed on a JEOL ARM300F (300 kV) with a cryo holder and transfer station (Gatan Inc., USA) operating at ~−170° C. UV-Vis spectra were recorded using a NanoDrop 2000c UV-Vis spectrophotometer. Fourier transform infrared spectrometry (FTIR) spectra were obtained on a Nexus 870 spectrometer (Thermo Nicolet). Electrospray ionization mass spectrometry (ESI-MS) spectra were acquired on a Bruker AmaZon SL. Liquid chromatography-mass spectrometry (LCMS) experiments were conducted on a Bruker AmaZon X. Analytical high-performance liquid chromatography (HPLC) analysis was performed on a Jupiter 4u Proteo 90A Phenomenex column (150×4.60 mm) using a Hitachi-Elite LaChrom L-2130 pump equipped with UV-Vis detector (Hitachi-Elite LaChrom L-2420). Matrix assisted laser desorption/ionization-time of flight mass spectrometry (MALDI-TOF MS) spectra were obtained on a Bruker AutoFlex-III. Solid-state NMR (ssNMR) spectra were recorded on a Mercury 400 (Bruker Avance III HD) equipped with Bruker 4 mm HX probe. Hydrodynamic diameters and zeta potentials were measured on a Zetasizer. Continuous wave electron paramagnetic resonance (EPR) spectra were obtained at X-band (9.5 GHz) fields using Bruker Elexsys E680 spectrometer equipped with a 4122SHQE resonator. Cyclic voltammetry (CV) measurements were carried out at room temperature with a Gamry Multipurpose instrument (Reference 600) interfaced to a PC. Cell viability assays were read on a Biotek Synergy Neo2 plate reader. Confocal images were obtained on a Leica SP5 laser scanning confocal microscope. Resin-embedded cells were microtomed using a Leica EM UC7/FC7 cryo-ultramicrotome and imaged on a Hitachi HD2300 cFEG STEM microscope with a high-angle annular dark field (HAADF) detector at an acceleration voltage of 80 kV. Cell irradiation was performed with a UVP 8 W, 365 nm UVLS-28 EL Series lamp.

MALDI-TOF Sample Preparation

MALDI-TOF measurements were performed on a Bruker AutoFlex-III time of flight instrument, operating in negative reflectron mode. AMNPs were suspended in ultrapure water to reach a final concentration of 0.01 mM. This solution was mixed with a saturated solution of the matrix (2,5-dihydroxybenzoinc acid, DHB) in water (50:50 volume ratio). This suspension was deposited on the stainless-steel sample holder and air-dried. Mass spectra were obtained by averaging the ions from 5000 laser shots.

Solid State NMR

AMNPs were dried under vacuum. Approximate 80 mg solid powder was loaded into a 4 mm rotor with special tools. The rotor was inserted into the probe from the top of the magnet, then a special cage was put immediately at the magnet top. The sample was spun to 15,000 Hz. After tuning $^{13}C$ first, then $^{1}H$, the proton decoupled $^{13}C$ data were acquired.

Electron Paramagnetic Resonance Spectroscopy

Continuous wave electron paramagnetic resonance (EPR) spectra were obtained at X-band (9.5 GHz) fields using Bruker Elexsys E680 spectrometer equipped with a 4122SHQE resonator. Scans were performed with magnetic field modulation amplitude of 2 G and non-saturating microwave power 1.544 mW, 32 scans of average. Samples were contained in quartz tubes with I.D. 1.50 mm and O.D. 1.80 mm.

Preparation of AMNP-Chitosan Film[1]

To prepare the AMNP-chitosan film, AMNPs (5 mg/mL) were suspended in a chitosan solution (0.5%, pH 5.5), and 20 μL of this suspension was spread onto a glassy carbon working electrode (0.071 $cm^2$). The films were vacuum-dried at room temperature for 30 min and then immersed in phosphate buffer (0.1 M, pH 7.0) for 10 min to neutralize the chitosan and form a hydrogel. In all studies, we used an AMNP-free chitosan film as a control.

Mediated Electrochemical Probing[1]

Cyclic voltammetry was performed using a three electrode system, which consisted of a glassy carbon electrode as a working electrode, Ag/AgCl as a reference electrode, and a Pt wire as a counter electrode. The glassy carbon electrode surface was polished routinely with a 0.3 μm alumina-water slurry on a felt surface immediately before use. The three electrodes were immersed into an electrochemical cell and each electrode connected with an electrochemical analyzer. During the experiment, air was excluded by purging $N_2$ through a tube in the cell. Two mediators in 0.1 M phosphate buffer (pH 7.0) including one oxidative mediator (300 μM ferrocene dimethanol, Fc, $E^0$=+0.25 V vs Ag/AgCl) and one reductive mediator (300 μM $Ru(NH_3)_6Cl_3$, $Ru^{3+}$, $E^0$=−0.20 V vs Ag/AgCl) were applied. The scan rate was 25 mV/s.

REFERENCES CORRESPONDING TO EXAMPLE 1

(1) Solano, F. Melanins: Skin Pigments and Much More-Types, Structural Models, Biological Functions, and Formation Routes. *New J. Sci.* 2014, 2014, 28.

(2) Hong, L.; Simon, J. D. Current Understanding of the Binding Sites, Capacity, Affinity, and Biological Significance of Metals in Melanin. *J. Phys. Chem. B* 2007, 111, 7938-7947.

(3) Liu, Y.; Hong, L.; Kempf, V. R.; Wakamatsu, K.; Ito, S.; Simon, J. D. Ion-Exchange and Adsorption of Fe(III) by Sepia *Melanin. Pigm. Cell Res.* 2004, 17, 262-269.

(4) Lian, H.; Yan, L.; D., S. J. Binding of Metal Ions to Melanin and Their Effects on the Aerobic Reactivity¶. *Photochem. Photobiol.* 2004, 80, 477-481.

(5) Tada, M.; Kohno, M.; Niwano, Y. Scavenging or Quenching Effect of Melanin on Superoxide Anion and Singlet Oxygen. *J. Clin. Biochem. Nutr.* 2010, 46, 224-228.

(6) Seagle, B.-L. L.; Rezai, K. A.; Gasyna, E. M.; Kobori, Y.; Rezaei, K. A.; Norris, J. R. Time-Resolved Detection of Melanin Free Radicals Quenching Reactive Oxygen Species. *J. Am. Chem. Soc.* 2005, 127, 11220-11221.

(7) Boulton, M.; Różanowska, M.; Różanowski, B. Retinal Photodamage. *J. Photochem. Photobiol. B: Biol.* 2001, 64, 144-161.

(8) Brenner, M.; Hearing, V. J. The Protective Role of Melanin Against UV Damage in Human Skin†. *Photochem. Photobiol.* 2007, 84, 539-549.

(9) Kobayashi, N.; Muramatsu, T.; Yamashina, Y.; Shirai, T.; Ohnishi, T.; Mori, T. Melanin Reduces Ultraviolet-Induced DNA Damage Formation and Killing Rate in Cultured Human Melanoma Cells. *J. Invest. Dermatol.* 1993, 101, 685-689.

(10) Tadokoro, T.; Kobayashi, N.; Zmudzka, B. Z.; Ito, S.; Wakamatsu, K.; Yamaguchi, Y.; Korossy, K. S.; Miller, S. A.; Beer, J. Z.; Hearing, V. J. UV-Induced DNA Damage and Melanin Content in Human Skin Differing in Racial/Ethnic Origin. *FASEB J.* 2003, 17, 1177-1179.

(11) Park, J.-Y.; Kim, S.-N.; Yoo, J.; Jang, J.; Lee, A.; Oh, J.-Y.; Kim, H.; Oh, S. T.; Park, S.-U.; Kim, J.; Park, H.-J.; Jeon, S. Novel Neuroprotective Effects of Melanin-Concentrating Hormone in Parkinson's Disease. *Mol. Neurobiol.* 2017, 54, 7706-7721.

(12) Marco, d. I.; Kazumasa, W.; Fabio, C.; Eduardo, D. M.; Carlos, G. B. J.; Stephane, C.; Ismael, G.; Ghanem, G.; Koike, K.; Paul, M.; Alessandro, P.; Clara, S.; Tadeusz, S.; D., S. J.; Luigi, Z.; A., Z. F.; Alessandra, N.; Shosuke, I. Melanins and Melanogenesis: from Pigment Cells to Human Health and Technological Applications. *Pigm. Cell Melanoma Res.* 2015, 28, 520-544.

(13) Hunt, G.; Kyne, S.; Ito, S.; Wakamatsu, K.; Todd, C.; Thody, A. J. Eumelanin and Phaeomelanin Contents of Human Epidermis and Cultured Melanocytes. *Pigm. Cell Res.* 1995, 8, 202-208.

(14) Alison, H.; Carol, O.; Brian, D.; Kazumasa, W.; Shosuke, I.; Jonathan, R. Eumelanin and Pheomelanin Concentrations in Human Epidermis before and after UVB Irradiation. *Pigm. Cell Res.* 2005, 18, 220-223.

(15) Wakamatsu, K.; Fujikawa, K.; Zucca, F. A.; Zecca, L.; Ito, S. The Structure of Neuromelanin as Studied by Chemical Degradative Methods. J. *Neurochem.* 2003, 86, 1015-1023.

(16) Schmaler-Ripcke, J.; Sugareva, V.; Gebhardt, P.; Winkler, R.; Kniemeyer, O.; Heinekamp, T.; Brakhage, A. A. Production of Pyomelanin, a Second Type of Melanin, via the Tyrosine Degradation Pathway in *Aspergillus fumigatus. Appl. Environ. Microbiol.* 2009, 75, 493-503.

(17) Haining, R.; Achat-Mendes, C. Neuromelanin, One of the Most Overlooked Molecules in Modern Medicine, is not a Spectator. *Neural Regen. Res.* 2017, 12, 372-375.

(18) D'Alba, L.; Shawkey, M. D. Melanosomes: Biogenesis, Properties, and Evolution of an Ancient Organelle. *Physiol. Rev.* 2019, 99, 1-19.

(19) Liu, Y. L.; Ai, K. L.; Lu, L. H. Polydopamine and Its Derivative Materials: Synthesis and Promising Applications in Energy, Environmental, and Biomedical Fields. *Chem. Rev.* 2014, 114, 5057-5115.

(20) Lee, H.; Dellatore, S. M.; Miller, W. M.; Messersmith, P. B. Mussel-Inspired Surface Chemistry for Multifunctional Coatings. *Science* 2007, 318, 426-430.

(21) Huang, L.; Liu, M. Y.; Huang, H. Y.; Wen, Y. Q.; Zhang, X. Y.; Wei, Y. Recent Advances and Progress on Melanin-like Materials and Their Biomedical Applications. *Biomacromolecules* 2018, 19, 1858-1868.

(22) Tokura, Y.; Harvey, S.; Chen, C.; Wu, Y.; Ng, D. Y. W.; Weil, T. Fabrication of Defined Polydopamine Nanostructures by DNA Origami-Templated Polymerization. *Angew. Chem. Int. Ed. Engl.* 2018, 57, 1587-1591.

(23) Lampel, A.; McPhee, S. A.; Park, H. A.; Scott, G. G.; Humagain, S.; Hekstra, D. R.; Yoo, B.; Frederix, P. W. J. M.; Li, T. D.; Abzalimov, R. R.; Greenbaum, S. G.; Tuttle, T.; Hu, C. H.; Bettinger, C. J.; Ulijn, R. V. Polymeric Peptide Pigments with Sequence-Encoded Properties. *Science* 2017, 356, 1064-1068.

(24) Huang, Y.; Li, Y.; Hu, Z.; Yue, X.; Proetto, M. T.; Jones, Y.; Gianneschi, N. C. Mimicking Melanosomes: Polydopamine Nanoparticles as Artificial Microparasols. *ACS Cent. Sci.* 2017, 3, 564-569.

(25) Wang, C.; Wang, D.; Dai, T.; Xu, P.; Wu, P.; Zou, Y.; Yang, P.; Hu, J.; Li, Y.; Cheng, Y. Skin Pigmentation-Inspired Polydopamine Sunscreens. *Adv. Funct. Mater.* 2018, 28, 1802127.

(26) Liu, X.; Cao, J.; Li, H.; Li, J.; Jin, Q.; Ren, K.; Ji, J. Mussel-Inspired Polydopamine: a Biocompatible and Ultrastable Coating for Nanoparticles in vivo. *ACS Nano* 2013, 7, 9384-9395.

(27) Zhang, X.; Wang, S.; Xu, L.; Feng, L.; Ji, Y.; Tao, L.; Li, S.; Wei, Y. Biocompatible Polydopamine Fluorescent Organic Nanoparticles: Facile Preparation and Cell Imaging. *Nanoscale* 2012, 4, 5581-5584.

(28) Wang, Z.; Xie, Y.; Li, Y.; Huang, Y.; Parent, L. R.; Ditri, T.; Zang, N.; Rinehart, J. D.; Gianneschi, N. C. Tunable, Metal-Loaded Polydopamine Nanoparticles Analyzed by Magnetometry. *Chem. Mater.* 2017, 29, 8195-8201.

(29) Xiao, M.; Li, Y.; Allen, M. C.; Deheyn, D. D.; Yue, X.; Zhao, J.; Gianneschi, N. C.; Shawkey, M. D.; Dhinojwala, A. Bio-Inspired Structural Colors Produced via Self-Assembly of Synthetic Melanin Nanoparticles. *ACS Nano* 2015, 9, 5454-5460.

(30) Nosanchuk, J. D.; Casadevall, A. The Contribution of Melanin to Microbial Pathogenesis. *Cell. Microbiol.* 2003, 5, 203-223.

(31) Nosanchuk, J. D.; Stark, R. E.; Casadevall, A. Fungal Melanin: What do We Know About Structure? *Front. Microbiol.* 2015, 6.

(32) Pihet, M.; Vandeputte, P.; Tronchin, G.; Renier, G.; Saulnier, P.; Georgeault, S.; Mallet, R.; Chabasse, D.; Symoens, F.; Bouchara, J.-P. Melanin is an Essential Component for the Integrity of the Cell Wall of *Aspergillus Fumigatus* Conidia. *BMC Microbiol.* 2009, 9, 177.

(33) Eisenman, H. C.; Nosanchuk, J. D.; Webber, J. B. W.; Emerson, R. J.; Camesano, T. A.; Casadevall, A. Microstructure of Cell Wall-Associated Melanin in the Human Pathogenic Fungus *Cryptococcus neoformans. Biochemistry* 2005, 44, 3683-3693.

(34) Robertson, K. L.; Mostaghim, A.; Cuomo, C. A.; Soto, C. M.; Lebedev, N.; Bailey, R. F.; Wang, Z. Adaptation of the Black Yeast *Wangiella dermatitidis* to Ionizing Radiation: Molecular and Cellular Mechanisms. *Plos One* 2012, 7.

(35) Pacelli, C.; Bryan, R. A.; Onofri, S.; Selbmann, L.; Shuryak, I.; Dadachova, E. Melanin is Effective in Protecting Fast and Slow Growing Fungi from Various Types of Ionizing Radiation. *Environ. Microbiol.* 2017, 19, 1612-1624.

(36) Dadachova, E.; Casadevall, A. Ionizing Radiation: How Fungi Cope, Adapt, and Exploit with the Help of Melanin. *Curr. Opin. Microbiol.* 2008, 11, 525-531.

(37) Dadachova, E.; Bryan, R. A.; Huang, X. C.; Moadel, T.; Schweitzer, A. D.; Aisen, P.; Nosanchuk, J. D.; Casadevall, A. Ionizing Radiation Changes the Electronic Properties of Melanin and Enhances the Growth of Melanized Fungi. *Plos One* 2007, 2.

(38) Schweitzer, A. D.; Revskaya, E.; Chu, P.; Pazo, V.; Friedman, M.; Nosanchuk, J. D.; Cahill, S.; Frases, S.; Casadevall, A.; Dadachova, E. Melanin-Covered Nanoparticles for Protection of Bone Marrow during Radiation Therapy of Cancer. *Int. J. Radiat. Oncol. Biol. Phys.* 2010, 78, 1494-1502.

(39) Cecchini, M. M.; Reale, S.; Manini, P.; d'Ischia, M.; DeAngelis, F. Modeling Fungal Melanin Buildup: Biomimetic Polymerization of 1,8-Dihydroxynaphthalene Mapped by Mass Spectrometry. *Chem. Eur. J.* 2017, 23, 8092-8098.

(40) Manini, P.; Bietti, M.; Galeotti, M.; Salamone, M.; Lanzalunga, O.; Cecchini, M. M.; Reale, S.; Crescenzi, O.; Napolitano, A.; De Angelis, F.; Barone, V.; d'Ischia, M. Characterization and Fate of Hydrogen-Bonded Free-Radical Intermediates and Their Coupling Products from the Hydrogen Atom Transfer Agent 1,8-Naphthalenediol. *ACS Omega* 2018, 3, 3918-3927.

(41) Song, B.; Wei, H.; Wang, Z.; Zhang, X.; Smet, M.; Dehaen, W. Supramolecular Nanofibers by Self-Organization of Bola-amphiphiles through a Combination of Hydrogen Bonding and π-π Stacking Interactions. *Adv. Mater.* 2007, 19, 416-420.

(42) Kim, E.; Kang, M.; Tschirhart, T.; Malo, M.; Dadachova, E.; Cao, G.; Yin, J. J.; Bentley, W. E.; Wang, Z.; Payne, G. F. Spectroelectrochemical Reverse Engineering Demonstrates That Melanin's Redox and Radical Scavenging Activities Are Linked. *Biomacromolecules* 2017, 18, 4084-4098.

(43) Kang, M.; Kim, E.; Temocin, Z.; Li, J. Y.; Dadachova, E.; Wang, Z.; Panzella, L.; Napolitano, A.; Bentley, W. E.; Payne, G. F. Reverse Engineering To Characterize Redox Properties: Revealing Melanin's Redox Activity through Mediated Electrochemical Probing. *Chem. Mater.* 2018, 30, 5814-5826.

(44) Liu, H.; Qu, X.; Tan, H.; Song, J.; Lei, M.; Kim, E.; Payne, G. F.; Liu, C. Role of Polydopamine's Redox-activity on Its Pro-oxidant, Radical-scavenging, and Antimicrobial Activities. *Acta Biomater.* 2019, 88, 181-196.

(45) Kim, E.; Liu, Y.; Shi, X. W.; Yang, X. H.; Bentley, W. E.; Payne, G. F. Biomimetic Approach to Confer Redox Activity to Thin Chitosan Films. *Adv. Funct. Mater.* 2010, 20, 2683-2694.

(46) Ju, K. Y.; Lee, Y.; Lee, S.; Park, S. B.; Lee, J. K. Bioinspired Polymerization of Dopamine to Generate Melanin-Like Nanoparticles Having an Excellent Free-Radical-Scavenging Property. *Biomacromolecules* 2011, 12, 625-632.

(47) Kobayashi, N.; Nakagawa, A.; Muramatsu, T.; Yamashina, Y.; Shirai, T.; Hashimoto, M. W.; Ishigaki, Y.; Ohnishi, T.; Mori, T. Supranuclear Melanin Caps Reduce Ultraviolet Induced DNA Photoproducts in Human Epidermis. *J. Invest. Dermatol.* 1998, 110, 806-810.

(48) Byers, H. R.; Maheshwary, S.; Amodeo, D. M.; Dykstra, S. G. Role of Cytoplasmic Dynein in Perinuclear Aggregation of Phagocytosed Melanosomes and Supranuclear Melanin Cap Formation in Human Keratinocytes. *J. Invest. Dermatol.* 2003, 121, 813-820.

(49) Bikle, D. D.; Xie, Z.; Tu, C. L. Calcium Regulation of Keratinocyte Differentiation. *Expert Rev. Endocrinol. Metab.* 2012, 7, 461-472.

(50) Xiao, M.; Hu, Z.; Wang, Z.; Li, Y.; Tormo, A. D.; Le Thomas, N.; Wang, B.; Gianneschi, N. C.; Shawkey, M. D.; Dhinojwala, A. Bioinspired Bright Noniridescent Photonic Melanin Supraballs. *Sci. Adv.* 2017, 3, e1701151.

Additional relevant references include: BMC Microbiology 2009, 9, 177; PLOS ONE 9(3): e91616; PLoS One. 2007; 2(5): e457; and Environ Microbiol, 19: 1612-1624.

REFERENCES CORRESPONDING TO SUPPLEMENTAL INFORMATION FOR EXAMPLE 1

(1) Kang, M.; Kim, E.; Temocin, Z.; Li, J. Y.; Dadachova, E.; Wang, Z.; Panzella, L.; Napolitano, A.; Bentley, W. E.; Payne, G. F. Reverse Engineering To Characterize Redox Properties: Revealing Melanin's Redox Activity through Mediated Electrochemical Probing. *Chem. Mater.* 2018, 30, 5814-5826.

Example 2: Structural Color

FIG. 40. Photographs and SEM images showing layers of artificial melanin nanoparticles exhibiting structural color. The larger photograph is captured using an optical microscope and the smaller inset photograph is captured using a cellphone camera. A layer of artificial melanin nanoparticles was formed by depositing artificial melanin nanoparticles from a solution and allowing the layer to form during evaporation of the solvent(s), such as illustrated in FIG. 42. The layer is characterized by a plurality of regions, indicated by the number annotations in the photographs, each indicated region having a different thickness. The corresponding SEM images next to the numbered photographs showing a cross-section of the corresponding numbered region of the layer, where each region has a different thickness and a different color due to the effect of structural color, or interference of light with the corresponding region of the layer of artificial melanin nanoparticles. For example: region #2 appears orange in the optical microscope photograph with SEM images showing a layer thickness of 295±16 nm; region #3 appears green in the optical microscope photograph with SEM images showing a layer thickness of 417±7 nm; region #4 appears purple in the optical microscope photograph with SEM images showing a layer thickness of 519±7 nm; and region #5 appears dark green in the optical microscope photograph with SEM images showing a layer thickness of 637±13 nm.

FIG. 41. A top-view of a region of the layer of artificial melanin nanoparticles of FIG. 40.

FIG. 42. An illustration of a method for forming the layer of FIG. 40. The layer is formed by self-assembly via evaporative deposition, where artificial melanin nanoparticles are deposited from a solution and the solvent(s) is allowed to evaporate thereby forming the layer. The layer of FIG. 40 is formed on a silicon wafer substrate having a native silica layer of approximately 2.4 nm thereon. For example, the solution has AMNP-1 artificial melanin nanoparticles at a concentration of 0.5 mg/mL. For example, the particles are approximately 140-170 nm in size. For example, the substrate temperature is approximately 21° C. and the relative humidity of the ambient air is 26% to 33%.

FIGS. 43A-43D. Each panel shows an SEM image and an inset photograph corresponding to a centrifuged pellet of artificial melanin nanoparticles (e.g., AMNP-1), where each different pellet has a different color due to exhibiting the effect of structural color. For example, the pellet of FIG. 43A appears blue in the inset photograph, the pellet of FIG. 43B appears purple in the inset photograph, the pellet of FIG. 43C appears green in the inset photograph, and the pellet of FIG. 43D appears yellow in the inset photograph.

Example 3: Synthetic, Porous DHN Allomelanin

This example provides technical characterization and synthetic information for a novel class of porous synthetic melanin particles, including synthetic, porous DHN allomelanin. Synthetic porous melanins include materials having well-defined, and optionally selectable and/or tunable, porosity, for example, melanin materials exhibiting substantially uniform pore structures and/or substantially ordered pore morphologies. Synthetic porous melanins are optionally biocompatible, degradability, non-toxic, metal free or any combination of these properties. In some embodiments, synthetic porous melanins materials are easy to synthesize via scalable processes, for example, utilizing environmentally friendly solvents, such as water, wherein the starting materials are commercially available. Synthesizing porous and hollow versions of synthetic melanins, such as allomelanins, is achieved in some embodiments via facile, template-free synthesis with few starting materials, for example, via inexpensive, easy, scalable, green processes requiring no template etching steps. In some embodiments, the porosity of the materials is also tunable for the required application.

Summary of Technology

Synthetic melanins have been used as multi-functional, biocompatible materials inspired by nature. Most synthetic melanin based materials have centered around polydopamine (PDA) to create mimics of eumelanin, but recently new materials have been created to mimic other types of melanin such as allomelanin, a class of nitrogen-free melanin. Allomelanin is commonly found in fungi where it serves as a radiation protection agent and rigid, cell wall protectant. Synthetic allomelanin has also been shown to serve as a radiation agent and antioxidant.

In the present example, synthesize porous and hollow versions of allomelanin materials are synthesized using a very simple methodology and characterized with respect to porosity. Synthetic melanins include biocompatible, degradable, non-toxic materials which are easy to synthesize and scalable, utilizing environmentally friendly solvents such as water. Synthesizing porous and hollow versions of synthetic allomelanins may be carried out using inexpensive, easy, scalable, green techniques that do not requires template etching steps. In some embodiments, the porosity of the materials is tunable or selectable, for example, over useful ranges. In some embodiments, for example, tunability or selectability is achieved by incubating the newly synthesized allomelanin materials with acetonitrile, acetic acid, or more efficiently, an alcoholic solvent, and then returning the particles back to water via a solvent switch after a period of time. Although we refer to this organic solvent incubation as "etching," or partial dissolution, the process does not involve the etching of a template which is created in a second step, or with separate chemistry, independent of the synthesis of the main material. In addition, this partial dissolution process is tunable, creating the desired structure (solid but porous, lacey porous, or hollow porous) for a given application.

Synthesis of Allomelanin Nanoparticles (MNPs)

Solid MNPs were synthesized largely based on the protocol for "AMNP-1" from previous work (doi: 10.1021/acsnano.9b02160). 150 mg of 1,8-DHN was dissolved in 7.5 mL of acetonitrile (ACN) and then diluted in 142.5 mL of ultrapure water. The mixture was stirred for 5 min at room temperature, and then 1 mL of 1 N $NaIO_4$ was quickly injected into the solution while stirring vigorously. After 20 hours, the solution was washed three times in ultrapure water by centrifugation at 10,000 rpm for 10 minutes.

Hollow MNPs were synthesized from a fresh batch of purified, solid MNPs which were left in a closed tube (containing ambient air) on the benchtop for 48 hours. They were centrifuged at 11,000 rpm for 15 minutes to remove water, and then resuspended in MeOH at 0.5 mg/mL. The suspension was agitated for 2-6 days and then dialyzed into ultrapure water.

Lacey MNPs were synthesized from a fresh batch of purified, solid MNPs which were left in a closed tube (containing ambient air) on the benchtop for 72 hours. They were centrifuged at 11,000 rpm for 15 minutes to remove water, and then resuspended in MeOH at 0.5 mg/mL. The suspension was agitated for 2-6 days and then dialyzed into ultrapure water.

TABLE 1

SAXS measurements for MNPs (Solid, Lacey, Hollow, and Fresh Solid). The particles are analyzed assuming a "core-shell" model whereby the solid particles have a negligible shell thickness, with a "shell rho" identical to that of pure water. Lacey and Hollow MNPs contain shells with different thicknesses, owing to the growth mechanism during formation, but similar shell rho values, indicating that they have similar composition/density. Pore volume per mass values ranging from 0.35 $cm^3/g$ to 0.60 $cm^3/g$ were determined.

| Particles | Core Radius (Å) | Shell Thickness (Å) | Core Rho ($\times10^{10}$ $cm^{-2}$) | Shell Rho ($\times10^{10}$ $cm^{-2}$) | Solvent Rho ($\times10^{10}$ $cm^{-2}$) |
|---|---|---|---|---|---|
| Solid | 612 ± 61 | 0.001 | 13.541 | 9.42 | 9.42 |
| Lacey | 517 ± 56 | 168 | 11.095 | 12.718 | 9.42 |
| Hollow | 482 ± 61 | 227 | 9.197 | 13.689 | 9.42 |
| Fresh Solid | 606 ± 55 | 0.001 | 12.423 | 9.42 | 9.42 |

TABLE 2

Brunauer-Emmett-Teller (BET) surface measurements and calculate pore dimensions/volumes for MNPs.

| Particles | BET Area ($m^2/g$) | Pore Volume ($cm^3/g$) | Microporous Size (nm) | Secondary Micropore Size (nm) |
|---|---|---|---|---|
| Solid | 680 | 0.35 | 0.6 | 1.2 |
| Lacey | 860 | 0.60 | 0.7 | 1.2 |
| Hollow | 645 | 0.36 | 0.5 | 1.3 |

FIG. 44 provides a schematic of "etching" or partial dissolution process to synthesize lacey and hollow MNPs from solid MNPs. This approach has found to be efficient for creating well-defined structures with the use of MeOH and can be performed using other alcoholic solvents such as isopropanol or ethanol, and/or non-alcoholic solvents such as acetonitrile or acetic acid. The Hollow MNPs are formed at an earlier timepoint where the original solid particle is "fresher" and overall less oxidized and may be less cross-linked, therefore MeOH treatment causes a leaching of more material from the particle core, which is likened to an oxidized "crust" which is still porous enough to allow small oligomers and monomers to leach out. In an embodiment, these particles are incubated with the etching solution for 6 days, therefore no leached material is removed. It re-deposits onto the surface of the particle, increasing the size of the particle by the same amount that leached out. Lacey MNPs are partially dissolved at a later stage (24 hours later), therefore the starting solid particle precursors are more fully oxidized, and less material can leach out upon MeOH treatment. This results in a particle midway between the Solid and Hollow MNPs, and is of an intermediate diameter, as there is less material leaching out that can re-deposit onto the surface. Hollow and Lacey particles are then dialyzed into water after the 6 day incubation with MeOH, where they remain stored in solution.

FIGS. 45A-45F provide STEM and SEM micrographs of MNPs. Bright-field STEM images of MNPs (top row, with high-angle annular dark-field (HAADF) STEM image insets) and SEM images of MNPs (bottom row) of Solid NMPs (FIGS. 45A-45B), Lacey MNPs (FIGS. 45C-45D), and Hollow MNPs (FIGS. 45E-45F). Scale bars in FIGS. 45A-45F are 500 nm, inset scale bars in FIGS. 45A, 45C and 45E are 20 nm.

FIGS. 46A-46D provide STEM imaging and particle size/growth analysis. FIG. 46A. Representative HAADF STEM micrograph of 1:1:1 Solid:Lacey:Hollow MNPs for analysis. FIG. 46B. Frequency distribution of Solid, Lacey, and Hollow MNP outer diameter (OD) and Hollow MNP inner diameter (ID). FIG. 46C. MNP density analysis. FIG. 46D. Normalized intensity as a function of MNP diameter. These images show that the growth mechanism after partial dissolution of the original solid particles to form "lacey" or "hollow" structures is consistent with a leaching of material, mainly small oligomers, from the center of the particle which are then redeposited onto the outer surface of the particle in a manner that conserves matter. Lacey and Hollow MNPs are slightly larger than their precursor solid particles due to this formation mechanism.

FIG. 47 provides Small Angle X-Ray Scattering (SAXS) measurements of MNPs (Solid, Lacey, Hollow, and Fresh Solid).

FIGS. 48A-48B provide Sorption (closed markers) and desorption (open markers) isotherms for Solid (square marker), Lacey (triangle marker) and Hollow (circle marker) MNPs as well as pore measurements. FIG. 48A. $N_2$ sorption measurements at 77 K. FIG. 48B. Pore size and volume measurements.

FIG. 49 provides solvent screening conditions for formation of hollow MNPs. Acetonitrile (ACN), acetic acid, and alcoholic solvents isopropanol (IPA), ethanol (EtOH) and methanol (MeOH) all etch solid particles to some extent, but MeOH is the most efficient at creating uniform structures. Less polar solvents ethyl acetate (EtOAc), dichloromethane (DCM), acetone, N,N-dimethylformamide (DMF), and 1-octanol do not etch the structures to any appreciable amount.

Commercialization

Large scale production of stable, well-defined, amorphous, porous materials. Other high surface area materials (such as MOFS) are typically delicate and chemically sensitive due to the reactivity of the metal center, and they often require costly, environmentally unfriendly metals, and more complicated linkers for their synthesis. In addition, MOFs and COFs suffer from scalability issues which impede their applicability for generating large quantities.

While some of the present "etched" or partially solubilized DHN melanins are susceptible to organic solvent directly following their synthesis, after several days (typically less than one week) they are fully stable in most organic solvents (e.g., alcohols MeOH and EtOH), and the materials so far have shown to be stable in water at room temperature for at least one year.

The present synthetic methods allows large scale production of well-defined nanomaterials starting from commercially available starting materials at low cost, using only water and alcohol as solvents. The synthesis is relatively environmentally friendly, using few materials and no harsh solvents. In addition, the resulting material is biocompatible and non-toxic to human skin cells.

REFERENCES RELATED TO EXAMPLE 3

Yi, B.; Shen, H. F., Liquid-immune structural colors with angle-independence inspired from hollow melanosomes. Chem Commun 2017, 53 (66), 9234-9237.

Wang, Y.; Su, J.; Li, T.; Ma, P. M.; Bai, H. Y.; Xie, Y.; Chen, M. Q.; Dong, W. F., A Novel UV-Shielding and Transparent Polymer Film: When Bioinspired Dopamine-Melanin Hollow Nanoparticles Join Polymers. Acs Appl Mater Inter 2017, 9 (41), 36281-36289.

Manini, P.; Lucci, V.; Lino, V.; Sartini, S.; Rossella, F.; Falco, G.; Chiappe, C.; d'Ischia, M., Synthetic mycomelanin thin films as emergent bio-inspired interfaces controlling the fate of embryonic stem cells. J Mater Chem B 2020, 8 (20), 4412-4418.

Manini, P.; Lino, V.; Franchi, P.; Gentile, G.; Sibillano, T.; Giannini, C.; Picardi, E.; Napolitano, A.; Valgimigli, L.; Chiappe, C.; d'Ischia, M., (2019). "A Robust Fungal Allomelanin Mimic: An Antioxidant and Potent pi-Electron Donor with Free-Radical Properties that can be Tuned by Ionic Liquids." Chempluschem 84 (9): 1331-1337.

Example 4: Synthetic, Porous Polydopamine

This example provides technical characterization and synthetic information for a novel class of porous synthetic melanin particles, including synthetic, porous polydopamine particles. Porous materials have broad potential utility and are used in myriad applications. However, many of the porous materials currently available are not scalable, require harsh conditions or expensive reagents to produce, are not solution processable, and are not stable under aqueous conditions. The present example provides technical characterization and synthetic information for a porous melanin material that is biocompatible, scalable, stable in many solutions and conditions, and uses non-expensive starting reagents. Using templating methods allows for porosity and size to be tuned or selected and demonstrate versatility with respect to applicability to a broad range of melanin monomers to be used in the synthesis.

Summary of Technology

The present porous synthetic melanin represents a novel and versatile biomimetic material. As opposed to other synthetic porous materials, melanin as a natural product has positive implications for the environment as it is degradable, multifunctional, and has low-to-no toxicity to cells/tissues. Additionally, the synthetic process is inexpensive and can be scaled for industrial purposes. The porous melanin may be synthesized using a templation method. The porosity as well as the size of the material could be tuned or selected based on the template used. Additionally, a templation method demonstrates applicability for a diverse range of melanin monomers to be used in the synthesis. In the example, porous polydopamine melanin particles are synthesized using a mesoporous silica template in water where the template is subsequentlyetched to leave the remaining porous melanin particles.

Synthesis of Porous Polydopamine

Synthetic Porous Melanin (SPM) was synthesized through a templation strategy. 250 mg of mesoporous silica (MS) and 225 mg of dopamine were stirred together for an hour in 250 mL of ultrapure water. Then trizma@base was added to make a 10 mM Tris buffer solution (pH 8.5) and the solution was further stirred for either four hours or twenty-one hours. After stirring, the particles were washed three times with ultrapure water by centrifugation at 11,000 rpm for 10 minutes. The mesoporous silica template was removed by etching with 10 wt % hydrofluoric acid for 15 hours. The particles were washed five times with ultrapure water by centrifugation at 11,000 rpm for 10 minutes to remove any remaining silica and hydrofluoric acid. The particles are resuspended in water. The four hour polymerization time led to a 5% loaded synthetic porous melanin where 5% of the polydopamine (PDA) remained after etching. The twenty-one hour polymerization time led to a 25% loaded synthetic porous melanin where 25% of the polydopamine remained after etching.

TABLE 3

Synthetic Porous Melanin Characterization and Porosity Parameters

| Particles | Zeta Potential (mV) | BET area ($m^2/g$) | Pore Volume ($cm^3/g$) | Microporous Size (Å) | Mesoporous Size (Å) |
|---|---|---|---|---|---|
| 5% Loaded SPM | −27.7 | 215 | 0.33 | 13 | 150 |
| 25% Loaded SPM | 10.4 | 140 | 0.30 | 14 | 130 |
| PDA | −14.6 | 20 | 0.02 | — | — |

REFERENCES ASSOCIATED WITH EXAMPLE 4

Chen, F.; Xing, Y.; Wang, Z.; Zheng, X.; Zhang, J.; Cai, K., Nanoscale Polydopamine (PDA) Meets pi-pi Interactions: An Interface-Directed Coassembly Approach for Mesoporous Nanoparticles. *Langmuir* 2016, 32 (46), 12119-12128.

FIG. 50 provides a schematic of templated synthesis of synthetic porous polydopamine.

FIGS. 51A-51J provide TEM and SEM micrographs of representative oxidatively polymerized polydopamine nanoparticles. Mesoporous silica with 5% loaded polydopamine before etching (FIG. 51A) and (FIG. 51B). Mesoporous silica with 5% loaded polydopamine after etching (5% Loaded SPM) (FIG. 51C) and (FIG. 51D). Mesoporous silica with 25% loaded polydopamine before etching (FIG. 51E) and (FIG. 51F). Mesoporous silica with 25% loaded polydopamine after etching (25% Loaded SPM) (FIG. 51G) and (FIG. 51H). Solid polydopamine nanoparticles (FIG. 51I) and (FIG. 51J). All scale bars 1 micron.

FIGS. 52A-52B provide Cryogenic TEM micrographs of SPM. FIG. 52A. 5% Loaded SPM. FIG. 52B. 25% Loaded SPM. All scale bars 1 micron.

FIGS. 53A-53F provide TEM micrographs of 5% Loaded SPM with different ratios of dopamine to mesoporous silica in milligrams. FIG. 53A. 5:10 FIG. 53B. 6:10 FIG. 53C. 7:10 FIG. 53D. 8:10 FIG. 53E. 9:10 FIG. 53F. 10:10. All scale bars 1 micron. Dopamine was polymerized on mesoporous silica for four hours.

FIGS. 54A-54F provide energy-dispersive X-ray spectroscopy (EDS) of 5% Loaded SPM. FIG. 54A. TEM of mesoporous silica coated with dopamine (SPM before etching). FIG. 54B. EDS of silica overlay of SPM before etching. FIG. 54C. EDS of silica of SPM before etching. FIG. 54D. TEM of SPM. FIG. 54E. EDS of silica overlay of SPM. FIG. 54F. EDS of silica of SPM.

FIGS. 55A-55D provide characterization of 5% Loaded SPM (blue), 25% Loaded SPM (red), PDA (green), and MS (purple). FIG. 55A. Dynamic light scattering. FIG. 55B. Fourier-transform infrared spectroscopy. FIG. 55C. Ultraviolet visible spectroscopy. FIG. 55D. Thermogravimetric analysis.

FIGS. 56A-56B provide $N_2$ sorption characterization. FIG. 56A. Nitrogen adsorption (solid) and desorption (open) of 5% Loaded SPM (blue), 25% SPM (red), and PDA (green). FIG. 56B. Pore size distribution of 5% (blue) and 25% (red) Loaded SPM determined using DFT.

Commercialization

Porous materials that are scalable, stable, tunable, biocompatible, and amorphous. Other porous materials are typically unstable in many solutions, are not scalable without the formation of defects or a decrease in porosity, are bioincompatible, and are synthesized from costly and environmentally unfriendly materials.

The synthesis of a porous melanin through templation methods allows for an adaptable material made from a few commercially available starting materials. The templation method allows for many types of melanin monomers to be utilized, and the porosity as well as size of the resulting particles can be tuned. We have shown the synthesis of a porous polydopamine to be synthesized utilizing this method. The porous polydopamine is scalable, biocompatible, and its porosity enhances its adsorption properties.

STATEMENTS REGARDING INCORPORATION BY REFERENCE AND VARIATIONS

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, exemplary embodiments and optional features, modification and variation of the concepts herein disclosed may be resorted to by those skilled in the art, and that such modifications and variations are considered to be within the scope of this invention as defined by the appended claims. The specific embodiments provided herein are examples of useful embodiments of the present invention and it will be apparent to one skilled in the art that the present invention may be carried out using a large number of variations of the devices, device components, methods steps set forth in the present description. As will be obvious to one of skill in the art, methods and devices useful for the present methods can include a large number of optional composition and processing elements and steps.

As used herein and in the appended claims, the singular forms “a”, “an”, and “the” include plural reference unless the context clearly dictates otherwise. Thus, for example, reference to “a cell” includes a plurality of such cells and equivalents thereof known to those skilled in the art. As well, the terms “a” (or “an”), “one or more” and “at least one” can be used interchangeably herein. It is also to be noted that the terms “comprising”, “including”, and “having” can be used interchangeably. The expression “of any of claims XX-YY” (wherein XX and YY refer to claim numbers) is intended to provide a multiple dependent claim in the alternative form, and is interchangeable with the expression “as in any one of claims XX-YY.”

When a group of substituents is disclosed herein, it is understood that all individual members of that group and all subgroups, including any isomers, enantiomers, and diastereomers of the group members, are disclosed separately. When a Markush group or other grouping is used herein, all individual members of the group and all combinations and sub-combinations possible of the group are intended to be individually included in the disclosure. When a compound is described herein such that a particular isomer, enantiomer or diastereomer of the compound is not specified, for example, in a formula or in a chemical name, that description is intended to include each isomers and enantiomer of the compound described individual or in any combination. Additionally, unless otherwise specified, all isotopic variants of compounds disclosed herein are intended to be encompassed by the disclosure. For example, it will be understood that any one or more hydrogens in a molecule disclosed can be replaced with deuterium or tritium. Isotopic variants of a molecule are generally useful as standards in assays for the molecule and in chemical and biological research related to the molecule or its use. Methods for making such isotopic variants are known in the art. Specific names of compounds are intended to be exemplary, as it is known that one of ordinary skill in the art can name the same compounds differently.

Certain molecules disclosed herein may contain one or more ionizable groups [groups from which a proton can be removed (e.g., —COOH) or added (e.g., amines) or which can be quaternized (e.g., amines)]. All possible ionic forms of such molecules and salts thereof are intended to be included individually in the disclosure herein. With regard to salts of the compounds herein, one of ordinary skill in the art can select from among a wide variety of available counterions those that are appropriate for preparation of salts of this invention for a given application. In specific applications, the selection of a given anion or cation for preparation of a salt may result in increased or decreased solubility of that salt.

Every device, system, formulation, plurality of nanoparticles, combination of components, or methods described or exemplified herein can be used to practice the invention, unless otherwise stated.

Whenever a range is given in the specification, for example, a temperature range, a time range, or a composition or concentration range, all intermediate ranges and subranges, as well as all individual values included in the ranges given are intended to be included in the disclosure. It will be understood that any subranges or individual values in a range or subrange that are included in the description herein can be excluded from the claims herein.

All patents and publications mentioned in the specification are indicative of the levels of skill of those skilled in the art to which the invention pertains. References cited herein are incorporated by reference herein in their entirety to indicate the state of the art as of their publication or filing date and it is intended that this information can be employed herein, if needed, to exclude specific embodiments that are in the prior art. For example, when composition of matter are claimed, it should be understood that compounds known and available in the art prior to Applicant’s invention, including compounds for which an enabling disclosure is provided in the references cited herein, are not intended to be included in the composition of matter claims herein.

As used herein, “comprising” is synonymous with “including,” “containing,” or “characterized by,” and is inclusive or open-ended and does not exclude additional, unrecited elements or method steps. As used herein, “consisting of” excludes any element, step, or ingredient not specified in the claim element. As used herein, “consisting essentially of” does not exclude materials or steps that do not materially affect the basic and novel characteristics of the claim. In each instance herein any of the terms “comprising”, “consisting essentially of” and “consisting of” may be replaced with either of the other two terms. The invention illustratively described herein suitably may be practiced in the absence of any element or elements, limitation or limitations which is not specifically disclosed herein.

One of ordinary skill in the art will appreciate that starting materials, biological materials, reagents, synthetic methods, purification methods, analytical methods, assay methods, and biological methods other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

We claim:

1. A material comprising a plurality of artificial melanin nanoparticles, wherein:

each melanin nanoparticle of the plurality of artificial melanin nanoparticles comprises a plurality of melanin oligomers;

each melanin oligomer comprises a plurality of covalently-bonded melanin base units;

each melanin oligomer has a molecular weight of 10,000 Da or less;

each melanin base unit comprises substituted or unsubstituted naphthalene;

each melanin oligomer is free of nitrogen;

the plurality of artificial melanin nanoparticles is characterized by a polydispersity index being less than or equal to 0.10;

each melanin nanoparticle of the plurality of artificial melanin nanoparticles has a diameter selected from the range of 100 nm to 300 nm, and wherein at least 50 wt. % of the plurality of melanin oligomers are selected from the group consisting of dimers, trimers, tetramers, pentamers, and any combination thereof.

2. The material of claim 1, wherein:

the plurality of artificial melanin nanoparticles are in the form of a packed and/or ordered structure and exhibit a structural color.

3. The material of claim 1, wherein:

each nanoparticle has a sphericity of less than 0.90 and has a shape characterized as at least one of: walnut-like, a collapsed sphere or collapsed ellipsoid, and a sphere or ellipsoid having a plurality of indentations.

4. The material of claim 1, wherein:

the plurality of artificial melanin nanoparticles are characterized by a radical scavenging activity greater than that of polydopamine nanoparticles having the same diameter as the plurality of artificial melanin nanoparticles under otherwise identical condition.

5. The material of claim 1, wherein each melanin base unit comprises dihydroxynaphthalene.

6. The material of claim 1, wherein each melanin base unit comprises a structure having the formula FX1:

(FX1)

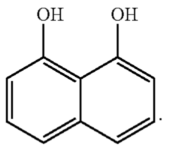

7. The material of claim 1, wherein 20 wt. % to 80 wt. % of the plurality of melanin oligomers are dimers having two covalently-bonded melanin base units.

8. The material of claim 1, wherein each melanin oligomer is non-covalently associated with at least one other melanin oligomer or a melanin monomer via at least one of hydrogen bonding and TT-TT stacking of naphthalene rings; wherein the melanin monomer comprises the melanin base unit.

9. The material of claim 8, wherein each nanoparticle is characterized by a sphericity of greater than 0.90.

10. The material of claim 1, wherein the plurality of artificial melanin nanoparticles are characterized by a peak size selected from the range of 100 nm to 300 nm.

11. The material of claim 1 being dispersed in a solvent or solvent mixture, thereby forming an artificial nanoparticle dispersion.

12. The material of claim 11, wherein the solvent or solvent mixture is at least 50% water.

13. The material of claim 11, wherein the nanoparticles in the artificial nanoparticle dispersion are characterized by a zeta potential selected from the range of −50 to −10 mV.

14. The material of claim 11, wherein the nanoparticles in the artificial nanoparticle dispersion are stably dispersed without forming precipitates after at least 5 hours at a concentration selected from the range of 0.01 mg/ml to 1 mg/mL.

15. The material of claim 1 characterized by a radical scavenging activity at least 0.15 times greater than that of polydopamine nanoparticles having the same diameter as the plurality of artificial melanin nanoparticles under otherwise identical condition.

16. The material of claim 1 characterized by a radical scavenging activity of at least 0.012 mol/g using an assay of 2,2-diphenyl-1-(2,4,6-trinitrophenyl) hydrazyl (DPPH).

17. A method for making a material comprising a plurality of artificial melanin nanoparticles, the method comprising:

polymerizing a plurality of melanin monomers via oxidative oligomerization, each melanin monomer comprising a melanin base unit;

wherein:

each melanin nanoparticle of the plurality of artificial melanin nanoparticles comprises a plurality of melanin oligomers;

each melanin oligomer has a molecular weight of 10,000 Da or less;

each melanin oligomer comprises a plurality of the melanin base units being covalently-bonded;

each melanin base unit comprises substituted or unsubstituted naphthalene;

each melanin oligomer is free of nitrogen;

the plurality of artificial melanin nanoparticles is characterized by a polydispersity index being less than or equal to 0.10;

each melanin nanoparticle of the plurality of artificial melanin nanoparticles has a diameter selected from the range of 100 nm to 300 nm; and at least 50 wt. % of the plurality of melanin oligomers are selected from the group consisting of dimers, trimers, tetramers, pentamers, and any combination thereof.

18. The material of claim 2, wherein the structural color comprises orange, green, purple, blue, yellow, or any combination thereof.

19. The material of claim 1, wherein at least 80 wt. % of the plurality of melanin oligomers are selected from the group consisting of dimers, trimers, tetramers, pentamers, and any combination thereof.

20. The material of claim 1, wherein each melanin nanoparticle of the plurality of artificial melanin nanoparticles further comprises a plurality of melanin polymers; wherein:

each melanin polymer comprises a plurality of covalently-bonded melanin base units;

each melanin polymer has a molecular weight of greater than 10,000 Da;

each melanin base unit comprises substituted or unsubstituted naphthalene; and each melanin polymer is free of nitrogen.

* * * * *